United States Patent
Gauthier et al.

(10) Patent No.: US 11,845,795 B2
(45) Date of Patent: *Dec. 19, 2023

(54) NKP46 BINDING PROTEINS

(71) Applicant: INNATE PHARMA, Marseilles (FR)

(72) Inventors: Laurent Gauthier, Marseilles (FR); Nadia Anceriz, Aubagne (FR); Ariane Morel, Marseilles (FR); Benjamin Rossi, Marseilles (FR)

(73) Assignee: INNATE PHARMA, Marseilles (FR)

( * ) Notice: Subject to any disclaimer, the term of this patent is extended or adjusted under 35 U.S.C. 154(b) by 746 days.

This patent is subject to a terminal disclaimer.

(21) Appl. No.: 16/677,709

(22) Filed: Nov. 8, 2019

(65) Prior Publication Data
US 2020/0131268 A1 Apr. 30, 2020

Related U.S. Application Data

(62) Division of application No. 15/321,650, filed as application No. PCT/EP2015/064063 on Jun. 23, 2015, now Pat. No. 10,519,234.

(60) Provisional application No. 62/017,886, filed on Jun. 27, 2014, provisional application No. 62/108,088, filed on Jan. 27, 2015.

(51) Int. Cl.
C07K 16/28 (2006.01)

(52) U.S. Cl.
CPC ...... C07K 16/2803 (2013.01); C07K 16/2866 (2013.01); C07K 2317/31 (2013.01); C07K 2317/71 (2013.01); C07K 2317/92 (2013.01); C07K 2319/30 (2013.01)

(58) Field of Classification Search
None
See application file for complete search history.

(56) References Cited

U.S. PATENT DOCUMENTS

| | | |
|---|---|---|
| 5,229,275 A | 7/1993 | Goroff |
| 5,565,332 A | 10/1996 | Hoogenboom et al. |
| 5,567,610 A | 10/1996 | Borrebaeck et al. |
| 5,573,905 A | 11/1996 | Lerner et al. |
| 6,162,963 A | 12/2000 | Kucherlapati et al. |
| 6,737,056 B1 | 5/2004 | Presta |
| 6,821,505 B2 | 11/2004 | Ward |
| 7,122,637 B2 | 10/2006 | Presta |
| 7,183,387 B1 | 2/2007 | Presta |
| 7,332,581 B2 | 2/2008 | Presta |
| 7,355,742 B2 | 2/2008 | Presta |
| 7,355,008 B2 | 4/2008 | Stavenhagen et al. |
| 7,371,826 B2 | 5/2008 | Presta |
| 7,416,727 B2 | 8/2008 | Presta |
| 7,425,619 B2 | 9/2008 | Koenig et al. |
| 7,521,542 B2 | 4/2009 | Johnson et al. |
| 7,632,497 B2 | 12/2009 | Stavenhagen |
| 7,825,085 B2 * | 11/2010 | Mandelboim .... C07K 14/70503 514/19.3 |
| 10,113,003 B2 | 10/2018 | Gauthier et al. |
| 2002/0161201 A1 | 10/2002 | Filpula et al. |
| 2004/0242851 A1 | 12/2004 | Zhu |
| 2005/0136050 A1 | 6/2005 | Kufer et al. |
| 2005/0238646 A1 | 10/2005 | Ledbetter et al. |
| 2006/0074225 A1 | 4/2006 | Chamberlain et al. |
| 2006/0275254 A1 | 12/2006 | Kim et al. |
| 2007/0178106 A1 | 8/2007 | Romagne |
| 2009/0155275 A1 | 6/2009 | Wu et al. |
| 2010/0316645 A1 | 12/2010 | Imhof-Jung et al. |
| 2012/0201746 A1 | 8/2012 | Liu et al. |
| 2014/0234342 A1 | 8/2014 | Narni-Mancinelli et al. |
| 2016/0369002 A1 | 12/2016 | Gauthier et al. |
| 2018/0355036 A1 | 12/2018 | Gauthier et al. |
| 2018/0369373 A1 | 12/2018 | Anceriz et al. |
| 2019/0048093 A1 | 2/2019 | Gauthier et al. |
| 2019/0055315 A1 | 2/2019 | Gauthier et al. |

FOREIGN PATENT DOCUMENTS

| | | |
|---|---|---|
| EP | 1176195 | 1/2002 |
| WO | WO 9211018 | 7/1992 |
| WO | WO 9954342 | 10/1999 |
| WO | WO 0042072 | 7/2000 |
| WO | WO 03035835 | 5/2003 |
| WO | WO 04063351 | 7/2004 |
| WO | WO 04099249 | 11/2004 |
| WO | WO 2005000086 | 1/2005 |
| WO | WO 05047327 | 5/2005 |
| WO | WO 2005040219 | 5/2005 |
| WO | WO 2005061547 | 7/2005 |
| WO | WO 05110474 | 11/2005 |
| WO | WO 2005105858 | 11/2005 |
| WO | WO 05115452 | 12/2005 |
| WO | WO 2006031994 | 3/2006 |

(Continued)

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Yu et al., Investigative Ophthalmology & Visual Science 49(2): 522-527 (Year: 2009).*
Holmes TD, et al. "A human NK cell activation/inhibition threshold allows small changes in the target cell surface phenotype to dramatically alter susceptibility to NK cells," The J Immunol. Feb. 1, 2011;186(3):1538-45.
Kim HR, et al. "Anti-cancer activity and mechanistic features of a NK cell activating molecule," Cancer Immunology, Immunother. Oct. 2009;58(10):1691-700.

(Continued)

Primary Examiner — Phuong Huynh
(74) Attorney, Agent, or Firm — Robin L. Teskin; Baker, Donelson, Bearman, Caldwell & Berkowitz PC

(57) ABSTRACT

Multispecific proteins that bind and specifically redirect NK cells to lyse a target cell of interest are provided without non-specific activation of NK cells in absence of target cells. The proteins have utility in the treatment of disease, notably cancer or infectious disease.

12 Claims, 27 Drawing Sheets
Specification includes a Sequence Listing.

(56) References Cited

FOREIGN PATENT DOCUMENTS

| WO | WO 2006053301 | 5/2006 |
|---|---|---|
| WO | WO 2006064136 | 6/2006 |
| WO | WO 06088494 | 8/2006 |
| WO | WO 06133148 | 12/2006 |
| WO | WO 2007021841 | 2/2007 |
| WO | WO 07024249 | 3/2007 |
| WO | WO 2007073499 | 6/2007 |
| WO | WO 2007106707 | 9/2007 |
| WO | WO 2008002933 | 1/2008 |
| WO | WO 2008105886 | 9/2008 |
| WO | WO 2008119353 | 10/2008 |
| WO | WO 2009089004 | 7/2009 |
| WO | WO 2010032269 | 3/2010 |
| WO | WO 2011063348 | 5/2011 |
| WO | WO 2011066501 | 6/2011 |
| WO | WO 2011069104 | 6/2011 |
| WO | WO 2011109400 | 9/2011 |
| WO | WO 2011131746 | 10/2011 |
| WO | WO 2011133886 | 10/2011 |
| WO | WO 2012089814 | 7/2012 |
| WO | WO 2014044686 | 3/2014 |
| WO | WO 2015197593 | 12/2015 |
| WO | WO 2015197598 | 12/2015 |
| WO | WO 2016207273 | 12/2016 |
| WO | WO 2016207278 | 12/2016 |

OTHER PUBLICATIONS

Torres and Casadevall. "The immunoglobulin constant region contributes to affinity and specificity," Trends Immunol. Feb. 2008;29(2):91-7.
Vyas M, et al. "Natural ligands and antibody-based fusion proteins: harnessing the immune system against cancer," Trends Mol Med. Feb. 2014;20(2):72-82.
Weidle UH, et al. "The intriguing options of multispecific antibody formats for treatment of cancer," Cancer Genomics & Proteomics. Jan. 1, 2013;10(1):1-18.
Weiner GJ. Rituximab: mechanism of action, Semin Hematol. Apr. 2010;47(2)115-23.
Feige MJ, et al. "An unfolded CH1 domain controls the assembly and secretion of IgG antibodies," Molecular cell. Jun. 12, 2009;34(5):569-79.
Chung S, et al. "Quantitative evaluation of fucose reducing effects in a humanized antibody on Fcγ receptor binding and antibody-dependent cell-mediated cytotoxicity activities,"MAbs May-Jun. 2012;4(3):326-340.
Barb AW, et al. "NMR analysis demonstrates immunoglobulin G N-glycans are accessible and dynamic," Nat Chem Biol. Mar. 2011;7(3):147-153.
Communication from the International Searching Authority received in PCT/EP2016/064537 dated Sep. 7, 2016.
Rozan C, et al., "Single domain antibody-based and linker-free bispecific antibodies targeting FcγRIII induce potent anti-tumor activity without recruiting regulatory T cells," Mol Cancer Ther. Aug. 2013;12;(8)1481-91.
Müller KM, et al., "The first constant domain (CH1 and CL) of an antibody used as heterodimerization domain for bispecific miniantibodies," FEBS Lett. Jan. 30, 1998;422(2):259-64.
Kufer P, et al., "A revival of bispecific antibodies," Trends Biotechnol. May 2004:22(5):238-44.
Low S, et al., "Inhibitors of the FcRn: IgG protein-protein interaction." AAPS J. Sep. 2009;11(3):432.
Hollander, N. "Bispecific antibodies for cancer therapy." Immunotherapy, Mar. 2009; 1(2):211-22.
Ying T. et al., "Soluble monomeric IgG1 Fc." J Biol Chem. Jun. 1, 2012;287(23):19399-408.
Idusogie EE, et al., "Mapping of the C1q binding site on rituxan, a chimeric antibody with a human IgG1 Fc," J Immunol. Apr. 15, 2000;164(8):4178-84.

Armour KL, et al., "Recombinant human IgG molecules lacking Fcγ receptor I binding and monocyte triggering activities," Eur J immunol. Aug. 1999;29(8):2613-24.
Presta, L. G., et al., Engineering therapeutic antibodies for improved function. (2002): 487-490.
Shields RL, et al., "Lack of fucose on human IgG1 N-linked oligosaccharide improves binding to human FcγRIII and antibody-dependent cellular toxicity," J Biol Chem. Jul. 26, 2002;277(30):26733-40. Epub May 1, 2002.
Shields RL, et al., "High resolution mapping of the binding site on human IgG1 for Fc gamma RI, Fc gamma RII, Fc gamma RIII, and FcRn and design of IgG1 variants with improved binding to the Fc gamma R." J Biol Chem. Mar. 2, 2001;276(9):6591-60. Epub Nov. 28, 2000.
Devereux J, et al., A comprehensive set of sequence analysis programs for the VAX. Nucleic Acids Res. Jan. 11, 1984;12(1 Pt 1):387-95.
Altschul SF, et al., "Basic local alignment search tool," J Mol Biol. Oct. 5, 1990;215(3):403-10.
Winter, C. C., et al., "Natural Killer Cells Protocols (edited by Campbell KS and Colonna M)." (2000): 219-238.
Gebauer M, et al., "Engineered protein scaffolds as next-generation antibody therapeutics," Curr Opin Chem Biol, Jun. 2009; 13(3):245-55. Epub Jun. 6, 2009.
Jakobovitz A, et al., "Germ-line transmission and expression of a human-derived yeast artificial chromosome," Nature. Mar. 18, 1993;362(6417):255-8.
Ward ES, et al., "Binding activities of a repertoire of single immunoglobulin variable domains secreted from *Escherichia coli*," Nature. Oct. 12, 1989;341(6242):544-6.
McCafferty J, et al., "Phage antibodies: filamentous phage displaying antibody variable domains," Nature. Dec. 1990;348(6301):552-53.
Griffiths AD, et al., "Human anti-self antibodies with high specificity from phage display libraries," EMBO J. Feb. 1993;12(2):725-34.
McDonagh CF, et al., "Antitumor activity of a novel bispecific antibody that targets the ErbB2/ErbB3 oncogenic unit and inhibits heregulin-induced activation of ErbB3," Mol. Cancer Ther. Mar. 2012;11(3):582-93.
Jones PT, et al., "Replacing the complementarity-determining regions in a human antibody with those from a mouse," Nature. May39-Jun. 4, 1986;321(6069):522-525.
Verhoeyen et al,. "Reshaping human antibodies: grafting an antilysozyme activity," Science. Mar. 25, 1988;239(4847):1534-6.
Kabat EA, et al. "Identical V region amino acid sequences and segments of sequences in antibodies of different specificities. Relative contributions of VH and VL genes, minigenes, and complementarity-determining regions to binding of antibody-combining sites," J Immunol. Sep. 1, 1991;147(5):1709-19.
Müller R., "Determination of affinity and specificity of anti-hapten antibodies by competitive radioimmunoassay," Methods Enzymol. 1983;92:589-601.
Jackman J et al., "Development of a two-part strategy to identify a therapeutic human bispecific antibody that inhibits IgE receptor signaling," J. Biol Chem. Jul. 2, 2010;285(27):20850-9.
Baeuerle PA, et al., "Bispecific T-cell engaging antibodies for cancer therapy," Cancer Res. Jun. 15, 2009;69(12):4941-4. Epub Jun. 9, 2009.
III CR, et al., "Design and construction of hybrid immunoglobulin domain with properties of both heavy and light chain variable regions," Protein Eng. Aug. 1997;10(8):949-57.
Holliger et al., "Engineered antibody fragments and the rise of single domains," Nat Biotechnol. Sep. 2005;23(9);1126-36.
Chothia c, et al., "Canonical structures for the hypervariable regions of immunoglobulins." J. Mol Biol. Aug. 20, 1987,196(4):901-17.
Plückthun, A. "Antibodies from *Escherichia coli*." The Pharmacology of Monoclonal Antibodies. Springer, Berlin, Heidelberg, 1994. 269-315.
Bolzhauser M., *Immuntherapie der kindlichen ALL: Einfluss eines bispezifischen CD19\* NKp46-Antikörpers auf die zytotoxische Aktivität von NK-Zellen gegenüber CD19_1hn+-ALL-Blasten pädiatrischer Patienten.* Diss. 2010.

(56) References Cited

OTHER PUBLICATIONS

Germain C, et al., "Redirecting NK cells mediated tumor cell lysis by a new recombinant bifunctional protein," Protein Eng Des Sel. Nov. 2008;21(11):665-72.

Chames P, et al., "Bispecific antibodies for cancer therapy: the light at the end of the tunnel?". MAbs Nov.Dec. 2009:1(6):539-547.

Kellner C, et al., "Heterodimeric bispecific antibody-derivatives against CD19 and CD16 induce effective antibody-dependent cellular cytotoxicity against B-lymphoid tumor cells," Cancer Lett. Apr. 28, 2011:303(2):128-39.

Pessino A, et al., "Molecular cloning of NKp46: a novel member of the immunoglobulin superfamily involved in triggering of natural cytotoxicity," J Exp Med. Sep. 7, 1998;188(5):953-60.

Sivori S, et al., "NKp46 is the major triggering receptor involved in the natural cytotoxicity of fresh or cultured human NK cells. Correlation between surface density of NKp46 and natural cytotoxicity against autologous, allogeneic or xenogeneic target cells," Eur J Immunol. May 1999;29(5):1656-66.

Brando C, et al., "Receptors and lytic mediators regulating anti-tumor activity by the leukemic killer T cell line TALL-104," J Leukocyte Biol. Aug. 2005;78(2):359-71.

El-Sherbiny YM, et al., "The requirement for DNAM-1, NKG2D, and NKp46 in the natural killer cell-mediated killing of myeloma cells," Cancer Res. Sep. 15, 2007;67(18):8444-9.

Nolte EN, et al., "Increased surveillance of cells in mitosis by human NK cells suggests a novel strategy for limiting tumor growth and viral replication," Blood. Jan. 15, 2007;109(2):670-3.

Schleinitz N, et al., "Expression of the CD85j (leukocyte Ig-like receptor 1, Ig-like transcript 2) receptor for class I major histocompatibility complex molecules in idiopathic inflammatory myopathies," Arthritis & Rheum.: Official Journal of the American College of Rheumatology. Oct. 2008;58(10):3216-23.

Umaña P, et al., "Engineered glycoforms of an antineuroblastoma IgG1 with optimized antibody-dependent cellular cytotoxic activity," Nat Biotechnol. Feb. 1999;17(2):176.

Jaron-Mendelson M, et al., "Dimerization of NKp46 receptor is essential for NKp46-mediated lysis: characterization of the dimerization site by epitope mapping," J Immunol. Jun. 15, 2012;188(12):6165-74.

\* cited by examiner

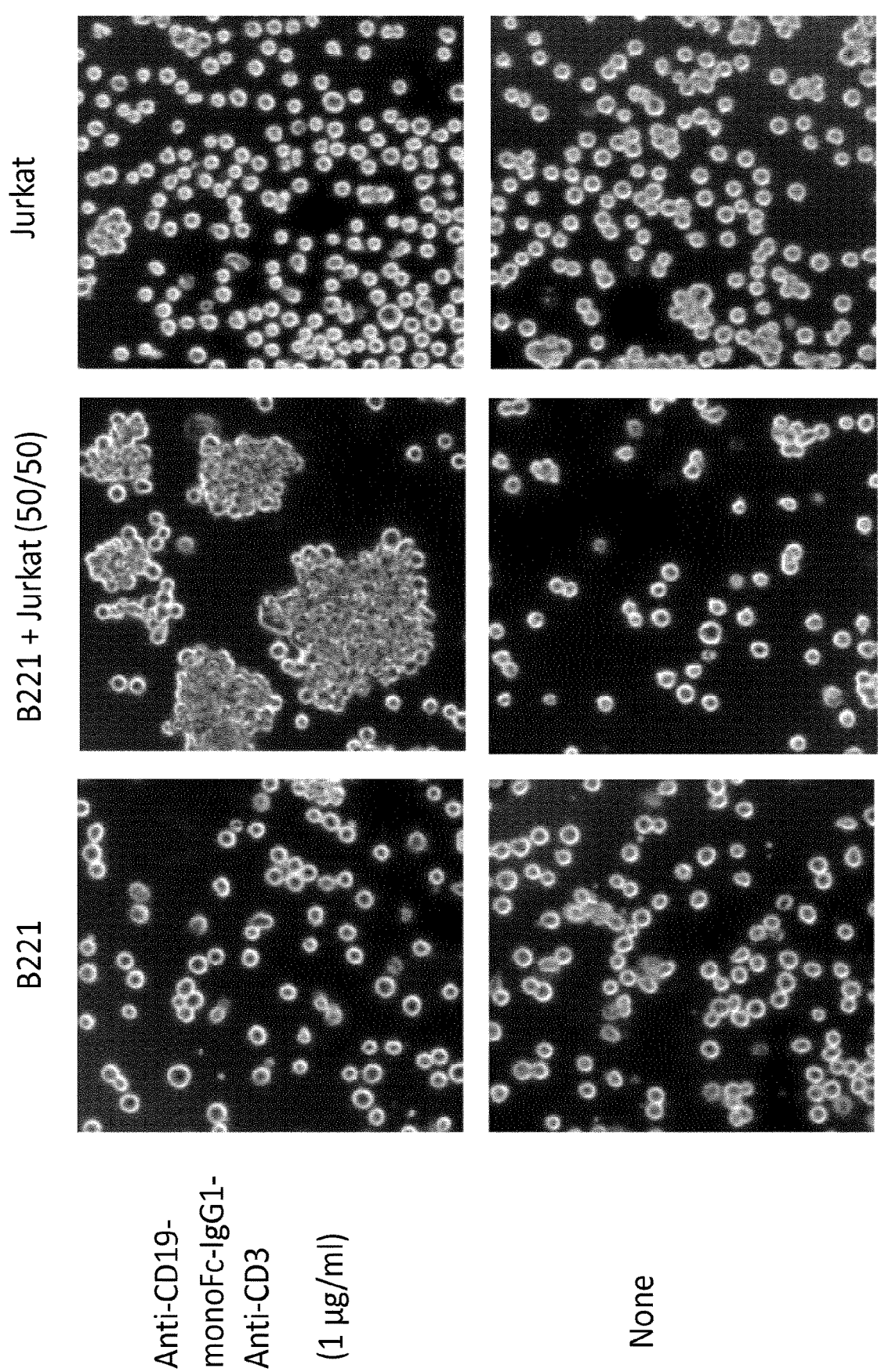

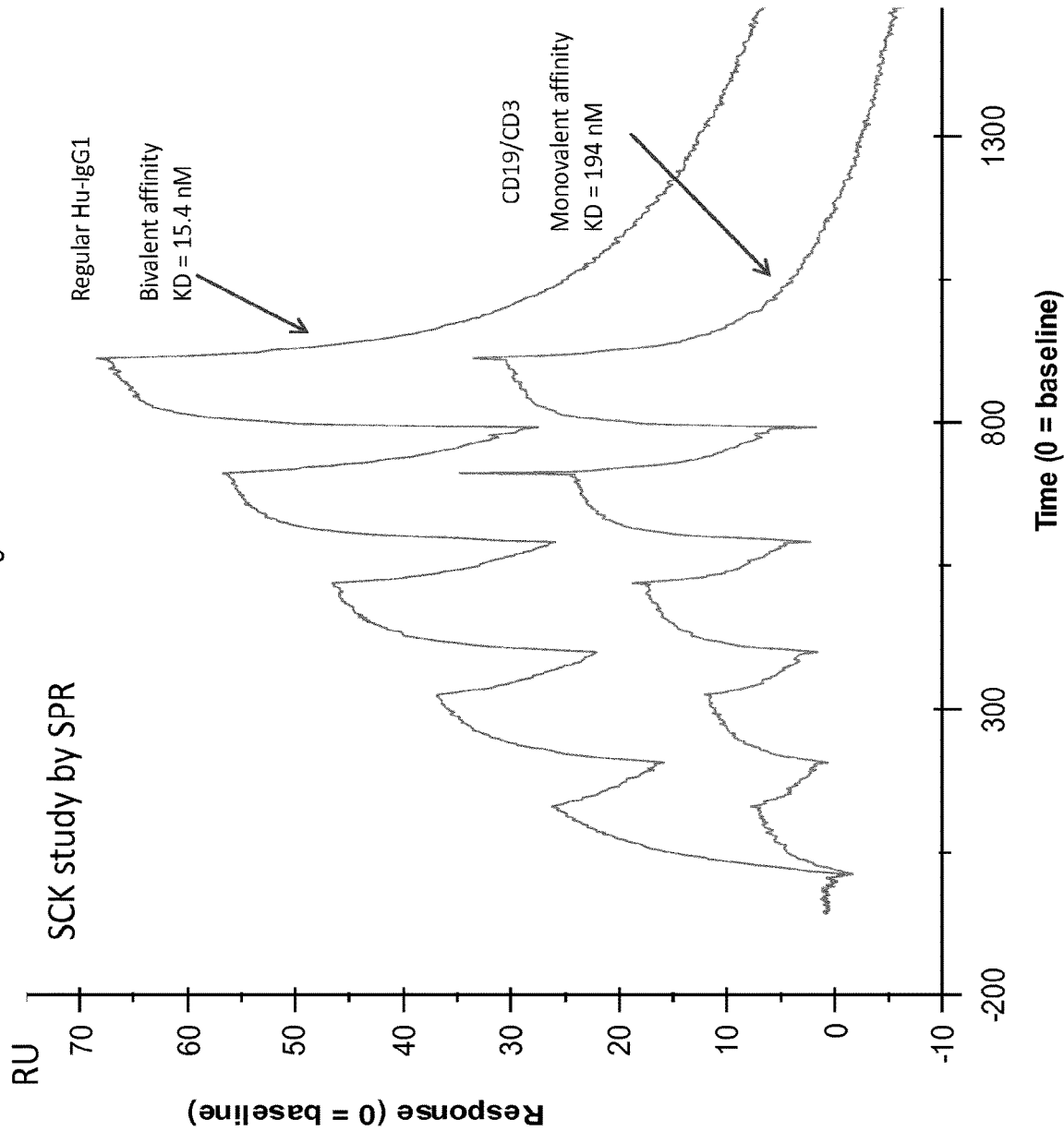

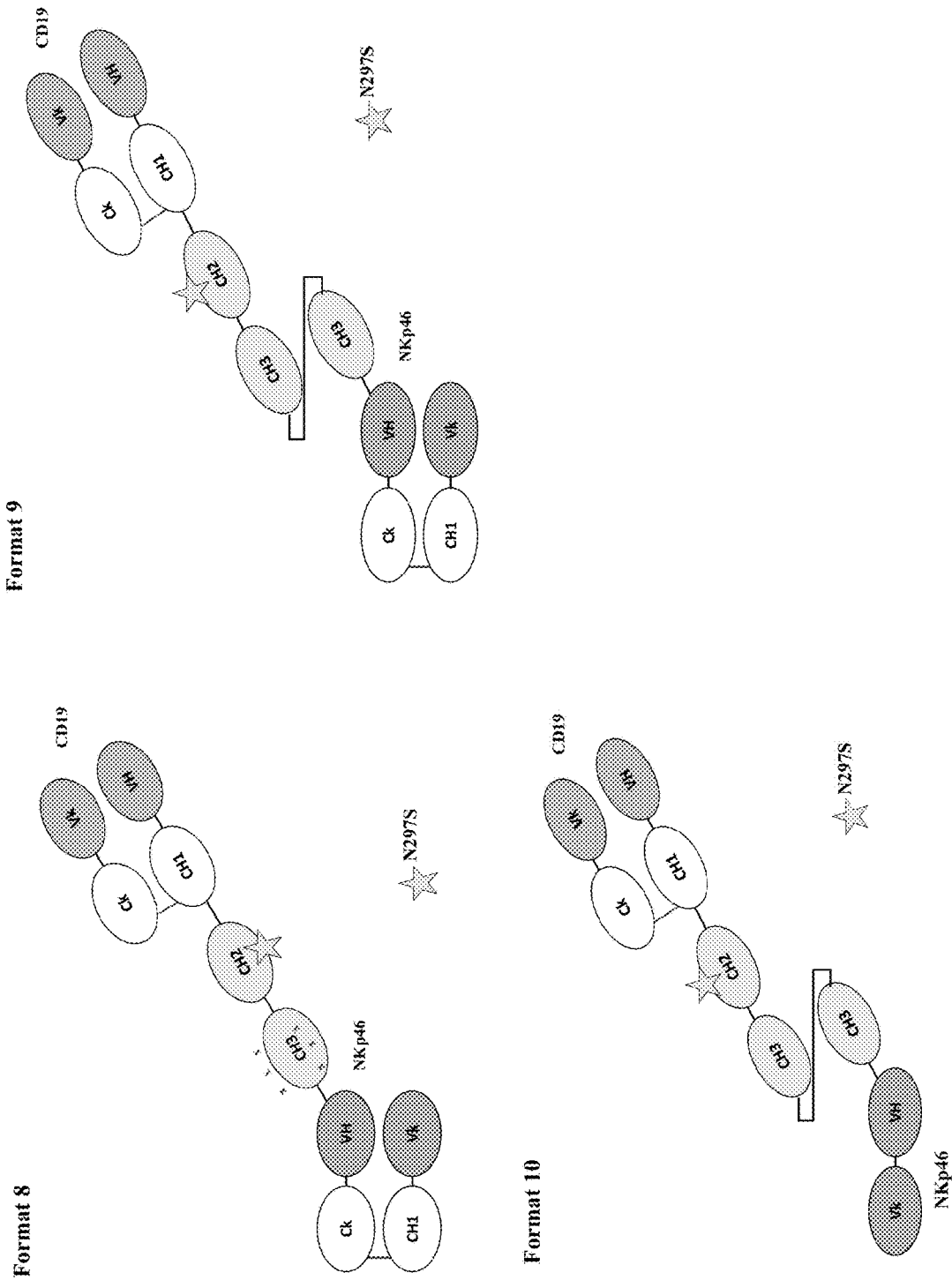

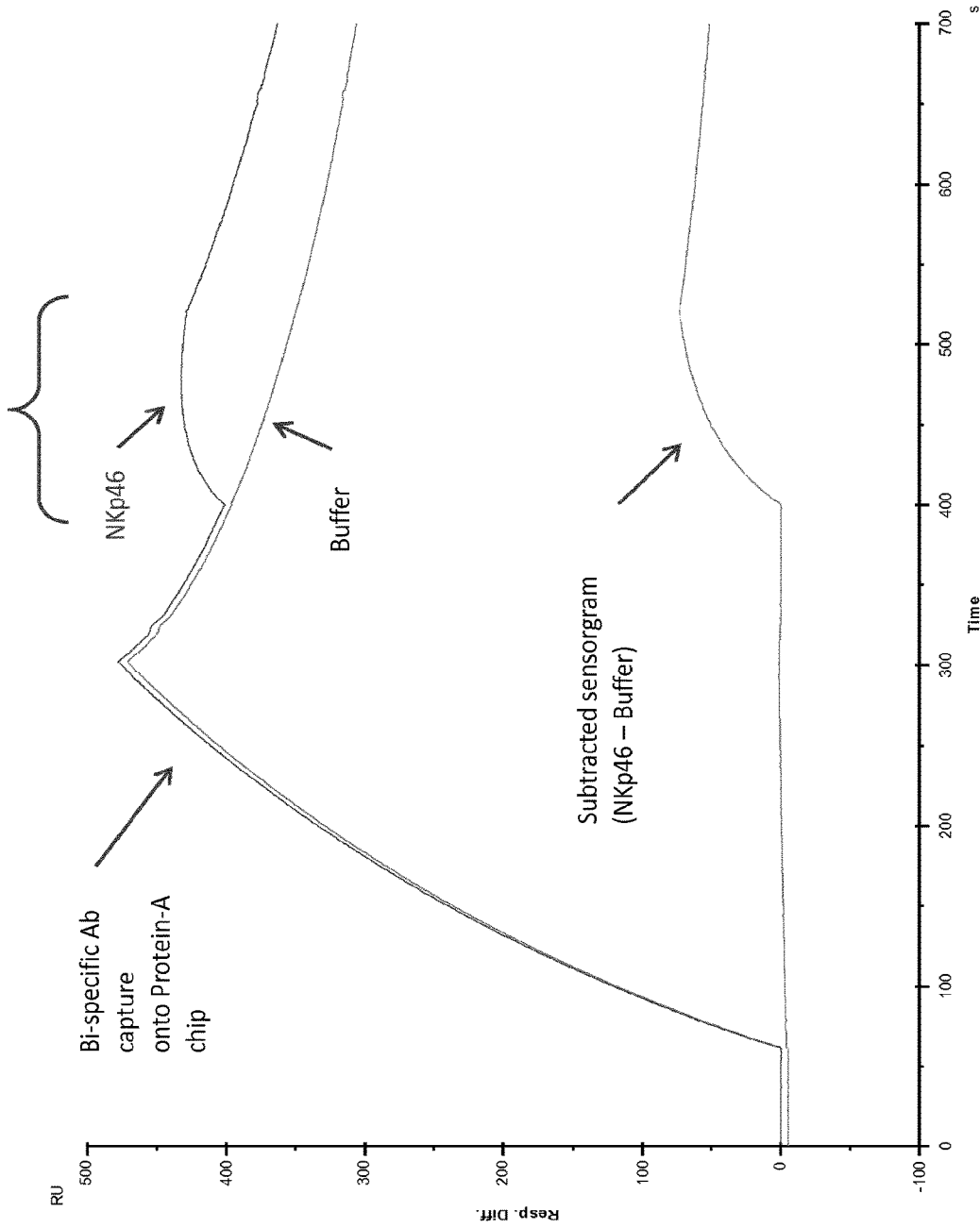

Figure 9A
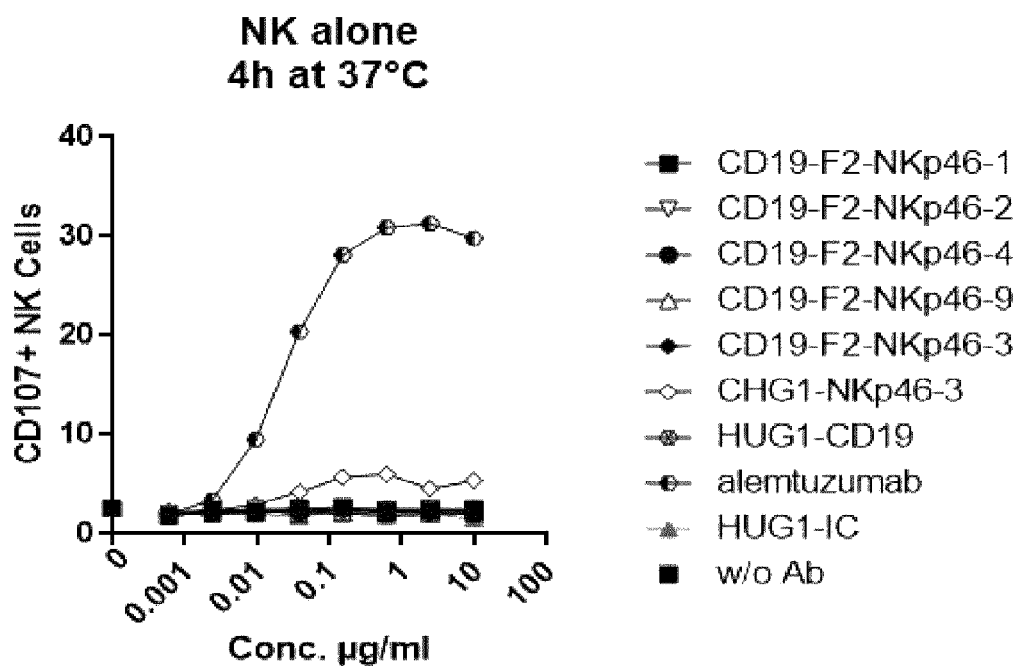
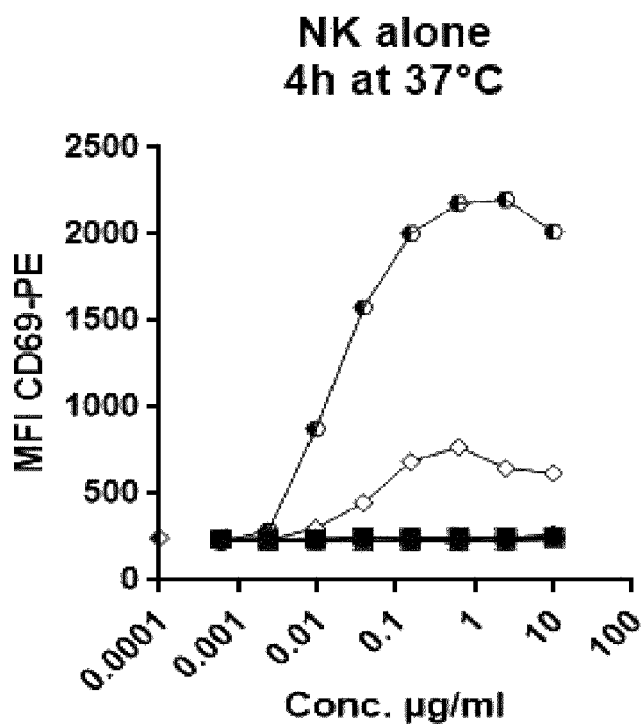

Figure 9B
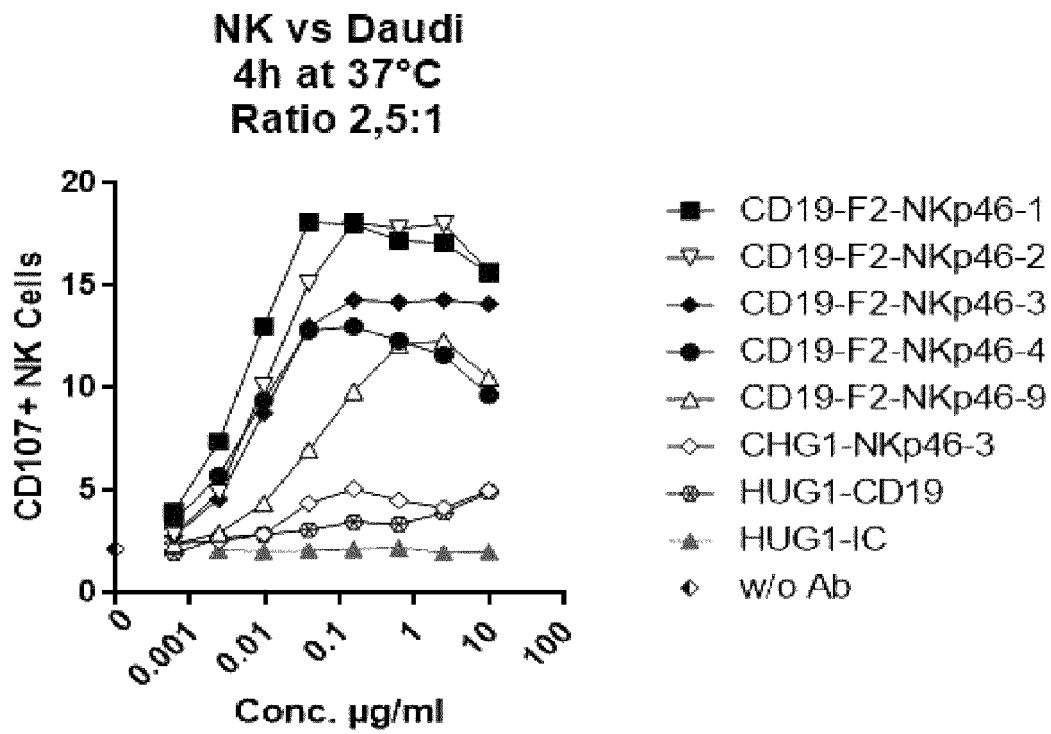
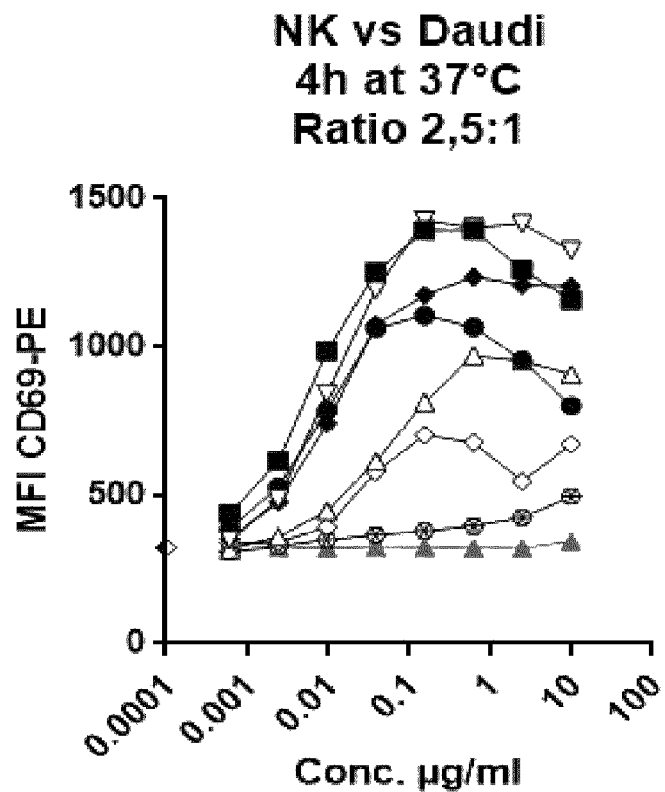

NKp46 WT

NKp46 Mutant 19

NKp46 WT

NKp46 Mutant 6

NKp46 WT

NKp46 Mutant S6

NKP46 BINDING PROTEINS

CROSS-REFERENCE TO RELATED APPLICATIONS

This application is a divisional application of U.S. application Ser. No. 15/321,650, filed Dec. 22, 2016, which is a U.S. National Phase Application of Int'l Appl. No. PCT/EP2015/064063, filed Jun. 23, 2015, which claims priority to U.S. Provisional Application No. 62/108,088, filed Jan. 27, 2015, and U.S. Provisional Application No. 62/017,886, filed Jun. 27, 2014, each of which is incorporated herein by reference.

REFERENCE TO THE SEQUENCE LISTING

This application includes as part of its disclosure a biological sequence listing which is being concurrently submitted through EFS-Web. Said biological sequence listing is contained in a file named "11562150001202.txt" which was created on Jul. 5, 2023, and has a size of 313,388 bytes, and is hereby incorporated by reference in its entirety.

FIELD OF THE INVENTION

Multispecific proteins that bind and specifically redirect NK cells to lyse a target cell of interest are provided without non-specific activation of NK cells in absence of target cells. The proteins have utility in the treatment of disease, notably cancer or infectious disease.

BACKGROUND

Bispecific antibodies binding two different epitopes offer opportunities for increasing specificity, broadening potency, and utilizing novel mechanisms of action that cannot be achieved with a traditional monoclonal antibody. A variety of formats for bispecific antibodies that bind to two targets simultaneously have been reported. Cross-linking two different receptors using a bispecific antibody to inhibit a signaling pathway has shown utility In a number of applications (see, e.g., Jackman, et al., (2010) J. Biol. Chem. 285:20850-20859). Bispecific antibodies have also been used to neutralize two different receptors. In other approaches, bispecific antibodies have been used to recruit immune effector cells, where T-cell activation is achieved in proximity to tumor cells by the bispecific antibody which binds receptors simultaneously on the two different cell types (see Baeuerle, P. A., et al. (2009) Cancer Res 69(12): 4941-4). Approaches developed to date have primarily involved bispecific antibodies that link the CD3 complex on T cells to a tumor-associated antigen. However in other examples, bispecific antibodies having one arm which binds CD16 (FcγRIIIa) and another which bound to an antigen of interest such as CD19 have been developed (see Kellner et al. (2011) Cancer Lett. 303(2): 128-139).

Natural killer (NK) cells are a subpopulation of lymphocytes that are involved in non-conventional immunity. NK cells provide an efficient immunosurveillance mechanism by which undesired cells such as tumor or virally-infected cells can be eliminated. Characteristics and biological properties of NK cells include the expression of surface antigens including CD16, CD56 and/or CD57, the absence of the alpha/beta or gamma/delta TCR complex on the cell surface; the ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

NK cell activity is regulated by a complex mechanism that involves both activating and inhibitory signals. Several distinct NK cell receptors have been identified that play an important role in the NK cell mediated recognition and killing of HLA Class I deficient target cells. One receptor, although not specific to NK cells, is FcγR3a (CD16) which is responsible for NK cell mediated ADCC. Another NK cell receptor is NKp46, a member of the Ig superfamily. It is specific to NK cells and its cross-linking, induced by specific mAbs, leads to a strong NK cell activation resulting in increased intracellular $Ca^{++}$ levels, triggering of cytotoxicity, and lymphokine release. International patent publication number WO2005/105858 (Innate Pharma) discloses use of monospecific full-length IgG anti-NKp46 antibodies that bind Fcγ receptors for treating hematological malignancies that are Fcγ-positive. Fc gamma receptors on tumor cells (e.g. B cell malignancies) were proposed to interact with the Fc domain of the anti-NKp46 antibodies which bound NK cells, such that the activated NK cells are brought into close proximity with their target cells via the two reactive portions of the antibody (e.g. the antigen-recognizing domain and the Fc domain), thereby enhancing the efficiency of the treatment.

To date, no NK cell specific bispecific antibodies have been developed. The depleting agents that recruit NK cytotoxicity such as anti-tumor antibodies are typically full-length IgG1 that mediate ADCC via CD16. Despite the existence of a variety of formats for bispecific antibodies, there remains a need in the art for proteins with new and well-defined mechanisms of action that can provide benefits over and can be used in addition to full-length antibodies.

SUMMARY OF THE INVENTION

The present invention arises from the discovery of functional multi-specific proteins (e.g. a polypeptide, a single chain protein, a multi-chain protein, including but not limited to antibody-based protein formats) that binds NKp46 on NK cells and to an antigen of interest on a target cell, and is capable of redirecting NK cells to lyse a target cell that expresses the antigen of interest, e.g. a cell that contributes to disease.

Advantageously, in on embodiment, the presence of NK cells and target cells, the multi-specific protein can bind (i) to antigen of interest on target cells and (ii) to NKp46 on NK cells, and, when bound to both antigen of interest on target cells and NKp46, can induce signaling in and/or activation of the NK cells through NKp46 (the protein acts as an NKp46 agonist), thereby promoting activation of NK cells and/or lysis of target cells, notably via the activating signal transmitted by NKp46. In specific advantageous embodiments, the multi-specific protein binds to NKp46 in monovalent fashion and, when bound to both antigen of interest on target cells and NKp46, induces signaling in the NK cells through NKp46. In one embodiment, the protein comprises a first antigen binding domain and a second antigen binding domain, wherein one of the first or second antigen binding domains binds to a human NKp46 polypeptide and the other of the first or second antigen binding domains binds an antigen of interest expressed on a target cell.

The multi-specific protein does not, however, substantially induce NKp46 signaling (and/or NK activation that results therefrom) in NK cells when the protein is not bound to the antigen of interest on target cells (e.g. in the absence of antigen of interest and/or target cells). By lacking agonist activity at NKp46 (NK cell activation is not substantially induced as a result of binding to NKp46) In the absence of target cells the multi-specific proteins can avoid unwanted NK cell activation (e.g. other than at the site of disease). In one embodiment, the bispecific protein binds more strongly (has a greater binding affinity) for the antigen of interest (e.g. a cancer antigen) than for NKp46.

In view of the NK-cell selective expression pattern of human NKp46, the multi-specific proteins can direct an immune effector response (e.g., cytotoxic response) toward a target cell that is substantially limited to NK cells (e.g., NKp46-expressing cells). Furthermore, because FcγRIIIa (CD16) is not present on all NK cells, conventional therapeutic antibodies (e.g. of human isotypes IgG1) designed to exert antibody-dependent cellular toxicity (ADCC) via FcγRIIIa may not mobilize all NK cells; the present proteins on the other hand enable all NK cells to be solicited via NKp46. Because the proteins of the invention promote lysis of target cells via the activating signal transmitted by NKp46 and not FcγRs, proteins of the invention can therefore also be used advantageously in combination with therapeutic agents such as antibodies that induce ADCC via FcγRIIIa (CD16) thereby targeting two separate NK cell cytotoxicity pathways.

In one aspect of any embodiment herein, a multi-specific protein described herein can for example be characterized by:
  (a) agonist activity at NKp46, when incubated in the presence of NKp46-expressing NK cells and target cells; and
  (b) lack of agonist activity at NKp46 when incubated with NK cells, e.g. NKp46-expressing NK cells, In the absence of target cells. Optionally, the NK cells are purified NK cells.

Determining whether a protein has agonist activity at NKp46 when incubated in the presence of NKp46-expressing cells and target cells can for example be evaluated by incubating the protein together with: (a) NKp46-expressing (e.g., NK cells or reporter cells), and (b) target cells that do not, in the absence of the multi-specific protein, induce NKp46 signaling in the reporter cells, and assessing whether the protein causes NKp46 signaling, NK cell activation and/or NK cytotoxicity toward the target cell. In one embodiment, assessing whether the protein causes NKp46 signaling by measuring a change in a NKp46 signaling pathway, e.g. by monitoring phosphorylation. In one embodiment, reporter cells are used with are designed to produce a detectable signal if NKp46 signaling is triggered.

Determining whether a protein lacks agonist activity when incubated with NK cells in the absence of target cells can for example be evaluated by incubating the protein together with purified NKp46-expressing NK cells. If the protein does not cause NK cell activation (e.g. of NKp46-expressing NK cells) the protein lacks agonist activity at NKp46. In another embodiment, If the protein does not cause NKp46 signaling the protein lacks agonist activity at NKp46.

In one aspect of any embodiment herein, a multi-specific protein described herein can for example be characterized by:
  (a) ability to activate NKp46-expressing NK cells, when incubated with NKp46-expressing NK cells and target cells; and
  (b) lack of ability to activate NKp46-expressing NK cells when incubated with NKp46-expressing NK cells, in the absence of target cells. Optionally, the NK cells are purified NK cells.

In one aspect of any embodiment herein, a multi-specific protein described herein can for example be characterized by:
  (a) ability to induce NKp46-expressing NK cells to lyse target cells, when incubated with NKp46-expressing NK cells and target cells; and
  (b) lack of ability to activate NKp46-expressing NK cells, when incubated with NKp46-expressing NK cells, in the absence of target cells (e.g., NKp46-expressing NK cells alone). Optionally, the NK cells are purified NK cells.

In one aspect of any embodiment herein, a multi-specific protein described herein can for example be characterized by:
  (a) ability to activate NKp46-expressing NK cells and/or mediate NK cell cytotoxicity, when incubated with NKp46-expressing NK cells and target cells; and
  (b) lack of ability to activate NKp46-negative, CD16-positive (NKp46+CD16−) NK cells and/or mediate NK cell cytotoxicity, when incubated with NKp46-CD16+ NK cells and target cells. Optionally, the NK cells are purified NK cells.

In one embodiment, a multi-specific protein has reduced (or lacks) binding to a human Fcγ receptor (e.g. CD16). For example, a multi-specific protein may lack an Fc domain.

In one embodiment, provided are multi-specific protein formats adapted for use in a NKp46-based NK cell engager, including antibody-based formats comprising antigen binding domain(s) and/or constant region domain(s) from immunoglobulins. By combining the NK-selective expression of NKp46 with multi-specific (e.g. bispecific) antibody formats in which the multi-specific proteins have reduced (or lack) binding to human Fcγ receptor but maintain at least part of an Fc domain, the inventors provide multi-specific antibody formats with favorable pharmacology due to at least partial FcRn binding and that direct NK cell cytotoxicity to a target of interest, without activating inhibitory Fcγ receptors nor blocking activating Fcγ receptors on NK cells (which could reduce efficacy of NK cells) and without triggering inhibitory and/or activatory Fcγ receptors on other immune cells (e.g. CD16 on monocyte-derived macrophages) which could lead to unwanted immunosuppressive effects or unwanted toxicity (e.g. cytokine mediated toxicity) and reduced specificity of the overall multi-specific protein, and/or to other unwanted effects such as pro-tumoral effects mediated by Fcγ receptor-expressing cells.

In another aspect of any embodiment herein, a multi-specific protein described herein can be characterized by lack of agonist activity at NKp46 when incubated with NK cells in the presence of Fcγ receptor-expressing cells (e.g., Fcγ receptor-expressing lymphocytes), and in the absence of target cells (e.g. cells expressing the antigen of interest). In one aspect, a multi-specific protein described herein can be characterized by lack of ability to activate NKp46-expressing NK cells when incubated with NKp46-expressing NK cells in the presence of Fcγ receptor-expressing cells (e.g., Fcγ receptor-expressing lymphocytes, Fcγ receptor-expressing NK cells), and in the absence of target cells (e.g. cells expressing the antigen of interest).

In one embodiment, a multi-specific protein can for example be characterized by:

(a) agonist activity at NKp46, when incubated in the presence of NKp46-expressing cells (e.g. NK cells) and target cells; and
(b) lack of agonist activity at NKp46 when incubated with NK cells in the presence of Fcγ receptor-expressing cells (e.g., Fcγ receptor-expressing lymphocytes), and In the absence of target cells (cells expressing the antigen of interest).

In one embodiment, a multi-specific protein can for example be characterized by:
(a) ability to activate NKp46-expressing NK cells, when incubated in the presence of NKp46-expressing cells (e.g. NK cells) and target cells; and
(b) lack of ability to activate NKp46-expressing NK cells, when incubated with NK cells in the presence of Fcγ receptor-expressing cells (e.g., Fcγ receptor-expressing lymphocytes), and in the absence of target cells (cells expressing the antigen of interest).

Determining whether a protein lacks agonist activity when incubated with NK cells in the presence of Fcγ receptor-expressing cells and in the absence of target cells can for example be evaluated by incubating the protein together with NK cells in the presence of Fcγ receptor-expressing lymphocytes (e.g. by incubating the protein with PBMC), but without target cells.

In one embodiment, provided is a method for identifying, testing and/or producing a multispecific protein that binds NKp46 on an NK cell and an antigen of interest expressed by a target cell, the method comprising:
(a) assessing whether the multispecific protein has agonist activity at NKp46, when incubated in the presence of NKp46-expressing cells (e.g. NK cells) and target cells; and
(b) assessing whether the multispecific protein has agonist activity at NKp46 when incubated with NK cells (optionally further in the presence of Fcγ receptor-expressing cells), in the absence of target cells.

Optionally, the NK cells are purified NK cells.

In one embodiment, provided is a method for identifying, testing and/or producing a multispecific protein, the method comprising providing a plurality of multispecific proteins protein that bind NKp46 on an NK cell and an antigen of interest expressed by a target cell:
(a) assessing each multispecific protein for agonist activity at NKp46, when incubated in the presence of NKp46-expressing cells (e.g. NK cells) and target cells;
(b) assessing each multispecific protein for agonist activity at NKp46 when incubated with NK cells (optionally further in the presence of Fcγ receptor-expressing cells), in the absence of target cells; and
(c) selecting a multispecific protein (e.g. for use as a medicament, for further evaluation, for further production, etc.) if the multispecific protein:
  a. has agonist activity at NKp46, when incubated in the presence of NKp46-expressing cells (e.g. NK cells) and target cells, and
  b. lacks agonist activity at NKp46 when incubated with NK cells (optionally further with Fcγ receptor-expressing cells), in the absence of target cells.

In any of the embodiments, agonist activity (or lack thereof) can be characterized by the ability (or lack thereof) to activate NKp46-expressing NK cells, e.g. as assessed by expression of NK cell activation markers, the induction of NK cytotoxicity, or other suitable assays of increased NK cell activity.

Further provided are certain epitopes on NKp46 are well suited for targeting with NKp46 binding moieties that lead to bispecific proteins with advantageous properties, notably high efficacy In directed NK cells to lyse target cells (e.g. via NKp46-mediated signaling). Provided also are CDRs of different anti-NKp46 antibodies suitable for use in construction of efficient multi-specific proteins, and amino acid sequences of exemplary multi-specific proteins.

In one embodiment, provided is a multispecific protein (e.g. polypeptide, a non-antibody polypeptide, an antibody) comprising: (a) a first antigen binding domain; and (b) a second antigen binding domain, wherein one of the first antigen binding domains binds NKp46 and the other binds an antigen of interest on a target cell (other than NKp46), wherein the multispecific protein is capable of directing NKp46-expressing NK cells to lyse said target cell. In one embodiment, the protein comprises at least a portion of a human Fc domain, e.g. an Fc domain that is bound by FcRn, optionally wherein the multispecific antibody is designed to have decreased or substantially lack FcγR binding; in one embodiment, the Fc domain is interposed between the two ABDs (one ABD is placed N-terminal and the other is C-terminal to the Fc domain).

In one aspect, the multispecific protein is a single chain protein. In one aspect, the multispecific protein comprises two or more polypeptide chains, i.e. a multi-chain polypeptide. For example, the multispecific protein or multi-chain protein is a dimer, trimer or tetramer.

An antigen binding domain positioned on a polypeptide chain can binds its target (i.e., NKp46 or an antigen of interest) as such or can optionally binds its target together with a complementary protein domain (antigen binding domain) positioned on a different polypeptide chain, wherein the two polypeptide chains associate to form a multimer (e.g. dimer, trimer, etc.).

In one aspect, the multispecific protein binds an NKp46 polypeptide (e.g. of the surface of a NK cell) in monovalent fashion. In one aspect, the protein binds the antigen of interest monovalent fashion.

In one aspect, the protein (and/or the antigen binding domain thereof that binds NKp46) competes for binding to a NKp46 polypeptide with any one or any combination of monoclonal antibodies NKp46-1, -2, -3, -4, -6 or -9 or the Anti-CD19-F2-Anti-NKp46-1, -2, -3, -4, -6 or -9 bispecific antibodies. In one embodiment, the antigen binding domain that binds NKp46 binds an epitope on an NKp46 polypeptide of SEQ ID NO:1 comprising one, two, three or more residues selected from the residues bound by any one or combination of antibodies NKp46-1, -2, -3, -4, -6 or -9 or the Anti-CD19-F2-Anti-NKp46-1, -2, -3, -4, -6 or -9 bispecific antibodies. In one embodiment the multispecific protein is capable of binding to human neonatal Fc receptor (FcRn). In one embodiment the multispecific protein has decreased or abolished binding to a human and/or non-human primate (e.g. cynomolgus monkey) Fcγ receptor, e.g., compared to a full length wild type human IgG1 antibody. In one embodiment the multispecific protein has decreased (e.g. partial or complete loss of) antibody dependent cytotoxicity (ADCC), complement dependent cytotoxicity (CDC), antibody dependent cellular phagocytosis (ADCP), FcR-mediated cellular activation (e.g. cytokine release through FcR cross-linking), and/or FcR-mediated platelet activation/depletion mediated by NKp46-negative effector cells.

In another embodiment, provided is a monomeric or multimeric multispecific single or multi-chain protein comprising: (a) a first antigen binding domain (ABD); (b) a second antigen binding domain, wherein one of the first or second antigen binding domains binds to NKp46 and the other binds to an antigen of interest on a target cell (other than NKp46); and (c) at least a portion of a human Fc domain, wherein the Fc domain is capable of binding to human neonatal Fc receptor (FcRn) and has decreased binding to a human Fcγ receptor, e.g., compared to a full length wild type human IgG1 antibody. In one embodiment the multispecific protein has decreased (e.g. partial or complete loss of) antibody dependent cytotoxicity (ADCC), complement dependent cytotoxicity (CDC), antibody dependent cellular phagocytosis (ADCP), FcR-mediated cellular activation (e.g. cytokine release through FcR crosslinking), and/or FcR-mediated platelet activation/depletion mediated by NKp46-negative effector cells. In one embodiment the multispecific protein is monomeric. In one embodiment the multispecific Fc-derived protein is a dimer, e.g. a heterodimer. In one embodiment, the monomeric or dimeric protein comprises a protein with a domain structure in which an Fc domain is interposed between the first antigen binding domain (ABD) that binds to NKp46 and the second antigen binding domain that binds an antigen of interest. In one embodiment the multispecific Fc-derived polypeptide is a bispecific antibody.

In one embodiment of any of the protein herein, the antigen binding domain that binds to an antigen of interest binds to an antigen (e.g. polypeptide) expressed by a target cell which sought to be lysed by an NK cell. Optionally such an antigen is expressed by a cancer cell, a virally infected cell, or a cell that contributes to an autoimmunity or inflammatory disease.

In one embodiment, the multispecific protein binds NKp46 in monovalent fashion. In one embodiment, the multispecific protein binds to the antigen of interest in monovalent fashion. In one embodiment, the multispecific protein binds both NKp46 and the antigen of interest in monovalent fashion.

In one embodiment, the first antigen binding domain comprises an antibody heavy chain variable domain and a light chain variable domain. Optionally, both said heavy and light chain variable domains are involved in binding interactions with NKp46.

In one embodiment, the second antigen binding domain comprises an antibody heavy chain variable domain and a light chain variable domain. Optionally, both said heavy and light chain variable domains are involved in binding interactions with the antigen bound by the second antigen binding domain.

Optionally, the Fc domain comprises at least a portion of a CH2 domain and at least a portion of a CH3 domain.

In one embodiment, the CH2 domain comprises an amino acid modification, compared to a wild-type CH2 domain. In one embodiment, the CH2 modification reduces binding of the bispecific polypeptide to a human Fcγ receptor. In one embodiment, the CH2 domain comprises a N297X mutation (EU numbering as in Kabat), wherein X is any amino acid other than asparagine. In one embodiment, the CH3 domain comprises an amino acid modification, compared to a wild-type CH3 domain.

In one embodiment, the CH2 domain and/or CH3 domains are naturally occurring (non-mutated) human CH2 and/or CH3 domains. In one embodiment, the multispecific protein comprises an Fc derived polypeptide lacks N-iinked glycosylation or has modified N-linked glycosylation.

In one embodiment, the Fc-derived polypeptide is a monomer.

In one embodiment, the Fc-derived polypeptide is a dimer, optionally a homodimer or a heterodimer. In one embodiment, the Fc-derived polypeptide is a heterotrimer. In one embodiment, the Fc-derived polypeptide is a heterotetramer.

In one embodiment, the CH3 domain is does not dimerize with another Fc-derived polypeptide (e.g. does not substantially form a homodimer with another identical Fc polypeptide but remains as a heterodimer or heterotrimer; does not form a homodimer and remains as a monomer). In one embodiment, the CH3 domain comprises amino acid mutations (e.g. substitutions) in the CH3 dimer interface to prevent formation of CH3-CH3 dimers.

Examples of monomeric bispecific protein are shown in FIGS. 1-3 and FIGS. 6A-6C. In one embodiment, provided is a monomeric bispecific protein comprising: (a) a first antigen binding domain that binds to an antigen of interest; (b) a second antigen binding domain that binds NKp46; and (c) at least a portion of a human Fc domain, wherein the Fc domain does not dimerize with another Fc-derived polypeptide (e.g. does not dimerize with an identical monomeric bispecific polypeptide). In one embodiment, the monomeric bispecific protein is capable of binding to human FcRn and has decreased binding to a human Fcγ receptor compared to a wild type full length human IgG1 antibody. In one embodiment, the monomeric bispecific protein has decreased binding to a human Fcγ receptor compared to a polypeptide having a full length wild-type human IgG1 Fc domain but otherwise identical. Optionally, the Fc domain comprises a CH2 domain and a modified CH3 domain to prevent CH3-CH3 dimerization (e.g. does not dimerize via interactions with another CH3 domain in an identical monomeric bispecific polypeptide).

In one embodiment, the Fc domain is interposed between the first antigen binding domain and the second binding domain on the polypeptide chain, e.g., the polypeptide has a domain arrangement: $(ABD_1)$-CH2-CH3-$(ABD_2)$, or further wherein the polypeptide has a domain arrangement: $(ABD_1)$-linker-CH2-CH3-linker-$(ABD_2)$; optionally intervening amino acid sequences are present between any protein domains. In one embodiment, $ABD_1$ is the antigen binding domain that binds an antigen of interest and $ABD_2$ is the antigen binding domain that binds to NKp46

In one aspect of any embodiment, the first antigen binding domain and/or the second antigen binding domain comprise a heavy and/or light chain variable domain. In one aspect of any embodiment, the first antigen binding domain and/or the second antigen binding domain comprise a scFv, optionally where the scFv comprises human framework amino acid sequences.

Optionally the monomeric polypeptide is capable of binding to human FcRn with intermediate affinity, e.g. binds to FcRn but has decreased binding to a human FcRn receptor compared to a full length wild type human IgG1 antibody; optionally the monomeric polypeptide further has decreased binding to a human FcγR (e.g. CD16, CD32A, CD32B and/or CD64) compared to a full length wild type human IgG1 antibody.

In one embodiment, a heteromultimeric protein or polypeptide is a tetrameric antibody made up of two heavy chains comprising variable regions (or 1, 2 or 3 CDRs thereof) derived from two different parental antibodies, and two light chains comprising variable regions (or 1, 2 or 3 CDRs thereof) derived from two different parental antibodies. Such a tetramer may comprise (a) two heavy chains each comprising a variable region, a CH1 domain, hinge and an Fc domain, and (b) two antibody light chains each comprising a light chain variable region and a CK domain, wherein one heavy chain variable region together with a light chain variable region binds to NKp46 and the other heavy chain variable region together with a light chain variable region bind an antigen of interest. Optionally the Fc domains are of IgG4 isotype or modified (e.g. with an amino acid substitution or produced in an appropriate host cell) to retain FcRn binding but lack of have decrease FcγR binding.

In one embodiment, provided is a heteromultimeric, e.g. heterodimeric, bispecific protein comprising: (a) a first polypeptide chain comprising a first variable region (V), fused to a CH1 or CK domain, wherein the V-(CH1/CK) unit is in turn fused to a first terminus (N- or C-terminus) of a human Fc domain (a full Fc domain or a portion thereof); (b) a second polypeptide chain comprising a first variable region (V) fused to a CH1 or CK domain that is complementary with the CH1 or CK of the first chain to form a CH1-CK dimer, optionally wherein the V-(CH1/CK) unit is fused to at least a human Fc domain (a full Fc domain or a portion thereof), wherein the two first variable regions form an antigen binding domain that binds a first antigen of interest in monovalent fashion, and (c) an antigen binding domain that binds a second antigen (optionally together with a complementary antigen binding domain), and optionally a second CH1 or CK domain, fused to a second terminus (N- or C-terminus) of the Fc domain of the first polypeptide such that the Fc domain is interposed between the V-(CH1/CK) unit and the antigen binding domain that binds a second antigen, wherein one of the first and second antigens is NKp46. Optionally the first and second polypeptide chains are bound by interchain disulfide bonds, e.g. formed between respective CH1 and CK domains. Optionally a V-(CH1/CK) unit is fused to a human Fc domain directly, or via intervening sequences, e.g. linkers, other protein domain(s), etc.

In one embodiment of the above heteromultimeric polypeptide or protein, the polypeptide or protein is a heterodimer, wherein the antigen binding domain for a second antigen is an scFv, optionally an scFv that binds NKp46.

In one embodiment of the above heteromultimeric polypeptide or protein, the polypeptide or protein is a heterotrimer, wherein the antigen binding domain for a second antigen is an heavy or light chain variable region, and the heteromultimeric polypeptide or protein further comprises a third polypeptide chain comprising a variable region (V) fused to a CH1 or CK domain that is complementary with the CH1 or CK of the first chain to form a CH1-CK dimer wherein the variable region that is the antigen binding domain for a second antigen of the first polypeptide and the variable region of the third chain form an antigen binding domain. The three polypeptide chains formed from the double dimerization yields a trimer. The CH1 or CK constant region of the third polypeptide is selected to be complementary to the second CH1 or CK constant region of the first polypeptide chain (but not complementary to the first CH1/CK of the first polypeptide chain).

In one aspect provided is an isolated heterodimeric polypeptide that binds a first and second antigen of interest in monovalent fashion, wherein one of the antigens is NKp46 and the other is an antigen of interest, comprising:
(a) a first polypeptide chain comprising, from N- to C-terminus, a first variable domain (V), a CH1 of CK constant region, a Fc domain or portion thereof, a second variable domain and third variable domain; and
(b) a second polypeptide chain comprising, from N- to C-terminus, a first variable domain (V), a CH1 or CK constant region, and optionally a Fc domain or portion thereof, wherein the CH1 or CK constant region is selected to be complementary to the CH1 or CK constant region of the first polypeptide chain such that the first and second polypeptides form a CH1-CK heterodimer in which the first variable domain of the first polypeptide chain and the first variable domain of the second polypeptide form an antigen binding domain that binds the first antigen of interest; and wherein a second variable domain and third variable domain forms an antigen binding domain that binds the second antigen of interest. When the second polypeptide chain lacks an Fc domain, the first polypeptide chain will comprise an Fc domain modified to prevent CH3-CH3 dimerization (e.g., substitutions or tandem CH3 domain).

In one aspect provided is an isolated heterodimeric polypeptide that binds a first and second antigen of interest in monovalent fashion, wherein one of the antigens is NKp46 and the other is an antigen of interest, comprising:
(a) a first polypeptide chain comprising, from N- to C-terminus, a second variable domain and third variable domain, a Fc domain or portion thereof, a first variable domain (V), and a CH1 of CK constant region; and
(b) a second polypeptide chain comprising, from N- to C-terminus, a first variable domain (V), a CH1 or CK constant region, and optionally a Fc domain or portion thereof, wherein the CH1 or CK constant region is selected to be complementary to the CH1 or CK constant region of the first polypeptide chain such that the first and second polypeptides form a CH1-CK heterodimer in which the first variable domain of the first polypeptide chain and the first variable domain of the second polypeptide form an antigen binding domain that binds the first antigen of interest; and wherein a second variable domain and third variable domain forms an antigen binding domain that binds the second antigen of interest. When the second polypeptide chain lacks an Fc domain, the first polypeptide chain will comprise an Fc domain modified to prevent CH3-CH3 dimerization (e.g., substitutions or tandem CH3 domain).

In one embodiment, provided is a trimeric polypeptide that binds a first and second antigen of interest in monovalent fashion, wherein one of the antigens is NKp46 and the other is an antigen of interest, comprising:
(a) a first polypeptide chain comprising, from N- to C-terminus, a first variable domain (V) fused to a first CH1 or CK constant region, an Fc domain or portion thereof, and a second variable domain (V) fused to a second CH1 or CK constant region;
(b) a second polypeptide chain comprising, from N- to C-terminus, a variable domain fused to a CH1 or CK constant region selected to be complementary to the first (but not the second) CH1 or CK constant region of the first polypeptide chain such that the first and second polypeptides form a CH1-CK heterodimer, and optionally an Fc domain or portion thereof; and
(c) a third polypeptide chain comprising, from N- to C-terminus, a variable domain fused to a CH1 or CK constant region, wherein the CH1 or CK constant region is selected to be complementary to the second (but not the first) variable domain and second CH1 or CK constant region of the first polypeptide chain. The first and third polypeptides will therefore form a CH1-CK heterodimer formed between the CH1 or CK constant region of the third polypeptide and the second CH1 or CK constant region of the first polypeptide, but not between the CH1 or CK constant region of the third polypeptide and the first CH1 or CK constant region of the first polypeptide. The first, second and third polypeptides form a CH1-CK heterotrimer, and wherein the first variable domain of the first polypeptide chain and the variable domain of the second polypeptide chain form an antigen binding domain specific for a first antigen of interest, and the second variable domain of the first polypeptide chain and the variable domain on the third polypeptide chain form an antigen binding domain specific for a second antigen of interest.

In one embodiment, the above heteromultimeric polypeptide or protein comprises one or more additional polypeptide chains.

In one embodiment, a heteromultimeric polypeptide or protein comprises a monomeric Fc domain (e.g. the second polypeptide does not comprise an Fc domain), optionally wherein the Fc domain comprises a CH3 domain with an amino acid mutation to prevent CH3-CH3 dimerization or a tandem CH3 domain.

In one embodiment, the above heteromultimeric polypeptide or protein comprises a dimeric Fc domain.

Optionally the heterodimeric polypeptide or protein is capable of binding to human FcRn with intermediate affinity, e.g. binds to FcRn but has decreased binding to a human FcRn receptor compared to a full length wild type human IgG1 antibody; optionally the monomeric polypeptide further has decreased binding to a human FcγR receptor (e.g. CD16, CD32A, CD32B and/or CD64) compared to a full length wild type human IgG1 antibody.

Optionally, the CH1 and/or CK domain are fused via a hinge region to the Fc domain. Optionally the hinge, CH2 and/or CH3 comprise an amino acid modification to reduce or substantially abolish binding to a human Fcγ receptor (e.g. CD16, CD32A, CD32B and/or CD64). Optionally such mutation decreases (e.g. partial or complete loss of) antibody dependent cytotoxicity (ADCC), complement dependent cytotoxicity (CDC), antibody dependent cellular phagocytosis (ADCP), FcR-mediated cellular activation (e.g. cytokine release through FcR cross-linking), and/or FcR-mediated platelet activation/depletion by NKp46-negative cells. Preferably, in any embodiment herein, CH1 and CK domains are of human origin.

In one aspect of any of the embodiments herein, the bispecific protein binds more strongly (has a greater binding affinity) for the antigen of interest (e.g. a cancer antigen) than for NKp46. Such antibodies will provide for advantageous pharmacological properties. In one aspect of any of the embodiments herein, the polypeptide has a Kd for binding (monovalent) to NKp46 of less than $10^{-7}$ M, preferably less than $10^{-8}$ M, or preferably less than $10^{-9}$ M for binding to a NKp46 polypeptide; optionally the polypeptide has a Kd for binding (monovalent) to a cancer, viral or bacterial antigen that is less than (i.e. has better binding affinity than) the Kd for binding (monovalent) to a NKp46 polypeptide. In one aspect of any of the embodiments herein, the polypeptide has a Kd for binding (monovalent) to NKp46 of between $10^{-7}$ M (100 nanomolar) and $10^{-10}$ M (0.1 nanomolar) for binding to a NKp46 polypeptide. In one aspect of any of the embodiments herein, the polypeptide has a Kd for binding (monovalent) to NKp46 of between $10^{-8}$ M (10 nanomolar) and $10^{-10}$ M (0.1 nanomolar) for binding to a NKp46 polypeptide. In one aspect of any of the embodiments herein, the polypeptide has a Kd for binding (monovalent) to NKp46 of between $10^{-8}$ M (10 nanomolar) and $10^{-9}$ M (1 nanomolar) for binding to a NKp46 polypeptide.

In one aspect of any of the embodiments of the invention, the antigen binding domain that binds NKp46 binds to at least one residue on NKp46 corresponding to an amino acid residues bound by any one of monoclonal antibodies NKp46-1, -2, -3, -4, -6 or -9 or the Anti-CD19-Anti-NKp46-1, -2, -3, -4, -6 or -9 bispecific antibodies. In one aspect, the antigen binding domain that binds NKp46 binds at least 1, 2, 3, 4 or more amino acids of NKp46 within the epitope bound by any one or combination of monoclonal antibodies NKp46-1, -2, -3, -4, -6 or -9 or the Anti-CD19-Anti-NKp46-1, -2, -3, -4, -6 or -9 bispecific antibodies. In one aspect of any of the embodiments of the invention, the antigen binding domain that binds NKp46 binds to the same epitope on a NKp46 polypeptide as any of monoclonal antibodies NKp46-1, -2, -3, -4, -6 or -9 or the Anti-CD19-Anti-NKp46-1, -2, -3, -4, -6 or -9 bispecific antibodies. In one embodiment, the antigen binding domain that binds NKp46 binds an epitope on an NKp46 polypeptide of SEQ ID NO:1 comprising one, two, three or more residues selected from the group of residues bound by any of antibodies NKp46-1, -2, -3, -4, -6 or -9.

In some embodiments, the protein that binds NKp46 exhibits significantly lower binding for a mutant NKp46 polypeptide in which a residue bound by any of antibodies NKp46-1, -2, -3, -4, -6 or -9 is substituted with a different amino acid, compared to a wild-type NKp46 polypeptide of SEQ ID NO: 1.

In one aspect of any of the embodiments of the invention, the protein that binds NKp46 competes for binding to a NKp46 polypeptide with any one or any combination of monoclonal antibodies NKp46-1, NKp46-2, NKp46-3, NKp46-4, NKp46-6 or NKp46-9, or the Anti-CD19-Anti-NKp46-1, -2, -3, -4, -6 or -9 bispecific antibodies. In one embodiment, the protein that binds NKp46 competes for binding to a NKp46 polypeptide with an antibody selected from the group consisting of:
  (a) an antibody having respectively a VH and VL region of SEQ ID NOS: 3 and 4 (NKp46-1);
  (b) an antibody having respectively a VH and VL region of SEQ ID NOS: 5 and 6 (NKp46-2);
  (c) (a) an antibody having respectively a VH and VL region of SEQ ID NOS: 7 and 8 (NKp46-3);
  (d) (a) an antibody having respectively a VH and VL region of SEQ ID NOS: 9 and 10 (NKp46-4);
  (e) an antibody having respectively a VH and VL region of SEQ ID NOS:11 and 12 (NKp46-6); and
  (f) an antibody having respectively a VH and VL region of SEQ ID NOS: 13 and 14 (NKp46-9).

In one embodiment, provided is an isolated protein that specifically binds NKp46 (e.g. a monospecific monoclonal antibody, a multispecific polypeptide, a bispecific antibody) that competes for binding to a NKp46 polypeptide with an antibody selected from the group consisting of:
  (a) an antibody having respectively a VH and VL region of SEQ ID NOS: 3 and 4 (NKp46-1);
  (b) an antibody having respectively a VH and VL region of SEQ ID NOS: 5 and 6 (NKp46-2);
  (c) (a) an antibody having respectively a VH and VL region of SEQ ID NOS: 7 and 8 (NKp46-3);
  (d) (a) an antibody having respectively a VH and VL region of SEQ ID NOS: 9 and 10 (NKp46-4);
  (e) an antibody having respectively a VH and VL region of SEQ ID NOS:11 and 12 (NKp46-6); and
  (f) an antibody having respectively a VH and VL region of SEQ ID NOS: 13 and 14 (NKp46-9).

In one aspect of any of the embodiments of the invention, the antigen binding domain that binds NKp46 comprises the hypervariable regions of any one of monoclonal antibodies NKp46-1, NKp46-2, NKp46-3, NKp46-4, NKp46-6 or NKp46-9.

In one aspect of any of the embodiments of the invention, the antigen binding domain that binds NKp46 has a heavy and/or light chain variable region having one, two or three CDRs of the respective heavy and/or light chain of an antibody selected from the group consisting of antibody NKp46-1, NKp46-2, NKp46-3, NKp46-4, NKp46-6 and NKp46-9.

In one aspect, provided is an isolated multispecific protein (a monomeric or multimeric polypeptide) that specifically binds (i) NKp46 and (ii) an antigen of interest (other than NKp46), wherein the multispecific protein comprises a monomeric Fc domain comprising an amino acid sequence which is at least 60%, 70%, 80%, 85%, 90%, 95% or 98% identical to the sequence of SEQ ID NOS: 2, optionally wherein one, two, three, four, five or more amino acids are substituted by a different amino acid, optionally comprising a substitution at 1, 2, 3, 4, 5, 6 of residues 121, 136, 165, 175, 177 or 179 of SEQ ID NO: 2.

In one embodiment, an isolated multispecific protein that binds NKp46 according to the disclosure comprises or an antigen binding domain thereof comprises heavy chain CDR1, 2 and 3 and light chain CDR 1, 2 and 3 of any of the antibodies selected from the group consisting of:
(a) an antibody having respectively a VH and VL region of SEQ ID NOS: 3 and 4 (NKp46-1);
(b) an antibody having respectively a VH and VL region of SEQ ID NOS: 5 and 6 (NKp46-2);
(c) (a) an antibody having respectively a VH and VL region of SEQ ID NOS: 7 and 8 (NKp46-3);
(d) (a) an antibody having respectively a VH and VL region of SEQ ID NOS: 9 and 10 (NKp46-4);
(e) an antibody having respectively a VH and VL region of SEQ ID NOS:11 and 12 (NKp46-6); and
(f) an antibody having respectively a VH and VL region of SEQ ID NOS: 13 and 14 (NKp46-9).

In one embodiment, an antibody or antigen binding domain according to the disclosure that binds NKp46 comprises:
(a) (i) a heavy chain comprising a CDR 1, 2 and 3 of the heavy chain variable region of NKp46-1 of Table A, and (ii) a light chain comprising a CDR 1, 2 and 3 of the light chain variable region of NKp46-1 of Table A;
(b) (i) a heavy chain comprising a CDR 1, 2 and 3 of the heavy chain variable region of NKp46-2 of Table A and (ii) a light chain comprising a CDR 1, 2 and 3 of the light chain variable region of NKp46-2 of Table A;
(c) (i) a heavy chain comprising a CDR 1, 2 and 3 of the heavy chain variable region of NKp46-3 of Table A and (ii) a light chain comprising a CDR 1, 2 and 3 of the light chain variable region of NKp46-3 of Table A;
(d) (i) a heavy chain comprising a CDR 1, 2 and 3 of the heavy chain variable region of NKp46-4 of Table A and (ii) a light chain comprising a CDR 1, 2 and 3 of the light chain variable region of NKp46-4 of Table A;
(e) (i) a heavy chain comprising a CDR 1, 2 and 3 of the heavy chain variable region of NKp46-6 of Table A and (ii) a light chain comprising CDR 1, 2 and 3 of the light chain variable region of NKp46-6 of Table A; or
(f) (i) a heavy chain comprising a CDR 1, 2 and 3 of the heavy chain variable region of NKp46-9 of Table A and (ii) a light chain comprising a CDR 1, 2 and 3 of the light chain variable region of NKp46-9 of Table A.

In one aspect, provided is an isolated polypeptide (a monomeric or multimeric polypeptide) that specifically binds NKp46 (e.g. a monospecific monoclonal antibody, a multispecific polypeptide, a bispecific antibody) that binds the same epitope on NKp46 as an antibody selected from the group consisting of antibody NKp46-1, NKp46-2, NKp46-3, NKp46-4, NKp46-6 and NKp46-9. The Isolated polypeptide may be, for example, a monospecific monoclonal antibody, a multispecific polypeptide or a bispecific antibody In one aspect, provided is an isolated polypeptide (a monomeric or multimeric polypeptide) that specifically binds NKp46 (e.g. a monospecific monoclonal antibody, a multispecific polypeptide, a bispecific antibody) comprising:
(a) a heavy chain comprising CDR 1, 2 and 3 of the heavy chain variable region of SEQ ID NO: 3 and a light chain comprising CDR 1, 2 and 3 of the light chain variable region of SEQ ID NO: 4;
(b) a heavy chain comprising CDR 1, 2 and 3 of the heavy chain variable region of SEQ ID NO: 5 and a light chain comprising CDR 1, 2 and 3 of the light chain variable region of SEQ ID NO: 6;
(c) a heavy chain comprising CDR 1, 2 and 3 of the heavy chain variable region of SEQ ID NO: 7 and a light chain comprising CDR 1, 2 and 3 of the light chain variable region of SEQ ID NO: 8;
(d) a heavy chain comprising CDR 1, 2 and 3 of the heavy chain variable region of SEQ ID NO: 9 and a light chain comprising CDR 1, 2 and 3 of the light chain variable region of SEQ ID NO: 10;
(e) a heavy chain comprising CDR 1, 2 and 3 of the heavy chain variable region of SEQ ID NO: 11 and a light chain comprising CDR 1, 2 and 3 of the light chain variable region of SEQ ID NO: 12; or
(f) a heavy chain comprising CDR 1, 2 and 3 of the heavy chain variable region of SEQ ID NO: 13 and (a light chain comprising CDR 1, 2 and 3 of the light chain variable region of SEQ ID NO: 14.

In one aspect, provided is an isolated multispecific heterodimeric protein comprising a first polypeptide chain comprising a first amino acid sequence which is at least 50%, 60%, 70%, 80%, 85%, 90%, 95% or 98% identical to the sequence of a first polypeptide chain of a F1 to F17 polypeptides disclosed herein; and a second amino acid sequence which is at least 50%, 60%, 70%, 80%, 85%, 90%, 95% or 98% identical to the sequence of a second polypeptide chain of the respective F1 to F17 polypeptide disclosed herein. Optionally any or all of the variable regions or CDRs of the first and second chains are substituted with different variable regions, optionally where variable regions or CDRs are excluded from the sequences that are considered for computing identity, optionally wherein the anti-NKp46 variable regions or CDRs are included for computing identity and the variable regions or CDRs for the antigen binding domain that binds the other antigen are excluded from the sequences that are considered for computing identity.

In one aspect, provided is an isolated multispecific heterotrimeric protein comprising a first polypeptide chain comprising a first amino acid sequence which is at least 50%, 60%, 70%, 80%, 85%, 90%, 95% or 98% identical to the sequence of a first polypeptide chain of the F1 to F17 polypeptides disclosed herein; a second amino acid sequence which is at least 50%, 60%, 70%, 80%, 85%, 90%, 95% or 98% identical to the sequence of a second polypeptide chain of the respective F1 to F17 polypeptide disclosed herein; and a third amino acid sequence which is at least 50%, 60%, 70%, 80%, 85%, 90%, 95% or 98% identical to the sequence of a third polypeptide chain of the respective F1 to F17 polypeptide disclosed herein. Optionally any or all of the variable regions or CDRs of the first and second chains are substituted with different variable regions, optionally where variable regions or CDRs are excluded from the sequences that are considered for computing identity, optionally wherein the anti-NKp46 variable regions or CDRs are included for computing identity and the variable regions or CDRs for the antigen binding domain that binds the other antigen are excluded from the sequences that are considered for computing identity.

In one embodiment of any of the polypeptides herein, the multispecific polypeptide is capable of directing NKp46-expressing NK cells to lyse a target cell of interest (e.g. a target cell expressing an antigen other than NKp46).

In one aspect of any of the embodiments herein, provided is a recombinant nucleic acid encoding a first polypeptide chain, and/or a second polypeptide chain and/or a third polypeptide chain of any of the proteins of the disclosure. In one aspect of any of the embodiments herein, provided is a recombinant host cell comprising a nucleic acid encoding a first polypeptide chain, and/or a second polypeptide chain and/or a third polypeptide chain of any of the proteins of the disclosure, optionally wherein the host cell produces a protein of the disclosure with a yield (final productivity after purification) of at least 1, 2, 3 or 4 mg/L. Also provided is a kit or set of nucleic acids comprising a recombinant nucleic acid encoding a first polypeptide chain of the disclosure, a recombinant nucleic acid encoding a second polypeptide chain of the disclosure, and, optionally, a recombinant nucleic acid encoding a third polypeptide chain of the disclosure. Also provided are methods of making monomeric, heterodimeric and heterotrimeric proteins of the disclosure.

Any of the methods can further be characterized as comprising any step described in the application, including notably in the "Detailed Description of the Invention"). The invention further relates to methods of identifying, testing and/or making proteins described herein. The invention further relates to a multispecific protein obtainable by any of present methods. The disclosure further relates to pharmaceutical or diagnostic formulations of the multispecific protein disclosed herein. The disclosure further relates to methods of using the multispecific protein in methods of treatment or diagnosis.

In one embodiment, the multispecific protein are administered to an individual having a disease (e.g. cancer, a viral or bacterial disease) in combination with a therapeutically effective amount of an ADCC-inducing antibody. The ADCC-inducing antibody can be, for example, an antibody that binds to a cancer antigen, viral antigen or bacterial antigen comprising an Fc domain that is bound by a human Fcγ receptor (e.g. CD16). In some embodiments, the ADCC-inducing antibody comprises a native or modified Fc domain from a human IgG1 or IgG3 isotype antibody. In some embodiments, the ADCC-inducing antibody has enhanced ADCC activity, e.g. comprising an Fc domain that comprises one or more amino acid modifications such as amino acid substitutions or hypofucosylation, compared to a native human IgG Fc domain.

These and additional advantageous aspects and features of the Invention may be further described elsewhere herein.

BRIEF DESCRIPTION OF THE FIGURES

FIG. 4 shows that Anti-CD19-F1-Anti-CD3 does not cause T/B cell aggregation in the presence of B221 (CD19) or JURKAT (CD3) cell lines when separate, but it does cause aggregation of cells when both B221 and JURKAT cells are co-incubated.

FIG. 5 shows Anti-CD19-F1-Anti-CD3 retains binding to FcRn, with a 1:1 ratio (1 FcRn for each monomeric Fc) (KD=194 nM), in comparison to a chimeric full length antibody having human IgG1 constant regions (KD=15.4 nM) which binds to FcRn with a 2:1 ration (2 FcRn for each antibody).

FIG. 6A to 6E shows different domain arrangements of bispecific anti-NKp46 proteins produced.

FIG. 7A shows superimposed sensorgrams showing the raw data curves, sample (NKp46) and blank (Buffer), which were used to generate each subtracted sensorgrams of FIG. 7B.

FIG. 9A shows bispecific antibodies having NKp46 and CD19 binding regions in an F2 format protein do not activate resting NK cells in the absence of target cells, however full length anti-NKp46 antibodies as well as positive control alemtuzumab did activate NK cells.

FIG. 9A. FIG. 9B shows that bispecific anti-NKp46×anti-CD19 antibodies (including each of the NKp46-1, NKp46-2, NKp46-3 or NKp46-4 binding domains) activated resting NK cells in presence of Daudi target cells, while full-length anti-CD19 showed at best only very low activation of NK cells and neither full-length anti-NKp46 antibodies or alemtuzumab showed substantial increase in activation beyond what was observed in presence of NK cells alone.

Figure 16A:
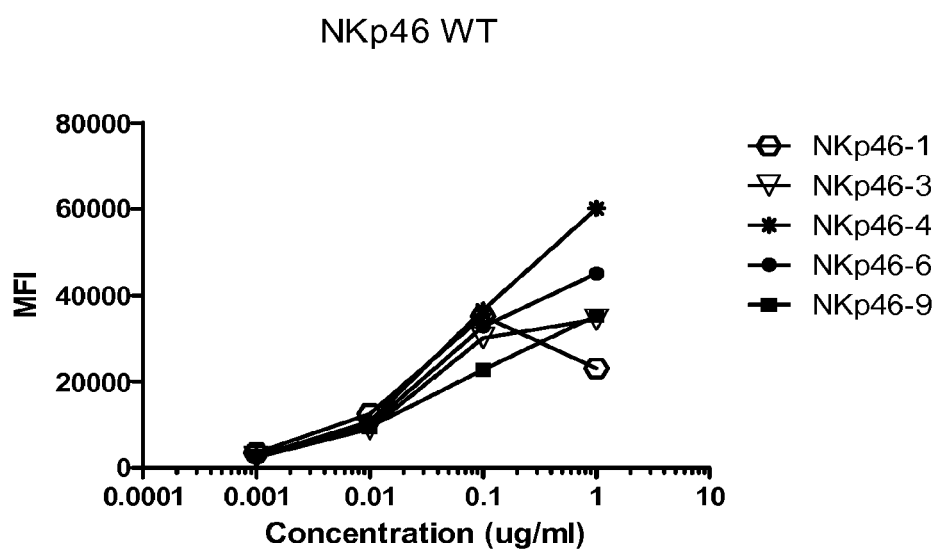
Figure 16B:
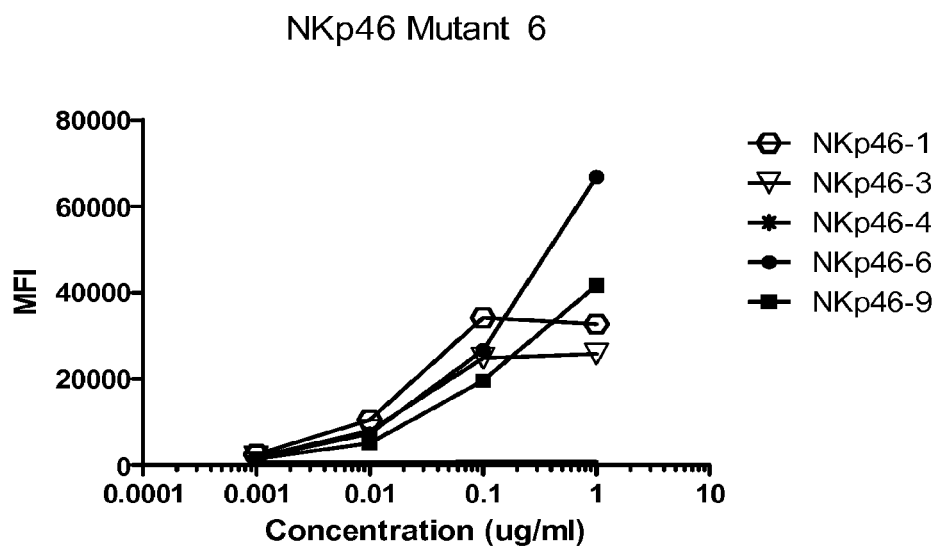
Figure 17A:
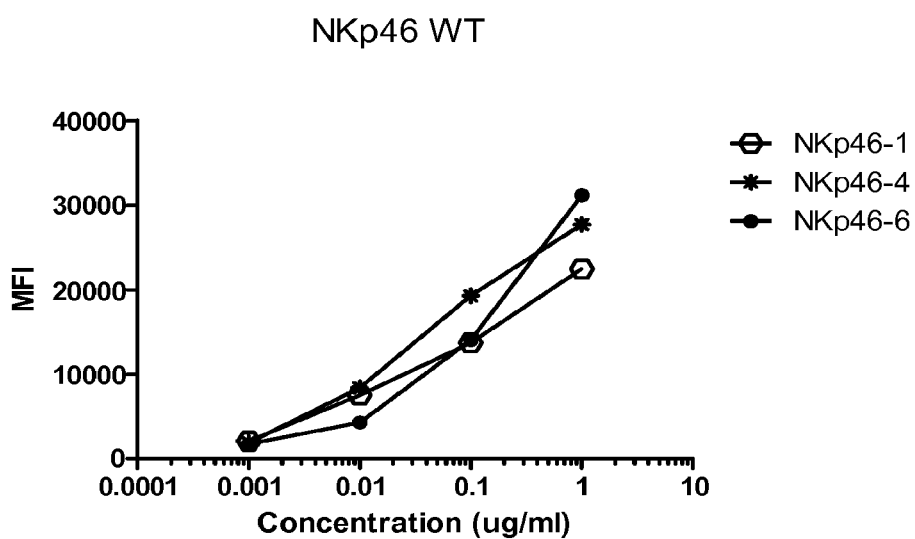
Figure 17B:
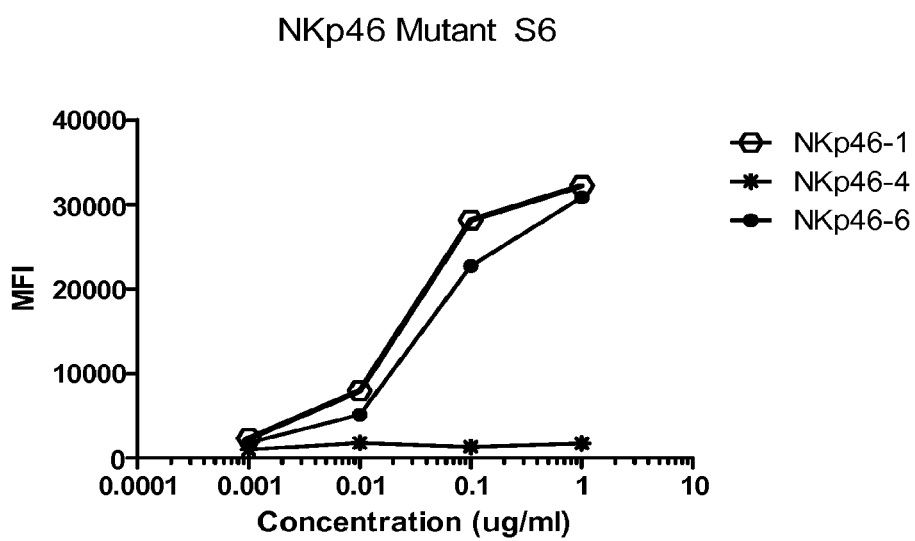

Antibody NKp46-4 had decreased binding to the mutant 6 (FIG. 16B) compared to wild-type NKp46 (FIG. 16A), and decreased binding to the supplementary mutant Supp6 (FIG. 17B) compared to wild-type NKp46 (FIG. 17A).

Figure 18:
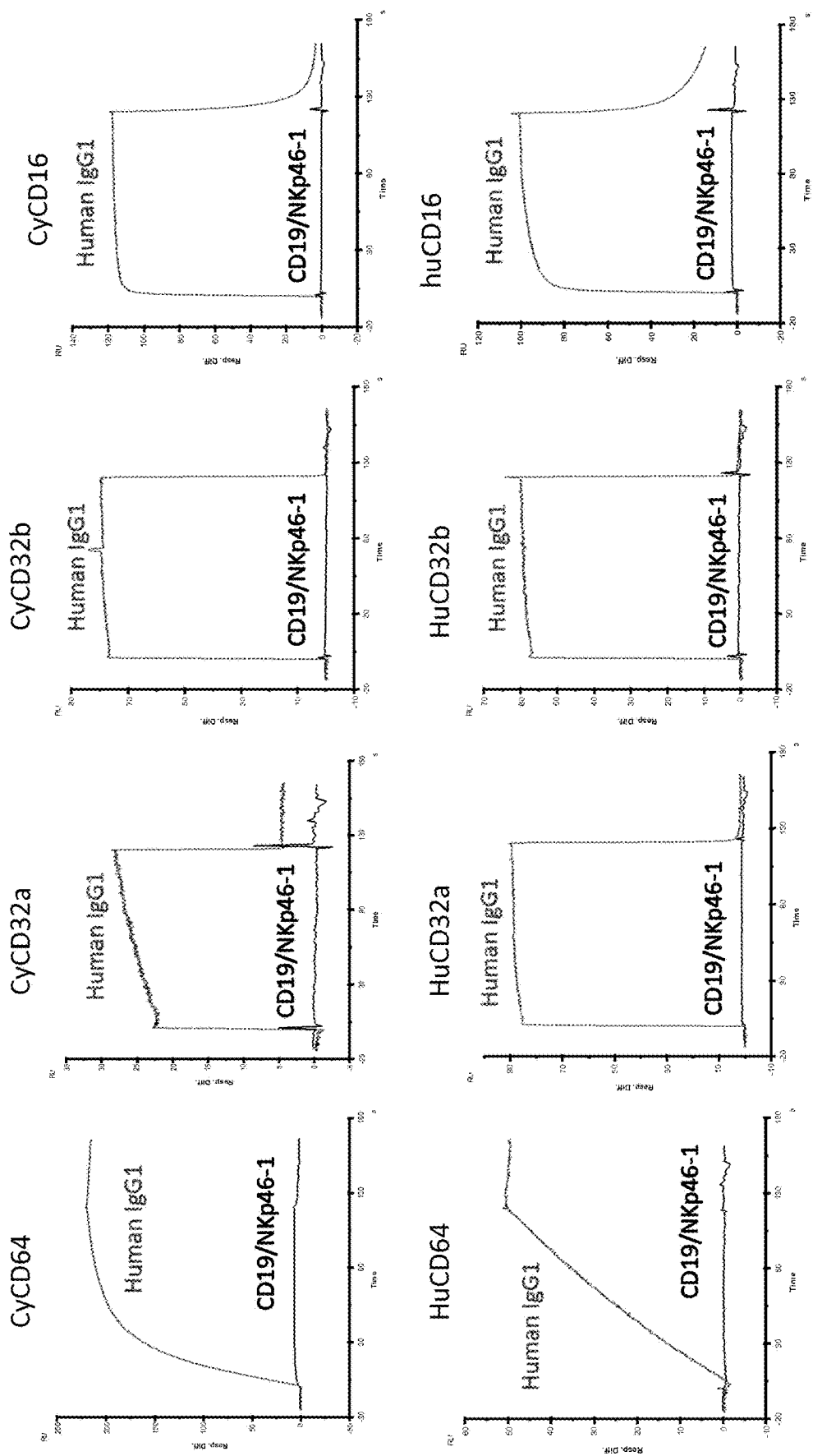

FIG. 18 shows superimposed sensorgrams showing the binding of *Macaca fascicularis* recombinant FcgRs (upper panels: CyCD64, CyCD32a, CYCD32b, CyCD16) and of human recombinant FcgRs (lower panels: HuCD64, HuCD32a, HuCD32b, HUCD16a) to the immobilized human IgG1 control (grey) and CD19/NKp46-1 bi-specific antibody (black). While full length wild type human IgG1 bound to all cynomolgus and human Fcy receptors, the CD19/NKp46-1 bi-specific antibodies did not bind to any of the receptors.

Figure 19A:
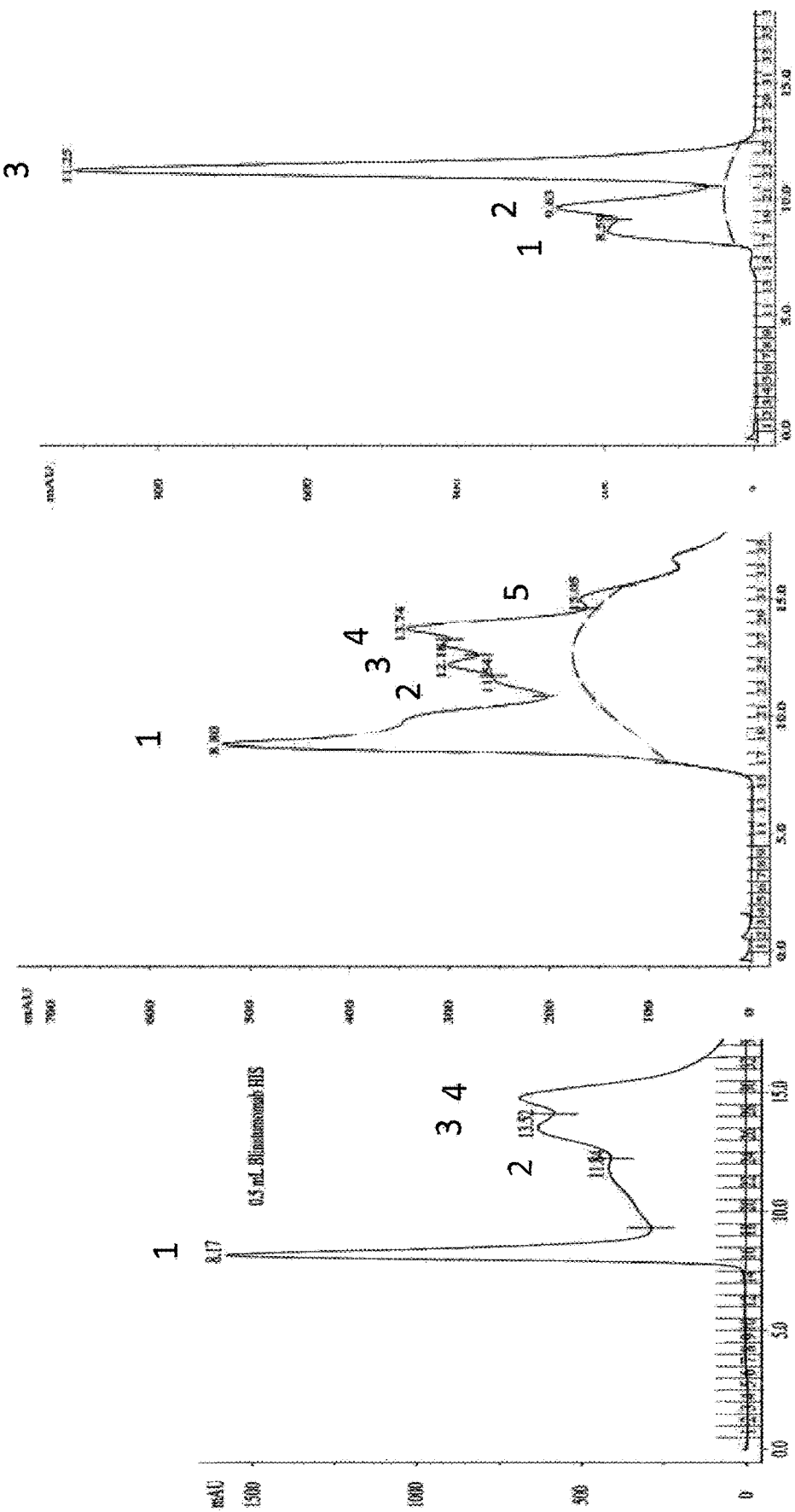
Figure 19B:
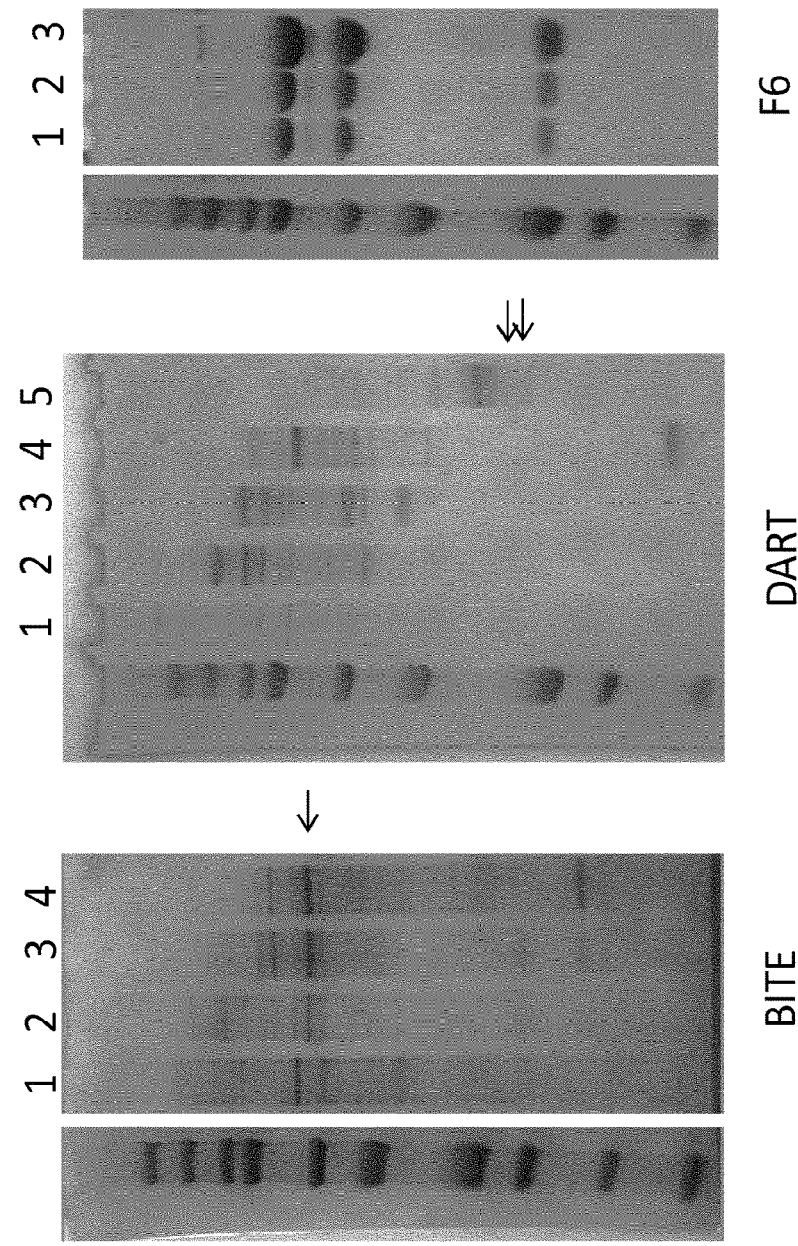

FIG. 19A shows results of purification by SEC of proteins format 6 (F6), compared with DART and BITE. BITE and DART showed a very low production yield compared to F6 and have a very complex SEC profile. FIG. 19B shows SOS-PAGE after Coomassie staining in the expected SEC fractions (3 and 4 for BITE and 4 and 5 for DART), whereas F6 format showed clear and simple SEC and SOS-PAGE profiles with a major peak (fraction 3) containing the desired bispecific proteins.

DETAILED DESCRIPTION OF THE INVENTION

Definitions

As used in the specification, "a" or "an" may mean one or more. As used in the claim(s), when used in conjunction with the word "comprising", the words "a" or "an" may mean one or more than one.

Where "comprising" is used, this can optionally be replaced by "consisting essentially of", more optionally by "consisting of".

As used herein, the term "antigen binding domain" refers to a domain comprising a three-dimensional structure capable of immunospecifically binding to an epitope. Thus, in one embodiment, said domain can comprise a hypervariable region, optionally a VH and/or VL domain of an antibody chain, optionally at least a VH domain. In another embodiment, the binding domain may comprise at least one complementarity determining region (CDR) of an antibody chain. In another embodiment, the binding domain may comprise a polypeptide domain from a non-immunoglobulin scaffold.

The term "antibody" herein is used in the broadest sense and specifically includes full-length monoclonal antibodies, polyclonal antibodies, multispecific antibodies (e.g., bispecific antibodies), and antibody fragments and derivatives, so long as they exhibit the desired biological activity. Various techniques relevant to the production of antibodies are provided in, e.g., Harlow, et al., ANTIBODIES: A LABO- RATORY MANUAL, Cold Spring Harbor Laboratory Press, Cold Spring Harbor, N.Y., (1988). An "antibody fragment" comprises a portion of a full-length antibody, e.g. antigen-binding or variable regions thereof. Examples of antibody fragments Include Fab, Fab', F(ab)$_2$, F(ab')$_2$, F(ab)$_3$, Fv (typically the VL and VH domains of a single arm of an antibody), single-chain Fv (scFv), dsFv, Fd fragments (typically the VH and CH1 domain), and dAb (typically a VH domain) fragments; VH, VL, VhH, and V-NAR domains; minibodies, diabodies, triabodies, tetrabodies, and kappa bodies (see, e.g., III et al., Protein Eng 1997; 10: 949-57); camel IgG; IgNAR; and multispecific antibody fragments formed from antibody fragments, and one or more isolated CDRs or a functional paratope, where isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23, 1126-1136; WO2005040219, and published U.S. Patent Applications 20050238646 and 20020161201.

The term "antibody derivative", as used herein, comprises a full-length antibody or a fragment of an antibody, e.g. comprising at least antigen-binding or variable regions thereof, wherein one or more of the amino acids are chemically modified, e.g., by alkylation, PEGylation, acylation, ester formation or amide formation or the like. This includes, but is not limited to, PEGylated antibodies, cysteine-PEGylated antibodies, and variants thereof.

The term "hypervariable region" when used herein refers to the amino acid residues of an antibody that are responsible for antigen binding. The hypervariable region generally comprises amino acid residues from a "complementarity-determining region" or "CDR" (e.g. residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991) and/or those residues from a "hypervariable loop" (e.g. residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

By "framework" or "FR" residues as used herein is meant the region of an antibody variable domain exclusive of those regions defined as CDRs. Each antibody variable domain framework can be further subdivided into the contiguous regions separated by the CDRs (FR1, FR2, FR3 and FR4).

By "constant region" as defined herein is meant an antibody-derived constant region that is encoded by one of the light or heavy chain immunoglobulin constant region genes. By "constant light chain" or "light chain constant region" as used herein is meant the region of an antibody encoded by the kappa (Ckappa) or lambda (Clambda) light chains. The constant light chain typically comprises a single domain, and as defined herein refers to positions 108-214 of Ckappa, or Clambda, wherein numbering is according to the EU index (Kabat et al., 1991, Sequences of Proteins of Immunological Interest, 5th Ed., United States Public Health Service, National Institutes of Health, Bethesda). By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447, wherein numbering is according to the EU Index.

By "Fab" or "Fab region" as used herein is meant the polypeptide that comprises the VH, CH1, VL, and CL immunoglobulin domains. Fab may refer to this region in isolation, or this region in the context of a polypeptide, multispecific polypeptide or ABD, or any other embodiments as outlined herein.

By "single-chain Fv" or "scFv" as used herein are meant antibody fragments comprising the VH and VL domains of an antibody, wherein these domains are present in a single polypeptide chain. Generally, the Fv polypeptide further comprises a polypeptide linker between the VH and VL domains which enables the scFv to form the desired structure for antigen binding. Methods for producing scFvs are well known in the art. For a review of methods for producing scFvs see Pluckthun in The Pharmacology of Monoclonal Antibodies, vol. 113, Rosenburg and Moore eds. Springer-Verlag, New York, pp. 269-315 (1994).

By "Fv" or "Fv fragment" or "Fv region" as used herein is meant a polypeptide that comprises the VL and VH domains of a single antibody.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cγ2 (CH2) and Cγ3 (CH3) and the hinge between Cγ1 and Cγ2. Although the boundaries of the Fc region may vary, the human IgG heavy chain Fc region is usually defined to comprise residues C226, P230 or A231 to its carboxyl-terminus, wherein the numbering is according to the EU index. Fc may refer to this region in isolation, or this region in the context of an Fc polypeptide, as described below. By "Fc polypeptide" or "Fc-derived polypeptide" as used herein is meant a polypeptide that comprises all or part of an Fc region. Fc polypeptides include but is not limited to antibodies, Fc fusions and Fc fragments.

By "variable region" as used herein is meant the region of an antibody that comprises one or more Ig domains substantially encoded by any of the VL (including Vkappa (VK) and Vlambda) and/or VH genes that make up the light chain (including kappa and lambda) and heavy chain immunoglobulin genetic loci respectively. A light or heavy chain variable region (VL or VH) consists of a "framework" or "FR" region interrupted by three hypervariable regions referred to as "complementarity determining regions" or "CDRs". The extent of the framework region and CDRs have been precisely defined, for example as in Kabat (see "Sequences of Proteins of Immunological Interest," E. Kabat et al., U.S. Department of Health and Human Services, (1983)), and as in Chothia. The framework regions of an antibody, that is the combined framework regions of the constituent light and heavy chains, serves to position and align the CDRs, which are primarily responsible for binding to an antigen.

The term "specifically binds to" means that an antibody or polypeptide can bind preferably in a competitive binding assay to the binding partner, e.g. NKp46, as assessed using either recombinant forms of the proteins, epitopes therein, or native proteins present on the surface of isolated target cells. Competitive binding assays and other methods for determining specific binding are further described below and are well known in the art.

When an antibody or polypeptide is said to "compete with" a particular monoclonal antibody (e.g. NKp46-1, -2, -4, -6 or -9 in the context of an anti-NKp46 mono- or bi-specific antibody), it means that the antibody or polypeptide competes with the monoclonal antibody in a binding assay using either recombinant target (e.g. NKp46) molecules or surface expressed target (e.g. NKp46) molecules. For example, if a test antibody reduces the binding of NKp46-1, -2, -4, -6 or -9 to a NKp46 polypeptide or NKp46-expressing cell in a binding assay, the antibody is said to "compete" respectively with NKp46-1, -2, -4, -6 or -9.

The term "affinity", as used herein, means the strength of the binding of an antibody or polypeptide to an epitope. The affinity of an antibody is given by the dissociation constant $K_D$, defined as $[Ab] \times [Ag]/[Ab-Ag]$, where $[Ab-Ag]$ is the molar concentration of the antibody-antigen complex, $[Ab]$ is the molar concentration of the unbound antibody and $[Ag]$ is the molar concentration of the unbound antigen. The affinity constant $K_A$ is defined by $1/K_D$. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of surface plasmon resonance (SPR) screening (such as by analysis with a BiAcore™ SPR analytical device).

Within the context of this invention a "determinant" designates a site of interaction or binding on a polypeptide.

The term "epitope" refers to an antigenic determinant, and is the area or region on an antigen to which an antibody or polypeptide binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

By "amino acid modification" herein is meant an amino acid substitution, insertion, and/or deletion in a polypeptide sequence. An example of amino acid modification herein is a substitution. By "amino acid modification" herein is meant an amino acid substitution, insertion, and/or deletion in a polypeptide sequence. By "amino acid substitution" or "substitution" herein is meant the replacement of an amino acid at a given position in a protein sequence with another amino acid. For example, the substitution Y50W refers to a variant of a parent polypeptide, in which the tyrosine at position 50 is replaced with tryptophan. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or Insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of a polypeptide will exhibit 98%, 98%, or 99% homogeneity for polypeptides in the context of all present peptide species in the composition or at least with respect to substantially active peptide species in the context of proposed use.

In the context herein, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

As used herein, "NK cells" refers to a sub-population of lymphocytes that is involved in non-conventional Immunity. NK cells can be Identified by virtue of certain characteristics and biological properties, such as the expression of specific surface antigens including CD56 and/or NKp46 for human NK cells, the absence of the alpha/beta or gamma/delta TCR complex on the cell surface, the ability to bind to and kill cells that fall to express "self" MHC/HLA antigens by the activation of specific cytolytic machinery, the ability to kill tumor cells or other diseased cells that express a ligand for NK activating receptors, and the ability to release protein molecules called cytokines that stimulate or Inhibit the immune response. Any of these characteristics and activities can be used to identify NK cells, using methods well known in the art. Any subpopulation of NK cells will also be encompassed by the term NK cells. Within the context herein "active" NK cells designate biologically active NK cells, including NK cells having the capacity of lysing target cells or enhancing the immune function of other cells. NK cells can be obtained by various techniques known in the art, such as isolation from blood samples, cytapheresis, tissue or cell collections, etc. Useful protocols for assays involving NK cells can be found in Natural Killer Cells Protocols (edited by Campbell KS and Colonna M). Human Press. pp. 219-238 (2000).

As used herein, an agent that has "agonist" activity at Nkp46 is an agent that can cause or increase "NKp46 signaling". "Nkp46 signaling" refers to an ability of a NKp46 polypeptide to activate or transduce an intracellular signaling pathway. Changes in NKp46 signaling activity can be measured, for example, by assays designed to measure changes in NKp46 signaling pathways, e.g. by monitoring phosphorylation of signal transduction components, assays to measure the association of certain signal transduction components with other proteins or intracellular structures, or in the biochemical activity of components such as kinases, or assays designed to measure expression of reporter genes under control of NKp46-sensitive promoters and enhancers, or indirectly by a downstream effect mediated by the NKp46 polypeptide (e.g. activation of specific cytolytic machinery in NK cells). Reporter genes can be naturally occurring genes (e.g. monitoring cytokine production) or they can be genes artificially introduced into a cell. Other genes can be placed under the control of such regulatory elements and thus serve to report the level of NKp46 signaling.

"NKp46" refers to a protein or polypeptide encoded by the Ncr1 gene or by a cDNA prepared from such a gene. Any naturally occurring isoform, allele or variant is encompassed by the term NKp46 polypeptide (e.g., an NKp46 polypeptide 90%, 95%, 98% or 99% identical to SEQ ID NO 1, or a contiguous sequence of at least 20, 30, 50, 100 or 200 amino acid residues thereof). The 304 amino acid residue sequence of human NKp46 (isoform a) is shown as follows:

```
                                              (SEQ ID NO: 1)
MSSTLPALLC  VGLCLSQRIS  AQQQTLPKPF  IWAEPHFMVP

KEKQVTICCQ  GNYGAVEYQL  HFEGSLFAVD  RPKPPERINK

VKFYIPDMNS  RMAGQYSCIY  RVGELWSEPS  NLLDLVVTEM

YDTPTLSVHP  GPEVISGEKV  TFYCRLDTAT  SMFLLLKEGR

SSHVQRGYGK  VQAEFPLGPV  TTAHRGTYRC  FGSYNNHAWS

FPSEPVKLLV  TGDIENTSLA  PEDPTFPADT  WGTYLLTTET

GLQKDHALWD  HTAQNLLRMG  LAFLVLVALV  WFLVEDWLSR

KRTRERASRA  STWEGRRRLN  TQTL.
```

SEQ ID NO: 1 corresponds to NCBI accession number NP_004820, the disclosure of which is Incorporated herein by reference. The human NKp46 mRNA sequence is described in NCBI accession number NM_004829, the disclosure of which is incorporated herein by reference.

Producing Polypeptides

The antigen binding domains used in the proteins described herein can be readily derived a variety of immunoglobulin or non-immunoglobulin scaffolds, for example affibodies based on the Z-domain of staphylococcal protein A, engineered Kunitz domains, monobodies or adnectins based on the 10th extracellular domain of human fibronectin Ill, anticalins derived from lipocalins, DARPins (designed ankyrin repeat domains, multimerized LDLR-A module, avimers or cysteine-rich knottin peptides. See, e.g., Gebauer and Skerra (2009) Current Opinion in Chemical Biology 13:245-255, the disclosure of which is Incorporated herein by reference.

Variable domains are commonly derived from antibodies (immunoglobulin chains), for example in the form of associated VL and VH domains found on two polypeptide chains, or single chain antigen binding domains such as scFv, a $V_H$ domain, a $V_L$ domain, a dAb, a V-NAR domain or a $V_H$H domain. The an antigen binding domain (e.g., $ABD_1$ and $ABD_2$) can also be readily derived from antibodies as a Fab.

Typically, antibodies are initially obtained by immunization of a non-human animal, e.g., a mouse, with an immunogen comprising a polypeptide, or a fragment or derivative thereof, typically an immunogenic fragment, for which it is desired to obtain antibodies (e.g. a human polypeptide). The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, NY (1988), the entire disclosure of which is herein incorporated by reference). Other protocols may also be used as long as they result in the production of B cells expressing an antibody directed to the antigen used in immunization. Lymphocytes from a non-immunized non-human mammal may also be isolated, grown in vitro, and then exposed to the immunogen in cell culture. The lymphocytes are then harvested and the fusion step described below is carried out. For exemplary monoclonal antibodies, the next step is the Isolation of splenocytes from the immunized non-human mammal and the subsequent fusion of those splenocytes with an immortalized cell in order to form an antibody-producing hybridoma. The hybridoma colonies are then assayed for the production of antibodies that specifically bind to the polypeptide against which antibodies are desired. The assay is typically a colorimetric ELISA-type assay, although any assay may be employed that can be adapted to the wells that the hybridomas are grown in. Other assays Include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody. After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference).

Human antibodies may also be produced by using, for immunization, transgenic animals that have been engineered to express a human antibody repertoire (Jakobovitz et Nature 362 (1993) 255), or by selection of antibody repertoires using phage display methods. For example, a Xeno-Mouse (Abgenix, Fremont, CA) can be used for immunization. A XenoMouse is a murine host that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Antibodies may also be produced by selection of combinatorial libraries of immunoglobulins, as disclosed for instance in (Ward et al. Nature, 341 (1989) p. 544, the entire disclosure of which is herein incorporated by reference). Phage display technology (McCafferty et al (1990) Nature 348:552-553) can be used to produce antibodies from immunoglobulin variable (V) domain gene repertoires from unimmunized donors. See, e.g., Griffith et al (1993) EMBO J. 12:725-734; U.S. Pat. Nos. 5,565,332; 5,573,905; 5,567, 610; 5,229,275). When combinatorial libraries comprise variable (V) domain gene repertoires of human origin, selection from combinatorial libraries will yield human antibodies.

Additionally, a wide range of antibodies are available in the scientific and patent literature, including DNA and/or amino acid sequences, or from commercial suppliers. Antibodies will typically be directed to a pre-determined antigen. Examples of antibodies include antibodies that recognize an antigen expressed by a target cell that is to be eliminated, for example a proliferating cell or a cell contributing to a pathology. Examples include antibodies that recognize tumor antigens, microbial (e.g. bacterial) antigens or viral antigens.

Antigen binding domains that bind NKp46 can be derived from the anti-NKp46 antibodies provided herein (see section "CDR Sequences"). Variable regions can be used directly, or can be modified by selecting hypervariable or CDR regions from the NKp46 antibodies and placing them into an appropriate VL or VH framework, for example human frameworks. Antigen binding domains that bind NKp46 can also be derived de novo using methods for generating antibodies. Antibodies can be tested for binding to NKp46 polypeptides. In one aspect of any embodiment herein, a polypeptide (e.g. multispecific polypeptide, bispecific or monospecific antibody) that binds to NKp46 will be capable of binding NKp46 expressed on the surface of a cell, e.g. native NKp46 expressed by a NK cell.

Antigen binding domains (ABDs) that bind antigens of interest can be selected based on the desired cellular target, and may include for example cancer antigens, bacterial or viral antigens, etc. As used herein, the term "bacterial antigen" Includes, but is not limited to, intact, attenuated or killed bacteria, any structural or functional bacterial protein or carbohydrate, or any peptide portion of a bacterial protein of sufficient length (typically about 8 amino acids or longer) to be antigenic. Examples include gram-positive bacterial antigens and gram-negative bacterial antigens. In some embodiments the bacterial antigen is derived from a bacterium selected from the group consisting of *Helicobacter* species, in particular *Helicobacter pyloris; Borelia* species, in particular *Borelia burgdorferi; Legionella* species, in particular *Legionella pneumophilia; Mycobacteria* s species, in particular *M. tuberculosis, M. avium, M. intracellulare, M. kansasii, M. gordonae; Staphylococcus* species, in particular *Staphylococcus aureus; Neisseria* species, in particular *N. gonorrhoeae, N. meningitidis; Listeria* species, in particular *Listeria monocytogenes; Streptococcus* species, in particular *S. pyogenes, S. agalactiae; S. faecalis; S. bovis, S. pneumonias*; anaerobic *Streptococcus* species; pathogenic *Campylobacter* species; *Enterococcus* species; *Haemophilus* species, in particular *Haemophilus influenzue; Bacillus* species, in particular *Bacillus anthracis; Corynebacterium* species, in particular *Corynebacterium diphtheriae; Erysipelothrix* species, in particular *Erysipelothrix rhusiopathiae; Clostridium* species, in particular *C. perfringens, C. tetani; Enterobacter* species, in particular *Enterobacter aerogenes, Klebsiella* species, in particular *Klebsiella* 1*S pneumoniae, Pasteurella* species, in particular *Pasteurella multocida, Bacteroides* species; *Fusobacterium* species, in particular *Fusobacterium nucleatum; Streptobacillus* species, in particular *Streptobacillus moniliformis; Treponema* species, in particular *Treponema pertenue; Leptospira*; pathogenic *Escherichia* species; and *Actinomyces* species, in particular *Actinomyces israelli*.

As used herein, the term "viral antigen" includes, but is not limited to, intact, attenuated or killed whole virus, any structural or functional viral protein, or any peptide portion of a viral protein of sufficient length (typically about 8 amino acids or longer) to be antigenic. Sources of a viral antigen include, but are not limited to viruses from the families: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviruses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g., African swine fever virus); and unclassified viruses (e.g., the agent of delta hepatitis (thought to be a defective satellite of hepatitis B virus), Hepatitis C; Norwalk and related viruses, and astroviruses). Alternatively, a viral antigen may be produced recombinantly.

As used herein, the terms "cancer antigen" and "tumor antigen" are used interchangeably and refer to antigens that are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

The cancer antigens are usually normal cell surface antigens which are either over-expressed or expressed at abnormal times. Ideally the target antigen is expressed only on proliferative cells (e.g., tumor cells), however this is rarely observed in practice. As a result, target antigens are usually selected on the basis of differential expression between proliferative and healthy tissue. Antibodies have been raised to target specific tumor related antigens including: Receptor Tyrosine Kinase-like Orphan Receptor 1 (ROR1), Cripto, CD4, CD20, CD30, CD19, CD33, CD38, CD47, Glycoprotein NMB, CanAg, Her2 (ErbB2/Neu), CD22 (Siglec2), CD33 (Siglec3), CD79, CD138, CD171, PSCA, L1-CAM, PSMA (prostate specific membrane antigen), BCMA, CD52, CD56, CD80, CD70, E-selectin, EphB2, Melanotransferin, Mud 6 and TMEFF2. Examples of cancer antigens also include B7-H3, B7-H4, B7-H6, PD-L1, MAGE, MART-1/Melan-A, gp100, major histocompatibility complex class I-related chain A and B polypeptides (MICA and MICB), adenosine deaminase-binding protein (ADAbp), cyclophilin b, colorectal associated antigen (CRC)-C017-1A/GA733, Killer-Ig Like Receptor 3DL2 (KIR3DL2), protein tyrosine kinase 7(PTK7), receptor protein tyrosine kinase 3 (TYRO-3), nectins (e.g. nectin-4), major histocompatibility complex class I-related chain A and B polypeptides (MICA and MICB), proteins of the UL16-binding protein (ULBP) family, proteins of the retinoic acid early transcript-1 (RAET1) family, carcinoembryonic antigen (CEA) and its immunogenic epitopes CAP-1 and CAP-2, etv6, aml1, prostate specific antigen (PSA), T-cell receptor/CD3-zeta chain, MAGE-family of tumor antigens, GAGE-family of tumor antigens, anti-Mullerian hormone Type II receptor, delta-like ligand 4 (DLL4), DR5, ROR1 (also known as Receptor Tyrosine Kinase-Like Orphan Receptor 1 or NTRKR1 (EC 2.7.10.1), BAGE, RAGE, LAGE-1, NAG, GnT-V, MUM-1, CDK4, MUC family, VEGF, VEGF receptors, Angiopoietin-2, PDGF, TGF-alpha, EGF, EGF receptor, a member of the human EGF-like receptor family such as HER-2/neu, HER-3, HER-4 or a heterodimeric receptor comprised of at least one HER subunit, gastrin releasing peptide receptor antigen, Muc-1, CA125, αvß3 integrins, α5ß1 integrins, αIIbß3-integrins, PDGF beta receptor, SVE-cadherin, IL-8, hCG, IL-6, IL-6 receptor, IL-15, α-fetoprotein, E-cadherin, α-catenin, ß-catenin and γ-catenin, p120ctn, PRAME, NY-ESO-1, cdc27, adenomatous polyposis coli protein (APC), fodrin, Connexin 37, Ig-idiotype, p15, gp75, GM2 and GD2 gangliosides, viral products such as human papillomavirus proteins, imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2, although this is not intended to be exhaustive. In one aspect, the antigen of interest is a CD19 polypeptide; in one aspect, the multispecific protein comprises an scFv that binds CD19 comprising an amino acid sequence which is at least 60%, 70%, 80%, 85%, 90% or 95% identical to the sequence of the anti-CD19 scFv of the Examples herein, or that comprises the heavy and light chain CDR1, -2 and -3 of the anti-CD19 heavy and light chain variable regions shown herein.

In one embodiment, the ABD binds to a cancer antigen, a viral antigen, a microbial antigen, or an antigen present on an Infected cell (e.g. virally Infected) or on a pro-inflammatory immune cell. In one embodiment, said antigen is a polypeptide selectively expressed or overexpressed on a tumor cell, and infected cell or a pro-inflammatory cell. In one embodiment, said antigen is a polypeptide that when inhibited, decreases the proliferation and/or survival of a tumor cell, an infected cell or a pro-inflammatory cell. For example, a first and/or second antibody or fragment can respectively bind anti-Her1 and anti-Her2. Anti-Her2 can be for example an antibody comprising the CDRs derived from Herceptin® (trastuzumab) or 2C4 (pertuzumab). Anti-Her2 and anti-Her1 (antibodies D1-5 and C3-101) amino acid sequences are shown in WO2011/069104.

The ABD which are incorporated into the polypeptides can be tested for any desired activity prior to inclusion in a multispecific NKp46-binding protein, for example the ABD can be tested for binding to an antigen of interest.

An ABD derived from an antibody will generally comprise at minimum a hypervariable region sufficient to confer binding activity. It will be appreciated that an ABD may comprise other amino acids or functional domains as may be desired, including but not limited to linker elements (e.g. linker peptides, CH1, Cκ or Cλ domains, hinges, or fragments thereof). In one example an ABD comprises an scFv, a $V_H$ domain and a $V_L$ domain, or a single domain antibody (nanobody or dAb) such as a V-NAR domain or a $V_HH$ domain. Exemplary antibody formats are further described herein and an ABD can be selected based on the desired format.

In any embodiment, an antigen binding domain can be obtained from a humanized antibody in which residues from a complementary-determining region (CDR) of a human antibody are replaced by residues from a CDR of the original antibody (the parent or donor antibody, e.g. a murine or rat antibody) while maintaining the desired specificity, affinity, and capacity of the original antibody. The CDRs of the parent antibody, some or all of which are encoded by nucleic acids originating in a non-human organism, are grafted in whole or in part into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239:1534-1536. An antigen binding domain can thus have non-human hypervariable regions or CDRs and human frameworks region sequences (optionally with backmutations).

Once appropriate antigen binding domains having desired specificity and/or activity are Identified, DNA encoding each of the or ABD can be separately placed, in suitable arrangements, in an appropriate expression vector, together with DNA encoding any elements such as an enzymatic recognition tag, or CH2 and CH3 domains and any other optional elements (e.g. DNA encoding a hinge region) for transfection into an appropriate host. ABDs will be arranged in an expression vector, or in separate vectors as a function of which type of polypeptide is to be produced, so as to produce the Fc-polypeptides having the desired domains operably linked to one another. The host is then used for the recombinant production of the multispecific polypeptide.

For example, a polypeptide fusion product can be produced from a vector in which the first of the two ABD is operably linked (e.g. directly, via a heavy or light chain CH1, Cκ or Cλ constant region and/or hinge region) to the N-terminus of a CH2 domain, and the CH2 domain is operably linked at its C-terminus to the N-terminus a CH3 domain. The second of the two ABD can be linked to the polypeptide at either terminus, or can be on a second polypeptide chain that forms a dimer, e.g. heterodimer, with the polypeptide comprising the first ABD. The polypeptide may comprise a full length Fc domain.

The multispecific polypeptide can then be produced in an appropriate host cell or by any suitable synthetic process. A host cell chosen for expression of the multispecific polypeptide is an important contributor to the final composition, including, without limitation, the variation in composition of the oligosaccharide moieties decorating the protein in the immunoglobulin CH2 domain. Thus, one aspect of the invention involves the selection of appropriate host cells for use and/or development of a production cell expressing the desired therapeutic protein such that the multispecific polypeptide retains at least partial FcRn binding but with decreased binding to a Fcγ receptor compared, e.g., to a wild type full length human IgG1 antibody. The host cell may be of mammalian origin or may be selected from COS-1, COS-7, HEK293, BHK21, CHO, BSC-1, Hep G2, 653, SP2/0, 293, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as natural or engineered *E. coli* spp., *Klebsiella* spp., or *Pseudomonas* spp.

Monomeric Proteins

Monomeric multispecific proteins can be produced according to a variety of formats. In one example, a multispecific proteins comprises in a single polypeptide chain a first antigen binding domain that binds to NKp46 and a second antigen binding domain that binds an antigen other than NKp46. In one embodiment, the antibody is a tandem scFv, optionally fused to another polypeptide or amino acid sequence. In one embodiment, the single polypeptide chain further comprises an Fc domain (e.g. a full length Fc domain or a portion thereof), optionally wherein the Fc domain is Interposed between the first and second antigen binding domains.

Monomeric bispecific Fc-derived polypeptides having advantageous properties can be constructed that comprise: (a) an antigen binding domain that binds to NKp46; (b) an antigen binding domain that binds an antigen other than NKp46; and (c) at least a portion of a human Fc domain, wherein the Fc domain (i) does not dimerize with another Fc-derived polypeptide, (ii) is capable of binding to human FcRn and (iii) has decreased binding (or lacks binding) to a human Fcγ receptor compared to a wild type human IgG1 Fc domain. Optionally, the Fc domain is interposed between the first and second ABD.

In one aspect of any embodiment, the first antigen binding domain and/or the second antigen binding domain comprise a scFv, optionally where the scFv comprises human framework amino acid sequences. In one embodiment, provided is a monomeric bispecific Fc-derived polypeptide comprising: (a) a first scFv that binds to NKp46; (b) a second scFv that binds an antigen other than NKp46; and (c) at least a portion of a human Fc domain, wherein the Fc domain (i) does not dimerize with another Fc-derived polypeptide, (ii) is capable of binding to human FcRn and (iii) has decreased binding to a human Fcγ receptor compared to a wild type human IgG1 Fc domain. Optionally, the Fc domain is interposed between the first and second scFv.

When the polypeptide fusion product comprising the two ABDs and at least a portion of an Fc domain is a monomer, the CH3 domains may be arranged and/or comprise amino acid modification to prevent CH3-CH3 dimerization. In one embodiment, the CH3 domain comprises mutations in the dimer interface to prevent interchain CH3-CH3 dimerization. In another embodiment, the CH3 domain is a tandem CH3 domain (or the Fc domain comprises a tandem CH3 domain) to prevent interchain CH3-CH3 dimerization. Such monomers will retain partial FcRn binding (compared, e.g., to a wild type full length human IgG1 antibody), yet have decreased human Fcγ receptor binding. Optionally the monomeric polypeptide is capable of binding to human FcRn with intermediate affinity, e.g. retains binding to FcRn but has decreased binding to a human FcRn receptor compared to a full-length wild type human IgG1 antibody. The Fc moiety may further comprise one or more amino acid modifications, e.g. in the CH2 domain, that further decreases or substantially abolishes binding to one or more Fcγ receptors.

Optionally in any of the embodiments, the Fc domain comprises a CH2 domain and a CH3 domain comprising one or more amino acid modifications such that the Fc domain which does not dimerize with another Fc-derived polypeptide (e.g. does not dimerize via interactions with another CH3 domain).

In some embodiments of the polypeptides, the ABD that binds NKp46 will be operably linked to the ABD that binds an antigen other than NKp46 (e.g. the two ABDs are fused via a linker), and one of the two ABD will in turn be fused to a CH2 domain which is in turn fused (e.g. fused at its C-terminus) to a CH3 domain (or a CH3 which is in turn fused a CH2 domain). In some embodiments, the first ABD will be operably linked to the second ABD via a peptide linker such that a tandem antigen binding domain is formed that comprises both ABDs.

Examples of such polypeptides may comprise a domain arrangement of any one of the following:
(ABD$_1$)-(ABD$_2$)-CH2-CH3
(ABD$_2$)-(ABD$_1$)-CH2-CH3
CH2-CH3-(ABD$_1$)-(ABD$_2$)
CH2-CH3-(ABD$_2$)-(ABD$_1$)
wherein one of ABD$_1$ and ABD$_1$ binds an antigen of interest and the other binds NKp46, optionally wherein a CH1 domain or fragment thereof and/or hinge domain is placed between an ABD$_1$ and CH2 or between an ABD$_2$ and CH2. Optionally, each ABD comprises a VL and a VH domain. Optionally, any of the polypeptides comprises a tandem CH3 domain wherein a second CH3 domain fused via a flexible linker to the C-terminal of the first CH3 domain.

Optionally the ABDs are each scFv such that tandem scFv-containing polypeptides are produced. The first and second ABDs can be linked together by a linker of sufficient length to enable the ABDs to fold in such a way as to permit binding to the respective antigen for which the ABD is intended to bind. Suitable peptide linkers for use in linking ABD$_1$ to ABD$_2$, or for use in linking an ABD to a CH2 or CH3 are known in the art, see, e.g. WO2007/073499, the disclosure of which is incorporated herein by reference. Examples of linker sequences include $(G_4S)_x$ wherein x is an integer (e.g. 1, 2, 3, 4, or more). The tandem antigen binding domain can thus for example have the structure (ABD$_1$-peptide linker-ABD$_2$-peptide linker-(monomeric CH2-CH3 domain-containing polypeptide)). For example, the polypeptide may comprise, as a fusion product, the structure (scFv$_1$-peptide linker-scFv$_2$-peptide linker-CH2-CH3), wherein each element is fused to the following element.

In any domain arrangement presented herein, the ABD that binds NKp46 may be represented by either ABD$_1$ or ABD$_2$, and the ABD that binds an antigen of interest may be represented by either ABD$_1$ or ABD$_2$, so long as one of the ABD$_1$ or ABD$_2$ binds NKp46 and the other binds antigen of Interest.

In some embodiments of the polypeptides having a first antigen binding domain (ABD$_1$) and second antigen binding domain (ABD$_2$), one of the two ABD will in turn be fused, optionally via intervening amino acids, to one end of an Fc domain (e.g. comprising a full or partial CH2 and a full or partial CH3 domain) and the other of the two ABD is fused, optionally via Intervening amino acids, to opposite end of the Fc domain. In some embodiments, an ABD will be linked to the CH2 domain via a linker (e.g. comprising a full or partial hinge region and/or a full or partial CH1 domain). Such polypeptides will have the advantage, inter alia, that antibody VL and VH domains that are not functional when constructed as a tandem scFv but are functional in single scFv form can be readily used.

The polypeptides may comprise a domain arrangement of any one of the following:
(ABD$_1$)-CH2-CH3-(ABD$_2$)
(ABD$_2$)-CH2-CH3-(ABD$_1$)
wherein one of ABD$_1$ and ABD$_1$ binds an antigen of interest and the other binds NKp46, optionally wherein a CH1 domain and/or hinge domain is placed between an ABD$_1$ and CH2 or between an ABD$_2$ and CH2. Optionally, each ABD comprises a VL and a VH domain. Optionally, any of the polypeptides has a second CH3 domain fused via a flexible linker to the C-terminal of the first CH3 domain. Examples of such polypeptides are shown as formats 1, 3 and 4 in FIG. 6A.

The monomeric Fc-derived polypeptides that have at least a portion of a human Fc domain can advantageously comprise a CH2 domain that does not substantially bind to an FcγIIIA polypeptide (CD16) and a CH3 domain, wherein said CH3 domain comprises a modified CH3 dimer interface (e.g. a mutations in the CH3 dimer interface) to prevent dimerization with another Fc-derived polypeptide.

In one embodiment of any of the polypeptides or methods herein, the CH3 domain comprises an amino acid substitution at 1, 2, 3, 4, 5, 6 or 7 of the positions L351, T366, L368, P395, F405, T407 (or Y407) and/or K409 (EU numbering as in Kabat).

Figure 6A:
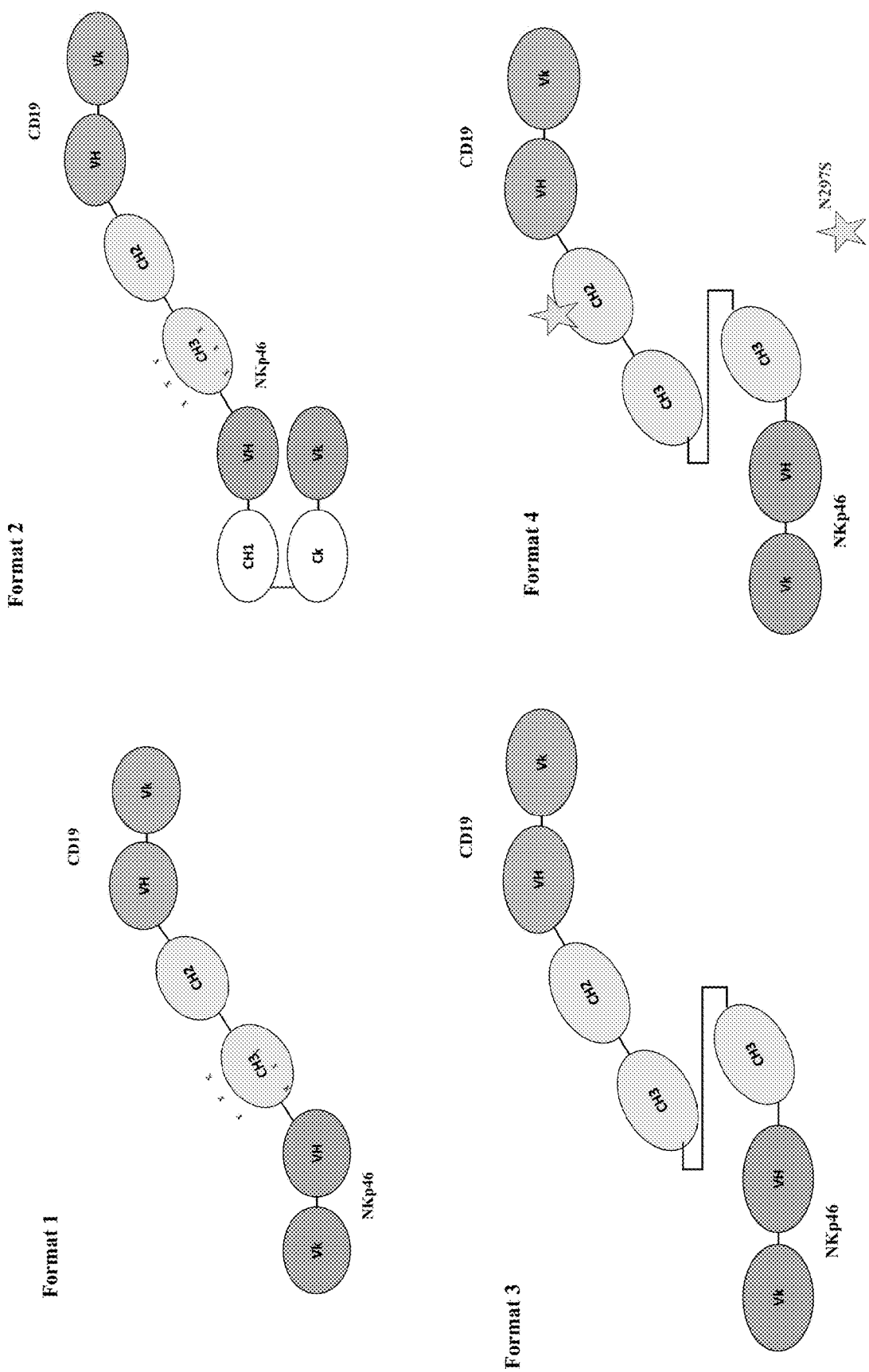

Another configuration for a CH3 domain that can be used in a monomeric multispecific protein is a tandem CH3 domain (see e.g. format 3 and 4 in FIG. 6A). A tandem CH3 domain comprises a first and a second CH3 domain, wherein the two CH3 domains associate with one another via non-covalent interactions. In one embodiment, the two CH3 domains associate with one another via the CH3 dimerization interface of each CH3 domain. In one embodiment, the polypeptide chain does not dimerize with another polypeptide chain comprising an Fc domain. An Fc domain that comprise a tandem CH3 domain will interact with neonatal Fc receptor (FcRn) but will have low or no binding to human Fcγ receptors, notably CD16.

In one embodiment of any aspect herein, a first CH3 domain is connected to a second CH3 domain by a linker. The tandem CH3 domains can thus be placed on the same polypeptide chain so as to have the domain arrangement, from N-terminus to C-terminus, as follows:
—CH3-linker-CH3-.

The linker will be a flexible linker (e.g. peptide linker). In one embodiment the linker permits the CH3 domains to associate with one another by non-covalent interactions. In one embodiment, the linker is a peptide linker having 10-50 amino acid residues. In one embodiment, the linker has the formula $(G_4S)_x$. Optionally, x is 2, 3, 4, 5 or 6. In any of the embodiments, each CH3 domain is independently a full-length and/or native CH3 domain, or a fragment or modified CH3 domain which retains a functional CH3 dimerization interface.

Examples of domain arrangements of monomeric proteins of the invention therefore include any one of the following:
$(ABD_1)$-CH2-CH3-linker-CH3-$(ABD_2)$
$(ABD_2)$-CH2-CH3-linker-CH3-$(ABD_1)$
$(ABD_1)$-$(ABD_2)$-CH2-CH3-linker-CH3
$(ABD_2)$-$(ABD_1)$-CH2-CH3-linker-CH3
CH2-CH3-linker-CH3-$(ABD_1)$-$(ABD_2)$
CH2-CH3-linker-CH3-$(ABD_2)$-$(ABD_1)$ Multimeric Proteins Multimeric bispecific proteins such as heterodimers, heterotrimers and tetramers (the latter including for example antibodies with two heavy chains and two light chains) can be produced according to a variety of formats.

In one advantageous format for NKp46 antibodies, the multimeric polypeptide is capable of binding to human FcRn and has decreased binding to a human Fcγ receptor (e.g. CD16, CD32 and/or CD64) compared, e.g., to a full length wild type human IgG1 antibody. When the polypeptide comprising the two ABDs is a multimer, Fc moieties with at least partial FcRn binding and decreased or abolished human Fcγ receptor binding can be obtained through the use of suitable CH2 and/or CH3 domains, as further described herein. In one embodiment, an Fc moiety is derived from a human IgG4 isotype constant region, as IgG4 based Fc domains will retain substantial FcRn binding but have reduced Fcγ receptor binding. In one embodiment, an Fc moiety may be obtained by production of the polypeptide in a host cell or by a process that does not yield N297-linked glycosylation, e.g. a bacterial cell. In one embodiment, an Fc moiety comprises one or more amino acid modifications, e.g. in the CH2 domain, that decreases binding to one or more Fcγ receptors and retains at least partial FcRn binding.

In one embodiment, exemplary heterodimer molecules can have a domain arrangement:

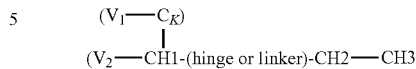

wherein $V_1$ and $V_2$ are single variable domains (e.g. $V_H$ domain, a $V_L$ domain, a dAb, a V-NAR domain or a $V_HH$ domain), and one of $V_1$ and $V_2$ binds NKp46 and the other binds an antigen of interest. Optionally, the CH3 domain is a tandem CH3 domain or a CH3 domain modified to prevent CH3-CH3 dimerization.

In one embodiment, exemplary heterodimer molecules can have a domain arrangement:

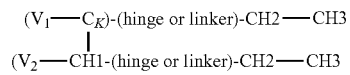

wherein $V_1$ and $V_2$ are single variable domains (e.g. $V_H$ domain, a $V_L$ domain, a dAb, a V-NAR domain or a $V_HH$ domain), and one of $V_1$ and $V_2$ binds NKp46 and the other binds an antigen of interest.

In one embodiment, exemplary heterodimer molecules can have a domain arrangement:

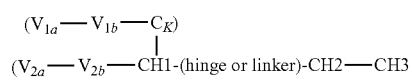

wherein $V_{1a}$, $V_{1b}$, $V_{2a}$ and $V_{2b}$ are each a $V_H$ domain or a $V_L$ domain, and wherein one of $V_{1a}$ and $V_{1b}$ is a VH and the other is a VL such that $V_{1a}$ and $V_{1b}$ form a first antigen binding domain (ABD), wherein one of $V_{2a}$ and $V_{2b}$ is a VH and the other is a VL such that $V_{2a}$ and $V_{2b}$ form a second ABD, wherein one of the ABD binds NKp46 and the other binds an antigen of interest. Optionally the CH3 domain is a tandem CH3 domain or a CH3 domain modified to prevent CH3-CH3 dimerization. Each pair of V domains can be separated by a linker peptide (e.g. to form an scFv).

In one embodiment, exemplary heterodimer molecules can have a domain arrangement:

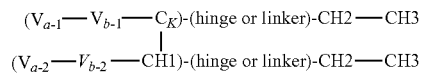

wherein $V_{a-1}$, $V_{b-1}$, $V_{a-2}$ and $V_{b-2}$ are each a $V_H$ domain or a $V_L$ domain, and wherein one of $V_{a-1}$ and $V_{b-1}$ is a VH and the other is a VL such that $V_{a-1}$ and $V_{b-1}$ form a first antigen binding domain (ABD), wherein one of $V_{a-2}$ and $V_{b-2}$ is a VH and the other is a VL such that $V_{a-2}$ and $V_{b-2}$ form a second antigen binding domain, wherein one of the ABD binds NKp46 and the other binds an antigen of interest. In one variant of the foregoing, any of, or each of the $V_{a-1}$, $V_{b-1}$, $V_{a-2}$ and $V_{b-2}$ are an scFv (made up of two variable domains). Each pair of V domains can be separated by a linker peptide (e.g. to form an scFv).

In similar approaches, trimers can be constructed. Exemplary heterotrimer molecules can have a domain arrangement:

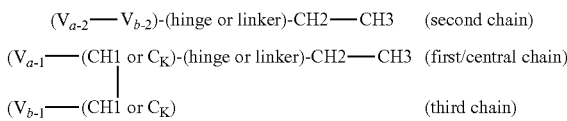

(V$_{a-2}$—V$_{b-2}$)-(hinge or linker)-CH2—CH3 (second chain)

(V$_{a-1}$—(CH1 or C$_K$)-(hinge or linker)-CH2—CH3 (first/central chain)

(V$_{b-1}$—(CH1 or C$_K$) (third chain)

wherein the first/central chain and the second chain associate by CH3-CH3 dimerization and first/central chain and the third chain associate by the CH1 or CK dimerization, wherein the domains of the first/central chain and the third chain are selected to be complementary to permit the first and third chains to associate by CH1-CK dimerization, and wherein V$_{a-1}$, V$_{b-1}$, V$_{a-2}$ and V$_{b-2}$ are each a V$_H$ domain or a V$_L$ domain, and wherein one of V$_{a-1}$ and V$_{b-1}$ is a VH and the other is a VL such that V$_{a-1}$ and V$_{b-1}$ form a first antigen binding domain (ABD), wherein one of V$_{a-2}$ and V$_{b-2}$ is a VH and the other is a VL such that V$_{a-2}$ and V$_{b-2}$ form a second antigen binding domain (e.g. an scFv wherein V$_{a-2}$ and V$_{b-2}$ are separated by a linker), wherein one of the ABD binds NKp46 and the other binds an antigen of interest. Optionally, CH3 domains comprise amino acid substitutions, wherein the CH3 domain interface of the antibody Fc region is mutated to create altered charge polarity across the Fc dimer interface such that co-expression of electrostatically matched Fc chains support favorable attractive Interactions thereby promoting desired Fc heterodimer formation, whereas unfavorable repulsive charge interactions suppress unwanted Fc homodimer formation.

In other aspects, heterodimeric or heterotrimeric polypeptides with two ABDs separated by an interposed Fc domain can be produced in which one or two chains each associate with a central chain by CH1-CK heterodimerization. Such multimers may be composed of a central (first) polypeptide chain comprising two immunoglobulin variable domains that are part of separate antigen binding domains of different antigen specificities, with an Fc domain interposed between the two immunoglobulin variable domains on the polypeptide chain, and a CH1 or CK constant domain placed on the polypeptide chain adjacent to a variable domain.

The first (central) polypeptide chain will provide one variable domain that will, together with a complementary variable domain on a second polypeptide chain, form an antigen binding domain specific for one (e.g. a first) antigen of interest. The first (central) polypeptide chain will also provide a second variable domain (placed on the opposite end of the interposed Fc domain) that will be paired with a complementary variable domain to form an antigen binding domain specific for another (e.g. a second) antigen of Interest; the variable domain that is complementary to the second variable domain can be placed on the central polypeptide (e.g. adjacent to the second variable domain in a tandem variable domain construct such as an scFv), or can be placed on a separate polypeptide chain, notably a third polypeptide chain. The second (and third, if present) polypeptide chains will associate with the central polypeptide chain by CH1-CK heterodimerization, forming interchain disulfide bonds between respective hinge domains and between complementary CH1 and CK domains, with a primary multimeric polypeptide being formed so long as CH/CK and VH/VK domains are chosen to give rise to a preferred dimerization configuration that results preferentially in the desired VH-VL pairings. Remaining unwanted pairings can remain minimal during production and removed during purification steps. In a trimer, or when polypeptides are constructed for preparation of a trimer, there will generally be one polypeptide chain that comprises a non-naturally occurring VH-CK or VK-CH1 domain arrangement.

Examples of the domain arrangements (N- to C-terminal) of central polypeptide chains for use in such heterodimeric proteins include:

V$_{a-1}$-(CH1 or CK)$_a$-Fc domain-V$_{a-2}$-V$_{b-2}$;

and

V$_{a-2}$-V$_{b-2}$-Fc domain-V$_{a-1}$-(CH1 or CK)$_a$ wherein V$_{a-1}$ is a light chain or heavy chain variable domain, and wherein one of V$_{a-2}$ and V$_{b-2}$ is a light chain variable domain and the other is a heavy chain variable domain.

Further examples include:

V$_{a-1}$-(CH1 or CK)$_a$-Fc domain-V$_b$;

and

V$_b$-Fc domain-V$_{a-1}$-(CH1 or CK)$_a$ wherein V$_b$ is a single variable domain (e.g. dAb, VhH).

The Fc domain of the central chain may be a full Fc domain (CH2-CH3) or a portion thereof sufficient to confer the desired functionality (e.g. FcRn binding). A second polypeptide chain will then be configured which will comprise an immunoglobulin variable domain and a CH1 or CK constant region, e.g., a (CH1 or CK)$_b$ unit, selected so as to permit CH1-CK heterodimerization with the central polypeptide chain; the immunoglobulin variable domain will be selected so as to complement the variable domain of the central chain that is adjacent to the CH1 or CK domain, whereby the complementary variable domains form an antigen binding domain for a first antigen of Interest.

For example, a second polypeptide chain can comprise a domain arrangement:

V$_{b-1}$-(CH1 or CK)$_b$, or

V$_{b-1}$-(CH1 or CK)$_b$-Fc domain such that the (CH1 or CK)$_2$ dimerizes with the (CH1 or CK)$_1$ on the central chain, and the V$_{b-1}$ forms an antigen binding domain together with V$_{a-1}$ of the central chain. If V$_{a-1}$ of the central chain is a light chain variable domain, V$_{b-1}$ will be a heavy chain variable domain; and if V$_{a-1}$ of the central chain is a heavy chain variable domain, V$_{b-1}$ will be a light chain variable domain.

The antigen binding domain for the second antigen of interest can then be formed from V$_{a-2}$ and V$_{b-2}$ which are configured as tandem variable domains on the central chain forming the antigen binding domain for the second antigen of interest (e.g. a heavy chain variable domain (VH) and a light chain (kappa) variable domain (VK), for example forming an scFv unit). The antigen binding domain for the second antigen of interest can also alternatively be formed from a single variable domain V$_b$ present on the central chain.

The resulting heterodimer can for example have the configuration as follows (see also Examples of such proteins shown as formats 2, 11 and 12 shown in FIGS. 6A and 6C):

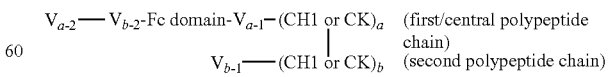

V$_{a-2}$—V$_{b-2}$-Fc domain-V$_{a-1}$-(CH1 or CK)$_a$ (first/central polypeptide chain)

V$_{b-1}$—(CH1 or CK)$_b$ (second polypeptide chain)

wherein one of V$_{a-1}$ of the first polypeptide chain and V$_{b-1}$ of the second polypeptide chain is a light chain variable domain and the other is a heavy chain variable domain, and wherein one of V$_{a-2}$ and V$_{b-2}$ is a light chain variable domain and the other is a heavy chain variable domain.

The resulting heterodimer can in another example have the configuration as follows (see also Examples of such proteins shown as format 10 shown in FIG. 6B):

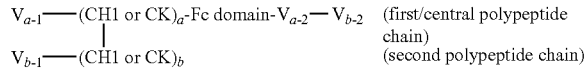

$V_{a\text{-}1}$——(CH1 or CK)$_a$-Fc domain-$V_{a\text{-}2}$—$V_{b\text{-}2}$ (first/central polypeptide chain)
$V_{b\text{-}1}$——(CH1 or CK)$_b$ (second polypeptide chain)

wherein one of $V_{a\text{-}1}$ of the first polypeptide chain and $V_{a\text{-}1}$ of the second polypeptide chain is a light chain variable domain and the other is a heavy chain variable domain, and wherein one of $V_{a\text{-}2}$ and $V_{b\text{-}2}$ is a light chain variable domain and the other is a heavy chain variable domain.

The resulting heterodimer can in another example have the configuration as follows (see also Examples of such proteins shown as formats 13 and 14 shown in FIGS. 6D and 6E):

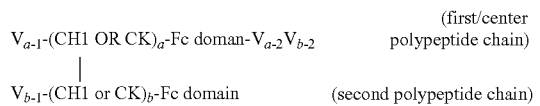

$V_{a\text{-}1}$-(CH1 OR CK)$_a$-Fc doman-$V_{a\text{-}2}V_{b\text{-}2}$ (first/center polypeptide chain)
$V_{b\text{-}1}$-(CH1 or CK)$_b$-Fc domain (second polypeptide chain)

wherein one of $V_{a\text{-}1}$ of the first polypeptide chain and $V_{b\text{-}1}$ of the second polypeptide chain is a light chain variable domain and the other is a heavy chain variable domain, and wherein one of $V_{a\text{-}2}$ and $V_{b\text{-}2}$ is a light chain variable domain and the other is a heavy chain variable domain.

In one embodiment, the heterodimeric bispecific Fc-derived polypeptide comprises a domain arrangement of one of the following, optionally wherein one or both hinge domains are replaced by a peptide linker, optionally wherein the Fc domain is fused to anti-NKp46 scFv via a peptide linker):

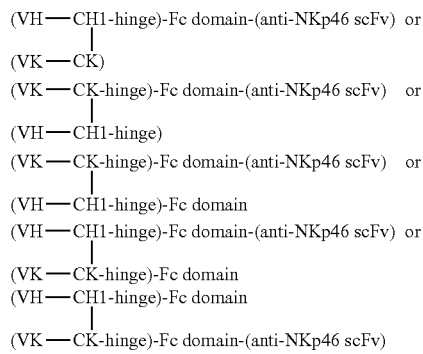

(VH—CH1-hinge)-Fc domain-(anti-NKp46 scFv) or
(VK—CK)
(VK—CK-hinge)-Fc domain-(anti-NKp46 scFv) or
(VH—CH1-hinge)
(VK—CK-hinge)-Fc domain-(anti-NKp46 scFv) or
(VH—CH1-hinge)-Fc domain
(VH—CH1-hinge)-Fc domain-(anti-NKp46 scFv) or
(VK—CK-hinge)-Fc domain
(VH—CH1-hinge)-Fc domain
(VK—CK-hinge)-Fc domain-(anti-NKp46 scFv)

Examples of domain arrangement for the heterodimeric polypeptide formed include but are not limited to those in the table below:

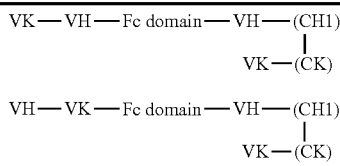

VK—VH—Fc domain—VH—(CH1)
           |
           VK—(CK)

VH—VK—Fc domain—VH—(CH1)
           |
           VK—(CK)

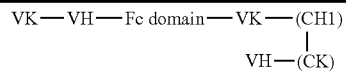
VK—VH—Fc domain—VK—(CH1)
           |
           VH—(CK)

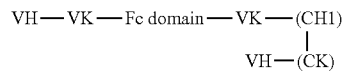
VH—VK—Fc domain—VK—(CH1)
           |
           VH—(CK)

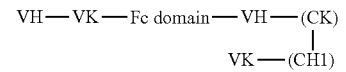
VH—VK—Fc domain—VH—(CK)
           |
           VK—(CH1)

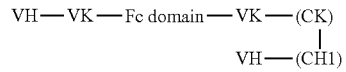
VH—VK—Fc domain—VK—(CK)
           |
           VH—(CH1)

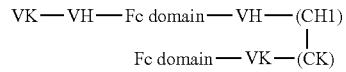
VK—VH—Fc domain—VH—(CH1)
           |
           Fc domain—VK—(CK)

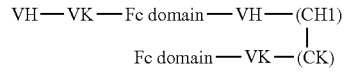
VH—VK—Fc domain—VH—(CH1)
           |
           Fc domain—VK—(CK)

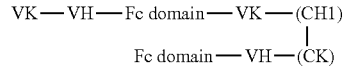
VK—VH—Fc domain—VK—(CH1)
           |
           Fc domain—VH—(CK)

VH—VK—Fc domain—VK—(CH1)
           |
           Fc domain—VH—(CK)

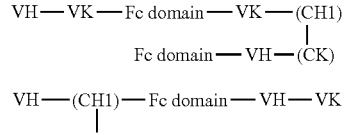
VH—(CH1)—Fc domain—VH—VK
   |
VK—(CK)—Fc domain

VH—(CH1)—Fc domain—VK—VH
   |
VK—(CK)—Fc domain

VK—(CH1)—Fc domain—VH—VK
   |
VH—(CK)—Fc domain

VK—(CH1)—Fc domain—VK—VH
   |
VH—(CK)—Fc domain

Heterotrimeric proteins can for example be formed by using a central (first) polypeptide chain comprising a first variable domain (V) fused to a first CH1 or CK constant region, a second variable domain (V) fused to a second CH1 or CK constant region, and an Fc domain or portion thereof interposed between the first and second variable domains (i.e. the Fc domain is interposed between the first and second (V-(CH 1/CK) units. For example, a central polypeptide chain for use in a heterotrimeric protein can have the domain arrangements (N- to C-terminal) as follows:

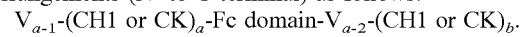
$V_{a\text{-}1}$-(CH1 or CK)$_a$-Fc domain-$V_{a\text{-}2}$-(CH1 or CK)$_b$.

A second polypeptide chain can then comprise a domain arrangement (N- to C-terminal):
$V_{b\text{-}1}$-(CH1 or CK)$_c$,
or
$V_{b\text{-}1}$-(CH1 or CK)$_c$-Fc domain
such that the (CH1 or CK)$_c$ dimerizes with the (CH1 or CK)$_1$ on the central chain, and the $V_{a\text{-}1}$ and $V_{b\text{-}1}$ form an antigen binding domain.

A third polypeptide chain can then comprise a domain arrangement (N- to C-terminal):
$V_{b\text{-}2}$-(CH1 or CK)$_d$,
such that the (CH1 or CK)$_d$ dimerizes with the (CH1 or CK)$_b$ unit on the central chain, and the $V_{a\text{-}2}$ and $V_{b\text{-}2}$ form an antigen binding domain.

An example of a configuration of a resulting heterotrimer with a dimeric Fc domain (also shown as formats 5, 6, 7 and 16 in FIGS. 6D and 6E) has a domain arrangement:

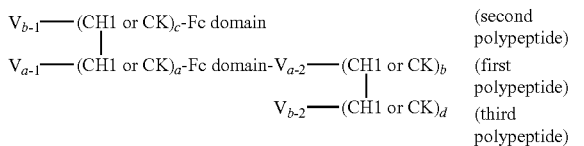

(second polypeptide) / (first polypeptide) / (third polypeptide)

An example of a configuration of a resulting heterotrimer with a monomeric Fc domain (also shown as formats 8, 9 and 17 in FIGS. 6B and 6C) has a domain arrangement:

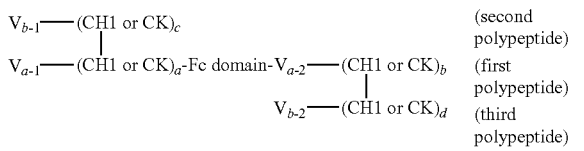

(second polypeptide) / (first polypeptide) / (third polypeptide)

Thus, in a configuration of a trimer polypeptide, the first polypeptide can have two variable domains that each form an antigen binding domain with a variable domain on a separate polypeptide chain (i.e. the variable domain of the second and third chains), the second polypeptide chain has one variable domain, and the third polypeptide has one variable domain.

A trimeric polypeptide may comprise:
(a) a first polypeptide chain comprising a first variable domain (V) fused to a first CH1 of CK constant region, a second variable domain (V) fused to a second CH1 of CK constant region, and an Fc domain or portion thereof interposed between the first and second variable domains;
(b) a second polypeptide chain comprising a variable domain fused at its C-terminus to a CH1 or CK constant region selected to be complementary to the first CH1 or CK constant region of the first polypeptide chain such that the first and second polypeptides form a CH1-CK heterodimer, and optionally an Fc domain; and
(c) a third polypeptide chain comprising a variable domain fused (e.g. at its C-terminus) to a CH1 or CK constant region, wherein the variable domain and the constant region are selected to be complementary to the second variable domain and second CH1 or CK constant region of the first polypeptide chain such that the first and third polypeptides form a CH1-CK heterodimer bound by disulfide bond(s) formed between the CH1 or CK constant region of the third polypeptide and the second CH1 or CK constant region of the first polypeptide, but not between the CH1 or CK constant region of the third polypeptide and the first CH1 or CK constant region of the first polypeptide wherein the first, second and third polypeptides form a CH1-CK heterotrimer, and wherein the first variable domain of the first polypeptide chain and the variable domain of the second polypeptide chain form an antigen binding domain specific for a first antigen of interest, and the second variable domain of the first polypeptide chain and the variable domain on the third polypeptide chain form an antigen binding domain specific for a second antigen of interest.

Examples of domain arrangement for the trimeric bispecific polypeptide formed from include but are not limited to:

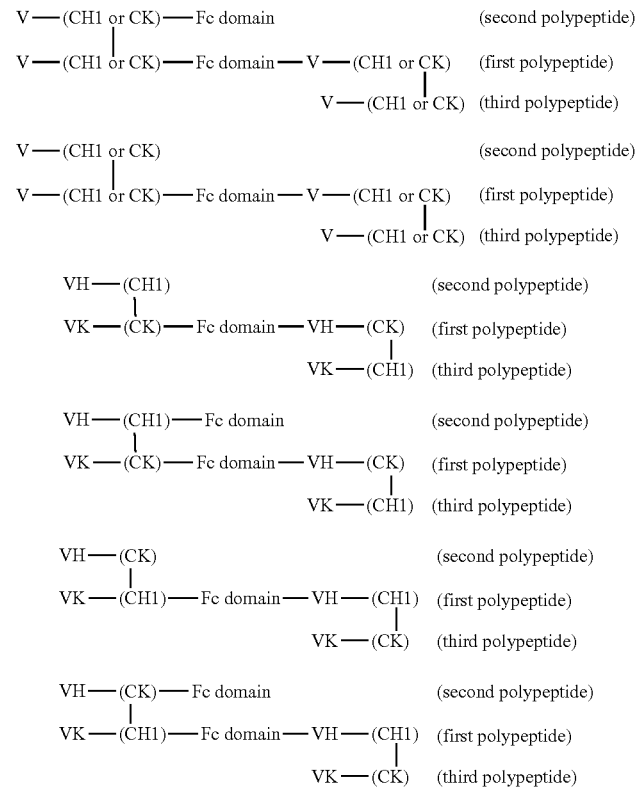

In any of the domain arrangements, the Fc domain may comprise a CH2-CH3 unit (a full length CH2 and CH3 domain or a fragment thereof). In heterodimers or heterotrimers comprising two chains with Fc domains (a dimeric Fc domain), the CH3 domain will be capable of CH3-CH3 dimerization (e.g. a wild-type CH3 domain). In heterodimers or heterotrimers comprising only one chain with an Fc domain (monomeric Fc domain), the Fc domain will be incapable of CH3-CH3 dimerization; for example the CH3 domain(s) will have amino acid modification(s) in the CH3 dimer interface or the Fc domain will comprise a tandem CH3 domain incapable of CH3-CH3 dimerization. In one embodiment of any aspect herein, a first CH3 domain is connected to a second CH3 domain by a linker. The tandem CH3 domain may have the domain arrangement, from N-terminus to C-terminus, as follows:

—CH3-linker-CH3-.

The linker in the tandem CH3 domain will be a flexible linker (e.g. peptide linker). In one embodiment the linker permits the CH3 domains to associate with one another by non-covalent interactions. In one embodiment, the linker is a peptide linker having 10-50 amino acid residues. In one embodiment, the linker has the formula $(G_4S)_x$. Optionally, x is 2, 3, 4, 5 or 6. In any of the embodiments, each CH3 domain is independently a full-length and/or native CH3 domain, or a fragment or modified CH3 domain which retains a functional CH3 dimerization interface.

In some exemplary configurations, the multispecific protein can be tetramers, e.g. tetramers with two heavy chains and two light chains. In some embodiments, a "Fab-exchange" approach is used in which heavy chains and attached light chains of different antibodies are swapped between two IgG4 or IgG4-like antibodies, see, e.g. WO2008/119353 and WO2011/131746, the disclosures of which are incorporated herein by reference. In some embodiments, a "knob-into-holes" approach is used in which the CH3 domain interface of the antibody Fc region is mutated so that antibodies preferentially form heterodimers (further Including the attached light chains). These mutations create altered charge polarity across the Fc dimer interface such that co-expression of electrostatically matched Fc chains support favorable attractive interactions thereby promoting desired Fc heterodimer formation, whereas unfavorable repulsive charge Interactions suppress unwanted Fc homodimer formation. See, e.g. WO2009/089004, the disclosure of which is incorporated herein by reference. When such hetero-multimeric antibodies have Fc regions derived from a human IgG4 Fc region, the antibodies will retain substantial FcRn binding but have reduced Fcγ receptor binding. In one embodiment, the antibody lacks N-linked glycosylation at residue N297 (Kabat EU numbering)

In some embodiments, one of the ABDs is linked to (e.g. comprises a variable region linked to) a CH1 domain and the other of the ABDs is linked to (e.g. comprises a variable region linked to) a complementary CK, (or CA) constant domain, wherein the CH1 and CK (or CA) constant domains associate to form a heterodimer molecule. For example, a first and second ABD can advantageously be single variable domains (e.g. VhH domains) having different antigen binding specificities (e.g., $VhH_1$ and $VhH_2$). $VhH_1$ can be fused to a CH1 domain and $VhH_2$ can be fused to a Cκ or Cλ domain. The $V_1$-Cκ (or Cλ) chain associates with a $V_2$-CH1 chain such that a Fab is formed. See, e.g., WO2006/064504 and WO2012/089814 for examples of such antibodies without Fc domains, the disclosures of which are Incorporated herein by reference. The CH1 and/or CK domains can then be linked to a CH2 domain, optionally via a hinge region (or a linker peptide, e.g., that has similar functional properties). The CH2 domain(s) is/are then linked to a CH3 domain. The CH2-CH3 domains can thus optionally be embodied as a full-length Fc domain.

In some embodiments the protein is a tetrameric antibody comprising two light chain and heavy chain pairs from different parental antibodies, comprising a modified CH3 domain interface so that antibodies preferentially form heterodimers, optionally further wherein the Fc domain is a human IgG4 Fc domain or a portion thereof, optionally comprising one or more amino acid modifications In one embodiment, tetrameric proteins are based two Fc containing chains (e.g. chains 1 and 2) to create a dimer via CH3-CH3 dimerization and/or hinge dimerization, and two further chains (e.g. chains 3 and 4) each comprising a V-CH/CK unit that dimerizes with one of the two Fc-containing chains. For example such an exemplary tetramer molecules can have a domain arrangement:

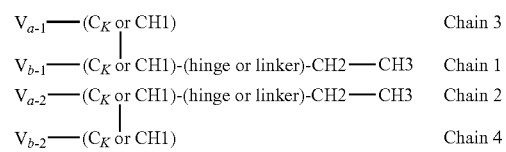

wherein $V_{a-1}$, $V_{b-1}$, $V_{a-2}$ and $V_{b-2}$ are each a $V_H$ domain or a $V_L$ domain, and wherein one of $V_{a-1}$ and $V_{b-1}$ is a VH and the other is a VL such that $V_{a-1}$ and $V_{b-1}$ form a first antigen binding domain (ABD), wherein one of $V_{a-2}$ and $V_{b-2}$ is a VH and the other is a VL such that $V_{a-2}$ and $V_{b-2}$ form a second antigen binding domain. The CH1 and CK are selected such that chain 3 is capable of associating with chain 1 and chain 4 with chain 2.

For example such an exemplary tetramer molecules can have a domain arrangement:

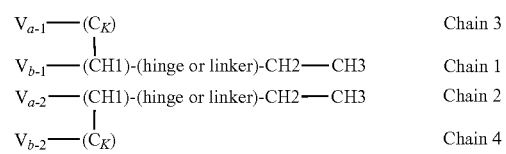

wherein $V_{a-1}$, $V_{b-1}$, $V_{a-2}$ and $V_{b-2}$ are each a $V_H$ domain or a $V_L$ domain, and wherein one of $V_{a-1}$ and $V_{b-1}$ is a VH and the other is a VL such that $V_{a-1}$ and $V_{b-1}$ form a first antigen binding domain (ABD), wherein one of $V_{a-2}$ and $V_{b-2}$ is a VH and the other is a VL such that $V_{a-2}$ and $V_{b-2}$ form a second antigen binding domain. The CH1 and CK are selected such that chain 3 is capable of associating with chain 1 and chain 4 with chain 2.

In any protein of the disclosure, a hinge region will typically be present on a polypeptide chain between a CH1 domain and a CH2 domain, and/or can be present between a CK domain and a CH2 domain. A hinge region can optionally be replaced for example by a suitable linker peptide.

The proteins domains described in the present disclosure can optionally be specified as being from N- to C-terminal. Protein arrangements of the disclosure for purposes of illustration are shown from N-terminus (on the left) to C-terminus. Domains can be referred to as fused to one another (e.g. a domain can be said to be fused to the C-terminus of the domain on its left, and/or a domain can be said to be fused to the N-terminus of the domain on its right).

The proteins domains described in the present disclosure can be fused to one another directly or via intervening amino acid sequences. For example, a CH1 or CK domain will be fused to an Fc domain (or CH2 or CH3 domain thereof) via a linker peptide, optionally a hinge region or a fragment thereof. In another example, a VH or VK domain will be fused to a CH3 domain via a linker peptide. VH and VL domains linked to another in tandem will be fused via a linker peptide (e.g. as an scFv). VH and VL domains linked to an Fc domain will be fused via a linker peptide. Two polypeptide chains will be bound to one another (indicated by "|"), preferably by interchain disulfide bonds formed between cysteine residues within complementary CH1 and CK domains.

Linkers for Variable Domains

In one embodiment, a peptide linker for use in linking an ABD (e.g. an scFv, a VH or VL domain) to a CH2 or CH3 comprises a fragment of a CH1 domain. For example, a N-terminal amino acid sequence of CH1 can be fused to an ABD (e.g. an scFv, a VH or VL domain, etc.) in order to mimic as closely as possible the natural structure of an antibody. In one embodiment, the linker may comprise a N-terminal CH1 amino acid sequence of between 2-4 residues, between 2-4 residues, between 2-6 residues, between 2-8 residues, between 2-10 residues, between 2-12 residues, between 2-14 residues, between 2-16 residues, between 2-18 residues, between 2-20 residues, between 2-22 residues, between 2-24 residues, between 2-26 residues, between 2-28 residues, or between 2-30 residues. In one embodiment linker comprises or consists of the amino acid sequence RTVA.

When an ABD is an scFv, the VH domain and VL domains (VL or VH domains or fragments thereof that retain binding specificity) that form a scFv are linked together by a linker of sufficient length to enable the ABD to fold in such a way as to permit binding to the antigen for which the ABD is intended to bind. Examples of linkers include, for example, linkers comprising glycine and serine residues, e.g., the amino acid sequence GEGTSTGS(G$_2$S)$_2$GGAD SEQ ID NO. 188. In another specific embodiment, the VH domain and VL domains of an svFv are linked together by the amino acid sequence (G$_4$S)$_3$ SEQ ID NO. 189.

Any of the peptide linkers may comprise a length of at least 5 residues, at least 10 residues, at least 15 residues, at least 20 residues, at least 25 residues, at least 30 residues or more. In other embodiments, the linkers comprises a length of between 2-4 residues, between 2-4 residues, between 2-6 residues, between 2-8 residues, between 2-10 residues, between 2-12 residues, between 2-14 residues, between 2-16 residues, between 2-18 residues, between 2-20 residues, between 2-22 residues, between 2-24 residues, between 2-26 residues, between 2-28 residues, or between 2-30 residues.

In one embodiment, the hinge region will be a fragment of a hinge region (e.g. a truncated hinge region without cysteine residues) or may comprise one or amino acid modifications to remove (e.g. substitute by another amino acid, or delete) a cysteine residue, optionally both cysteine residues in a hinge region. Removing cysteines can be useful to prevent formation of disulfide bridges in a monomeric polypeptide.

Constant Regions

Constant region domains can be derived from any suitable antibody. Of particular interest are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat. By "hinge" or "hinge region" or "antibody hinge region" is meant the flexible polypeptide comprising the amino acids between the first and second constant domains of an antibody. Structurally, the IgG CH1 domain ends at EU position 220, and the IgG CH2 domain begins at residue EU position 237. Thus for IgG the hinge is herein defined to include positions 221 (D221 in IgG1) to 236 (G236 in IgG1), wherein the numbering is according to the EU index as in Kabat. References to amino acid residue within constant region domains found within the polypeptides shall be, unless otherwise Indicated or as otherwise dictated by context, with reference to Kabat, in the context of an IgG antibody.

CH3 domains that can serve in the present antibodies can be derived from any suitable antibody. Such CH3 domains can serve as the basis for a modified CH3 domain. Optionally the CH3 domain is of human origin.

In certain embodiments herein (e.g. for monomeric, dimeric or trimeric bispecific antibodies with monomeric Fc domains), a CH3 domain may comprise one or more amino acid modifications (e.g. amino acid substitutions) to disrupt the CH3 dimerization interface. Optionally the CH3 domain modifications will prevent protein aggregation caused by the exposure of hydrophobic residues when the CH2-CH3 domains are in monomeric form. Optionally, the CH3 domain modifications will additionally not abolish the ability of the Fc-derived polypeptide to bind to neonatal Fc receptor (FcRn), e.g. human FcRn.

CH3 domains that can be used to prevent homodimer formation have been described in various publications. See, e.g. US 2006/0074225, WO2006/031994, WO2011/063348 and Ying et al. (2012) J. Biol. Chem. 287(23):19399-19407, the disclosures of each of which are Incorporated herein by reference. In order to discourage homodimer formation, one or more residues that make up the CH3-CH3 interface are replaced with a charged amino acid such that the interaction becomes electrostatically unfavorable. For example, WO2011/063348 provides that a positive-charged amino acid in the interface, such as lysine, arginine, or histidine, is replaced with a different (e.g. negative-charged amino acid, such as aspartic acid or glutamic acid), and/or a negative-charged amino acid in the interface is replaced with a different (e.g. positive charged) amino acid. Using human IgG as an example, charged residues within the interface that may be changed to the opposing charge include R355, D356, E357, K370, K392, D399, K409, and K439. In certain embodiments, two or more charged residues within the interface are changed to an opposite charge. Exemplary molecules include those comprising K392D and K409D mutations and those comprising D399K and D356K mutations. In order to maintain stability of the polypeptide in monomeric form, one or more large hydrophobic residues that make up the CH3-CH3 interface are replaced with a small polar amino acid. Using human IgG as an example, large hydrophobic residues of the CH3-CH3 interface include Y349, L351, L368, L398, V397, F405, and Y407. Small polar amino acid residues include asparagine, cysteine, glutamine, serine, and threonine. Thus in one embodiment, a CH3 domain will comprise an amino acid modification (e.g. substitution) at 1, 2, 3, 4, 5, 6, 7 or 8 of the positions R355, D356, E357, K370, K392, D399, K409, and K439. In WO2011/063348, two of the positively charged Lys residues that are closely located at the CH3 domain interface were mutated to Asp. Threonine scanning mutagenesis was then carried out on the structurally conserved large hydrophobic residues in the background of these two Lys to Asp mutations. Fc molecules comprising K392D and K409D mutations along with the various substitutions with threonine were analyzed for monomer formation. Exemplary monomeric Fc molecules include those having K392D, K409D and Y349T substitutions and those having K392D, K409D and F405T substitutions.

In Ying et al. (2012) J. Biol. Chem. 287(23):19399-19407, amino acid substitutions were made within the CH3 domain at residues L351, T366, L368, P395, F405, T407 and K409. Combinations of different mutations resulted in the disruption of the CH3 dimerization interface, without causing protein aggregation. Thus in one embodiment, a CH3 domain will comprise an amino acid modification (e.g. substitution) at 1, 2, 3, 4, 5, 6 or 7 of the positions L351, T366, L368, P395, F405, T407 and/or K409. In one embodiment, a CH3 domain will comprise amino acid modifications L351Y, T366Y, L368A, P395R, F405R, T407M and K409A. In one embodiment, a CH3 domain will comprise amino acid modifications L351S, T366R, L368H, P395K, F405E, T407K and K409A. In one embodiment, a CH3 domain will comprise amino acid modifications L351K, T366S, P395V, F405R, T407A and K409Y.

In one embodiment a CH2-CH3 portion comprising a CH3 domain modified to prevent homodimer formation comprises an amino acid sequence of SEQ ID NO: 2, or a sequence at least 90, 95% or 98% identical thereto: APELLGGPSVFLFPPKPKDTLMISRTPE-VTCVVVDVSHEDPEVKFNWYVDGVEVHNAKTKP REEQYN-STYRVVSVLTVLHQDWLNGKEYKCKVSNKALPA-PIEKTISKAKGQPREPQVYTLP PSREEMTKNQVSLT-CLVKGFYPSDIAVEWESNGQPENNYKTTPPVLDSDG-SFFLTSKLTVD KSRWQQGNVFSCSVMHEALHN-HYTQKSLSLSPG (SEQ ID NO: 2), optionally comprising a substitution at 1, 2, 3, 4, 5, 6 of residues 121, 136, 165, 175, 177 or 179 of SEQ ID NO: 2.

In certain embodiments herein for monomeric, dimeric or trimeric bispecific antibodies with monomeric Fc domains, an Fc domain comprises a tandem CH3 domain. A tandem CH3 domain comprises a first CH3 domain is connected to a second CH3 domain by a linker. The tandem CH3 domains can thus be placed on a polypeptide chain so as to have the domain arrangement, from N-terminus to C-terminus, as follows:

—CH3-linker-CH3-.

The linker will be a flexible linker (e.g. peptide linker). In one embodiment the linker permits the CH3 domains to associate with one another by non-covalent interactions. In one embodiment, the linker is a peptide linker having 10-50 amino acid residues. In one embodiment, the linker has the formula $(G_4S)_x$. Optionally, x is 2, 3, 4, 5 or 6. In any of the embodiments, each CH3 domain is independently a full-length and/or native CH3 domain, or a fragment or modified CH3 domain which retains a functional CH3 dimerization Interface.

An exemplary tandem CH3 with a flexible peptide linker (underlined) is shown below. An exemplary tandem CH3 domain can thus comprise an amino acid sequence of SEQ ID NO: 112, or a sequence at least 70%, 80%, 90%, 95% or 98% Identical thereto:

(SEQ ID NO: 112)
G Q P R E P Q V Y T L P P S R E E M T K N Q V S L T

C L V K G F Y P S D I A V E W E S N G Q P E N N Y K

T T P P V L D S D G S F F L Y S K L T V D K S R W Q

Q G N V F S C S V M H E A L H N H Y T Q K S L S L S

P G <u>G G G G S G G G G S G G G G S</u> G Q P R E P Q V Y

T L P P S R E E M T K N Q V S L T C L V K G F Y P S

D I A V E W E S N G Q P E N N Y K T T P P V L D S D

G S F F L Y S K L T V D K S R W Q Q G N V F S C S V

M H E A L H N H Y T Q K S L S L S P G

CH2 domains can be readily obtained from any suitable antibody. Optionally the CH2 domain is of human origin. A CH2 may or may not be linked (e.g. at its N-terminus) to a hinge of linker amino acid sequence. In one embodiment, a CH2 domain is a naturally occurring human CH2 domain of IgG1, 2, 4 or 4 subclass. In one embodiment, a CH2 domain is a fragment of a CH2 domain (e.g. at least 10, 20, 30, 40 or 50 amino acids).

In one embodiment, a CH2 domain, when present in a polypeptide described herein, will retain binding to a neonatal Fc receptor (FcRn), particularly human FcRn.

In one embodiment, a CH2 domain, when present in a polypeptide described herein, and the polypeptides described herein, will confer decreased or lack of binding to a Fcγ receptor, notably FcγRIIIA (CD16).

In one embodiment, the polypeptides described herein and their Fc domain(s) and/or a CH2 domain thereof, will have decreased or will substantially lack antibody dependent cytotoxicity (ADCC), complement dependent cytotoxicity (CDC), antibody dependent cellular phagocytosis (ADCP), FcR-mediated cellular activation (e.g. cytokine release through FcR cross-linking), and/or FcR-mediated platelet activation/depletion, as mediated by NKp46-negative immune cells.

In one embodiment, a CH2 domain in a polypeptide will have substantial loss of binding to activating Fcγ receptors, e.g., FcγRIIIA (CD16), FcγRIIA (CD32A) or CD64, or to an inhibitory Fc receptor, e.g., FcγRIIB (CD32B). In one embodiment, a CH2 domain in a polypeptide will furthermore have substantial loss of binding to the first component of complement (C1q).

The exemplary multispecific proteins described herein make use of wild-type CH2 domains in monomeric Fc domains, or with CH2 mutations in dimeric Fc domain proteins at reside N297 (Kabat numbering). However the person of skill in the art will appreciate that other configurations can be implemented. For example, substitutions into human IgG1 of IgG2 residues at positions 233-236 and IgG4 residues at positions 327, 330 and 331 were shown to greatly reduce binding to Fcγ receptors and thus ADCC and CDC. Furthermore, Idusogie et al. (2000) J Immunol. 164(8): 4178-84 demonstrated that alanine substitution at different positions, including K322, significantly reduced complement activation.

In one embodiment, a CH2 domain that retains binding to a FcRn receptor but has reduction of binding to Fcγ receptors will lack or have modified N-linked glycosylation, e.g. at residue N297 (Kabat EU). For example the polypeptide is expressed in a cell line which naturally has a high enzyme activity for adding fucosyl to the N-acetylglucosamine that binds to the Fc region of the polypeptides, or which does not yield glycosylation at N297 (e.g. bacterial host cells). In another embodiment, a polypeptide may have one or more substitution that result in lack of the canonical Asn-X-Ser/Thr N-linked glycosylation motif at residues 297-299, which can also thus also result in reduction of binding to Fcγ receptors. Thus, a CH2 domain may have a substitution at N297 and/or at neighboring residues (e.g. 298, 299).

In one embodiment, an Fc domain or a CH2 domain therefrom is derived from an IgG1, IgG3, IgG4 or IgG2 Fc mutant exhibiting diminished FcγR binding capacity but having conserved FcRn binding. In one aspect, the IgG2 Fc mutant or the derived multispecific polypeptide, Fc domain or CH2 domain comprises the mutations V234A, G237A, P238S according to the EU numbering system. In another aspect, the IgG2 Fc mutant or the derived multispecific polypeptide or Fc domain comprises mutations V234A, G237A, H268Q or H268A, V309L, A330S, P331S according to the EU numbering system. In a particular aspect, the IgG2 Fc mutant or the derived multispecific polypeptide or Fc domain comprises mutations V234A, G237A, P238S, H268A, V309L, A330S, P331S, and, optionally, P233S according to the EU numbering system. Optionally, a CH2 domain with loss of binding to Fcγ receptors may comprises residues 233, 234, 235, 237, and 238 (EU numbering system) that comprise a n amino acid sequence selected from PAAAP SEQ ID NO. 192, PAAAS SEQ ID NO. 193, and SAAAS SEQ ID NO. 194; optionally an Fc domain having such mutations can further comprise mutations H268A or H268Q, V309L, A330S and P331S (see WO2011/066501, the disclosure of which is incorporated herein by reference).

In one embodiment, a CH2 domain that loses binding to a Fcγ receptor will comprise at least one amino acid modification (for example, possessing 1, 2, 3, 4, 5, 6, 7, 8, 9, or more amino acid modifications) in the CH2 domain of the Fc region, optionally further in combination with one or more amino acid modification in other domains (e.g. in a hinge domain or a CH3 domain). Any combination of Fc modifications can be made, for example any combination of different modifications disclosed in Armour KL. et al., (1999) Eur J Immunol. 29(8):2613-24; Presta, L. G. et al. (2002) Biochem. Soc. Trans. 30(4):487-490; Shields, R. L. et al. (2002) J. Biol. Chem. 26; 277(30):26733-26740 and Shields, R. L. et al. (2001) J. Biol. Chem. 276(9):6591-6604). In one embodiment, a polypeptide of the invention that has decreased binding to a human Fcγ receptor will comprise at least one amino acid modification (for example, possessing 1, 2, 3, 4, 5, 6, 7, 8, 9, or more amino acid modifications) relative to a wild-type CH2 domain within amino acid residues 237-340 (EU numbering), such that the polypeptide comprising such CH2 domain has decreased affinity for a human Fcγ receptor of interest relative to an equivalent polypeptide comprising a wild-type CH2 domain, optionally wherein the variant CH2 domain comprises a substitution at any one or more of positions 233, 234, 235, 236, 237, 238, 268, 297, 238, 299, 309, 327, 330, 331 (EU numbering).

CDR Sequences and Epitopes

In one embodiment, the proteins and antibodies herein bind the D1 domain of NKp46, the D2 domain of NKp46, or to a region spanning both the D1 and D2 domains (at the border of the D1 and D2 domains, the D1/D2 junction), of the NKp46 polypeptide of SEQ ID NO: 1. In one embodiment, the proteins or antibodies have an affinity for human NKp46 characterized by a $K_D$ of less than $10^{-8}$ M, less than $10^{-9}$ M, or less than $10^{-10}$ M.

In another embodiment, the antibodies bind NKp46 at substantially the same epitope on NKp46 as antibody NKp46-1, NKp46-2, NKp46-3, NKp46-4, NKp46-6 or NKp46-. In another embodiment, the antibodies at least partially overlaps, or includes at least one residue in the segment bound by NKp46-1, NKp46-2, NKp46-3, NKp46-4, NKp46-6 or NKp46. In one embodiment, all key residues of the epitope are in a segment corresponding to domain D1 or D2. In one embodiment, the antibody binds a residue present in the D1 domain as well as a residue present in in the D2 domain. In one embodiment, the antibodies bind an epitope comprising 1, 2, 3, 4, 5, 6, 7 or more residues in the segment corresponding to domain D1 or D2 of the NKp46 polypeptide of SEQ ID NO: 1. In one embodiment, the antibodies bind domain D1 and bind an epitope comprising 1, 2, 3, or 4 of the residues R101, V102, E104 and/or L105.

In one embodiment, the antibodies bind domain D1/D2 junction and bind an epitope comprising 1, 2, 3, 4 or 5 of the residues K41, E42, E119, Y121 and/or Y194.

In one embodiment, the antibodies bind domain D2 and bind an epitope comprising 1, 2, 3, or 4 of the residues P132, E133, I135, and/or S136.

The Examples section herein describes the construction of a series of mutant human NKp46 polypeptides. Binding of anti-NKp46 antibody to cells transfected with the NKp46 mutants was measured and compared to the ability of anti-NKp46 antibody to bind wild-type NKp46 polypeptide (SEQ ID NO:1). A reduction in binding between an anti-NKp46 antibody and a mutant NKp46 polypeptide as used herein means that there is a reduction in binding affinity (e.g., as measured by known methods such FACS testing of cells expressing a particular mutant, or by Biacore testing of binding to mutant polypeptides) and/or a reduction in the total binding capacity of the anti-NKp46 antibody (e.g., as evidenced by a decrease in Bmax in a plot of anti-NKp46 antibody concentration versus polypeptide concentration). A significant reduction in binding indicates that the mutated residue is directly involved in binding to the anti-NKp46 antibody or is in close proximity to the binding protein when the anti-NKp46 antibody is bound to NKp46. An antibody epitope will thus preferably include such residue and may include additional residues adjacent to such residue.

In some embodiments, a significant reduction in binding means that the binding affinity and/or capacity between an anti-NKp46 antibody and a mutant NKp46 polypeptide is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody and a wild type NKp46 polypeptide (e.g., the polypeptide shown in SEQ ID NO:1). In certain embodiments, binding is reduced below detectable limits. In some embodiments, a significant reduction in binding is evidenced when binding of an anti-NKp46 antibody to a mutant NKp46 polypeptide is less than 50% (e.g., less than 45%, 40%, 35%, 30%, 25%, 20%, 15% or 10%) of the binding observed between the anti-NKp46 antibody and a wild-type NKp46 polypeptide (e.g., the polypeptide shown in SEQ ID NO: 1 (or the extracellular domain thereof)). Such binding measurements can be made using a variety of binding assays known in the art. A specific example of one such assay is described in the Example section.

In some embodiments, anti-NKp46 antibodies are provided that exhibit significantly lower binding for a mutant NKp46 polypeptide in which a residue in a wild-type NKp46 polypeptide (e.g., SEQ ID NO:1) is substituted. In the shorthand notation used here, the format is: Wild type residue: Position in polypeptide: Mutant residue, with the numbering of the residues as indicated in SEQ ID NO: 1.

In some embodiments, an anti-NKp46 antibody binds a wild-type NKp46 polypeptide but has decreased binding to a mutant NKp46 polypeptide having a mutation (e.g., an alanine substitution) any one or more of the residues R101, V102, E104 and/or L105 (with reference to SEQ ID NO:1) compared to binding to the wild-type NKp46).

In some embodiments, an anti-NKp46 antibody binds a wild-type NKp46 polypeptide but has decreased binding to a mutant NKp46 polypeptide having a mutation (e.g., an alanine substitution) any one or more of the residues K41, E42, E119, Y121 and/or Y194 (with reference to SEQ ID NO:1) compared to binding to the wild-type NKp46).

In some embodiments, an anti-NKp46 antibody binds a wild-type NKp46 polypeptide but has decreased binding to a mutant NKp46 polypeptide having a mutation (e.g., an alanine substitution) any one or more of the residues P132, E133, I135, and/or S136 (with reference to SEQ ID NO:1) compared to binding to the wild-type NKp46)

The amino acid sequence of the heavy chain variable region of antibodies NKp46-1, NKp46-2, NKp46-3, NKp46-4, NKp46-6 and NKp46-9 are listed herein in Table B (SEQ ID NOS: 3, 5, 7, 9, 11 and 13 respectively), the amino acid sequence of the light chain variable region of antibodies NKp46-1, NKp46-2, NKp46-3, NKp46-4, NKp46-6 and NKp46-9 are also listed herein in Table B (SEQ ID NOS: 4, 6, 8, 10, 12 and 14 respectively).

In a specific embodiment, provided is an antibody, e.g. a full length monospecific antibody, a multispecific or bispecific antibody, including a bispecific monomeric polypeptide, that binds essentially the same epitope or determinant as monoclonal antibody NKp46-1, NKp46-2, NKp46-3, NKp46-4, NKp46-6 or NKp46-9; optionally the antibody comprises a hypervariable region of antibody NKp46-1, NKp46-2, NKp46-3, NKp46-4, NKp46-6 or NKp46-9. In any of the embodiments herein, antibody NKp46-1, NKp46-2, NKp46-3, NKp46-4, NKp46-6 or NKp46-9 can be characterized by its amino acid sequence and/or nucleic acid sequence encoding it. In one embodiment, the antibody comprises the Fab or F(ab')$_2$ portion of NKp46-1, NKp46-2, NKp46-3, NKp46-4, NKp46-6 or NKp46-9. Also provided is an antibody that comprises the heavy chain variable region of NKp46-1, NKp46-2, NKp46-3, NKp46-4, NKp46-6 or NKp46-9. According to one embodiment, an antibody comprises the three CDRs of the heavy chain variable region of NKp46-1, NKp46-2, NKp46-3, NKp46-4, NKp46-6 or NKp46-9. Also provided is a polypeptide that further comprises one, two or three of the CDRs of the light chain variable region of NKp46-1, NKp46-2, NKp46-3, NKp46-4, NKp46-6 or NKp46-9. Optionally any one or more of said light or heavy chain CDRs may contain one, two, three, four or five or more amino acid modifications (e.g. substitutions, insertions or deletions). Optionally, provided is a polypeptide where any of the light and/or heavy chain variable regions comprising part or all of an antigen binding region of antibody NKp46-1, NKp46-2, NKp46-3, NKp46-4, NKp46-6 or NKp46-9 are fused to an immunoglobulin constant region of the human IgG type.

In another aspect, the invention provides a protein, e.g., an antibody, a full length monospecific antibody, a multispecific or a bispecific protein, or a polypeptide chain or fragment thereof, as well as a nucleic acid encoding any of the foregoing, wherein the protein comprises the heavy chain CDRs of NKp46-1, NKp46-2, NKp46-3, NKp46-4, NKp46-6 or NKp46-9, comprising, for the respective antibody: a HCDR1 region comprising an amino acid sequence as set forth in Table A, or a sequence of at least 4, 5, 6, 7, 8, 9 or 10 contiguous amino acids thereof, wherein one or more of these amino acids may be substituted by a different amino acid; a HCDR2 region comprising an amino acid sequence as set forth in Table A, or a sequence of at least 4, 5, 6, 7, 8, 9 or 10 contiguous amino acids thereof, wherein one or more of these amino acids may be substituted by a different amino acid; a HCDR3 region comprising an amino acid sequence as set forth in as set forth in Table A, or a sequence of at least 4, 5, 6, 7, 8, 9 or 10 contiguous amino acids thereof, wherein one or more of these amino acids may be substituted by a different amino acid.

In another aspect, the invention provides a protein, e.g., an antibody, a full length monospecific antibody, a multispecific or a bispecific protein, or a polypeptide chain or fragment thereof, as well as a nucleic acid encoding any of the foregoing, wherein the protein comprises light chain CDRs of NKp46-1, NKp46-2, NKp46-3, NKp46-4, NKp46-6 or NKp46-9, comprising, for the respective antibody: a LCDR1 region comprising an amino acid sequence as set forth in Table A, or a sequence of at least 4, 5, 6, 7, 8, 9 or 10 contiguous amino acids thereof, wherein one or more of these amino acids may be substituted by a different amino acid; a LCDR2 region comprising an amino acid sequence as set forth in Table A, or a sequence of at least 4, 5, 6, 7, 8, 9 or 10 contiguous amino acids thereof, wherein one or more of these amino acids may be substituted by a different amino acid; a LCDR3 region comprising an amino acid sequence as set forth in Table A, or a sequence of at least 4, 5, 6, 7, 8, 9 or 10 contiguous amino acids thereof, wherein one or more of these amino acids may be deleted or substituted by a different amino acid.

In another aspect, the invention provides a protein that binds human NKp46, comprising:

(a) the heavy chain variable region of NKp46-1, NKp46-2, NKp46-3, NKp46-4, NKp46-6 or NKp46-9 as set forth in Table B, optionally wherein one, two, three or more amino acids may be substituted by a different amino acid;

(b) the light chain variable region NKp46-1, NKp46-2, NKp46-3, NKp46-4, NKp46-6 or NKp46-9 as set forth in Table B, optionally wherein one, two, three or more amino acids may be substituted by a different amino acid;

(c) the heavy chain variable region of NKp46-1, NKp46-2, NKp46-3, NKp46-4, NKp46-6 or NKp46-9 as set forth in Table B, optionally wherein one or more of these amino acids may be substituted by a different amino acid; and the respective light chain variable region of NKp46-1, NKp46-2, NKp46-3, NKp46-4, NKp46-6 or NKp46-9 as set forth In Table B, optionally wherein one, two, three or more amino acids may be substituted by a different amino acid;

(d) the heavy chain CDR 1, 2 and 3 (HCDR1, HCDR2) amino acid sequence of NKp46-1, NKp46-2, NKp46-3, NKp46-4, NKp46-6 or NKp46-9 as shown in Table A, optionally wherein one, two, three or more amino acids in a CDR may be substituted by a different amino acid;

(e) the light chain CDR 1, 2 and 3 (LCDR1, LCDR2, LCDR3) amino acid sequence of NKp46-1, NKp46-2, NKp46-3, NKp46-4, NKp46-6 or NKp46-9 as shown in Table A, optionally wherein one, two, three or more amino acids in a CDR may be substituted by a different amino acid; or (f) the heavy chain CDR 1, 2 and 3 (HCDR1, HCDR2, HCDR3) amino acid sequence of NKp46-1, NKp46-2, NKp46-3, NKp46-4, NKp46-6 or NKp46-9 as shown in Table A, optionally wherein one, two, three or more amino acids in a CDR may be substituted by a different amino acid; and the light chain CDRs 1, 2 and 3 (LCDR1, LCDR2, LCDR3) amino acid sequence of the respective NKp46-1, NKp46-2, NKp46-3, NKp46-4, NKp46-6 or NKp46-9 antibody as shown In Table A, optionally wherein one, two, three or more amino acids in a CDR may be substituted by a different amino acid.

In one embodiment, the aforementioned CDRs are according to Kabat, e.g. as shown In Table A. In one embodiment, the aforementioned CDRs are according to Chotia numbering, e.g. as shown in Table A. In one embodiment, the aforementioned CDRs are according to IMGT numbering, e.g. as shown in Table A.

In another aspect of any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO or Table A.

In another aspect, the invention provides an antibody that competes for NKp46 binding with a monoclonal antibody of (a) to (f), above.

In another aspect, the invention provides a bispecific antibody comprising an antibody that binds human NKp46 of (a) to (f), above, or an antibody that competes for binding to NKp46 therewith, fused (optionally via intervening amino acid sequences) to a monomeric Fc domain, optionally further fused (optionally via intervening amino acid sequences) to a second antigen binding domain (e.g. a scFv, a $V_H$ domain, a $V_L$ domain, a dAb, a V-NAR domain or a $V_HH$ domain). Optionally the second antigen binding domain will bind a cancer antigen, a viral antigen or a bacterial antigen.

The sequences of the CDRs, according to IMGT, Kabat and Chothia definitions systems, have been summarized In Table A below. The sequences of the variable chains of the antibodies according to the invention are listed in Table B below. In any embodiment herein, a VL or VH sequence can be specified or numbered so as to contain or lack a signal peptide or any part thereof.

TABLE A

| mAb | CDR definition | HCDR1 SEQ ID | Sequence | HCDR2 SEQ ID | Sequence | HCDR3 SEQ ID | Sequence |
|---|---|---|---|---|---|---|---|
| NKp46-1 | Kabat | 15 | DYVIN | 18 | EIYPGSGTNYYNEKFKA | 21 | RGRYGLYAMDY |
|  | Chotia | 16 | GYTFTDY | 19 | PGSG | 22 | GRYGLYAMD |
|  | IMGT | 17 | GYTFTDYV | 20 | GYTFTDYVIYPGSGTN | 23 | ARRGRYGLYAMDY |
| NKp46-2 | Kabat | 31 | SDYAWN | 34 | YITYSGSTSYNPSLES | 36 | GGYYGSSWGVFAY |
|  | Chotia | 32 | GYSITSDY | | YSG | 37 | GYYGSSWGVFA |
|  | IMGT | 33 | GYSITSDYA | 35 | ITYSGST | 38 | ARGGYYGSSWGVFAY |
| NKp46-3 | Kabat | 46 | EYTMH | 49 | GISPNIGGTSYNQKFKG | 51 | RGGSFDY |
|  | Chotia | 47 | GYTFTEY | | PNIG | 52 | GGSFD |
|  | IMGT | 48 | GYTFTEYT | 50 | ISPNIGGT | 53 | ARRGGSFDY |
| NKp46-4 | Kabat | 60 | SFTMH | 63 | YINPSSGYTEYNQKFKD | 65 | GSSRGFDY |
|  | Chotia | 61 | GYTFTSF | | PSSG | 66 | SSRGFD |
|  | IMGT | 62 | GYTFTSFT | 64 | INPSSGYT | 67 | VRGSSRGFDY |
| NKp46-6 | Kabat | 73 | SSWMH | 76 | HIHPNSGISNYNEKFKG | 78 | GGRFDD |
|  | Chotia | 74 | GYTFTSS | | PNSG | | GRFD |
|  | IMGT | 75 | GYTFTSSW | 77 | IHPNSGIS | 79 | ARGGRFDD |
| NKp46-9 | Kabat | 85 | SDYAWN | 88 | YITYSGSTNYNPSLKS | 89 | CWDYALYAMDC |
|  | Chotia | 86 | GYSITSDY | | YSG | 90 | WDYALYAMD |
|  | IMGT | 87 | GYSITSDYA | 35 | ITYSGST | 91 | ARCWDYALYAMDC |
| Bab281 | Kabat | 97 | NYGMN | 100 | WINTNTGEPTYAEEFKG | 102 | DYLYYFDY |
|  | Chotia | 98 | GYTFTNY | | TNTG | 103 | YLYYFD |
|  | IMGT | 99 | GYTFTNYG | 101 | INTNTGEP | 104 | ARDYLYYFDY |

| mAb | CDR definition | LCDR1 SEQ ID | Sequence | LCDR2 SEQ ID | Sequence | LCDR3 SEQ ID | Sequence |
|---|---|---|---|---|---|---|---|
| NKp46-1 | Kabat | 24 | RASQDISNYLN | 27 | YTSRLHS | 28 | QQGNTRPWT |
|  | Chotia | 25 | SQDISNY | | YTS | 29 | YTSGNTRPW |
|  | IMGT | 26 | QDISNY | | YTS | 30 | YTSQQGNTRPWT |
| NKp46-2 | Kabat | 39 | RVSENIYSYLA | 42 | NAKTLAE | 43 | QHHYGTPWT |
|  | Chotia | 40 | SENIYSY | | NAK | 44 | HYGTPW |
|  | IMGT | 41 | ENIYSY | | NAK | 45 | QHHYGTPWT |
| NKp46-3 | Kabat | 54 | RASQSISDYLH | 57 | YASQSIS | 58 | QNGHSFPLT |
|  | Chotia | 55 | SQSISDY | | YAS | 59 | GHSFPL |
|  | IMGT | 56 | QSISDY | | YAS | | QNGHSFPLT |

TABLE A-continued

| | | | | | | | |
|---|---|---|---|---|---|---|---|
| NKp46-4 | Kabat | 68 | RASENIYSNLA | 70 | AATNLAD | 71 | QHFWGTPRT |
| | Chotia | | SENIYSN | | AAT | 72 | FWGTPR |
| | IMGT | 69 | ENIYSN | | AAT | | QHFWGTPRT |
| NKp46-6 | Kabat | 80 | RASQSISDYLH | | YASQSIS | 82 | QNGHSFLMYT |
| | Chotia | 81 | GRFDSQSISDY | | YAS | 83 | GHSFLMY |
| | IMGT | | QSISDY | | YAS | 84 | YASQNGHSFLMYT |
| NKp46-9 | Kabat | 92 | RTSENIYSYLA | 93 | NAKTLAE | 94 | QHHYDTPLT |
| | Chotia | | SENIYSY | | NAK | 95 | NAKHYDTPL |
| | IMGT | | ENIYSY | | NAK | 96 | QHHYDTPLT |
| Bab281 | Kabat | 105 | KASENVVTYVS | 108 | GASNRYT | 109 | GQGYSYPYT |
| | Chotia | 106 | SENVVTY | | GAS | 110 | GYSYPY |
| | IMGT | 107 | ENVVTY | | GAS | 111 | GQGYSYPYT |

TABLE B

| Antibody | SEQ ID NO | Amino acid sequence |
|---|---|---|
| NKp46-1 VH | 3 | QVQLQQSGPELVKPGASVKMSCKASGYTFTDYVINWKQRSGQGLEWIGEIYPGSGTNYYNEKFKAKATLTADKSSNIAYMQLSSLTSEDSAVYFCARRGRYGLYAMDYWGQGTSVTVSS |
| NKp46-1 VL | 4 | DIQMTQTTSSLSASLGDRVTISCRASQDISNYLNWYQQKPDGTVKLLIYYTSRLHSGVPSRFSGSGSGTDYSLTINNLEQEDIATYFCQQGNTRPWTFGGGTKLEIK |
| NKp46-2 VH | 5 | EVQLQESGPGLVKPSQSLSLTCTVTGYSITSDYAWNWIRQFPGNKLEWMGYITYSGSTSYNPSLESRISITRDTSTNQFFLQLNSVTTEDTATYYCARGGYYGSSWGVFAYWGQGTLVTVSA |
| NKp46-2 VL | 6 | DIQMTQSPASLSASVGETVTITCRVSENIYSYLAWYQQKQGKSPQLLVYNAKTLAEGVPSRFSGSGSGTQFSLKINSLQPEDEGSYYCQHHYGTPWTEGGGTKLEIK |
| NKp46-3 VH | 7 | EVQLQQSGPELVKPGASVKISCKTSGYTFTEYTMHWVKQSHGKSLEWIGGISPNIGGTSYNQKFKGKATLTVDKSSSTAYMELRSLTSEDSAVYYCARRGGSFDYWGQGTTLTVSS |
| NKp46-3 VL | 8 | DIVMTQSPATLSVTPGDRVSLSCRASQSISDYLHWYQQKSHESPRLLIKYASQSISGIPSRFSGSGSGSDFTLSINSVEPEDVGVYYCQNGHSFPLTFGAGTKLELK |
| NKp46-4 VH | 9 | QVQLQQSAVELARPGASVKMSCKASGYTFTSFTMHWVKQRPGQGLEWIGYINPSSGYTEYNQKFKDKTTLTADKSSSTAYMQLDSLTSDDSAVYYCVRGSSRGFDYWGQGTLVTVSA |
| NKp46-4 VL | 10 | DIQMIQSPASLSVSVGETVTITCRASENIYSNLAWFQQKQGKSPQLLVYAATNLADGVPSRFSGSGSGTQYSLKINSLQSEDFGIYYCQHFWGTPRTFGGGTKLEIK |
| NKp46-6 VH | 11 | QVQLQQPGSVLVRPGASVKLSCKASGYTFTSSWMHWAKQRPGQGLEWIGHIHPNSGISNYNEKFKGKATLTVDTSSSTAYVDLSSLTSEDSAVYYCARGGRFDDWGAGTTVTVSS |
| NKp46-6 VL | 12 | DIVMTQSPATLSVTPGDRVSLSCRASQSISDYLHWYQQKSHESPRLLIKYASQSISGIPSRFSGSGSGSDFTLSINSVEPEDVGVYYCQNGHSFLMYTEGGGTKLEIK |
| NKp46-9 VH | 13 | DVQLQESGPGLVKPSQSLSLTCTVTGYSITSDYAWNWIRQFPGNKLEWMGYITYSGSTNYNPSLKSRISITRDTSKNQFFLQLNSVTTEDTATYYCARCWDYALYAMDCWGQGTSVTVSS |
| NKp46-9 VL | 14 | DIQMTQSPASLSASVGETVTITCRTSENIYSYLAWCQQKQGKSPQLLVYNAKTLAEGVPSRFSGSGSGTHFSLKINSLQPEDFGIYYCQHHYDTPLTFGAGTKLELK |

Also provided, as shown in the Examples herein, is a protein comprising the amino acid sequences of monomeric bispecific polypeptides comprising scFv comprising the heavy and light chain CDR1, 2 and 3 of the respective heavy and light chain variable region listed as SEQ ID NOS: 3-14 of antibodies NKp46-1, NKp46-2, NKp46-3, NKp46-4, NKp46-6 and NKp46-9, a monomeric Fc domain, and scFv comprising the heavy and light chain CDR1, 2 and 3 of the heavy and light chain variable region of an anti-CD19 antibodies, e.g. the anti-CD19 shown in the Example herein.

Once the multispecific protein is produced it can be assessed for biological activity, such as agonist activity.

In one aspect of any embodiment herein, a multispecific protein is capable of inducing activation of an NKp46-expressing cell (e.g. an NK cell, a reporter cell) when the protein is incubated in the presence of the NKp46-expressing cell (e.g. purified NK cells) and a target cell that expresses the antigen of interest).

In one aspect of any embodiment herein, a multispecific protein is incapable of inducing substantial activation of an NKp46-expressing cell (e.g. an NK cell, a reporter cell) when incubated with NKp46-expressing cells (e.g., purified NK cells or purified reporter cells, optionally further in the presence of Fcγ receptor-expressing cells) in the absence of target cells.

In one aspect of any embodiment herein, a multispecific protein is capable of inducing NKp46 signaling in an NKp46-expressing cell (e.g. an NK cell, a reporter cell) when the protein is incubated in the presence of the NKp46-expressing cell (e.g. purified NK cells) and a target cell that expresses the antigen of Interest).

In one aspect of any embodiment herein, a multispecific protein is not capable of causing (or increasing) NKp46 signaling in an NKp46-expressing cell (e.g. an NK cell, a reporter cell) when Incubated with NKp46-expressing cells (e.g., purified NK cells or purified reporter cells, optionally further in the presence of Fcγ receptor-expressing cells) in the absence of target cells.

Optionally, NK cell activation or signaling in characterized by increased expression of a cell surface marker of activation, e.g. CD107, CD69, etc.

Activity can be measured for example by bringing target cells and NKp46-expressing cells into contact with one another, in presence of the multispecific polypeptide. In one example, aggregation of target cells and NK cells is measured. In another example, the multispecific protein may, for example, be assessed for the ability to cause a measurable increase In any property or activity known in the art as associated with NK cell activity, respectively, such as marker of cytotoxicity (CD107) or cytokine production (for example IFN-γ or TNF-α), increases in intracellular free calcium levels, the ability to lyse target cells in a redirected killing assay, etc.

In the presence of target cells (target cells expressing the antigen of interest) and NK cells that express NKp46, the multispecific protein will be capable of causing an increase in a property or activity associated with NK cell activity (e.g. activation of NK cell cytotoxicity, CD107 expression, IFNγ production) in vitro. For example, an multispecific protein of the disclosure can be selected for the ability to increase an NK cell activity by more than about 20%, preferably with at least about 30%, at least about 40%, at least about 50%, or more compared to that achieved with the same effector: target cell ratio with the same NK cells and target cells that are not brought into contact with the multispecific protein, as measured by an assay of NK cell activity, e.g., a marker of activation of NK cell cytotoxicity, CD107 or CD69 expression, IFNγ production, a classical In vitro chromium release test of cytotoxicity. Examples of protocols for activation and cytotoxicity assays are described in the Examples herein, as well as for example, in Pessino et al, J. Exp. Med, 1998, 188 (5): 953-960; Sivori et al, Eur J Immunol, 1999. 29:1656-1666; Brando et al, (2005) J. Leukoc. Biol. 78:359-371; El-Sherbiny et al, (2007) Cancer Research 67(18):8444-9; and Nolte-'t Hoen et al, (2007) Blood 109:670-673).

Activity can also be assed using a reporter assay can be used in which NKp46 ligand-expressing target cells are brought into contact with a NKp46 expressing reporter cell (e.g. an NK cell, a T cell), and the ability of the antibody to induce NKp46 signaling is assessed. For example, the NKp46-expressing reporter cell may be the DO.11.10 T cell hybridoma or similar cell transduced with retroviral particles encoding a chimeric NKp46 protein in which the intracytoplasmic domain of mouse CD3G is fused to the extracellular portion of NKp46 (see, e.g., DOMSP46 cells as described in Schleinitz et al., (2008) Arthritis Rheum. 58: 3216-3223). Engagement of the chimeric proteins at the cell surface triggers IL-2 secretion. After incubation, cell supernatants can be assayed for the presence of mouse IL-2 in a standard target cell survival assay. A target cell can be selected that does not, in the absence of the multispecific protein, induce NKp46 signaling in the reporter cell. The multispecific protein can then be brought into contact with the NKp46 expressing reporter cell in the presence of the target cell, and NKp46 signaling can be assessed. DOMSP46, or DO.11.10 (20,000 cells/well in 96-well plates) can be incubated with target cells and multispecific protein in 96-well plates. After 20 h, cell supernatants are assayed for the presence of mouse IL-2 in a standard CTLL-2 survival assay using Cell Titer-Glo Luminescent Cell Viability Assay (Promega).

In one embodiment, the invention provides methods of making a monomeric polypeptide (e.g. any monomeric protein described herein), comprising:
  a) providing a nucleic acid encoding a monomeric bispecific polypeptide described herein (e.g., a polypeptide comprising (a) a first antigen binding domain that binds to NKp46; (b) a second antigen binding domain that binds a polypeptide expressed on a target cell; and (c) at least a portion of a human Fc domain, wherein the multispecific polypeptide is capable of binding to human neonatal Fc receptor (FcRn) and has decreased binding to a human Fcγ receptor compared to a full length wild type human IgG1 antibody); and
  b) expressing said nucleic acid in a host cell to produce said polypeptide, respectively; and recovering the monomeric protein. Optionally step (b) comprises loading the protein produced onto an affinity purification support, optionally an affinity exchange column, optionally a Protein-A support or column, and collecting the monomeric protein.

In one embodiment, the invention provides methods of making a heterodimeric protein (e.g. any heterodimeric protein described herein), comprising:
  a) providing a first nucleic acid encoding a first polypeptide chain described herein (e.g., a polypeptide chain comprising a first variable domain (V) fused to a CH1 of CK constant region, a second variable domain (and optionally third variable domain, wherein the second and third variable domain form a first antigen binding domain), and an Fc domain or portion thereof interposed between the first and second variable domains);
  b) providing a second nucleic acid encoding a second polypeptide chain described herein (e.g., a polypeptide chain comprising a first variable domain (V) fused at its C-terminus to a CH1 or CK constant region selected to be complementary to the CH1 or CK constant region of the first polypeptide chain such that the first and second polypeptides form a CH1-CK heterodimer in which the first variable domain of the first polypeptide chain and the first variable domain of the second polypeptide form a second antigen binding domain); wherein one of the first or second antigen binding domains binds NKp46 and the other binds an antigen of interest; and
  c) expressing said first and second nucleic acids in a host cell to produce a protein comprising said first and second polypeptide chains, respectively; and recovering a heterodimeric protein. Optionally, the heterodimeric protein produced represents at least 20%, 25% or 30% of the total proteins (e.g. bispecific proteins) prior to purification. Optionally step (c) comprises loading the protein produced onto an affinity purification support, optionally an affinity exchange column, optionally a Protein-A support or column, and collecting the heterodimeric protein; and/or loading the protein produced (or the protein collected following loading onto an affinity exchange or Protein A column) onto an ion exchange column; and collecting the heterodimeric fraction. In one embodiment, the second variable domain (optionally together with the third variable domain) of the first polypeptide chain binds NKp46.

By virtue of their ability to be produced in standard cell lines and standardized methods with high yields, unlike BITE, DART and other bispecific formats, the proteins of the disclosure also provide a convenient tool for screening for the most effective variable regions to incorporated into a multispecific protein. In one aspect, the present disclosure provides a method for identifying or evaluating candidate variable regions for use in a heterodimeric protein, comprising the steps of:

a) providing a plurality of nucleic acid pairs, wherein each pair includes one nucleic acid encoding a heavy chain candidate variable region and one nucleic acid encoding a light chain candidate variable region, for each of a plurality of heavy and light chain variable region pairs (e.g., obtained from different antibodies binding the same or different antigen(s) of interest);

b) for each of the plurality nucleic acid pairs, making a heterodimeric protein by:
  (i) producing a first nucleic acid encoding a first polypeptide chain comprising one of the heavy or light chain candidate variable domains (V) fused to a CH1 or CK constant region, a second variable domain (and optionally third variable domain, wherein the second and third variable domain form a first antigen binding domain), and an Fc domain or portion thereof interposed between the candidate and second variable domains);
  (ii) producing a second nucleic acid encoding a second polypeptide chain comprising the other of the heavy or light chain candidate variable domains (V) fused at its C-terminus to a CH1 or CK constant region selected to be complementary to the CH1 or CK constant region of the first polypeptide chain such that the first and second polypeptides form a CH1-CK heterodimer in which the heavy and light chain candidate variable domains form a second antigen binding domain; and
  (iii) expressing said nucleic acids encoding the first and second polypeptide chains in a host cell to produce a protein comprising said first and second polypeptide chains, respectively; and recovering a heterodimeric protein; and c) evaluating the plurality of heterodimeric proteins produced for a biological activity of interest, e.g., an activity disclosed herein. In this method, one of the first or second antigen binding domains binds NKp46 and the other binds an antigen of interest. In one embodiment, the second variable domain (optionally together with the third variable domain) of the first polypeptide chain binds NKp46. Optionally, the heterodimeric protein produced represents at least 20%, 25% or 30% of the total proteins prior to purification. Optionally the recovering step in (iii) comprises loading the protein produced onto an affinity purification support, optionally an affinity exchange column, optionally a Protein-A support or column, and collecting the heterodimeric protein; and/or loading the protein produced (or the protein collected following loading onto a affinity exchange or Protein A column) onto an ion exchange column; and collecting the heterodimeric fraction. In one embodiment, the first antigen binding domain binds NKp46 and the second antigen binding domain binds an antigen of interest; optionally the first antigen binding domain is an anti-NKp46 scFv. In one embodiment, the second variable domain (optionally together with the third variable domain) of the first polypeptide chain binds NKp46.

In one embodiment, the invention provides methods of making a heterotrimeric protein (e.g. any heterotrimeric protein described herein), comprising:
  (a) providing a first nucleic acid encoding a first polypeptide chain described herein (e.g., a polypeptide chain comprising a first variable domain (V) fused to a first CH1 or CK constant region, a second variable domain fused to a second CH1 or CK constant region, and an Fc domain or portion thereof interposed between the first and second (V-CH1/CK) units);
  (b) providing a second nucleic acid encoding a second polypeptide chain described herein (e.g., a polypeptide chain comprising a variable domain (V) fused at its C-terminus to a CH1 or CK constant region selected to be complementary to the first CH1 or CK constant region of the first polypeptide chain such that the first and second polypeptides form a CH1-CK heterodimer in which the first variable domain of the first polypeptide chain and the variable domain of the second polypeptide form an antigen binding domain);
  (c) providing a third nucleic acid comprising a third polypeptide chain described herein (e.g., a polypeptide chain comprising a variable domain fused at its C-terminus to a CH1 or CK constant region, wherein the CH1 or CK constant region is selected to be complementary to the second variable domain and second CH1 or CK constant region of the first polypeptide chain such that the first and third polypeptides form a CH1-CK heterodimer in which the second variable domain of the first polypeptide and the variable domain of the third polypeptide form an antigen binding domain; and
  (d) expressing said first, second and third nucleic acids in a host cell to produce a protein comprising said first, second and third polypeptide chains, respectively; and recovering a heterotrimeric protein. Optionally, the heterotrimeric protein produced represents at least 20%, 25% or 30% of the total proteins prior to purification. Optionally step (d) comprises loading the protein produced onto an affinity purification support, optionally an affinity exchange column, optionally a Protein-A support or column, and collecting the heterotrimeric protein; and/or loading the protein produced (e.g., the protein collected following loading onto an affinity exchange or Protein A column) onto an ion exchange column; and collecting the heterotrimeric fraction. In this method, one of the antigen binding domains binds NKp46 and the other binds an antigen of interest. In one embodiment, the second or the third polypeptide further comprises and Fc domain or fragment thereof fused to the C-terminus of the CH1 or CK domain (e.g. via a hinge domain or linker). In one embodiment, the second variable domain of the first polypeptide and the variable domain of the third polypeptide form an antigen binding domain that binds NKp46.

In one aspect, the present disclosure provides a method for identifying or evaluating candidate variable regions for use in a heterotrimeric protein, comprising the steps of:
a) providing a plurality of nucleic acid pairs, wherein each pair includes one nucleic acid encoding a heavy chain candidate variable region and one nucleic acid encoding a light chain candidate variable region, for each of a plurality of heavy and light chain variable region pairs (e.g., obtained from different antibodies binding the same or different antigen(s) of interest);
b) for each of the plurality nucleic acid pairs, making a heterotrimeric protein by:
  (i) producing a first nucleic acid encoding a first polypeptide chain comprising one of the heavy or light chain candidate variable domains (V) fused to a first CH1 or CK constant region, a second variable domain fused to a second CH1 or CK constant region, and an Fc domain or portion thereof interposed between the first and second (V-CH1/CK) units);
  (ii) producing a second nucleic acid encoding a second polypeptide chain comprising the other of the heavy or light chain candidate variable domains (V) fused at its C-terminus to a CH1 or CK constant region selected to be complementary to the first CH1 or CK constant region of the first polypeptide chain such that the first and second polypeptides form a CH1-CK heterodimer in which the heavy and light chain candidate variable domains form an antigen binding domain;
  (ii) producing a third nucleic acid encoding a third polypeptide chain comprising a variable domain fused at its C-terminus to a CH1 or CK constant region, wherein the CH1 or CK constant region is selected to be complementary to the second variable domain and second CH1 or CK constant region of the first polypeptide chain such that the first and third polypeptides form a CH1-CK heterodimer in which the second variable domain of the first polypeptide and the variable domain of the third polypeptide form an antigen binding domain; and
  (iii) expressing said nucleic acids encoding the first and second polypeptide chains in a host cell to produce said first and second polypeptide chains, respectively; and recovering a heterodimeric protein; and
c) evaluating the plurality of heterodimeric proteins produced for a biological activity of Interest, e.g., an activity disclosed herein. In one embodiment, the second or the third polypeptide further comprises and Fc domain or fragment thereof fused to the C-terminus of the CH1 or CK domain (e.g. via a hinge domain or linker). Optionally, the heterotrimeric protein produced represents at least 20%, 25% or 30% of the total proteins prior to purification. Optionally the recovering step in (iii) loading the protein produced onto an affinity purification support, optionally an affinity exchange column, optionally a Protein-A support or column, and collecting the heterotrimeric protein; and/or loading the protein produced (e.g., the protein collected following loading onto an affinity exchange or Protein A column) onto an ion exchange column; and collecting the heterotrimeric fraction.

In the methods for identifying or evaluating candidate variable regions, it will be appreciated that the candidate variable regions can be from an anti-NKp46 antibody or from an antigen that binds an antigen of interest. It will also be appreciated that the position of the respective ABDs for the candidate variable region pair and the other variable region pair can be inverted. For example, in a trimeric protein the methods can be modified such that the heavy and light chain candidate variable domains are formed by the second V region of the first polypeptide and the V region of the second polypeptide, and the other variable region pair are formed by the first V region of the first polypeptide and the V region of the third polypeptide.

In one embodiment, the second variable domain of the first polypeptide and the variable domain of the third polypeptide form an antigen binding domain that binds NKp46.

Furthermore, by providing a panel of different multispecific protein formats that all can be produced in standard cell lines and standardized methods with high yields, yet have different properties (e.g. conformational flexibility, spacing between two antigen binding domains, etc.) that can affect functional activity of the protein, the protein formats of the disclosure can be used in a panel to screen proteins configurations or formats to identify the most effective configurations or formats for a given antigen of interest, or combination of first and second antigen of interest. Different proteins formats may access or engage their antigen targets differently.

In one aspect, the present disclosure provides a method for identifying or evaluating candidate protein configurations for use in a heterodimeric protein, comprising the steps of:
  producing, separately (e.g. In separate containers), a plurality of multispecific proteins of the disclosure, wherein the proteins differ in their domain arrangements, and
  evaluating the plurality of multispecific proteins produced for a biological activity of interest, e.g., an activity disclosed herein. In one embodiment, the proteins having different domain arrangements share antigen binding domains (e.g. the same CDRs or variable domains) for NKp46 and/or the antigen of interest. In one embodiment 1, 2, 3, 4, 5, 6, 7 or more different proteins are produced and evaluated. In one embodiment, one or more of (or all of) the proteins are selected from the group of proteins having a domain arrangement disclosed herein, e.g. that of formats F1, F2, F3, F4, F5, F6, F7, F8, F9, F10, F11, F12, F13, F14, F15, F16 and F17.In one embodiment the proteins are produced according to the methods disclosed herein. Optionally, the plurality of multispecific proteins includes one protein with a monomeric Fc domain and one protein with a dimeric Fc domain.

In one aspect, the present disclosure provides a library of at least 5, 10, 20, 30, 50 hetero-multimeric proteins of the disclosure, wherein the proteins share domain arrangements but differ in the amino acid sequence of the variable domain of one or both of their antigen binding domains.

In one aspect, the present disclosure provides a library of at least 2, 3, 4, 5 or 10 hetero-multimeric proteins of the disclosure, wherein the proteins share the amino acid sequence of the variable domain of one or both of their antigen binding domains, but differ in domain arrangements.

In one aspect of the any of the embodiments herein, recovering a monomeric, heterodimeric or heterotrimer protein can comprise introducing the protein to a solid phase so as to immobilize the protein. The immobilized protein can then subsequently be eluted. Generally, the solid support may be any suitable Insoluble, functionalized material to which the proteins can be reversibly attached, either directly or indirectly, allowing them to be separated from unwanted materials, for example, excess reagents, contaminants, and solvents. Examples of solid supports include, for example, functionalized polymeric materials, e.g., agarose, or its bead form Sepharose®, dextran, polystyrene and polypropylene, or mixtures thereof; compact discs comprising microfluidic channel structures; protein array chips; pipet tips; membranes, e.g., nitrocellulose or PVDF membranes; and microparticles, e.g., paramagnetic or non-paramagnetic beads. In some embodiments, an affinity medium will be bound to the solid support and the protein will be indirectly attached to solid support via the affinity medium. In one aspect, the solid support comprises a protein A affinity medium or protein G affinity medium. A "protein A affinity medium" and a "protein G affinity medium" each refer to a solid phase onto which is bound a natural or synthetic protein comprising an Fc-binding domain of protein A or protein G, respectively, or a mutated variant or fragment of an Fc-binding domain of protein A or protein G, respectively, which variant or fragment retains the affinity for an Fc-portion of an antibody. Protein A and Protein G are bacterial cell wall proteins that have binding sites for the Fc portion of mammalian IgG. The capacity of these proteins for IgG varies with the species. In general, IgGs have a higher affinity for Protein G than for Protein A, and Protein G can bind IgG from a wider variety of species. The affinity of various IgG subclasses, especially from mouse and human, for Protein A varies more than for Protein G. Protein A can, therefore, be used to prepare isotypically pure IgG from some species. When covalently attached to a solid matrix, such as cross-linked agarose, these proteins can be used to capture and purify antigen-protein complexes from biochemical solutions. Commercially available products include, e.g., Protein G, A or L bonded to agarose or sepharose beads, for example EZview™ Red Protein G Affinity Gel is Protein G covalently bonded to 4% Agarose beads (Sigma Aldrich Co); or POROS® A, G, and CaptureSelect® HPLC columns (Invitrogen Inc.). Affinity capture reagents are also described, for example, in the Antibody Purification Handbook, Biosciences, publication No. 18-1037-46, Edition AC, the disclosure of which is hereby incorporated by reference).

In one aspect of the any of the embodiments herein, evaluating monomeric, heterodimeric or heterotrimeric proteins for a characteristic of interest comprises evaluating the proteins for one or more properties selected from the group consisting of: binding to an antigen of interest, binding to NKp46, binding to a tumor, viral or bacterial antigen, binding to an FcRn receptor, binding to an Fcγ receptor, Fc-domain mediated effector function(s), agonistic or antagonistic activity at a polypeptide to which the multimeric proteins binds, ability to modulate the activity (e.g. cause the death of) a cell expressing the antigen of Interest, ability to direct a lymphocyte to a cell expressing the antigen of Interest, ability to activate a lymphocyte in the presence and/or absence of a cell expressing the antigen of interest, NK cell activation, activation of NKp46-expressing lymphocytes (e.g. NK cells) in presence but not In absence of target cells, lack of activation of NKp46-negative lymphocytes, stability or half-life in vitro or in vivo, production yield, purity within a composition, and susceptibility to aggregate in solution.

In one aspect, the present disclosure provides a method for identifying or evaluating an anti-NKp46 bispecific protein, comprising the steps of:

(a) providing nucleic acid(s) encoding an anti-NKp46 bispecific protein described herein;
(b) expressing said nucleic acid(s) in a host cell to produce said protein, respectively; and recovering said protein; and
(c) evaluating the protein produced for a biological activity of interest, e.g., an activity disclosed herein. In one embodiment, a plurality of different anti-NKp46 bispecific proteins are produced and evaluated.

In one embodiment, the step (c) comprises:
(i) testing the ability of the protein to activate effector cells that express NKp46, when incubated with such effector cells in the presence of target cells (that express antigen of Interest). Optionally, step (1) is followed by a step comprising: selecting a protein (e.g., for further development, for use as a medicament) that activates said effector cells.

In one embodiment, the step (c) comprises:
(i) testing the ability of the protein to activate effector cells that express NKp46, when incubated with such effector cells in the absence of target cells (that express antigen of interest). Optionally, step (i) is followed by a step comprising: selecting a protein (e.g., for further development, for use as a medicament) that does not substantially activate said effector cells.

In one embodiment, the step (c) comprises:
(i) testing the ability of the protein to activate effector cells that express NKp46, when incubated with such effector cells in the presence of target cells (that express antigen of interest); and
(ii) testing the ability of the protein to activate effector cells that express NKp46, when incubated with such effector cells in the absence of target cells (that express antigen of interest). Optionally, the method further comprises: selecting a protein (e.g., for further development, for use as a medicament) that does not substantially activate said effector cells when incubated in the absence of target cells, and that activates said effector cells when Incubated In the presence of target cells.

In one embodiment, the step (c) comprises:
(i) testing the ability of the polypeptide to induce effector cells that express NKp46 to lyse target cells (that express antigen of Interest), when Incubated such effector cells In the presence of target cells. Optionally, step (i) is followed by a step comprising: selecting a protein (e.g., for further development, for use as a medicament) that induces effector cells that express NKp46 to lyse the target cells, when incubated such effector cells in the presence of the target cells.

In one embodiment, the step (c) comprises:
(i) testing the ability of the protein to activate effector cells that express CD16 but do not express NKp46, when incubated with such effector cells in the presence of target cells. Optionally, step (i) is followed by a step comprising: selecting a protein (e.g., for further development, for use as a medicament) that do not substantially activate said effector cells, when incubated with such effector cells in the presence of target cells.

Uses of Compounds

In one aspect, provided are the use of any of the compounds defined herein for the manufacture of a pharmaceutical preparation for the treatment or diagnosis of a mammal in need thereof. Provided also are the use any of the compounds defined above as a medicament or an active component or active substance in a medicament. In a further aspect provided is a method for preparing a pharmaceutical composition containing a compound as defined above, to provide a solid or a liquid formulation for administration orally, topically, or by injection. Such a method or process at least comprises the step of mixing the compound with a pharmaceutically acceptable carrier.

In one aspect, provided is a method to treat, prevent or more generally affect a predefined condition by exerting a certain effect, or detect a certain condition using a multispecific protein described herein, or a (pharmaceutical) composition comprising such.

For example, in one aspect, the invention provides a method of restoring or potentiating the activity of NKp46+ NK cells in a patient in need thereof (e.g. a patient having a cancer or a viral or bacterial infection), comprising the step of administering a multispecific protein described herein to said patient. In one embodiment, the method is directed at increasing the activity of NKp46+ lymphocytes in patients having a disease in which increased lymphocyte (e.g. NK cell) activity is beneficial or which is caused or characterized by Insufficient NK cell activity, such as a cancer, or a viral or microbial/bacterial Infection.

The polypeptides described herein can be used to prevent or treat disorders that can be treated with antibodies, such as cancers, solid and non-solid tumors, hematological malignancies, infections such as viral infections, and inflammatory or autoimmune disorders.

In one embodiment, the antigen of interest (the non-NKp46 antigen) is an antigen expressed on the surface of a malignant cell of a type of cancer selected from the group consisting of: carcinoma, including that of the bladder, head and neck, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sezary syndrome (SS); Adult T-cell leukemia lymphoma (ATLL); a/d T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic (Ki 1+) large cell lymphoma; intestinal T-cell lymphoma; T-lymphoblastic; and lymphoma/leukaemia (T-Lbly/T-ALL).

In one embodiment, polypeptides described herein can be used to prevent or treat a cancer selected from the group consisting of: carcinoma, including that of the bladder, head and neck, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xeroderma pigmentosum, keratoacanthoma, seminoma, thyroid follicular cancer and teratocarcinoma. Other exemplary disorders that can be treated according to the invention include hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sezary syndrome (SS); Adult T-cell leukemia lymphoma (ATLL); a/d T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic (Ki 1+) large cell lymphoma; intestinal T-cell lymphoma; T-lymphoblastic; and lymphoma/leukaemia (T-Lbly/T-ALL).

In one example, the tumor antigen is an antigen expressed on the surface of a lymphoma cell or a leukemia cell, and the multispecific protein is administered to, and/or used for the treatment of, an individual having a lymphoma or a leukemia. Optionally, the tumor antigen is selected from CD19, CD20, CD22, CD30 or CD33.

In one aspect, the methods of treatment comprise administering to an individual a multispecific protein described herein in a therapeutically effective amount. A therapeutically effective amount may be any amount that has a therapeutic effect in a patient having a disease or disorder (or promotes, enhances, and/or induces such an effect in at least a substantial proportion of patients with the disease or disorder and substantially similar characteristics as the patient).

In one embodiment, the multispecific protein described herein may be used in combined treatments with one or more other therapeutic agents, including agents normally utilized for the particular therapeutic purpose for which the antibody is being administered.

The additional therapeutic agent will normally be administered in amounts and treatment regimens typically used for that agent in a monotherapy for the particular disease or condition being treated. Such therapeutic agents when used in the treatment of cancer, include, but are not limited to anti-cancer agents and chemotherapeutic agents; in the treatment of infections disease, include, but are not limited to anti-viral agents and anti-biotics.

In one embodiment, the additional therapeutic agent is an agent capable of inducing ADCC of a cell to which it is bound, e.g. via CD16 expressed by an NK cell. Typically, such protein will have an Fc domain or portion thereof and will exhibit binding to Fcγ receptors (e.g. CD16). In one embodiment, its ADCC activity will be mediated at least in part by CD16. In one embodiment, the additional therapeutic agent is an antibody having a native or modified human Fc domain, for example a Fc domain from a human IgG1 or IgG3 antibody. The term "antibody-dependent cell-mediated cytotoxicity" or "ADCC" is a term well understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC Include natural killer (NK) cells, macrophages, monocytes, neutrophils, and eosinophils. The term "ADCC-inducing antibody" refers to an antibody that demonstrates ADCC as measured by assay(s) known to those of skill in the art. Such activity is typically characterized by the binding of the Fc region with various FcRs. Without being limited by any particular mechanism, those of skill in the art will recognize that the ability of an antibody to demonstrate ADCC can be, for example, by virtue of it subclass (such as IgG1 or IgG3), by mutations introduced into the Fc region, or by virtue of modifications to the carbohydrate patterns in the Fc region of the antibody.

Certain modifications to the Fc region of an antibody, as compared to a wild type Fc region, are also known by those in the art to enhance ADCC activity. Combinations with such "ADCC-enhanced" antibodies as the additional therapeutic agent are particularly advantageous because such antibodies may induce high activation via CD16, and the multispecific proteins acting via NKp46 will induce NK cell activation and/or target cell lysis by a complementary mechanism without interfering with CD16 pathway utilized by ADCC-enhanced antibodies, and without causing additional immune-related toxicity. Typical modifications include modified human IgG1 constant regions comprising at least one amino acid modification (e.g. substitution, deletions, insertions), and/or altered types of glycosylation, e.g., hypofucosylation. Such modifications can affect interaction with Fc receptors: FcγRI (CD64), FcγRII (CD32), and FcγRIII (CD 16). FcγRI (CD64), FcγRIIA (CD32A) and FcγRIII (CD 16) are activating (i.e., immune system enhancing) receptors while FcγRIIB (CD32B) is an inhibiting (i.e., immune system dampening) receptor. A modification may, for example, increase binding of the Fc domain to FcγRIIIa on effector (e.g. NK) cells and/or decrease binding to FcγRIIB. Examples of modifications are provided in PCT/EP2013/069302 filed 17 Sep. 2013, the disclosure of which is incorporated herein by reference.

In some embodiments, the additional therapeutic agent is an antibody comprising a variant Fc region comprise at least one amino acid modification (for example, possessing 1, 2, 3, 4, 5, 6, 7, 8, 9, or more amino acid modifications) in the CH3 domain of the Fc region. In other embodiments, the antibodies comprising a variant Fc region comprise at least one amino acid modification (for example, possessing 1, 2, 3, 4, 5, 6, 7, 8, 9, or more amino acid modifications) in the CH2 domain of the Fc region, which is defined as extending from amino acids 231-341. In some embodiments, antibodies comprise at least two amino acid modifications (for example, possessing 2, 3, 4, 5, 6, 7, 8, 9, or more amino acid modifications), wherein at least one such modification is in the CH3 region and at least one such modification is in the CH2 region. Encompasses also are amino acid modification in the hinge region. In one embodiment, encompassed are amino acid modification in the CH1 domain of the Fc region, which is defined as extending from amino acids 216-230. Any combination of Fc modifications can be made, for example any combination of different modifications disclosed in U.S. Pat. Nos. 7,632,497; 7,521,542; 7,425,619; 7,416,727; 7,371,826; 7,355,008; 7,335,742; 7,332,581; 7,183,387; 7,122,637; 6,821,505 and 6,737,056; in PCT Publications Nos. WO2011/109400; WO 2008/105886; WO 2008/002933; WO 2007/021841; WO 2007/106707; WO 06/088494; WO 05/115452; WO 05/110474; WO 04/1032269; WO 00/42072; WO 06/088494; WO 07/024249; WO 05/047327; WO 04/099249 and WO 04/063351; and in Lazar et al. (2006) Proc. Nat. Acad. Sci. USA 103(11): 405-410; Presta, L. G. et al. (2002) Biochem. Soc. Trans. 30(4):487-490; Shields, R. L. et al. (2002) J. Biol. Chem. 26; 277(30):26733-26740 and Shields, R. L. et al. (2001) J. Biol. Chem. 276(9):6591-6604).

In some embodiments, the additional therapeutic agent is an antibody comprising a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, optionally wherein the variant Fc region comprises a substitution at any one or more of positions 221, 239, 243, 247, 255, 256, 258, 267, 268, 269, 270, 272, 276, 278, 280, 283, 285, 286, 289, 290, 292, 293, 294, 295, 296, 298, 300, 301, 303, 305, 307, 308, 309, 310, 311, 312, 316, 320, 322, 326, 329, 330, 332, 331, 332, 333, 334, 335, 337, 338, 339, 340, 359, 360, 370, 373, 376, 378, 392, 396, 399, 402, 404, 416, 419, 421, 430, 434, 435, 437, 438 and/or 439. In one embodiment, in some embodiments, the additional therapeutic agent is an antibody comprising a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, optionally wherein the variant Fc region comprises a substitution at any one or more of positions 239, 298, 330, 332, 333 and/or 334 (e.g. S239D, S298A, A330L, I332E, E333A and/or K334A substitutions).

In some embodiments, the additional therapeutic agent is an antibody comprising altered glycosylation patterns that Increase Fc receptor binding ability of antibodies. Such carbohydrate modifications can be accomplished by, for example, expressing the antibody in a host cell with altered glycosylation machinery. Cells with altered glycosylation machinery have been described in the art and can be used as host cells In which to express recombinant antibodies to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 06/133148; WO 03/035835; WO 99/54342, each of which is incorporated herein by reference in its entirety. In one aspect, the antibodies are hypofucosylated in their constant region. Such antibodies may comprise an amino acid alteration or may not comprise an amino acid alteration but be produced or treated under conditions so as to yield such hypofucosylation. In one aspect, an antibody composition comprises a chimeric, human or humanized antibody described herein, wherein at least 20, 30, 40, 50, 60, 75, 85, 90, 95% or substantially all of the antibody species in the composition have a constant region comprising a core carbohydrate structure (e.g. complex, hybrid and high mannose structures) which lacks fucose. In one embodiment, provided is an antibody composition which is free of antibodies comprising a core carbohydrate structure having fucose. The core carbohydrate will preferably be a sugar chain at Asn297.

Examples of ADCC-enhanced antibodies Include but are not limited to: GA-101 (hypofucosylated anti-CD20), margetuximab (Fc enhanced anti-HER2), mepolizumab, MEDI-551 (Fc engineered anti-CD19), obinutuzumab (glyco-engineered/hypofucosylated anti-CD20), ocaratuzumab (Fc engineered anti-CD20), XmAb5574/MOR208 (Fc engineered anti-CD19).

In one example, the additional therapeutic agent (e.g. antibody capable of inducing ADCC) binds a cancer antigen present on a lymphoma or a leukemia cell, e.g. CD19, CD20, CD22, CD30 or CD33, and the multispecific protein and the additional therapeutic agent are administered to, and/or are used in the treatment of, an Individual having a lymphoma or a leukemia.

"Combination therapy" embraces the administration of a second therapeutic agent (e.g. an ADCC-inducing antibody) and a multispecific protein described herein as part of a specific treatment regimen intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" generally is not Intended to encompass the administration of two or more of these therapeutic agents as part of separate monotherapy regimens that incidentally and arbitrarily result in the combinations of the present Invention. "Combination therapy" embraces administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, both the therapeutic agents may be administered orally or both therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different antineoplastic agent) and non-drug therapies (such as, but not limited to, surgery or radiation treatment).

The multispecific polypeptides can be included in kits. The kits may optionally further contain any number of polypeptides and/or other compounds, e.g., 1, 2, 3, 4, or any other number of multispecific polypeptide and/or other compounds. It will be appreciated that this description of the contents of the kits is not limiting in any way. For example, the kit may contain other types of therapeutic compounds. Optionally, the kits also include instructions for using the polypeptides, e.g., detailing the herein-described methods.

Also provided are pharmaceutical compositions comprising the compounds as defined above. A compound may be administered in purified form together with a pharmaceutical carrier as a pharmaceutical composition. The form depends on the intended mode of administration and therapeutic or diagnostic application. The pharmaceutical carrier can be any compatible, nontoxic substance suitable to deliver the compounds to the patient. Pharmaceutically acceptable carriers are well known in the art and include, for example, aqueous solutions such as (sterile) water or physiologically buffered saline or other solvents or vehicles such as glycols, glycerol, oils such as olive oil or injectable organic esters, alcohol, fats, waxes, and Inert solids A pharmaceutically acceptable carrier may further contain physiologically acceptable compounds that act for example to stabilize or to increase the absorption of the compounds Such physiologically acceptable compounds include, for example, carbohydrates, such as glucose, sucrose or dextrans, antioxidants, such as ascorbic acid or glutathione, chelating agents, low molecular weight proteins or other stabilizers or excipients One skilled in the art would know that the choice of a pharmaceutically acceptable carrier, Including a physiologically acceptable compound, depends, for example, on the route of administration of the composition Pharmaceutically acceptable adjuvants, buffering agents, dispersing agents, and the like, may also be incorporated into the pharmaceutical compositions.

The compounds can be administered parenterally. Preparations of the compounds for parenteral administration must be sterile. Sterilization is readily accomplished by filtration through sterile filtration membranes, optionally prior to or following lyophilization and reconstitution. The parenteral route for administration of compounds is in accord with known methods, e.g. injection or infusion by intravenous, intraperitoneal, intramuscular, intraarterial, or intralesional routes. The compounds may be administered continuously by infusion or by bolus injection. A typical composition for intravenous infusion could be made up to contain 100 to 500 ml of sterile 0.9% NaCl or 5% glucose optionally supplemented with a 20% albumin solution and 1 mg to 10 g of the compound, depending on the particular type of compound and its required dosing regimen. Methods for preparing parenterally administrable compositions are well known in the art.

EXAMPLES

Example 1

Generation of Anti-huNKp46 Antibodies

Balb/c mice were immunized with a recombinant human NKp46 extracellular domain recombinant-Fc protein. Mice received one primo-immunization with an emulsion of 50 μg NKp46 protein and Complete Freund Adjuvant, intraperitoneally, a 2nd immunization with an emulsion of 50 μg NKp46 protein and Incomplete Freund Adjuvant, intraperitoneally, and finally a boost with 10 μg NKp46 protein, intravenously. Immune spleen cells were fused 3 days after the boost with X63.Ag8.653 immortalized B cells, and cultured in the presence of irradiated spleen cells.

Primary screen: Supernatant (SN) of growing clones were tested in a primary screen by flow cytometry using a cell line expressing the human NKp46 construct at the cell surface. Briefly, for FACS screening, the presence of reacting antibodies in supernatants was revealed by Goat anti-mouse polyclonal antibody (pAb) labeled with PE.

A selection of antibodies that bound NKp46 were selected, produced and their variable regions further evaluated for their activity In the context of a bispecific molecule.

Example 2

Identification of a Bispecific Antibody Format that Binds FcRn but not FcγR for Targeting Effector Cell Receptors The aim of this experiment was to develop a new bispecific protein format that places an Fc domain on a polypeptide together with an anti-NKp46 binding domain and an anti-target antigen binding domain. The bispecific protein binds to NKp46 monovalently via its anti-NKp46 binding domain. The monomeric Fc domain retains at least partial binding to the human neonatal Fc receptor (FcRn), yet does not substantially bind human CD16 and/or other human Fcγ receptors. Consequently, the bispecific protein will not induce Fcγ-mediated (e.g. CD16-mediated) target cell lysis.

Example 2-1 Construction and Binding Analysis of Anti-CD19-IgG1-Fcmono-Anti-CD3

Since no anti-NKp46 bispecific antibody has been produced that could indicate whether such a protein could be functional, CD3 was used as a model antigen in place of NKp46 in order to investigate the functionality of a new monovalent bispecific protein format prior to targeting NK cells via NKp46.

Figure 1:
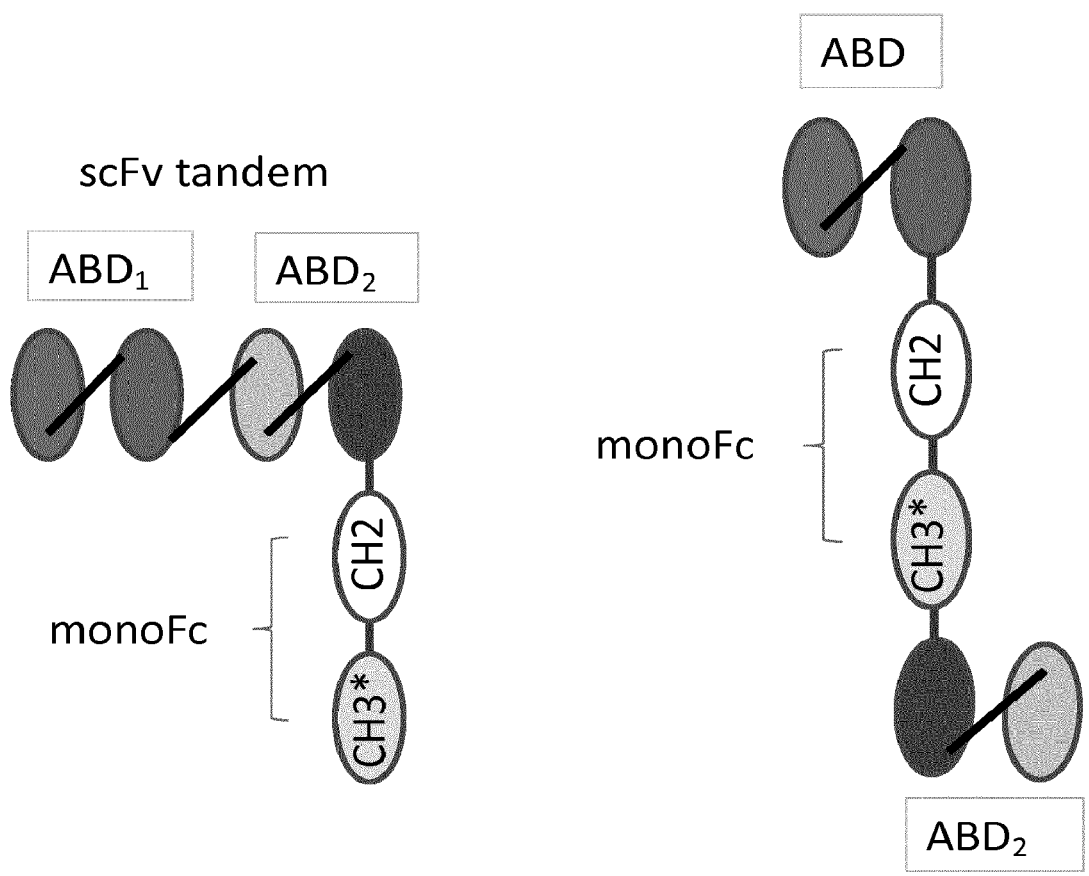
FIG. 1 shows two examples of multispecific polypeptides in which one of the antigen binding domains ($ABD_I$ or $ABD_2$) specifically binds to NKp46 and the other of the ABDs binds to an antigen of interest, wherein the drawing on the left has tandem scFv and the drawing on the right has two ABD with an Fc domain Interposed.
Figure 2:
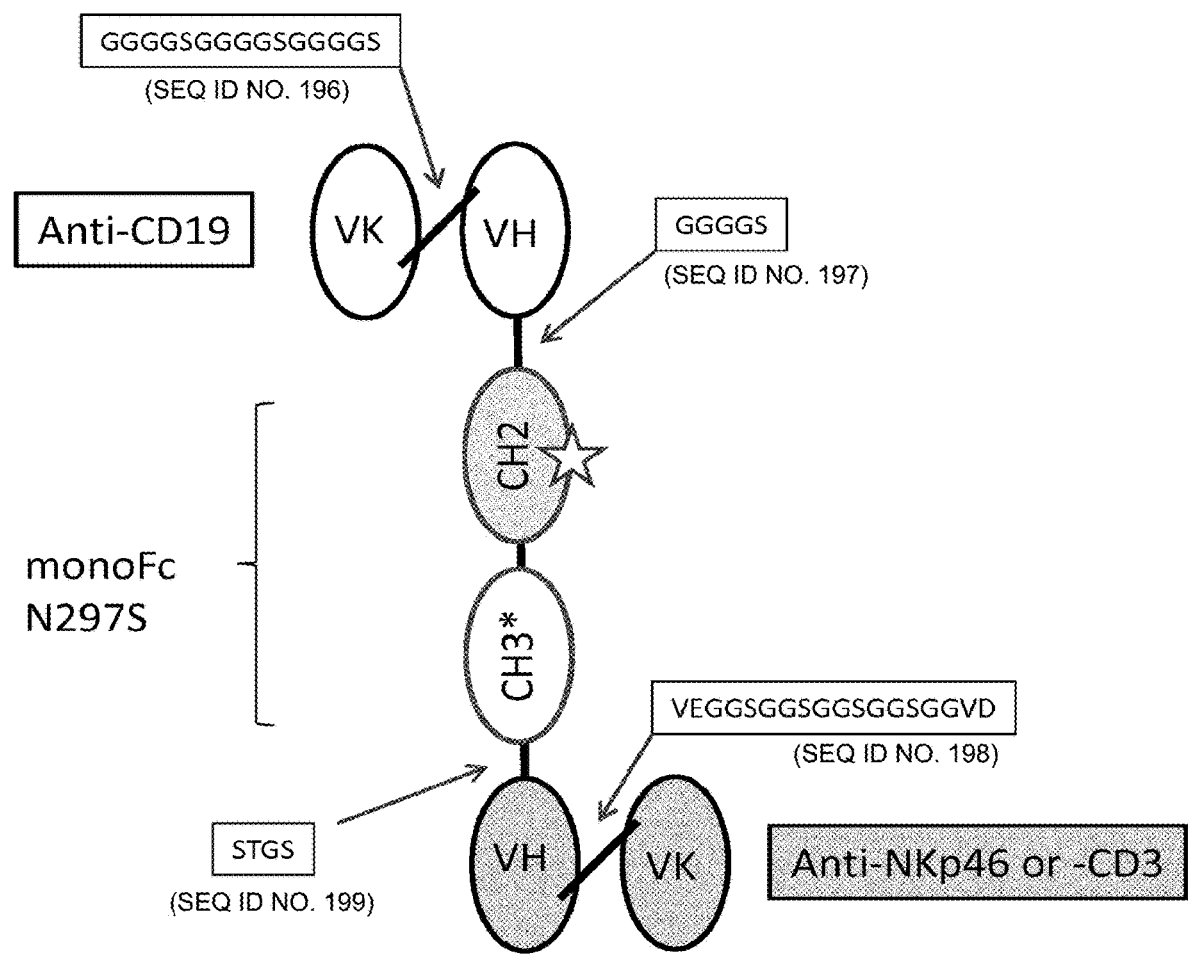
FIG. 2 shows a schematic of an anti-CD19-F1-Anti-NKp46 used in the Examples herein. The star in the CH2 domain indicates an option N297S mutation.
Figure 3:
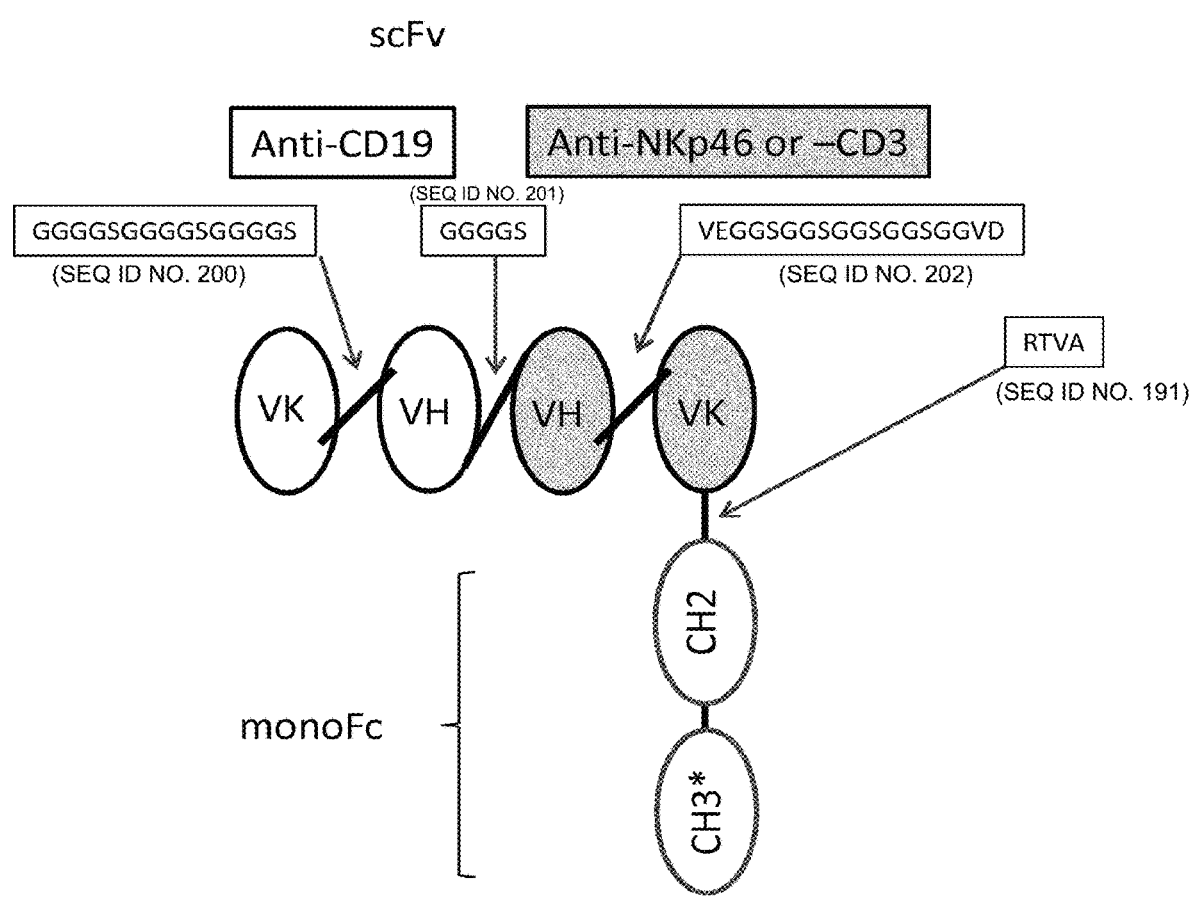
FIG. 3 shows a schematic of an anti-CD19-Anti-NKp46-IgG1-Fcmono. For the scFv tandem construct, the Anti-NKp46 VK domain (C-terminal) is linked to the CH2 domain (N-terminal) using a linker peptide (RTVA) that mimics the regular VK-CK elbow junction.

A bispecific Fc-based on a scFv specific for tumor antigen CD19 (anti-CD19 scFv) and a scFV specific for activating receptor CD3 on a T cell (anti-CD3 scFv) was used to assess FcRn binding and CD19-binding functions of a new monomeric bispecific polypeptide format. The domain arrangement of the final polypeptide is shown in FIG. 2 and is also referred to as the "F1" format (the star in the CH2 domain indicates an optional N297S mutation, not included in the polypeptide tested here).

A bispecific monomeric Fc-containing polypeptide was constructed based on an scFv specific for the tumor antigen CD19 (anti-CD19 scFv) and an scFV specific for an activating receptor CD3 on a T cell (anti-CD3 scFv). The CH3 domain incorporated the mutations (EU numbering) L351K, T366S, P395V, F405R, T407A and K409Y. The polypeptide has domains arranged as follows: anti-CD19-CH2-CH3-anti-CD3. DNA sequence coding for a CH3/VH linker peptide having the amino acid sequence STGS was designed in order to insert a specific SalI restriction site at the CH3-VH Junction.

The CH3 domain incorporated the mutations (EU numbering) L351K, T366S, P395V, F405R, T407A and K409Y. The CH2 domain was a wild-type CH2. DNA and amino acid sequences for the monomeric CH2-CH3 Fc portion and the anti-CD19 are shown below.

The light chain and heavy chain DNA and amino acid sequences corresponding to the anti-CD19 scFv were as follows:

| Sequence | SEQ ID NO |
|---|---|
| Anti-CD19-VK DNA | 113 |
| Anti-CD19-VK amino acid | 114 |
| Anti-CD19-VH DNA | 115 |
| Anti-CD19-VH amino acid | 116 |

The DNA sequences for the monomeric CH2-CH3 Fc portion and final bispecific IgG1-Fcmono polypeptide (the last K was removed in that construct) is shown In SEQ ID NO: 117. The amino acid sequence is shown in SEQ ID NO: 2. The Anti-CD19-F1-Anti-CD3 complete sequence (mature protein) is shown in SEQ ID NO: 118.

Cloning and Production of the Recombinant Proteins

Coding sequences were generated by direct synthesis and/or by PCR. PCR were performed using the PrimeSTAR MAX DNA polymerase (Takara, #R045A) and PCR products were purified from 1% agarose gel using the Nucleo-Spin gel and PCR clean-up kit (Macherey-Nagel, #740609.250). Once purified the PCR product were quantified prior to the In-Fusion ligation reaction performed as described in the manufacturer's protocol (ClonTech, #ST0345). The plasmids were obtained after a miniprep preparation run on an EVO200 (Tecan) using the Nucleospin 96 plasmid kit (Macherey-Nagel, #740625.4). Plasmids were then sequenced for sequences confirmation before to transfecting the CHO cell line.

CHO cells were grown in the CD-CHO medium (Invitrogen) complemented with phenol red and 6 mM GlutaMax. The day before the transfection, cells are counted and seeded at 175.000 cells/mi. For the transfection, cells (200.000 cells/transfection) are prepared as described in the AMAXA SF cell line kit (AMAXA, #V4XC-2032) and nucleofected using the DS137 protocol with the Nucleofector 4D device. All the transfections were performed using 300 ng of verified plasmids. After transfection, cells are seeded into 24 well plates in pre-warmed culture medium. After 24H, hygromycine B was added in the culture medium (200 µg/ml). Protein expression is monitored after one week in culture. Cells expressing the proteins are then sub-cloned to obtain the best producers. Sub-cloning was performed using 96 flat-bottom well plates in which the cells are seeded at one cell per well into 200 µl of culture medium complemented with 200 µg/ml of hygromycine B. Cells were left for three weeks before to test the clone's productivity.

Recombinant proteins which contain a IgG1-Fc fragment are purified using Protein-A beads (–rProteinA Sepharose fast flow, GE Healthcare, ref.: 17-1279-03). Briefly, cell culture supernatants were concentrated, clarified by centrifugation and injected onto Protein-A columns to capture the recombinant Fc containing proteins. Proteins were eluted at acidic pH (citric acid 0.1M pH3), Immediately neutralized using TRIS-HCL pH8.5 and dialyzed against 1×PBS. Recombinant scFv which contain a "six his" tag were purified by affinity chromatography using Cobalt resin. Other recombinant scFv were purified by size exclusion chromatography (SEC).

Example 2-2: Binding Analysis of Anti-CD19-IgG1-Fcmono-Anti-CD3 to B221, JURKAT, HUT78 and CHO Cell Lines Cells were harvested and stained with the cell supernatant of the anti-CD19-F1-anti-CD3 producing cells during 1 H at 4° C. After two washes in staining buffer (PBS1X/BSA 0.2%/EDTA 2 mM), cells were stained for 30 min at 4° C. with goat anti-human (Fc)-PE antibody (IM0550 Beckman Coulter-1/200). After two washes, stainings were acquired on a BD FACS Canto II and analyzed using the FlowJo software.

CD3 and CD19 expression were also controlled by flow cytometry: Cells were harvested and stained in PBS1X/BSA 0.2%/EDTA 2 mM buffer during 30 min at 4° C. using 5 µl of the anti-CD3-APC and 5 µl of the anti-CD19-FITC antibodies. After two washes, stainings were acquired on a BD FACS Canto II and analyzed using the FlowJo software.

The Anti-CD19-F1-Anti-CD3 protein binds to the CD3 cell lines (HUT78 and JURKAT cell lines) and the CD19 cell line (B221 cell line) but not to the CHO cell line used as a negative control.

Example 2-3

T- and B-Cell Aggregation by Purified Anti-CD19-F1-Anti-CD3

Purified Anti-CD19-F1-Anti-CD3 was tested in a T/B cell aggregation assay to evaluate whether the antibody is functional in bringing together CD19 and CD3 expressing cells. Results are shown in FIG. 4. The top panel shows that Anti-CD19-F1-Anti-CD3 does not cause aggregation in the presence of B221 (CD19) or JURKAT (CD3) cell lines, but it does cause aggregation of cells when both B221 and JURKAT cells are co-incubated, illustrating that the bispecific antibody is functional. The lower panel shows control without antibody.

Example 2-4

Binding of Bispecific Monomeric Fc Polypeptide to FcRn

Affinity Study by Surface Plasmon Resonance (SPR)
Biacore T100 General Procedure and Reagents SPR measurements were performed on a Biacore T100 apparatus (Biacore GE Healthcare) at 25° C. In all Biacore experiments Acetate Buffer (50 mM Acetate pH5.6, 150 mM NaCl, 0.1% surfactant p20) and HBS-EP+ (Biacore GE Healthcare) served as running buffer and regeneration buffer respectively. Sensorgrams were analyzed with Biacore T100 Evaluation software. Recombinant mouse FcRn was purchase from R&D Systems.
Immobilization of FcRn Recombinant FcRn proteins were immobilized covalently to carboxyl groups in the dextran layer on a Sensor Chip CM5. The chip surface was activated with EDC/NHS (N-ethyl-N'-(3-dimethylaminopropyl) carbodiimidehydrochloride and N-hydroxysuccinimide (Biacore GE Healthcare)). FcRn proteins were diluted to 10 μg/ml in coupling buffer (10 mM acetate, pH 5.6) and Injected until the appropriate Immobilization level was reached (i.e. 2500 RU). Deactivation of the remaining activated groups was performed using 100 mM ethanolamine pH 8 (Biacore GE Healthcare).
Affinity Study Monovalent affinity study was done following the Single Cycle Kinetic (SCK) protocol. Five serial dilutions of soluble analytes (antibodies and bi-specific molecules) ranging from 41.5 to 660 nM were injected over the FcRn (without regeneration) and allowed to dissociate for 10 min before regeneration. For each analyte, the entire sensorgram was fitted using the 1:1 SCK binding model.
Results Anti-CD19-F1-Anti-CD3 having its CH2-CH3 domains placed between two antigen binding domains, here two scFv, was evaluated to assess whether such bispecific monomeric Fc protein could retain binding to FcRn and thereby have improved in vivo half-lives compared to convention bispecific antibodies. Results showed that FcRn binding was retained, the model suggesting 1:1 ratio (1 FcRn for each monomeric Fc) instead of 2:1 ration (2 FcRn for each antibody) for a regular IgG. Results are shown in FIG. 5.

Affinity was evaluated using SPR, in comparison to a chimeric full length antibody having human IgG1 constant regions. Results are shown in FIG. 5. The monomeric Fc retained significant monomeric binding to FcRn (monomeric Fc: affinity of KD=194 nM; full length antibody with bivalent binding: avidity of KD=15.4 nM).

Example 3

Construction of Anti-CD19×Anti-NKp46 Bispecific Monomeric Fc Domain Polypeptides It was unknown what activating receptors on NK cells would contribute to lysis of target cells, and since anti-NKp46 antibodies may block NKp46, whether cytotoxicity could be mediated by NKp46 triggering. We investigated whether the bispecific protein format could induce NKp46 triggering, and moreover without inducing NKp46 agonism in the absence of target cells, which could lead to inappropriate NK activation distant from the target and/or decreased overall activity toward target cells.

A new bispecific protein format was developed as a single chain protein which binds to FcRn but not FcγR. Additionally, multimeric proteins that comprise two or three polypeptide chains, wherein the Fc domain remains monomeric, were developed that are compatible for use with antibody variable regions that do not maintain binding to their target when converted to scFv format. The latter formats can be used conveniently for antibody screening; by incorporating at least one binding region as a F(ab) structure, any anti-target (e.g. anti-tumor) antibody variable region can be directly expressed in a bispecific construct as the F(ab) format within the bispecific protein and tested, irrespective of whether the antibody would retain binding as an scFv, thereby simplifying screening and enhancing the number of antibodies available. These formats in which the Fc domain remains monomeric have the advantage of maintaining maximum conformational flexibility which may permit optimal binding to NKp46 or target antigens.

Different constructs were made for use in the preparation of a bispecific antibodies using the variable domains DNA and amino acid sequences from the scFv specific for tumor antigen CD19 described in Example 2-1, and different variable regions from antibodies specific for the NKp46 receptor identified in Example 1. A construct was also made using as anti-NKp46 the variable regions from existing antibody Bab281 (mIgG1, available commercially from Beckman Coulter, Inc. (Brea, CA, USA) (see also Pessino et al, J. Exp. Med, 1998, 188 (5): 953-960 and Sivori et al, Eur J Immunol, 1999. 29:1656-1666) specific for the NKp46 receptor.

For the Fc domain to remain monomeric in single chain polypeptides or multimers in which only one chain had an Fc domain, CH3-CH3 dimerization was prevented through two different strategies: (1) through the use of CH3 domain incorporating the mutations (EU numbering) L351K, T366S, P395V, F405R, T407A and K409Y; or (2) through the use of a tandem CH3 domain in which the tandem CH3 domains separated by a flexible linker associated with one another, in turn preventing interchain CH3-CH3 dimerization. The DNA and amino acid sequences for the monomeric CH2-CH3 Fc portion with point mutations were as in Example 2-1. The DNA and amino acid sequences for the monomeric CH2-CH3-linker-CH3 Fc portion with tandem CH3 domains is shown in FIGS. 6A-6D.

The light chain and heavy chain DNA and amino acid sequences for the anti-CD19 scFv were as in Example 2-1.

Proteins were cloned, produced and purified as in Example 2-1. Shown below are the light chain and heavy chain DNA and amino acid sequences for anti-NKp46 scFv.

A DNA sequence coding for a CH3/VH linker peptide having the amino acid sequence STGS was designed in order to insert a specific SalI restriction site at the CH3-VH Junction. The domain arrangement of the final polypeptide In shown in FIG. 2 (star In the CH2 domain indicates an optional N297S mutation), where the anti-CD3 scFv is replaced by an anti-NKp46 scFv. The (VK-VH) units include a linker between the VH and VK domains. Proteins were cloned, produced and purified as in Example 2-1. The amino acid sequences of the bispecific polypeptides (complete sequence (mature protein)) are shown in the corresponding SEQ ID NOS listed in the table 3 below.

TABLE 1

Amino acid sequences of different anti-NKp46 scFv

| scFv anti-NKp46 | scFV sequence (VHVK)/- stop |
|---|---|
| NKp46-1 | STGSQVQLQQSGPELVKPGASVKMSCKASGYTFTDYVINWGKQRSGQGLEWIGEI YPGSGTNYYNEKFKAKATLTADKSSNIAYMQLSSLTSEDSAVYFCARRGRYGLYA MDYWGQGTSVTVSSVEGGSGGSGGSGGSGGVDDIQMTQTTSSLSASLGDRVTISC RASQDISNYLNWYQQKPDGTVKLLIYYTSRLHSGVPSRFSGSGSGTDYSLTINNL EQEDIATYFCQQGNTRPWTFGGGTKLEIK- (SEQ ID NO: 119) |
| NKp46-2 | STGSEVQLQESGPGLVKPSQSLSLTCTVTGYSITSDYAWNWIRQFPGNKLEWMGY ITYSGSTSYNPSLESRISITRDTSTNQFFLQLNSVTTEDTATYYCARGGYYGSSW GVFAYWGQGTLVTVSAVEGGSGGSGGSGGSGGVDDIQMTQSPASLSASVGETVTI TCRVSENIYSYLAWYQQKQGKSPQLLVYNAKTLAEGVPSRFSGSGSGTQFSLKIN SLQPEDEGSYYCQHHYGTPWTEGGGTKLEIK- (SEQ ID NO: 120) |
| NKp46-3 | STGSEVQLQQSGPELVKPGASVKISCKTSGYTFTEYTMHWVKQSHGKSLEWIGGI SPNIGGTSYNQKFKGKATLTVDKSSSTAYMELRSLTSEDSAVYYCARRGGSFDYW GQGTTLTVSSVEGGSGGSGGSGGSGGVDDIVMTQSPATLSVTPGDRVSLSCRASQ SISDYLHWYQQKSHESPRLLIKYASQSISGIPSRFSGSGSGSDFTLSINSVEPED VGVYYCQNGHSFPLTFGAGTKLELK- (SEQ ID NO: 121) |
| NKp46-4 | STGSQVQLQQSAVELARPGASVKMSCKASGYTFTSFTMHWVKQRPGQGLEWIGYI NPSSGYTEYNQKFKDKTTLTADKSSSTAYMQLDSLTSDDSAVYYCVRGSSRGFDY WGQGTLVTVSAVEGGSGGSGGSGGSGGVDDIQMIQSPASLSVSVGETVTITCRAS ENIYSNLAWFQQKQGKSPQLLVYAATNLADGVPSRFSGSGSGTQYSLKINSLQSE DFGIYYCQHFWGTPRTFGGGTKLEIK- (SEQ ID NO: 122) |
| NKp46-6 | STGSQVQLQQPGSVLVRPGASVKLSCKASGYTFTSSWMHWAKQRPGQGLEWIGHI HPNSGISNYNEKFKGKATLTVDTSSSTAYVDLSSLTSEDSAVYYCARGGRFDDWG AGTTVTVSSVEGGSGGSGGSGGSGGVDDIVMTQSPATLSVTPGDRVSLSCRASQS ISDYLHWYQQKSHESPRLLIKYASQSISGIPSRFSGSGSGSDFTLSINSVEPEDV GVYYCQNGHSFLMYTEGGGTKLEIK- (SEQ ID NO: 123) |
| NKp46-9 | STGSDVQLQESGPGLVKPSQSLSLTCTVTGYSITSDYAWNWIRQFPGNKLEWMGY ITYSGSTNYNPSLKSRISITRDTSKNQFFLQLNSVTTEDTATYYCARCWDYALYA MDCWGQGTSVTVSSVEGGSGGSGGSGGSGGVDDIQMTQSPASLSASVGETVTITC RTSENIYSYLAWCQQKQGKSPQLLVYNAKTLAEGVPSRFSGSGSGTHFSLKINSL QPEDFGIYYCQHHYDTPLTFGAGTKLELK- (SEQ ID NO: 124) |
| Bab281 | STGSQIQLVQSGPELQKPGETVKISCKASGYTFTNYGMNWVKQAPGKGLKWMGWI NTNTGEPTYAEEFKGRFAFSLETSASTAYLQINNLKNEDTATYFCARDYLYYFDY WGQGTTLTVSSVEGGSGGSGGSGGSGGVDNIVMTQSPKSMSMSVGERVTLTCKAS ENVVTYVSWYQQKPEQSPKLLIYGASNRYTGVPDRFTGSGSATDFTLTISSVQAE DLADYHCGQGYSYPYTFGGGTKLEIK- (SEQ ID NO: 125) |

TABLE 2

DNA sequences corresponding to the different anti-NKp46 scFv

| scFv anti-NKp46 | scFV sequences |
|---|---|
| NKp46-1 | SEQ ID NO: 126 |
| NKp46-2 | SEQ ID NO: 127 |
| NKp46-3 | SEQ ID NO: 128 |
| NKp46-4 | SEQ ID NO: 129 |
| NKp46-6 | SEQ ID NO: 130 |
| NKp46-9 | SEQ ID NO: 131 |
| Bab281 | SEQ ID NO: 132 |

Format 1 (F1) (Anti-CD19-IgG1-Fcmono-Anti-NKp46 (scFv))

The domain structure of Format 1 (F1) is shown in FIG. 6A. A bispecific Fc-containing polypeptide was constructed based on an scFv specific for the tumor antigen CD19 (anti-CD19 scFv) and an scFV specific for the NKp46 receptor. The polypeptide is a single chain polypeptide having domains arranged (N- to C-terminal) as follows: (VK-VH)$^{anti\text{-}CD19}$-CH2-CH3-(VH-VK)$^{anti\text{-}NKp46}$

TABLE 3

| Sequence | SEQ ID NO |
|---|---|
| CD19-F1-NKp46-1 | 133 |
| CD19-F1-NKp46-2 | 134 |
| CD19-F1-NKp46-3 | 135 |
| CD19-F1-NKp46-4 | 136 |
| CD19-F1-NKp46-6 | 137 |
| CD19-F1-NKp46-9 | 138 |
| CD19-F1-Bab281 | 139 |

Format 2 (F2): CD19-F2-NKp46-3

The domain structure of F2 polypeptides is shown In FIG. 6A. The DNA and amino acid sequences for the monomeric CH2-CH3 Fc portion were as in Example 2-1 containing CH3 domain mutations (the mutations (EU numbering) L351K, T366S, P395V, F405R, T407A and K409Y. The heterodimer is made up of:
  (1) a first (central) polypeptide chain having domains arranged as follows (N- to C-terminal):
    (VK-VH)$^{anti-CD19}$-CH2-CH3-VH$^{anti-NKp46}$-CH1
  and
  (2) a second polypeptide chain having domains arranged as follows (N- to C-terminal): VK$^{anti-NKp46}$-CK.

The (VK-VH) unit was made up of a VH domain, a linker and a VK unit (i.e. an scFv). As with other formats of the bispecific polypeptides, the DNA sequence coded for a CH3/VH linker peptide having the amino acid sequence STGS designed in order to insert a specific SalI restriction site at the CH3-VH junction. Proteins were cloned, produced and purified as in Example 2-1. The amino acid sequences for the first and second chains of the F2 protein are shown in SEQ ID NO: 140 and 141.

Format 3 (F3): CD19-F3-NKp46-3

The domain structure of F3 polypeptides is shown in FIG. 6A. The DNA and amino acid sequences for the CH2-CH3 Fc portion comprised a tandem CH3 domain in which the two CH3 domains on the same polypeptide chain associated with one another, thereby preventing dimerization between different bispecific proteins.

The single chain polypeptide has domains arranged (N- to C-terminal) as follows: (VK-VH)$^{anti-CD19}$-CH2-CH3-CH3-(VH-VK)$^{anti-NKp46}$ The (VK-VH) units were made up of a VH domain, a linker and a VK unit (scFv). Proteins were cloned, produced and purified as in Example 2-1. Bispecific protein was purified from cell culture supernatant by affinity chromatography using prot-A beads and analysed and purified by SEC. The protein showed a high production yield of 3.4 mg/L and with a simple SEC profile. The amino acid sequence for the F3 protein is shown in SEQ ID NO: 142.

Format 4 (F4): CD19-F4-NKp46-3

The domain structure of F4 polypeptides is shown in FIG. 6A. The DNA and amino acid sequences for the CH2-CH3 Fc portion comprised a tandem CH3 domain as in Format F3, however additionally comprising a N297S mutation to prevent N-linked glycosylation and abolish FcγR binding. Proteins were cloned, produced and purified as in Example 2-1. Bispecific proteins was purified from cell culture supernatant by affinity chromatography using prot-A beads and analysed and purified by SEC. The protein showed a good production yield of 1 mg/L and with a simple SEC profile. The amino acid sequence for the F4 protein with NKp46-3 variable domains is shown in SEQ ID NO: 143.

Format 8 (F8)

The domain structure of F8 polypeptides is shown in FIG. 6B. The DNA and amino acid sequences for the monomeric CH2-CH3 Fc portion were as in Format F2 containing CH3 domain mutations (the mutations (EU numbering) L351K, T366S, P395V, F405R, T407A and K409Y, as well as a N297S mutation to prevent N-linked glycosylation and abolish FcγR binding. Three variants of F8 proteins were produced: (a) cysteine residues in the hinge region left intact (wild-type, referred to as F8A), (b) cysteine residues in the hinge region replaced by serine residues (F8B), and (c) a linker sequence GGGSS SEQ ID NO. 190 replacing residues DKTHTCPPCP in the hinge (F8C). Variants F8B and F8C provided advantages in production by avoiding formation of homodimers of the central chain. The heterotrimer is made up of;
  (1) a first (central) polypeptide chain having domains arranged as follows (N- to C-terminal):
    VH$^{anti-CD19}$-CH1-CH2-CH3-VH$^{anti-NKp46}$-CK
  and
  (2) a second polypeptide chain having domains arranged as follows (N- to C-terminal): VK$^{anti-NKp46}$-CH1
  and
  (3) a third polypeptide chain having domains arranged as follows (N- to C-terminal):
    VK$^{anti-CD19}$-CK Proteins were cloned, produced and purified as in Example 2-1. Bispecific proteins was purified from cell culture supernatant by affinity chromatography using prot-A beads and analysed and purified by SEC. The protein showed a high production yield of 3.7 mg/L (F8C) and with a simple SEC profile. The amino acid sequences of the three chains of the F8 protein (C variant) with NKp46-3 variable regions are shown in SEQ ID NOS: 144,145 and 146.

Format 9 (F9): CD19-F9-NKp46-3

The F9 polypeptide is a trimeric polypeptide having a central polypeptide chain and two polypeptide chains each of which associate with the central chain via CH1-CK dimerization. The domain structure of the trimeric F9 protein is shown in FIG. 6B, wherein the bonds between the CH1 and CK domains are interchain disulfide bonds. The two antigen binding domains have a F(ab) structure permitting the use of antibodies irrespective of whether they remain functional in scFv format. The DNA and amino acid sequences for the CH2-CH3 Fc portion comprised a tandem CH3 domain as in Format F4 and a CH2 domain comprising a N297S substitution. Three variants of F9 proteins were produced: (a) cysteine residues in the hinge region left intact (wild-type, referred to as F9A), (b) cysteine residues in the hinge region replaced by serine residues (F9B), and (c) a linker sequence GGGSS SEQ ID NO. 190 replacing residues DKTHTCPPCP SEQ ID NO. 195 in the hinge (F9C). Variants F9B and F9C provided advantages in production by avoiding formation of homodimers of the central chain. The heterotrimer is made up of:
  (1) a first (central) polypeptide chain having domains arranged as follows (N- to C-terminal):
    VH$^{anti-CD19}$-CH1-CH2-CH3-CH3-VH$^{anti-NKp46}$-CK
  and
  (2) a second polypeptide chain having domains arranged as follows (N- to C-terminal): VK$^{anti-NKp46}$-CH1
  and
  (3) a third polypeptide chain having domains arranged as follows (N- to C-terminal):
    VK$^{anti-CD19}$-CK Proteins were cloned, produced and purified as in Example 2-1. Bispecific proteins was purified from cell culture supernatant by affinity chromatography using prot-A beads and analysed and purified by SEC. The protein showed a high production yield of 8.7 mg/L (F9A) and 3.0 mg/L (F9B), and with a simple SEC profile.

The amino acid sequences of the three chains of the F9 protein variant F9A are shown in the SEQ ID NOS: 147, 148 and 149. The amino acid sequences of the three chains of the F9 protein variant F9B are shown in the SEQ ID NOS: 150, 151 and 152. The amino acid sequences of the three chains of the F9 protein variant F9C are shown in the SEQ ID NOS: 153, 154 and 155.

Format 10 (F10): CD19-F10-NKp46-3

The F10 polypeptide is a dimeric protein having a central polypeptide chain and a second polypeptide chain which associates with the central chain via CH1-CK dimerization. The domain structure of the dimeric F10 proteins is shown in FIG. 6B wherein the bonds between the CH1 and CK domains are interchain disulfide bonds. One of the two antigen binding domains has a Fab structure, and the other is a scFv. The DNA and amino acid sequences for the CH2-CH3 Fc portion comprised a tandem CH3 domain as in Format F4 and a CH2 domain with a N297S substitution. Additionally, three variants of F10 proteins were produced: (a) cysteine residues in the hinge region left intact (wild-type, referred to as F10A), (b) cysteine residues in the hinge region replaced by serine residues (F10B, and (c) a linker sequence GGGSS SEQ ID NO. 190 replacing residues DKTHTCPPCP SEQ ID NO. 195 in the hinge (F10C). Variants F10B an F10C provided advantages in production by avoiding formation of homodimers of the central chain. The (VK-VH) unit was made up of a VH domain, a linker and a VK unit (scFv). The heterodimer is made up of:
(1) a first (central) polypeptide chain having domains arranged as follows (N- to C-terminal):
VH$^{anti\text{-}CD19}$-CH1-CH2-CH3-CH3-(VH-VK)$^{anti\text{-}NKp46}$
and
(2) a second polypeptide chain having domains arranged as follows (N- to C-terminal):
VK$^{anti\text{-}CD19}$-CK.

Proteins were cloned, produced and purified as in Example 2-1. Bispecific proteins was purified from cell culture supernatant by affinity chromatography using prot-A beads and analysed and purified by SEC. The protein showed a good production yield of 2 mg/L (F10A) and with a simple SEC profile. The amino acid sequences of the two chains of the F10A protein variant are shown in the SEQ ID NOS: 156 (second chain) and 157 (first chain). The amino acid sequences of the two chains of the F10B protein variant are shown in the SEQ ID NOS: 158 (second chain) and 159 (first chain). The amino acid sequences of the two chains of the F10C protein variant are shown in the SEQ ID NOS: 160 (second chain) and 161 (first chain).

Format 11 (F11): CD19-F11-NKp46-3

Figure 6C:
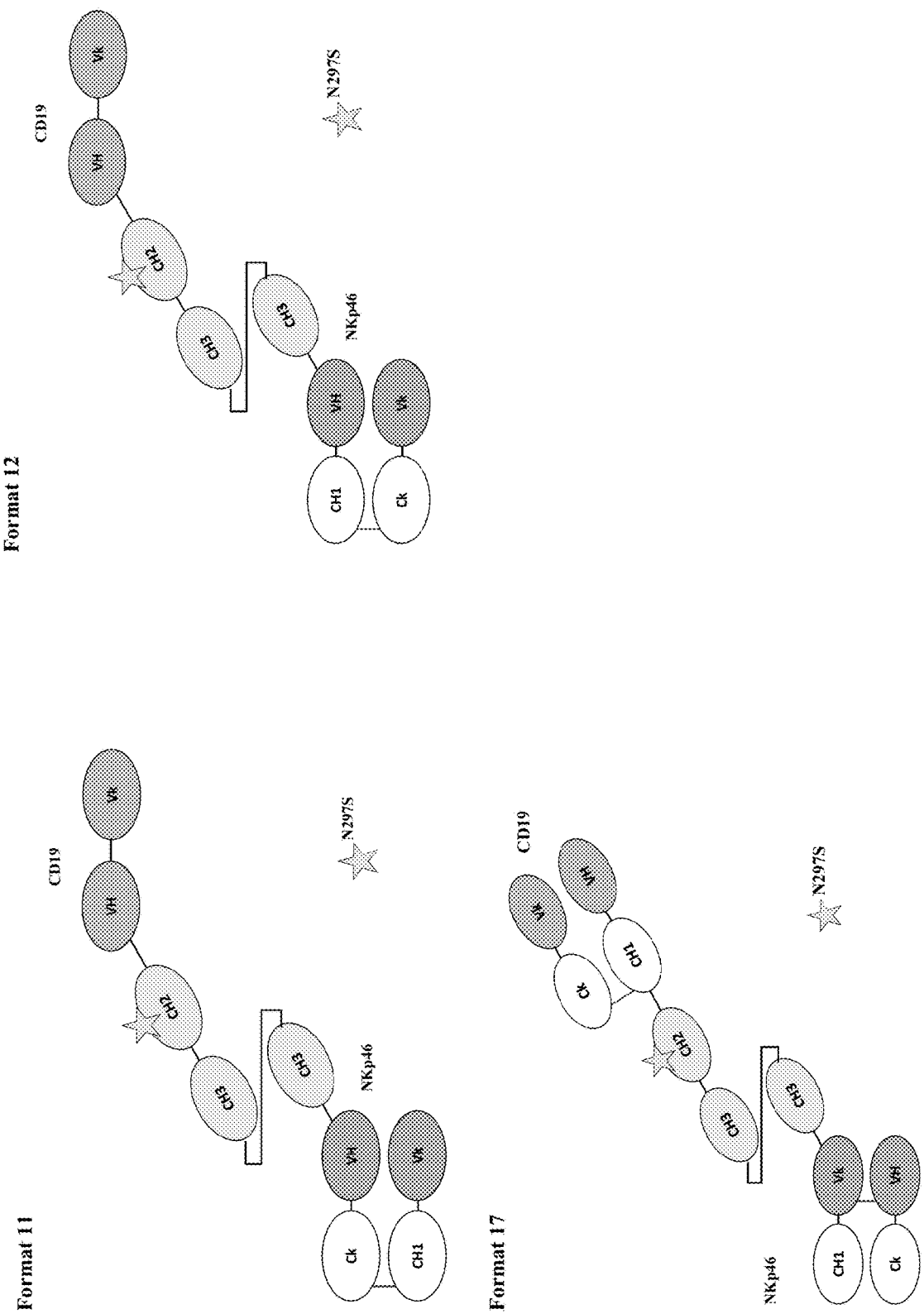

The domain structure of F11 polypeptides is shown in FIG. 6C. The heterodimeric protein is similar to F10 but the structures of the antigen binding domains are reversed. One of the two antigen binding domains has a Fab-like structure, and the other is a scFv. The heterodimer is made up of
(1) a first (central) polypeptide chain having domains arranged as follows (N- to C-terminal):
(VK-VH)$^{anti\text{-}CD19}$-CH2-CH3-CH3-VH$^{anti\text{-}NKp46}$-CK
and
(2) a second polypeptide chain having domains arranged as follows (N- to C-terminal): VK$^{anti\text{-}NKp46}$-CH1.

Proteins were cloned, produced and purified as in Example 2-1. Bispecific proteins was purified from cell culture supernatant by affinity chromatography using prot-A beads and analysed and purified by SEC. The protein showed a good production yield of 2 mg/L and with a simple SEC profile. The amino acid sequences of the two chains of the F11 protein are shown in SEQ ID NO: 162 (chain 1) and SEQ ID NO: 163 (chain 2).

Format 12 (F12): CD19-F12-NKp46-3

The domain structure of the dimeric F12 polypeptides is shown in FIG. 6C, wherein the bonds between the CH1 and CK domains are disulfide bonds. The heterodimeric protein is similar to F11 but the CH1 and CK domains within the F(ab) structure are inversed. The heterodimer is made up of:
(1) a first (central) polypeptide chain having domains arranged as follows (N- to C-terminal):
(VK-VH)$^{anti\text{-}CD19}$-CH2-CH3-CH3-VH$^{anti\text{-}NKp46}$-CH1
and
(2) a second polypeptide chain having domains arranged as follows (N- to C-terminal): VK$^{anti\text{-}NKp46}$-CK.

Proteins were cloned, produced and purified as in Example 2-1. Bispecific proteins was purified from cell culture supernatant by affinity chromatography using prot-A beads and analysed and purified by SEC. The protein showed a good production yield of 2.8 mg/L and with a simple SEC profile. The DNA and amino acid sequences for the F12 protein are shown below. The amino acid sequences of the two chains of the F12 protein are shown in SEQ ID NO: 164 (chain 1) and SEQ ID NO: 165 (chain 2).

Format 17 (F17): CD19-F17-NKp46-3

The domain structure of the trimeric F17 polypeptides is shown in FIG. 6C, wherein the bonds between the CH1 and CK domains are disulfide bonds. The heterodimeric protein is similar to F9 but the VH and VK domains, and the CH1 and CK, domains within the C-terminal F(ab) structure are each respectively inversed with their partner. The heterotrimer is made up of:
(1) a first (central) polypeptide chain having domains arranged as follows (N- to C-terminal):
VH$^{anti\text{-}CD19}$-CH1-CH2-CH3-CH3-VK$^{anti\text{-}NKp46}$-CH1
and
(2) a second polypeptide chain having domains arranged as follows (N- to C-terminal): VH$^{anti\text{-}NKp46}$-CK
and
(3) a third polypeptide chain having domains arranged as follows (N- to C-terminal):
VK$^{anti\text{-}CD19}$-CK Additionally, three variants of F17 proteins were produced: (a) cysteine residues in the hinge region left intact (wild-type, referred to as F17A), (b) cysteine residues in the hinge region replaced by serine residues (F10B, and (c) a linker sequence GGGSS replacing residues DKTHTCPPCP in the hinge (F17C). Proteins were cloned, produced and purified as in Example 2-1. The amino acid sequences of the three chains of the F17B protein are shown in SEQ ID NOS: 166, 167 and 168.

Example 4

Bispecific NKp46 Antibody Formats with Dimeric Fc Domains

New protein constructions with dimeric Fc domains were developed that share advantages of the monomeric Fc domain proteins of Example 3 but bind to FcRn with greater affinity, but which also have low or substantially lack of binding to FcγR. The polypeptide formats were tested to investigate the functionality of heterodimeric proteins comprising a central chain with a (VH-(CH1/CK)-CH2-CH3-) unit or a (VK-(CH1 or CK)-CH2-CH3-) unit. One of both of the CH3 domains will then be fused, optionally via intervening amino acid sequences or domains, to a variable domain(s) (a single variable domain that associates with a variable domain on a separated polypeptide chain, a tandem variable domain (e.g., an scFv), or a single variable domain that is capable of binding antigen as a single variable domain. The two chains then associate by CH1-CK dimerization to form disulfide linked dimers, or if associated with a third chain, to form trimers. Members of this family of formats may have less conformational flexibility compared to native antibodies or other bispecific constructs.

Different constructs were made for use in the preparation of a bispecific antibody using the variable domains DNA and amino acid sequences derived from the scFv specific for tumor antigen CD19 described in Example 2-1 and different variable regions from antibodies specific for NKp46 Identified in Example 1. Proteins were cloned, produced and purified as in Example 2-1. Domains structures are shown in FIGS. 6A-6D.

Format 5 (F5): CD19-F5-NKp46-3

Figure 6D:
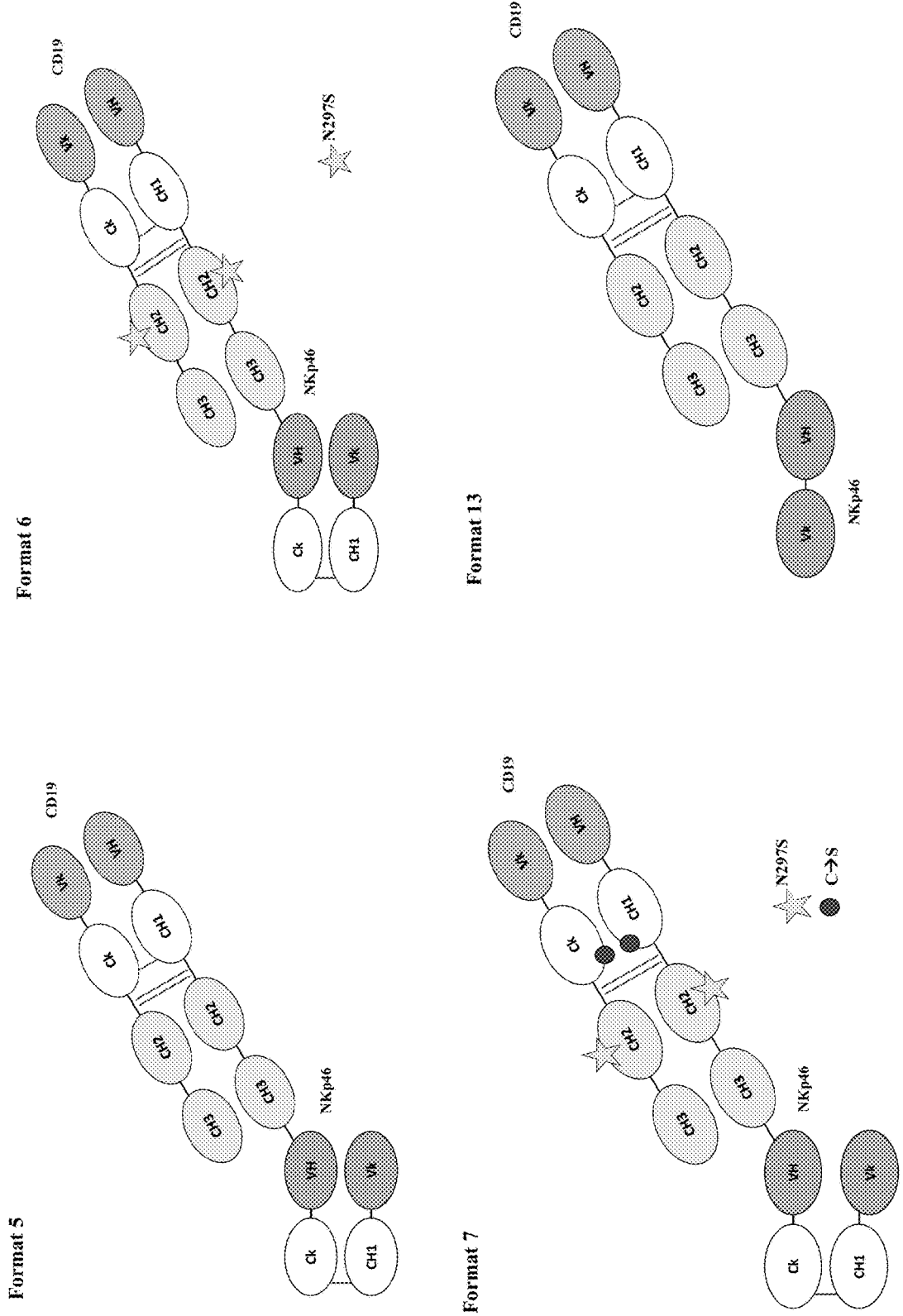

The domain structure of the trimeric F5 polypeptide is shown in FIG. 6D, wherein the interchain bonds between hinge domains (indicated in the figures between CH1/CK and CH2 domains on a chain) and interchain bonds between the CH1 and CK domains are Interchain disulfide bonds. The heterotrimer is made up of:
(1) a first (central) polypeptide chain having domains arranged as follows (N- to C-terminal):
$VH^{anti-CD19}$-CH1-CH2-CH3-$VH^{anti-NKp46}$-CK
and
(2) a second polypeptide chain having domains arranged as follows (N- to C-terminal): $VK^{anti-CD19}$-CK-CH2-CH3
and
(3) a third polypeptide chain having domains arranged as follows (N- to C-terminal):
$VK^{anti-NKp46}$-CH1

Proteins were cloned, produced and purified as in Example 2-1. Bispecific proteins was purified from cell culture supernatant by affinity chromatography using prot-A beads and analysed and purified by SEC. The protein showed a high production yield of 37 mg/L and with a simple SEC profile. The amino acid sequences of the three polypeptide chains are shown In SEQ ID NOS 169 (second chain), 170 (first chain) and 171 (third chain).

Format 6 (F6): CD19-F6-NKp46-3

The domain structure of heterotrimeric F6 polypeptides is shown In FIG. 6D. The F6 protein is the same as F5, but with a N297S substitution to avoid N-linked glycosylation. Proteins were cloned, produced and purified as in Example 2-1. Bispecific proteins was purified from cell culture supernatant by affinity chromatography using prot-A beads and analysed and purified by SEC. The protein showed a high production yield of 12 mg/L and with a simple SEC profile. The amino acid sequences of the three polypeptide chains are shown in SEQ ID NOS: 172 (second chain), 173 (first chain) and 174 (third chain).

Format 7 (F7): CD19-F7-NKp46-3

The domain structure of heterotrimeric F7 polypeptides is shown in FIG. 6D. The F7 protein is the same as F6, but with cysteine to serine substitutions in the CH1 and CK domains that are linked at their C-termini to the Fc domains, to prevent formation of a minor population of dimeric species of the central chain with the $VK^{anti-NKp46}$-CH1 chain. Proteins were cloned, produced and purified as in Example 2-1. Bispecific proteins was purified from cell culture supernatant by affinity chromatography using prot-A beads and analysed and purified by SEC. The protein showed a high production yield of 11 mg/L and with a simple SEC profile. The amino acid sequences of the three polypeptide chains are shown in SEQ ID NOS: 175 (second chain), 176 (first chain) and 177 (third chain).

Format 13 (F13): CD19-F13-NKp46-3

The domain structure of the dimeric F13 polypeptide is shown in FIG. 6D, wherein the interchain bonds between hinge domains (indicated between CH1/CK and CH2 domains on a chain) and interchain bonds between the CH1 and CK domains are interchain disulfide bonds. The heterodimer is made up of:
(1) a first (central) polypeptide chain having domains arranged as follows (N- to C-terminal):
$VH^{anti-CD19}$-CH1-CH2-CH3-$(VH-VK)^{anti-NKp46}$
and
(2) a second polypeptide chain having domains arranged as follows (N- to C-terminal): $VK^{anti-CD19}$-CK-CH2-CH3.

The (VH-VK) unit was made up of a VH domain, a linker and a VK unit (scFv).

Proteins were cloned, produced and purified as in Example 2-1. Bispecific proteins was purified from cell culture supernatant by affinity chromatography using prot-A beads and analysed and purified by SEC. The protein showed a high production yield of 6.4 mg/L and with a simple SEC profile. The amino acid sequences of the two polypeptide chains are shown in SEQ ID NOS: 178 (second chain) and 179 (first chain).

Format 14 (F14): CD19-F14-NKp46-3

Figure 6E:
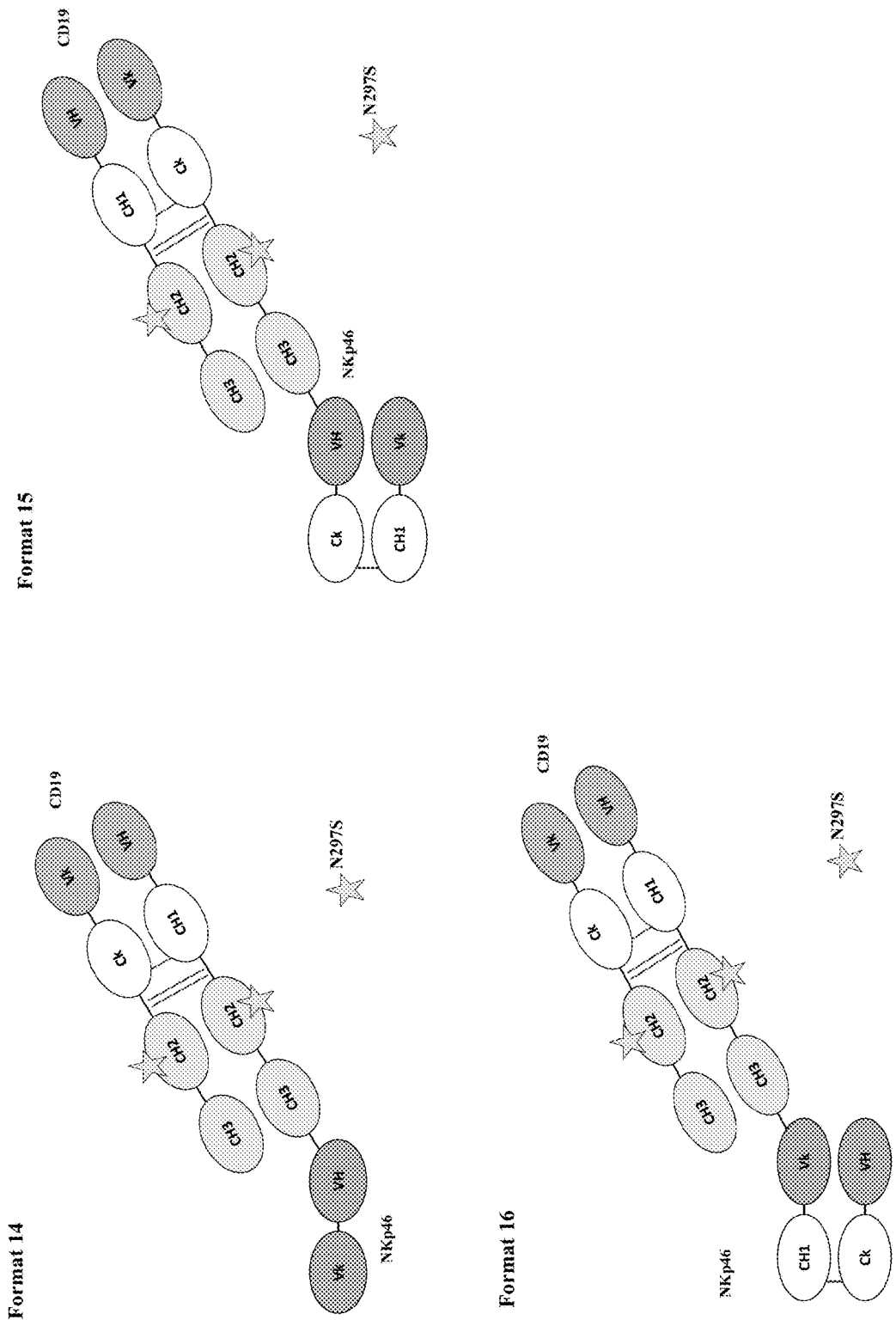

The domain structure of the dimeric F14 polypeptide is shown in FIG. 6E. The F14 polypeptide is a dimeric polypeptide which shares the structure of the F13 format, but instead of a wild-type Fc domain (CH2-CH3), the F14 has CH2 domain mutations N297S to abolish N-iinked glycosylation. Proteins were cloned, produced and purified as in Example 2-1. Bispecific proteins was purified from cell culture supernatant by affinity chromatography using prot-A beads and analysed and purified by SEC. The protein showed a high production yield of 2.4 mg/L and with a simple SEC profile. The amino acid sequences of the two polypeptide chains are shown in SEQ ID NOS: 180 (second chain) and 181 (first chain).

Format 15 (F15): CD19-F15-NKp46-3

The domain structure of the trimeric F15 polypeptides is shown in FIG. 6E. The F15 polypeptide is a dimeric polypeptide which shares the structure of the F6 format, but differs by Inversion of the N-terminal VH-CH1 and VK-CK units between the central and second chains. Proteins were cloned, produced and purified as in Example 2-1. Bispecific proteins was purified from cell culture supernatant by affinity chromatography using prot-A beads and analysed and purified by SEC. The protein showed a good production yield of 0.9 mg/L and with a simple SEC profile. The amino acid sequences of the three polypeptide chains are shown in SEQ ID NOS: 182 (second chain), 183 (first chain) and 184 (third chain).

Format 16 (F16): CD19-F16-NKp46-3

The domain structure of the trimeric F16 polypeptide is shown in FIG. 6E. The F16 polypeptide is a dimeric polypeptide which shares the structure of the F6 format, but differs by inversion of the C-terminal VH-CK and VK-CH1 units between the central and second chains. Proteins were cloned, produced and purified as in Example 2-1. The amino acid sequences of the three polypeptide chains are shown in SEQ ID NOS: 185 (second chain), 186 (first chain) and 187 (third chain).

Example 5

NKp46 Binding Affinity by Bispecific Proteins by Surface Plasmon Resonance (SPR)

Biacore T100 General Procedure and Reagents

SPR measurements were performed on a Biacore T100 apparatus (Biacore GE Healthcare) at 25° C. In all Biacore experiments HBS-EP+(Biacore GE Healthcare) and NaOH 10 mM served as running buffer and regeneration buffer respectively. Sensorgrams were analyzed with Biacore T100 Evaluation software. Protein-A was purchase from (GE Healthcare). Human NKp46 recombinant proteins were cloned, produced and purified at Innate Pharma.

Immobilization of Protein-A

Protein-A proteins were immobilized covalently to carboxyl groups in the dextran layer on a Sensor Chip CM5. The chip surface was activated with EDC/NHS (N-ethyl-N'-(3-dimethylaminopropyl) carbodiimidehydrochloride and N-hydroxysuccinimide (Biacore GE Healthcare)). Protein-A was diluted to 10 µg/ml in coupling buffer (10 mM acetate, pH 5.6) and Injected until the appropriate Immobilization level was reached (i.e. 2000 RU). Deactivation of the remaining activated groups was performed using 100 mM ethanolamine pH 8 (Biacore GE Healthcare).

Binding Study

The bispecific proteins were first tested in Format F1 described in Example 2 having different anti-NKp46 variable regions from NKp46-1, NKp46-2, NKp46-3 or NKp46-4 antibodies. Antibodies were next tested as different formats F3, F4, F5, F6, F9, F10, F11, F13, F14 having the anti-NKp46 variable regions from the NKp46-3 antibody, and compared to the NKp46-3 antibody as a full-length human IgG1.

Bispecific proteins at 1 µg/mL were captured onto Protein-A chip and recombinant human NKp46 proteins were injected at 5 µg/mL over captured bispecific antibodies. For blank subtraction, cycles were performed again replacing NKp46 proteins with running buffer.

The Bab281 antibody was separately tested for binding to NKp46 by SPR, and additionally by flow cytometry using a cell line expressing the human NKp46 construct at the cell surface. For FACS screening, the presence of reacting antibodies in supernatants was revealed by Goat anti-mouse polyclonal antibody (pAb) labeled with PE. SPC and FACS results showed that the Bab281 based antibody did not bind the NKp46 cell line or NKp46-Fc proteins. Bab281 lost binding to its target when presented in the bispecific format.

Affinity Study

Monovalent affinity study was done following a regular Capture-Kinetic protocol recommended by the manufacturer (Biacore GE Healthcare kinetic wizard). Seven serial dilutions of human NKp46 recombinant proteins, ranging from 6.25 to 400 nM were sequentially injected over the captured BI-Specific antibodies and allowed to dissociate for 10 min before regeneration. The entire sensorgram sets were fitted using the 1:1 kinetic binding model.

Results

SPR showed that the bispecific polypeptides of format F1 having the NKp46-1, 2, 3 and 4 scFv binding domains bound to NKp46, while other bispecific polypeptides having the scFv of other anti-NK46 antibodies did not retain NKp46 binding. The binding domains that did not retain binding in monomeric bispecific format initially bound to NKp46 but lost binding upon conversion to the bispecific format. All of the bispecific polypeptides of formats F1, F2 F3, F4, F5, F6, F9, F10, F11, F13, F14 retained binding to NKp46 when using the NKp46-3 variable regions.

Figure 7B:
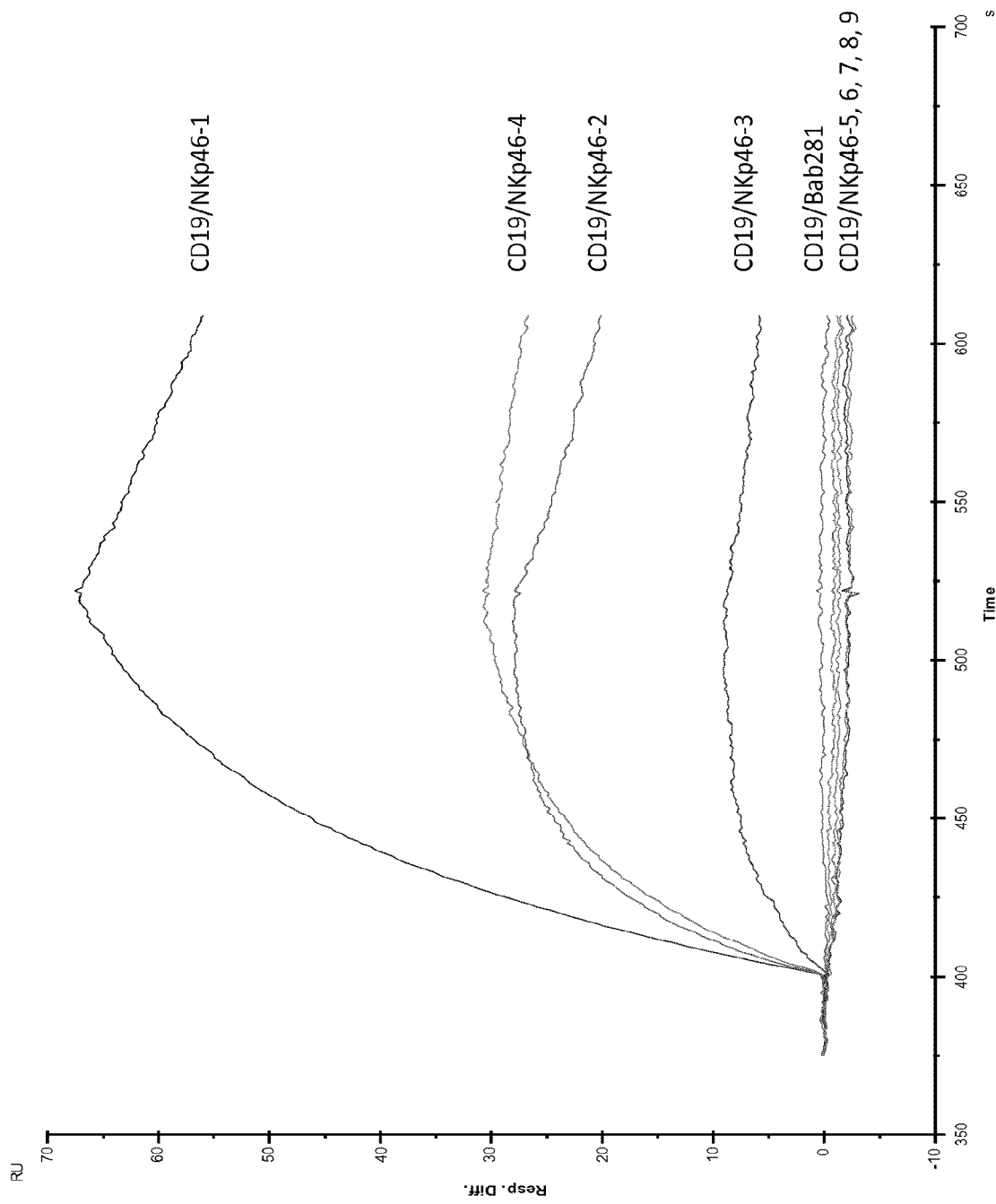
FIG. 7B shows superimposed substracted sensorgrams showing the binding of NKp46 recombinant proteins to the captured bispecific monomeric polypeptide.

FIG. 7A shows representative superimposed sensorgrams showing the raw data curves, sample (CD19-F1-NKp46-1) and blank (Buffer), which were used to generate each subtracted sensorgrams of FIG. 7B. Subtracted sensorgrams were obtained by subtracting the blank sensorgram to the sample sensorgram. Sensorgrams were aligned to zero in the y and x axis at the capture step injection start before blank subtraction.

FIG. 7B shows representative superimposed substracted sensorgrams showing the binding of CD19-F1-NKp46-1 recombinant proteins to the captured bispecific monomeric polypeptide. Sensorgrams were aligned to zero In the y and x axis at the sample step injection start.

Monovalent affinities and kinetic association and dissociation rate constants are shown below In the table 3 below.

TABLE 3

| Bispecific mAb | ka (1/Ms) | kd (1/s) | KD (M) |
|---|---|---|---|
| CD19-F1-Bab281 | n/a | n/a | n/a (loss of binding) |
| CD19-F1-NKp46-1 | 1.23E+05 | 0.001337 | 1.09E−08 |
| CD19-F1-NKp46-2 | 1.62E+05 | 0.001445 | 8.93E−09 |
| CD19-F1-NKp46-3 | 7.05E+04 | 6.44E−04 | 9.14E−09 |
| CD19-F1-NKp46-4 | 1.35E+05 | 6.53E−04 | 4.85E−09 |
| CD19-F3-NKp46-3 | 3.905E+5 | 0.01117 | 28E−09 |
| CD19-F4-NKp46-3 | 3.678E+5 | 0.01100 | 30E−09 |
| CD19-F5-NKp46-3 | 7.555E+4 | 0.00510 | 67E−09 |
| CD19-F6-NKp46-3 | 7.934E+4 | 0.00503 | 63E−09 |
| CD19-F9A-NKp46-3 | 2.070E+5 | 0.00669 | 32E−09 |
| CD19-F10A-NKp46-3 | 2.607E+5 | 0.00754 | 29E−09 |
| CD19-F11A-NKp46-3 | 3.388E+5 | 0.01044 | 30E−09 |
| CD19-F13-NKp46-3 | 8.300E+4 | 0.00565 | 68E−09 |
| CD19-F14-NKp46-3 | 8.826E+4 | 0.00546 | 62E−09 |
| NKp46-3 IgG1 | 2.224E+5 | 0.00433 | 20E−09 |

Example 6

Engagement of NK Cells Against Daudi Tumor Target with Fc-Containing NKp46×CD19 Bispecific Protein Bispecific antibodies having a monomeric Fc domain and a domain arrangement according to the single chain F1 or dimeric F2 formats described In Example 3, and a NKp46 binding region based on NKp46-1, NKp46-2, NKp46-3 or NKp46-4 were tested for functional ability to direct NK cells to lyse 0019-positive tumor target cells (Daudi, a well characterized B lymphoblast cell line). The F2 proteins additionally Included NKp46-9 variable regions which lost binding to NKp46 in the scFv format but which retained binding in the F(ab)-like format of F2.

Briefly, the cytolytic activity of each of (a) resting human NK cells, and (b) human NK cell line KHYG-1 transfected with human NKp46, was assessed in a classical 4-h $^{51}$Cr-release assay in U-bottom 96 well plates. Daudi cells were labelled with $^{51}$Cr (50 µCi (1.85 MBq)/1×10$^6$ Cells), then mixed with KHYG-1 transfected with hNKp46 at an effector/target ratio equal to 50 for KHYG-1, and 10 (for F1 proteins) or 8.8 (for F2 proteins) for resting NK cells, in the presence of monomeric bi-specific antibodies at different concentrations. After brief centrifugation and 4 hours of incubation at 37° C., samples of supernatant were removed and transferred into a LumaPlate (Perkin Elmer Life Sciences, Boston, MA), and $^{51}$Cr release was measured with a TopCount NXT beta detector (PerkinElmer Life Sciences, Boston, MA). All experimental conditions were analyzed in triplicate, and the percentage of specific lysis was determined as follows: 100×(mean cpm experimental release−mean cpm spontaneous release)/(mean cpm total release−mean cpm spontaneous release). Percentage of total release is obtained by lysis of target cells with 2% Triton X100 (Sigma) and spontaneous release corresponds to target cells in medium (without effectors or Abs).

Results

In the KHYG-1 hNKp46 NK experimental model, each bi-specific antibody NKp46-1, NKp46-2, NKp46-3, NKp46-4 or NKp46-9 induced specific lysis of Daudi cells by human KHYG-1 hNKp46 NK cell line compared to negative controls (Human IgG1 isotype control (IC) and CD19/CD3 bi-specific antibodies), thereby showing that these antibodies induce Daudi target cell lysis by KHYG-1 hNKp46 through CD19/NKp46 cross-linking.

Figure 8A:
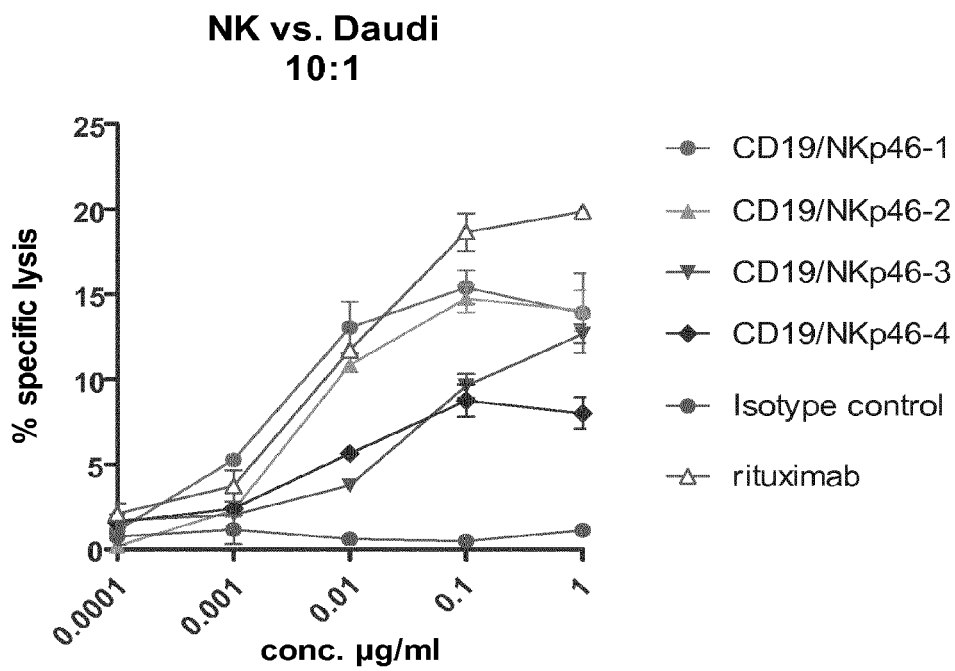
FIGS. 8A and 8B show respectively bispecific F1 and F2 antibodies having NKp46 binding region based on NKp46-1, NKp46-2, NKp46-3 or NKp46-4 are able to direct resting NK cells to their CD19-positive Daudi tumor target cells, while isotype control antibody did not lead to elimination of the Daudi cells. Rituximab (RTX) served as positive control of ADCC, where the maximal response obtained with RTX (at 10 μg/ml in this assay) was 21.6% specific lysis.
Figure 8B:
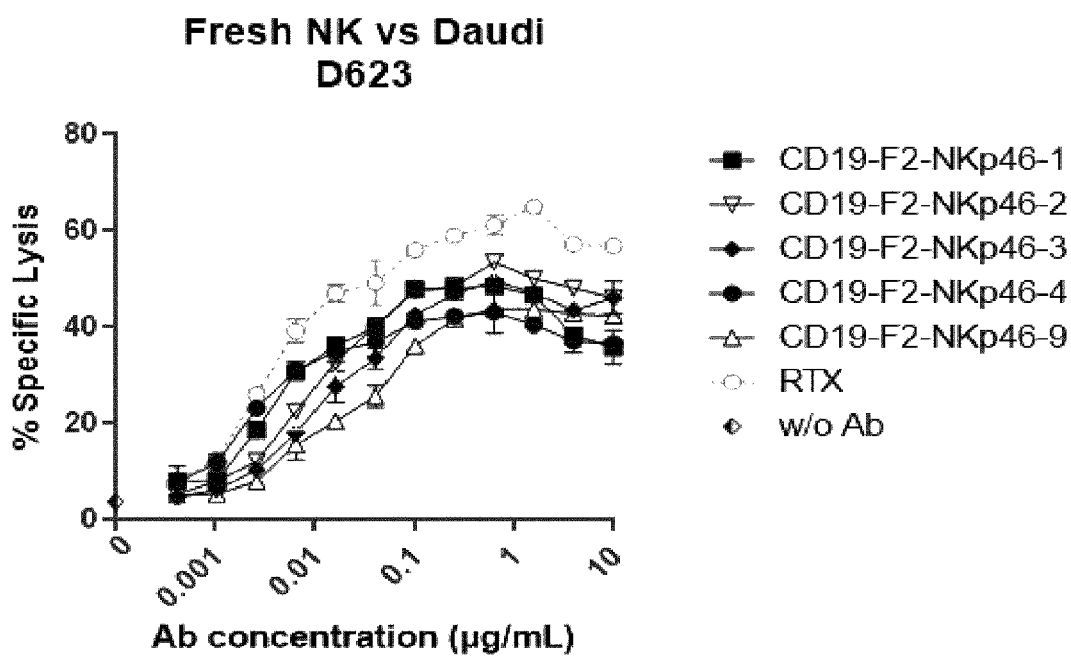

When resting NK cells were used as effectors, each bi-specific antibody NKp46-1, NKp46-2, NKp46-3, NKp46-4 or NKp46-9 again induced specific lysis of Daudi cells by human NK cells compared to negative control (Human IgG1 isotype control (IC) antibody), thereby showing that these antibodies Induce Daudi target cell lysis by human NK cells through CD19/NKp46 cross-linking. Rituximab (RTX, chimeric IgG1) was used as a positive control of ADCC (Antibody-Dependent Cell Cytotoxicity) by resting human NK cells. The maximal response obtained with RTX (at 10 µg/ml in this assay) was 21.6% specific lysis illustrating that the bispecific antibodies have high target cell lysis activity. Results for experiments with resting NK cells are shown in FIG. 8A for the single chain F1 proteins and 8B for the dimeric F2 proteins.

Example 7

Comparison with Full Length Anti-NKp46 mAbs and Depleting Anti-Tumor mAbs: Only NKp46×CD19 Bispecific Proteins Prevent Non-Specific NK Activation These studies aimed to investigate whether bispecific antibodies can mediate NKp46-mediated NK activation toward cancer target cells without triggering non-specific NK cell activation.

NKp46×CD19 bispecific proteins having an arrangement according to the F2 format described in Example 3 with anti-NKp46 variable domains from NKp46-1, NKp46-2, NKp46-3, NKp46-4 or NKp46-9 were compared to:

(a) full-length monospecific anti-NKp46 antibodies (NKp46-3 as human IgG1), and (b) the anti-CD19 antibody as a full-length human IgG1 as ADCC Inducing antibody comparator.

The experiments further included as controls: rituximab, an anti-CD20 ADCC Inducing antibody control for a target antigen with high expression levels; anti-CD52 antibody alemtuzumab, a human IgG1, binds CD52 target present on both targets and NK cells; and negative control isotype control therapeutic antibody (a human IgG1 that does not bind a target present on the target cells (HUG1-IC).

The different proteins were tested for functional effect on NK cell activation in the presence of CD19-positive tumor target cells (Daudi cells), in the presence of CD19-negative, CD16-positive target cells (HUT78 T-lymphoma cells), and in the absence of target cells.

Briefly, NK activation was tested by assessing CD69 and CD107 expression on NK cells by flow cytometry. The assay was carried out in 96 U well plates in completed RPMI, 150 µL final/well. Effector cells were fresh NK cells purified from donors. Target cells were Daudi (CD19-positive), HUT78 (CD19-negative) or K562 (NK activation control cell line). In addition to K562 positive control, three conditions were tested, as follows:

NK cell alone
NK cells vs Daudi (CD19+)
NK cells vs HUT78 (CD19−)

Effector:Target (E:T) ratio was 2.5: 1 (50 000 E:20 000 T), with an antibody dilution range starting to 10 µg/mL with 1/4 dilution (n=8 concentrations). Antibodies, target cells and effector cells were mixed; spun 1 min at 300 g; incubated 4h at 37° C.; spun 3 min at 500 g; washed twice with Staining Buffer (SB); added 50 µL of staining Ab mix; incubated 30 min at 300 g; washed twice with SB resuspended pellet with CellFix; stored overnight at 4° C.; and fluorescence revealed with Canto II (HTS).

Results

1. NK Cells Alone

Results are shown in FIG. 9A. In the absence of target-antigen expressing cells, none of the bispecific anti-NKp46× anti-CD19 antibody (including each of the NKp46-1, NKp46-2, NKp46-3, NKp46-4 and NKp46-9 variable regions) activated NK cells as assessed by CD69 or CD107 expression. Full-length anti-CD19 also did not activate NK cells. However, the full-length anti-NKp46 antibodies caused detectable activation of NK cells. Alemtuzumab also induced activation of NK cells, at a very high level. Isotype control antibody did not Induce activation.

2. NK Cells Vs Daudi (CD19+)

Results are shown in FIG. 9B. In the presence of target-antigen expressing cells, each of the bispecific anti-NKp46× anti-CD19 antibodies (Including each of the NKp46-1, NKp46-2, NKp46-3, NKp46-4 and NKp46-9 binding domains) activated NK cells. Full-length anti-CD19 showed at best only very low activation of NK cells. Neither full-length anti-NKp46 antibodies or alemtuzumab showed substantial Increase In activation beyond what was observed in presence of NK cells alone. FIG. 9 shows full-length anti-NKp46 antibodies showed a similar level of baseline activation observed in presence of NK cells alone. Alemtuzumab also induced activation of NK cells a similar level of activation observed in presence of NK cells alone, and at higher antibody concentrations in this setting (ET 2.5:1) the activation was greater than with the bispecific anti-NKp46×anti-CD19 antibody. Isotype control antibody did not induce activation.

3. NK Cells Vs HUT78 (CD19−)

Figure 9C:
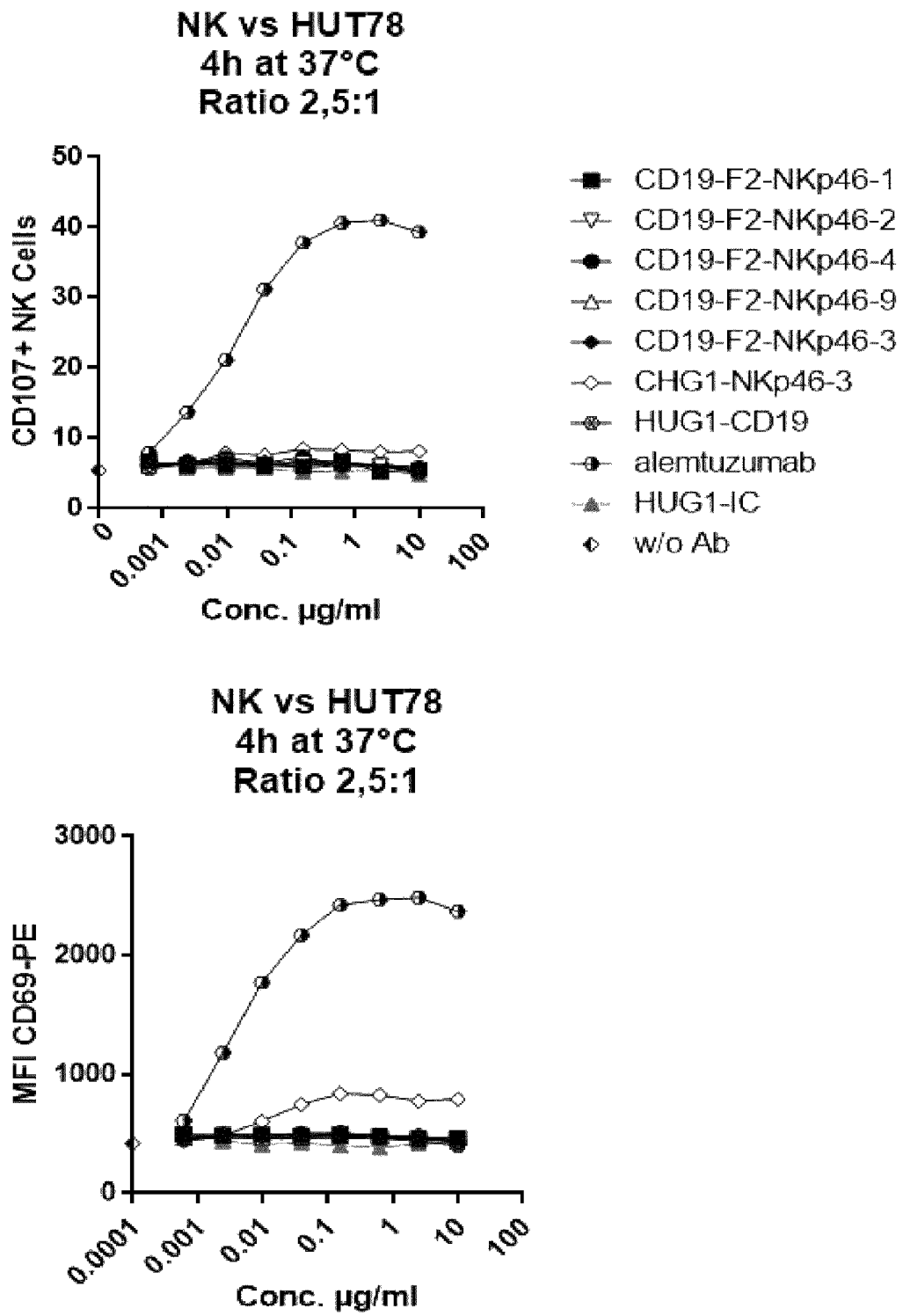
FIG. 9C shows that In the presence of CD19-negative HUT78 cells, none of the bispecific anti-NKp46×anti-CD19 antibody (including each of the NKp46-1, NKp46-2, NKp46-3 or NKp46-4 variable regions) activated NK cells. However, the full-length anti-NKp46 antibodies and alemtuzumab caused detectable activation of NK cells at a similar level observed in presence of NK cells alone. Isotype control antibody did not induce activation.

Results are shown in FIG. 9C. In the presence of target-antigen-negative HUT78 cells, none of the bispecific anti-NKp46×anti-CD19 antibody (including each of the NKp46-1, NKp46-2, NKp46-3, NKp46-4 and NKp46-9 variable regions) activated NK cells. However, the full-length anti-NKp46 antibodies and alemtuzumab caused detectable activation of NK cells at a similar level observed in presence of NK cells alone. Isotype control antibody did not induce activation.

In conclusion, the bispecific anti-NKp46 proteins are able to activate NK cells in a target-cell specific manner, unlike full-length monospecific anti-NKp46 antibodies and full-length antibodies of depleting IgG isotypes which also activate NK cells in the absence of target cells. The NK cell activation achieved with anti-NKp46 bispecific proteins was higher than that observed with full length anti-CD19 IgG1 antibodies.

Example 8

Comparative Efficacy with Depleting Anti-Tumor mAbs: NKp46×CD19 Bispecific Proteins at Low ET Ratio These studies aimed to investigate whether bispecific antibodies can mediate NKp46-mediated NK cell activation toward cancer target cells at lower effector:target ratios. The ET ratio used in this Example was 1:1 which is believed to be closer to the setting that would be encountered in vivo than the 2.5:1 ET ratio used in Example 7 or the 10:1 ET ratio of Example 6.

NKp46×CD19 bispecific proteins having an arrangement according to the F2 format described in Example 3 with anti-NKp46 variable domains from NKp46-1, NKp46-2, NKp46-3, NKp46-4 or NKp46-9 were compared to:
(a) full-length monospecific anti-NKp46 antibodies (NKp46-3 as human IgG1), and
(b) the anti-CD19 antibody as a full-length human IgG1 as ADCC inducing antibody control comparator.

The experiments further included as controls: rituximab (an anti-CD20 ADCC inducing antibody control for a target antigen with high expression levels); anti-CD52 antibody alemtuzumab (a human IgG1, binds CD52 target present on both targets and NK cells), and negative control isotype control therapeutic antibody (a human IgG1 that does not bind a target present on the target cells (HUG1-IC). The different proteins were tested for functional effect on NK cell activation as assessed by CD69 or CD107 expression in the presence of CD19-positive tumor target cells (Daudi cells), in the presence of CD19-negative, CD16-positive target cells (HUT78 T-lymphoma cells), and in the absence of target cells. The experiments were carried out as in Example 7 except that the ET ratio was 1:1.

Results

Figure 10A:
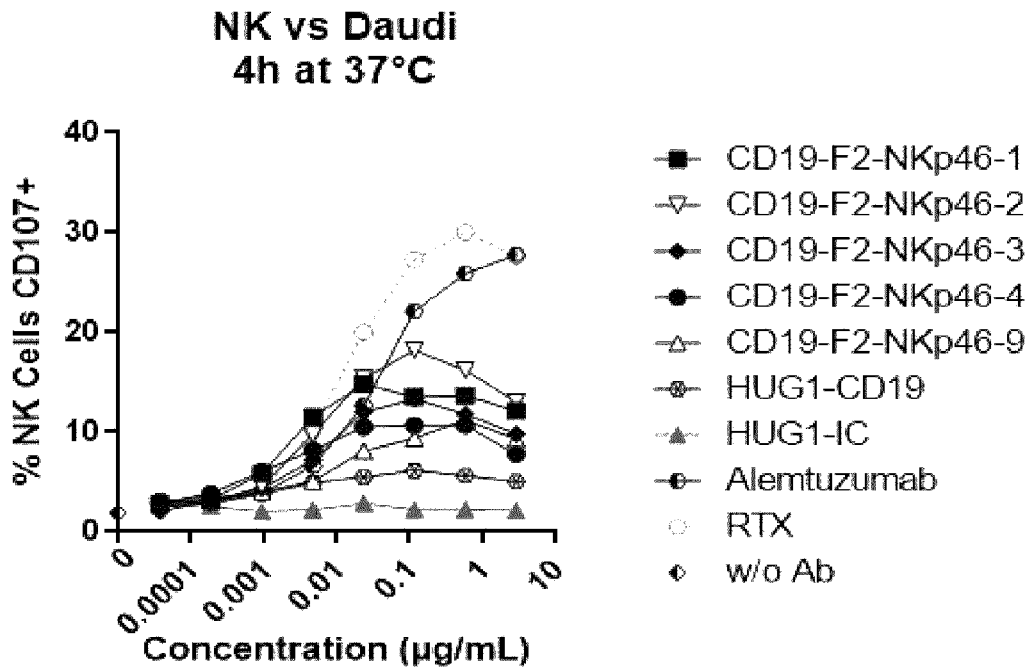
FIGS. 10A and B shows that at low effector:target ratio of 1:1 each of the bispecific anti-NKp46×anti-CD19 antibody activated NK cells in the presence of Daudi cells, and that bispecific anti-NKp46×anti-CD19 were far more potent than the anti-CD19 antibody as a full-length human IgG1 as ADCC inducing antibody.
Figure 10B:
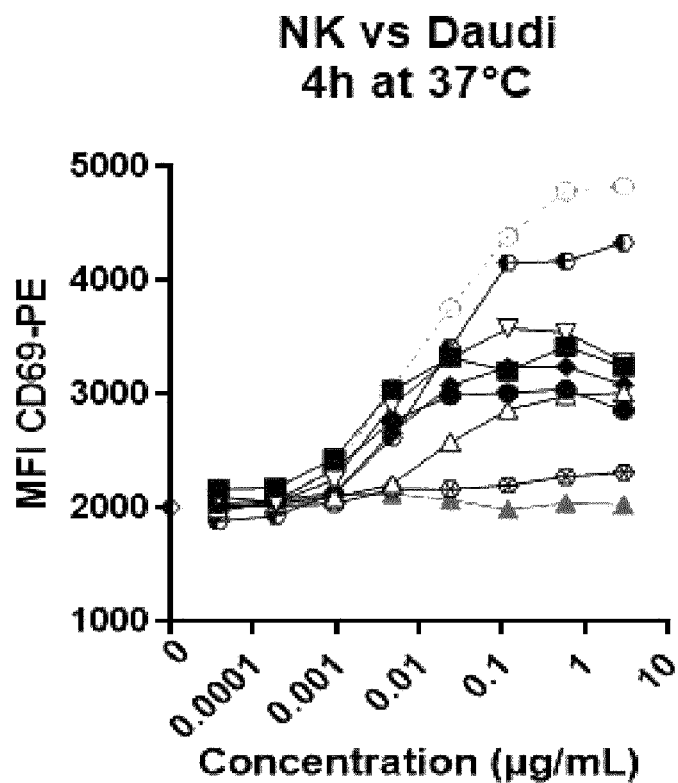

Results are shown in FIG. 10 (10A: CD107 and 10B: CD69). In the presence of target-antigen expressing cells, each of the bispecific anti-NKp46×anti-CD19 antibody (including each of the NKp46-1, NKp46-2, NKp46-3, NKp46-4 and NKp46-9 variable regions) activated NK cells in the presence of Daudi cells.

The activation Induced by bispecific anti-NKp46×anti-CD19 antibody In the presence of Daudi cells was far more potent than the full-length human IgG1 anti-CD19 antibody as ADCC inducing antibody which had low activity in this setting. Furthermore, in this low E:T ratio setting the activation Induced by bispecific anti-NKp46×anti-CD19 antibody was as potent as anti-CD20 antibody rituximab, with a difference being observed only at the highest concentrations that were 10 fold higher than concentrations in which differences were observed at the 2.5:1 ET ratio.

In the absence of target cells or in the in the presence of target antigen-negative HUT78 cells, full-length anti-NKp46 antibodies and alemtuzumab showed a similar level of baseline activation observed in the presence of Daudi cells. Anti-NKp46×anti-CD19 antibody did not activate NK cells in presence of HUT78 cells.

In conclusion, the bispecific anti-NKp46 proteins are able to activate NK cells in a target-cell specific manner and at lower effector:target ratio are more effective in mediating NK cell activation that traditional human IgG1 antibodies.

Example 9

Mechanism of Action Studies

NKp46×CD19 bispecific proteins having an arrangement according to the F2, F3, F5 or F6 formats described in Examples 3 or 4 with anti-NKp46 variable domains from NKp46-3 were compared to rituximab (anti-CD20 ADCC inducing antibody), and a human IgG1 isotype control antibody for functional ability to direct CD16−/NKp46+NK cell lines to lyse CD19-positive tumor target cells.

Briefly, the cytolytic activity of the CD16−/NKp46+ human NK cell line KHYG-1 was assessed in a classical 4-h $^{51}$Cr-release assay in U-bottom 96 well plates. Daudi or B221 cells were labelled with $^{51}$Cr (50 µCi (1.85 MBq)/1× 10$^6$ cells), then mixed with KHYG-1 at an effector/target ratio equal to 50:1, in the presence of test antibodies at dilution range starting from 10$^{-7}$ mol/L with 1/5 dilution (n=8 concentrations)

After brief centrifugation and 4 hours of incubation at 37° C., 50 µL of supernatant were removed and transferred into a LumaPlate (Perkin Elmer Life Sciences, Boston, MA), and $^{51}$Cr release was measured with a TopCount NXT beta detector (PerkinElmer Life Sciences, Boston, MA). All experimental conditions were analyzed in triplicate, and the percentage of specific lysis was determined as follows: 100×(mean cpm experimental release−mean cpm spontaneous release)/(mean cpm total release−mean cpm spontaneous release). Percentage of total release is obtained by lysis of target cells with 2% Triton X100 (Sigma) and spontaneous release corresponds to target cells in medium (without effectors or Abs).

Results

Figure 11A:
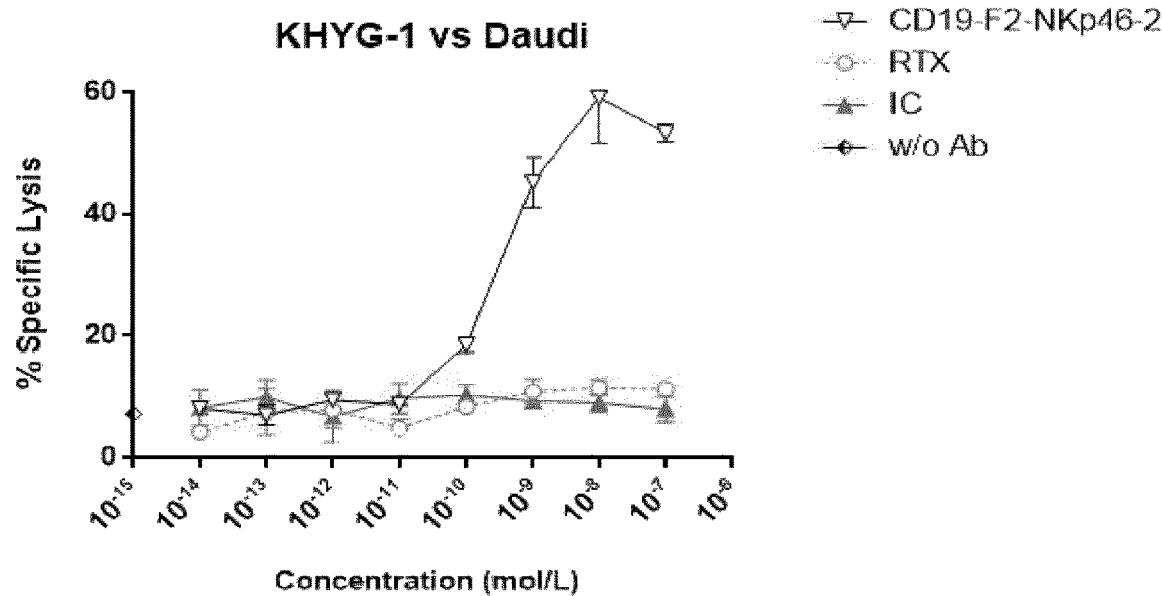
FIGS. 11A and 11B shows that each NKp46×CD19 bispecific protein (Format F3, F5 and F6) induced specific lysis of Daudi or B221 cells by human KHYG-1 CD16-negative hNKp46-positive NK cell line, while rituximab and human IgG1 isotype control (IC) antibodies did not.
Figure 11B:
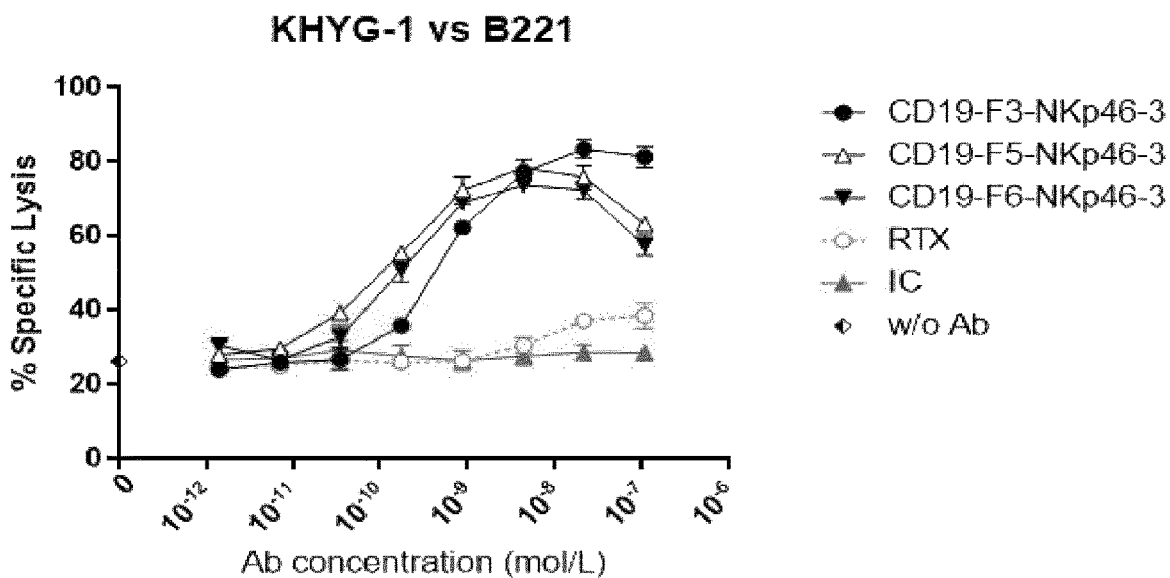
Figure 12A:
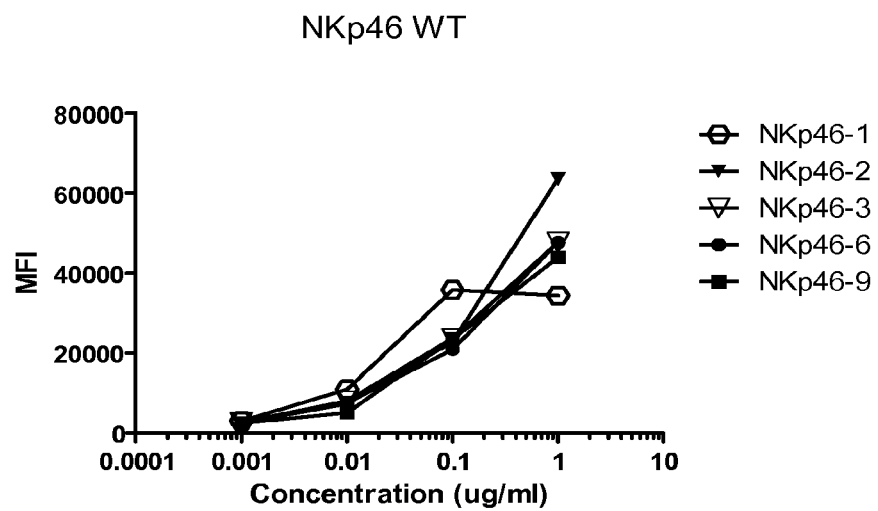
FIGS. 12A-12B, 13A-13B, 14A-14B, 15A-15B, 16A-16B, 17A-17B show binding of antibodies to different NKp46 mutants. Antibody NKp46-1 had decreased binding to the mutant 2 (FIG. 12B) compared to wild-type NKp46 (FIG. 12A), and decreased binding to the supplementary mutant Supp7 (FIG. 13B) compared to wild-type NKp46 (FIG. 13A). Antibody NKp46-3 had decreased binding to the mutant Supp8 (FIG. 14B) compared to wild-type NKp46 (FIG. 14A), and decreased binding to the supplementary mutant 19 (FIG. 15B) compared to wild-type NKp46 (FIG. 15A).
Figure 12B:
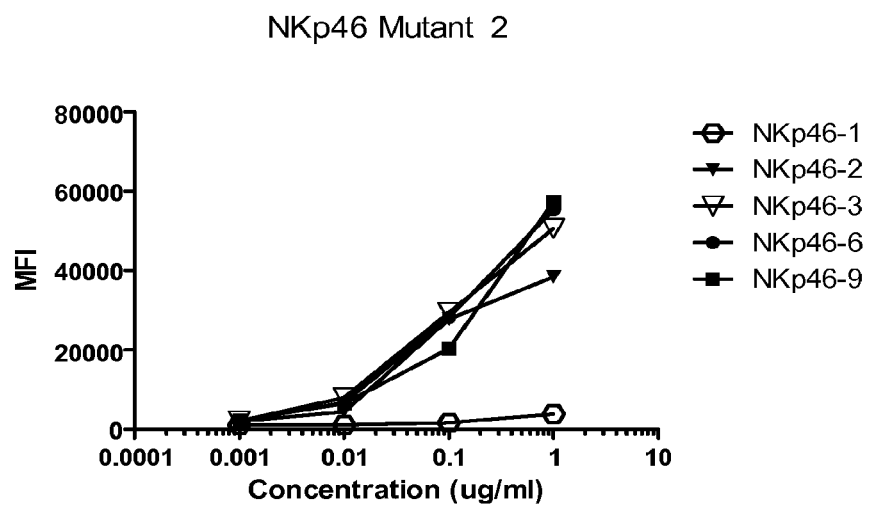
Figure 13A:
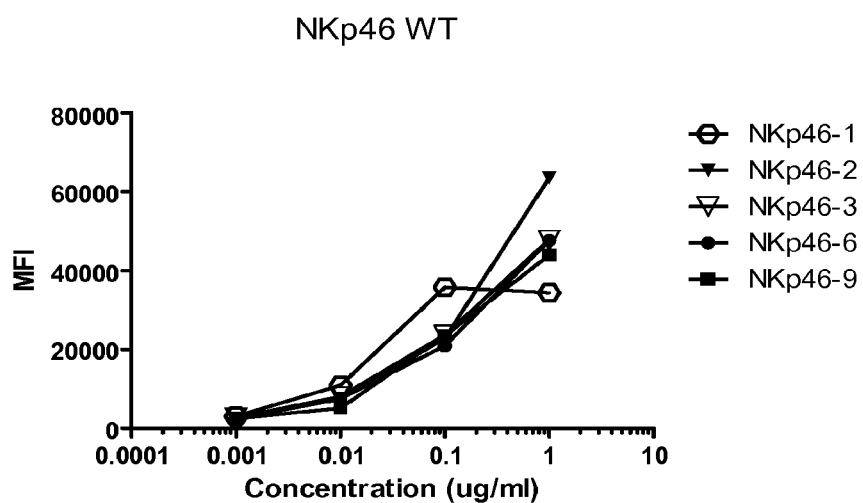
Figure 13B:
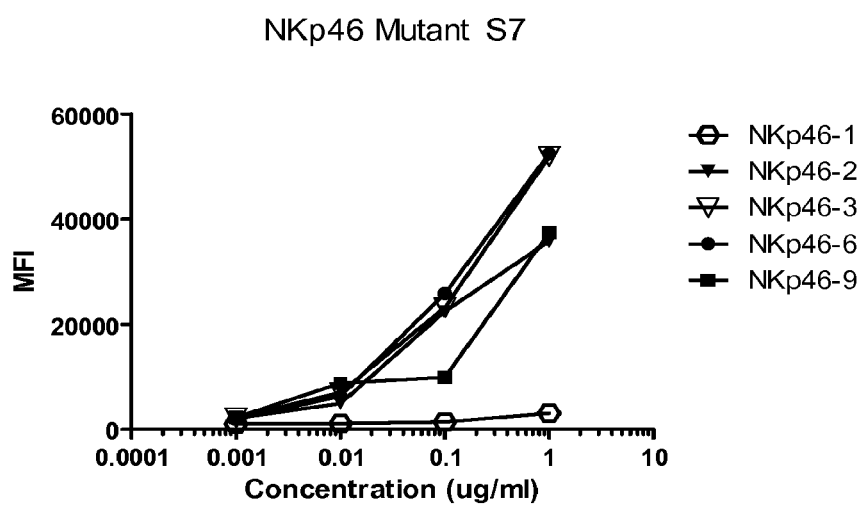

Results are shown In FIGS. 11A (KHYG-1 vs Daudi) and 11B (KHYG-1 vs B221). In the KHYG-1 hNKp46 NK experimental model, each NKp46×CD19 bispecific protein (Format F2, F3, F5 and F6) induced specific lysis of Daudi or B221 cells by human KHYG-1 hNKp46 NK cell line, while rituximab and human IgG1 isotype control (IC) antibodies did not.

Example 10

Binding of Different Bispecific Formats to FcRn

Affinity of different antibody formats for human FcRn was studied by Surface Plasmon Resonance (SPR) by immobilizing recombinant FcRn proteins covalently to carboxyl groups in the dextran layer on a Sensor Chip CM5, as described in Example 2-6.

A chimeric full length anti-CD19 antibody having human IgG1 constant regions and NKp46×CD19 bispecific proteins having an arrangement according to the F3, F4, F5, F6, F9, F10, F11, F13 or F14 formats described in Examples 3 or 4 with anti-NKp46 variable domains from NKp46-3 (NKp46-2 for F2) were tested; for each analyte, the entire sensorgram was fitted using the steady state or 1:1 SCK binding model.

Results are shown in Table 4 below. The bispecific proteins having dimeric Fc domains (formats F5, F6, F13, F14) bound to FcRn with affinity similar to that of the full-length IgG1 antibody. The bispecific proteins with monomeric Fc domains (F3, F4, F9, F10, F11) also displayed binding to FcRn, however with lower affinity that the bispecific proteins having dimeric Fc domains.

TABLE 4

| Antibody/Bispecific | SPR method | KD nM |
| --- | --- | --- |
| Human IgG1/K Anti-CD19 | SCK/Two state reaction | 7.8 |
| CD19-F5-NKp46-3 | SCK/Two state reaction | 2.6 |
| CD19-F6-NKp46-3 | SCK/Two state reaction | 6.0 |
| CD19-F13-NKp46-3 | SCK/Two state reaction | 15.2 |
| CD19-F14-NKp46-3 | SCK/Two state reaction | 14.0 |
| CD19-F3-NKp46-3 | Steady State | 474.4 |
| CD19-F4-NKp46-3 | Steady State | 711.7 |
| CD19-F9A-NKp46-3 | Steady State | 858.5 |
| CD19-F10A-NKp46-3 | Steady State | 432.8 |
| CD19-F11-NKp46-3 | Steady State | 595.5 |

Example 11

Binding to FcγR

Anti-CD19-F1-Anti-NKp46 having its CH2-CH3 domains placed between two antigen binding domains, here two scFv, was evaluated to assess whether such bispecific monomeric Fc protein could retain binding to Fcγ receptors.

Human IgG1 antibodies and CD19/NKp46-1 bi-specific antibodies were immobilized onto a CM5 chip. Recombinant FcγRs (cynomolgus monkey and human CD64, CD32a, CD32b, and CD16) were cloned, produced and purified at Innate Pharma. FIG. 18 shows superimposed sensorgrams showing the binding of *Macaca fascicularis* recombinant FcgRs (upper panels; CyCD64, CyCD32a, CYCD32b, CyCD16) and of Human recombinant FcgRs (lower panels; HuCD64, HuCD32a, HuCD32b, HuCD16a) to the immobilized human IgG1 control (grey) and CD19/NKp46-1 bi-specific antibody (black). Sensorgrams were aligned to zero in the y and x axis at the sample injection start.

FIG. 18 shows that while full length wild type human IgG1 bound to all cynomolgus and human Fcγ receptors, the CD19/NKp46-1 bi-specific antibodies did not bind to any of the receptors

Example 12

Epitope Mapping of Anti-NKp46 Antibodies

A. Competition Assays

Competition assays were conducted by Surface Plasmon Resonance (SPR according to the methods described below.
Biacore T100 General Procedure and Reagents SPR measurements were performed on a Biacore T100 apparatus (Biacore GE Healthcare) at 25° C. In all Biacore experiments HBS-EP+ (Biacore GE Healthcare) and NaOH 10 mM NaCl 500 mM served as running buffer and regeneration buffer respectively. Sensorgrams were analyzed with Biacore T100 Evaluation software. Anti-6×His tag antibody was purchased from QIAGEN. Human 6×His tagged NKp46 recombinant proteins (NKp46-His) were cloned, produced and purified at Innate Pharma.
Immobilization of Anti-6×His Tag Antibodies Anti-His antibodies were immobilized covalently to carboxyl groups in the dextran layer on a Sensor Chip CM5. The chip surface was activated with EDC/NHS (N-ethyl-N'-(3-dimethylaminopropyl) carbodiimidehydrochloride and N-hydroxysuccinimide (Biacore GE Healthcare)). Protein-A and Anti-His antibodies were diluted to 10 μg/ml in coupling buffer (10 mM acetate, pH 5.6) and injected until the appropriate immobilization level was reached (i.e. 2000 to 2500 RU). Deactivation of the remaining activated groups was performed using 100 mM ethanolamine pH 8 (Biacore GE Healthcare).
Competition Study Parental regular human IgG1 chimeric antibodies having NKp46 binding region corresponding to NKp46-1, NKp46-2, NKp46-3 or NKp46-4 were used for the competition study which has been performed using an Anti-6×His tag antibody chip.

Bispecific antibodies having NKp46 binding region based on NKp46-1, NKp46-2, NKp46-3 or NKp46-4 at 1 μg/mL were captured onto Protein-A chip and recombinant human NKp46 proteins were injected at 5 μg/mL together with a second test bispecific antibody of the NKp46-1, NKp46-2, NKp46-3 or NKp46-4 group.

None of NKp46-1, NKp46-2, NKp46-3 or NKp46-4 competed with one another for binding to NKp46, these antibodies each representing a different epitope.

B. Binding to NKp46 Mutants

In order to define the epitopes of anti NKp46 antibodies, we designed NKp46 mutants defined by one, two or three substitutions of amino acids exposed at the molecular surface over the 2 domains of NKp46. This approach led to the generation of 42 mutants transfected in Hek-293T cells, as shown in the table below. The targeted amino acid mutations in the table 5 below are shown both using numbering of SEQ ID NO: 1 (also corresponding to the numbering used In Jaron-Mendelson et al. (2012) J. Immunol. 88(12):6165-74.

TABLE 5

| Mutant | Substitution (Numbering according to Jaron-Mendelson and SEQ ID NO 1) | | |
|---|---|---|---|
| 1 | P40A | K43S | Q44A |
| 2 | K41S | E42A | E119A |
| 3 | P86A | D87A | |
| 4 | N89A | R91A | |
| 5 | K80A | K82A | |
| 5 bis | E34A | T46A | |
| 6 | R101A | V102A | |
| 7 | N52A | Y53A | |
| 8 | V56A | P75A | E76A |
| 9 | R77A | I78A | |
| 10 | S97A | I99A | |
| 10 bis | Q59A | H61A | |
| 11 | L66A | V69A | |
| 12 | E108A | | |
| 13 | N111A | L112A | |
| 14 | D114A | | |
| 15 | T125A | R145S | D147A |
| 16 | S127A | Y143A | |
| 17 | H129A | K139A | |
| 18 | K170A | V172A | |
| 19 | I135A | S136A | |
| 19 bis | T182A | R185A | |
| 20 | R160A | | |
| 21 | K207A | | |
| 22 | M152A | R166A | |
| 23 | N195A | N196A | |
| Stalk1 | D213A | I214A | T217A |
| Stalk2 | F226A | T233A | |
| Stalk3 | L236A | T240A | |
| Supp1 | F30A | W32A | |
| Supp2 | F62A | F67A | |
| Supp3 | E63A | Q95A | |
| Supp4 | R71A | K73A | |
| Supp5 | Y84A | | |
| Supp6 | E104A | L105A | |
| Supp7 | Y121A | Y194A | |
| Supp8 | P132A | E133A | |
| Supp9 | S151A | Y168A | |
| Supp10 | S162A | H163A | |
| Supp11 | E174A | P176A | |
| Supp12 | P179A | H184A | |
| Supp13 | R189A | E204A | P205A |

Generation of Mutants

NKp46 mutants were generated by PCR. The sequences amplified were run on agarose gel and purified using the Macherey Nagel PCR Clean-Up Gel Extraction kit (reference 740609). The two or three purified PCR products generated for each mutant were then ligated into an expression vector, with the ClonTech InFusion system. The vectors containing the mutated sequences were prepared as Miniprep and sequenced. After sequencing, the vectors containing the mutated sequences were prepared as Midiprep using the Promega PureYield™ Plasmid Midiprep System. HEK293T cells were grown in DMEM medium (Invitrogen), transfected with vectors using Invitrogen's Lipofectamine 2000 and incubated at 37° C. in a CO2 incubator for 24 hours prior to testing for transgene expression.

Flow Cytometry Analysis of Anti-NKp46 Binding to the HEK293T Transfected Cells

All the anti-NKp46 antibodies were tested for their binding to each mutant by flow cytometry. A first experiment was performed to determine antibodies that lose their binding to one or several mutants at one concentration (10 µg/ml). To confirm a loss of binding, titration of antibodies was done on antibodies for which binding seemed to be affected by the NKp46 mutations (1-0.1-0.01-0.001 µg/ml).

Results

Results are shown in FIGS. 12 to 17. Antibody NKp46-1 had decreased binding to the mutant 2 (having a mutation at residues K41, E42 and E119, as shown in FIG. 12A (NKp46wild-type) compared to 12B (mutant 2). Similarly, NKp46-1 also had decreased binding to the supplementary mutant Supp7 (having a mutation at residues Y121 and Y194, as shown in FIG. 13A (NKp46 wild-type) compared to 13B (mutant Supp7).

Figures 14A, 14B:
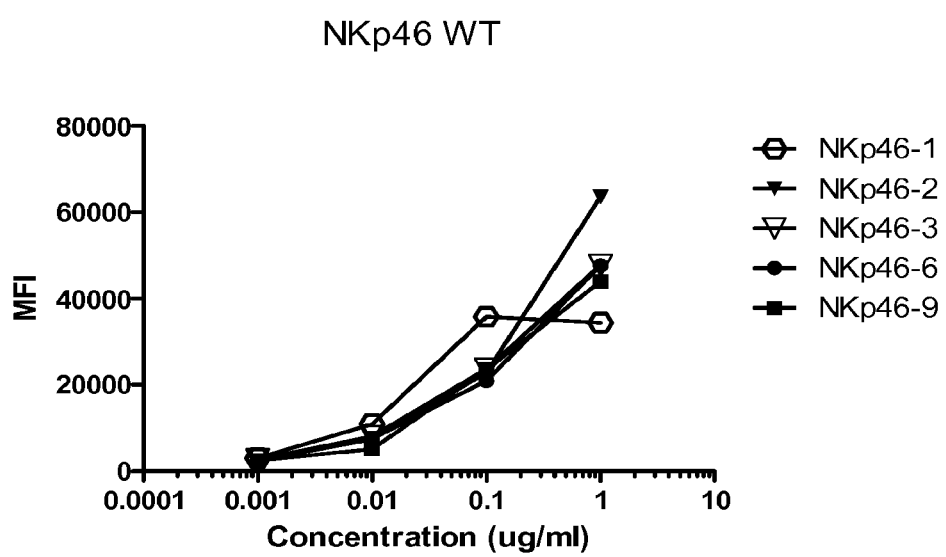
Figure 15A:
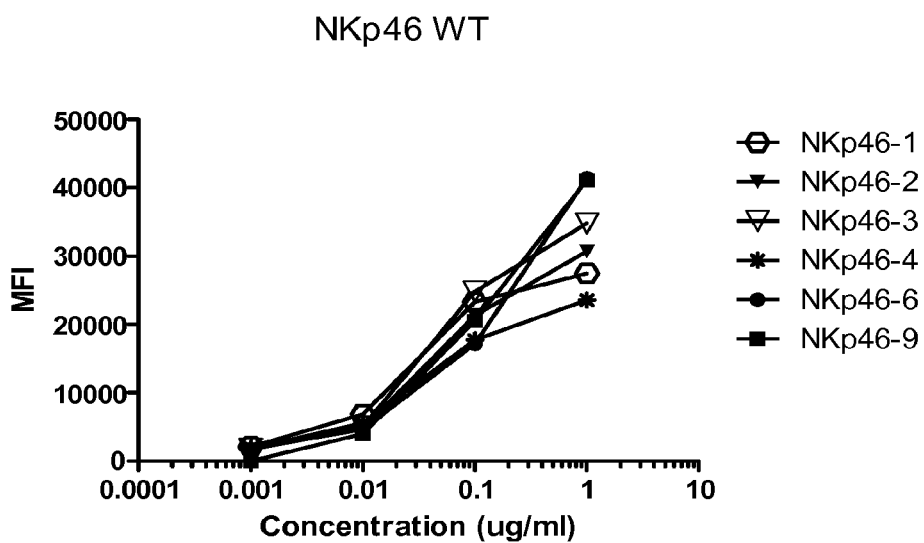
Figure 15B:
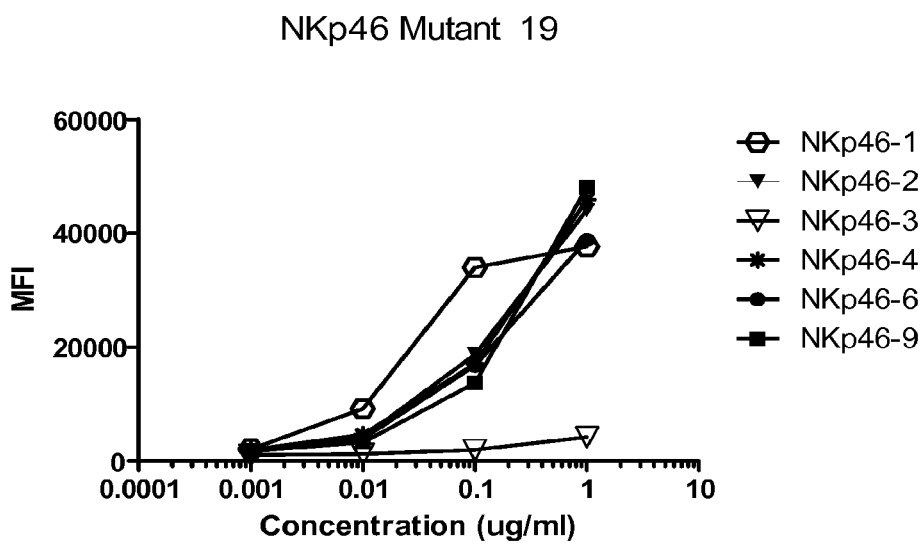

Antibody NKp46-3 had decreased binding to the mutant 19 (having a mutation at residues I135, and S136, as shown in FIG. 15A (NKp46 wild-type) compared to 15B (mutant 19). Similarly, NKp46-1 also had decreased binding to the supplementary mutant Supp8 (having a mutation at residues P132 and E133, as shown in FIG. 14A (NKp46 wild-type) compared to 14B (mutant Supp8).

Antibody NKp46-4 had decreased binding to the mutant 6 (having a mutation at residues R101, and V102, as shown in FIG. 16A (NKp46 wild-type) compared to 16B (mutant 6). Similarly, NKp46-1 also had decreased binding to the supplementary mutant Supp6 (having a mutation at residues E104 and L105, as shown in FIG. 17A (NKp46 wild-type) compared to 17B (mutant Supp6).

In this study, we identified epitopes for anti-NKp46 antibodies (NKp46-1, NKp46-3 and NKp46-4). Epitopes of NKp46-4, NKp46-3 and NKp46-1 are on NKp46 D1 domain, D2 domain and D1/D2 junction, respectively. R101, V102, E104 and L105 are essential residues for NKp46-4 binding and defined a part of NKp46-4 epitope. The epitope of NKp46-1 epitope includes K41, E42, E119, Y121 and Y194 residues. The epitope of NKp46-3 includes P132, E133, I135, and S136 residues.

Example 13

Improved Product Profile and Yield of Different Bispecific Formats Compared to Existing Formats Blinatumomab and two bispecific antibodies having NKp46 and CD19 binding regions based on F1 to F17 formats and NKp46-3, and blinatumomab, respectively were cloned and produced under format 6 (F6), DART and BITE formats following the same protocol and using the same expression system. F6, DART and BITE bispecific proteins were purified from cell culture supernatant by affinity chromatography using prot-A beads for F6 or Ni-NTA beads for DART and BITE. Purified proteins were further analysed and purified by SEC (FIG. 19-A). BITE and DART showed a very low production yield compared to F6 and have a very complex SEC profile. As shown in FIG. 19-B (arrows), DART and BITE are barely detectable by SDS-PAGE after Coomassie staining in the expected SEC fractions (3 and 4 for BITE and 4 and 5 for DART), whereas F6 format showed clear and simple SEC and SDS-PAGE profiles with a major peak (fraction 3) containing the multimeric bispecific proteins. The major peak for the F6 format corresponded to about 30% of the total proteins. These observations are also true for F1 to F17 proteins (data not shown) indicating that the Fc domain (or Fc-derive domain) present in those formats facilitate the production and improve the quality and solubility of bispecific proteins.

Moreover, the Fc domains present in proteins F1 to F17 have the advantage of being adapted to affinity chromatography without the need for incorporation of peptide tags that will thereafter remain present as an unwanted part of a therapeutic product, such as in the case of BiTe and DART antibodies which cannot be purified by protein A. F1 to F17 antibodies are all bound by protein A. Table 6 below shows productivity of different formats.

TABLE 6

| Format | SEC | SDS PAGE Reduced | SDS PAGE Non Reduced | Final « productivity » yield |
|---|---|---|---|---|
| F3 | 2 peaks | ✓ | ✓ | 3.4 mg/L |
| F4 | 2 peaks | ✓ | ✓ | 1 mg/L |
| F5 | ✓ | ✓ | ✓ | 37 mg/L |
| F6 | ✓ | ✓ | ✓ | 12 mg/L |
| F7 | ✓ | ✓ | ✓ | 11 mg/L |
| F8C | ✓ | ✓ | ✓ | 3.7 mg/L |
| F9A | ✓ | ✓ | ✓ | 8.7 mg/L |
| F9B | ✓ | ✓ | ✓ | 3.0 mg/L |
| F10A | ✓ | ✓ | ✓ | 2.0 mg/L |
| F11 | ✓ | ✓ | ✓ | 2.0 mg/L |
| F12 | ✓ | ✓ | ✓ | 2.8 mg/L |
| F13 | ✓ | ✓ | ✓ | 6.4 mg/L |
| F14 | ✓ | ✓ | ✓ | 2.4 mg/L |
| F15 | ✓ | ✓ | ✓ | 0.9 mg/L |
| BiTe | — | — | — | — |
| DART | — | — | — | — |

All headings and sub-headings are used herein for convenience only and should not be construed as limiting the invention in any way. Any combination of the above-described elements in all possible variations thereof is encompassed by the invention unless otherwise Indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e. g., all exact exemplary values provided with respect to a particular factor or measurement can be considered to also provide a corresponding approximate measurement, modified by "about," where appropriate). All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise Indicated. No language in the specification should be construed as indicating any element is essential to the practice of the invention unless as much is explicitly stated.

The description herein of any aspect or embodiment of the invention using terms such as reference to an element or elements is intended to provide support for a similar aspect or embodiment of the Invention that "consists of," "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent applications cited in this specification are herein incorporated by reference in their entireties as if each individual publication or patent application were specifically and individually indicated to be incorporated by reference.

Although the foregoing invention has been described in some detail by way of Illustration and example for purposes of clarity of understanding, it will be readily apparent to one of ordinary skill in the art in light of the teachings of this invention that certain changes and modifications may be made thereto without departing from the spirit or scope of the appended claims.

The invention claimed is:

1. A method of treating cancer in a subject in need thereof comprising administering to the subject a multispecific protein comprising a first antigen binding domain (ABD) and a second ABD, wherein the first or second ABD[s] binds to a human NKp46 polypeptide and the other binds a cancer antigen expressed by cancer cells of the treated subject,
   wherein the first or second ABD binds to human NKp46 polypeptide monovalently, and
   wherein the multispecific protein directs an NKp46-expressing NK cell to lyse the cancer cells expressing the cancer antigen; and further wherein:
   (a) the first and second ABDs in the multispecific protein comprise variable heavy chain and variable light chain polypeptides, respectively comprising heavy and light chain CDRs specific to human Nkp46 or to the cancer antigen expressed on human cancer cells; and
   (b) wherein the first or second ABD in the multispecific protein which binds to a human NKp46 polypeptide is selected from the group consisting of:
   (1) a polypeptide comprising a variable heavy chain polypeptide comprising CDR 1, 2 and 3 peptides of the heavy chain variable region of SEQ ID NO: 3 and a variable light chain polypeptide comprising CDR 1, 2 and 3 peptides of the light chain variable region of SEQ ID NO: 4;
   (2) a polypeptide comprising a variable heavy chain polypeptide comprising CDR 1, 2 and 3 peptides of the heavy chain variable region of SEQ ID NO: 5 and a variable light chain polypeptide comprising CDR 1, 2 and 3 peptides of the light chain variable region of SEQ ID NO: 6;
   (3) a polypeptide comprising a variable heavy chain polypeptide comprising CDR 1, 2 and 3 peptides of the heavy chain variable region of SEQ ID NO: 7 and a variable light chain polypeptide comprising CDR 1, 2 and 3 peptides of the light chain variable region of SEQ ID NO: 8;
   (4) a polypeptide comprising a variable heavy chain polypeptide comprising CDR 1, 2 and 3 peptides of the heavy chain variable region of SEQ ID NO: 9 and a variable light chain polypeptide comprising CDR 1, 2 and 3 peptides of the light chain variable region of SEQ ID NO: 10;
   (5) a polypeptide comprising a variable heavy chain polypeptide comprising CDR 1, 2 and 3 peptides of the heavy chain variable region of SEQ ID NO: 11 and a variable light chain polypeptide comprising CDR 1, 2 and 3 peptides of the light chain variable region of SEQ ID NO: 12; and
   (6) a polypeptide comprising a variable heavy chain polypeptide comprising CDR 1, 2 and 3 peptides of the heavy chain variable region of SEQ ID NO: 13 and a variable light chain polypeptide comprising CDR 1, 2 and 3 peptides of the light chain variable region of SEQ ID NO: 14.

2. The method according to claim 1, wherein the multispecific protein is administered in combination with a second therapeutic agent, wherein the second therapeutic agent is an antibody that is capable of mediating ADCC toward a cell that expresses an antigen bound by the antibody.

3. The method according to claim 1, wherein:
   (i) said multispecific protein mediates lysis of the target cancer cells expressing the cancer antigen of interest by NKp46-signaling;
   (ii) the multispecific protein does not exhibit activation of NKp46-expressing NK cells when incubated with such NK cells in the absence of cells expressing the cancer antigen of interest;
   (iii) the multispecific protein does not exhibit activation of NKp46-negative, CD16-positive lymphocytes when incubated with such NK cells in the presence of cancer cells expressing the cancer antigen of interest;

(iv) the multispecific protein (a) activates NK cells, when incubated with NKp46-expressing NK cells and target cancer cells expressing the cancer antigen of interest; and (b) does not activate NKp46-expressing NK cells when incubated with NK cells in the absence of target cancer cells expressing the cancer antigen of interest; and (v) the multispecific protein does not exhibit activation of NKp46-expressing NK cells when incubated with NK cells and target cancer cells expressing the cancer antigen of interest, in the presence of Fcγ-expressing cells.

4. The method according to claim 1, wherein the multispecific protein:
(1) is an isolated heterodimeric polypeptide comprising:
  (a) a first polypeptide chain comprising, from N- to C-terminus, a first variable domain (V), a CH1 or CK constant region, a Fc domain or CH3 domain thereof, a second variable domain and a third variable domain; and
  (b) a second polypeptide chain comprising, from N- to C-terminus, a first variable domain (V), a CH1 or CK constant region, and a Fc domain or CH3 domain thereof, wherein the CH1 or CK constant region is selected to be complementary to the CH1 or CK constant region of the first polypeptide chain such that the first and second polypeptides form a CH1-CK heterodimer in which the first variable domain of the first polypeptide chain and the first variable domain of the second polypeptide form an antigen binding domain that binds human NKp46; and wherein a second variable domain and third variable domain forms an antigen binding domain that binds the cancer antigen; or
(2) is an isolated heterodimeric polypeptide comprising:
  (a) a first polypeptide having a domain arrangement selected from:
  Va-1-(CH1 or CK)a-Fc domain-Va-2-Vb-2, and
  Va-2-Vb-2-Fc domain-Va-1-(CH1 or CK)b,
  and
  (b) a second polypeptide chain having a domain arrangement:
  Vb-1-(CH1 or CK)b, and
  wherein one of Va-1 and Vb-1 is a light chain variable domain and the other is a heavy chain variable domain, and one of Va-2 and Vb-2 is a light chain variable domain and the other is a heavy chain variable domain;
  wherein (CH1 or CK)b dimerizes with the (CH1 or CK)a on the central chain, and the Vb-1 forms a first antigen binding domain together with Va-1 of the central chain, and wherein Va-2 and Vb-2 together form a second antigen binding domain, wherein either the first or the second antigen binding domain binds to human NKp46, and the other binds to the cancer antigen; or
(3) is an isolated heterodimeric polypeptide comprising:
  a first polypeptide having a domain arrangement:
  $V_{a-1}$-(CH1 or CK)$_a$-Fc domain-$V_{a-2}$-$V_{b-2}$,
  and
  (b) a second polypeptide chain having a domain arrangement:
  $V_{b-1}$-(CH1 or CK)$_b$-Fc domain
  wherein one of Va-1 and Vb-1 is a light chain variable domain and the other is a heavy chain variable domain, one of Va-2 and Vb-2 is a light chain variable domain and the other is a heavy chain variable domain; said (CH1 or CK)b dimerizes with the (CH1 or CK)a on the central chain, and the Vb-1 forms a first antigen binding domain together with Va-1 of the central chain; and Va-2 and Vb-2 together form a second antigen binding domain, wherein either the first or the second antigen binding domain binds to human NKp46, and the other binds to the cancer antigen.

5. The method according to claim 4, wherein in said multispecific protein Va-2 and Vb-2 together form an antigen binding domain that binds NKp46.

6. The method according to claim 1, wherein the multispecific protein:
(1) is an isolated heterotrimeric polypeptide comprising
  (a) a first polypeptide chain comprising, from N- to C-terminus, a first variable domain (V) fused to a first CH1 or CK constant region, an Fc domain or CH3 domain thereof, and a second variable domain (V) fused to a second CH1 or CK constant region;
  (b) a second polypeptide chain comprising, from N- to C-terminus, a third variable domain (V) fused to a CH1 or CK constant region selected to be complementary to the first (but not the second) CH1 or CK constant region of the first polypeptide chain such that the first and second polypeptides form a CH1-CK heterodimer, and an Fc domain or CH3 domain thereof; and
  (c) a third polypeptide chain comprising, from N- to C-terminus, a fourth variable domain (V) fused to a CH1 or CK constant region, wherein the CH1 or CK constant region is selected to be complementary to the second (but not the first) variable domain and second CH1 or CK constant region of the first polypeptide chain, wherein the first and the third variable domains and the second and fourth variable domains respectively associate to form a first antigen binding domain and a second antigen binding domain, wherein either the first or the second antigen binding domain binds to human NKp46, and the other binds to the cancer antigen; or
(2) is an isolated heterotrimeric polypeptide comprising:
  (a) a first polypeptide chain having a domain arrangement:
  Va-1-(CH1 or CK)a-Fc domain-Va-2-(CH1 or CK)b,
  (b) a second polypeptide chain having a domain arrangement:
  Vb-1-(CH1 or CK)c,
  and
  (c) a third polypeptide chain having a domain arrangement:
  Vb-2-(CH1 or CK)d,
  wherein one of Va-1 and Vb-1 is a light chain variable domain and the other is a heavy chain variable domain, one of Va-2 and Vb-2 is a light chain variable domain and the other is a heavy chain variable domain;
  wherein (CH1 or CK)c dimerizes with the (CH1 or CK)a on the central chain, and the Va-1 and Vb-1 form the first antigen binding domain; and
  wherein (CH1 or CK)d dimerizes with the (CH1 or CK)b unit on the central chain, and the Va-2 and Vb-2 form the second antigen binding domain, wherein either the first or the second antigen binding domain binds to human NKp46, and the other binds to the cancer antigen.

7. The method according to claim 6, wherein:
the Fc domain of the multispecific protein comprises
   (a) a CH2 domain, and
   (b) a CH3 domain comprising an amino acid mutation that prevents CH3-CH3 dimerization or
the Fc domain comprises
   (a) a CH2 domain, and
   (b) a first and a second CH3 domain separated by a linker peptide, wherein the two CH3 domains associate with one another via non-covalent interactions.

8. The method according to claim 1, wherein the multispecific protein:
   (1) is a heterotrimeric polypeptide which comprises
      (a) a first polypeptide chain having a domain arrangement:
      Va-1-(CH1 or CK)a-Fc domain-Va-2-(CH1 or CK)b,
      (b) a second polypeptide chain having a domain arrangement:
      Vb-1-(CH1 or CK)c-Fc domain,
      and
      (c) a third polypeptide chain having a domain arrangement:
      Vb-2-(CH1 or CK)d, wherein one of Va-1 and Vb-1 is a light chain variable domain and the other is a heavy chain variable domain, one of Va-2 and Vb-2 is a light chain variable domain and the other is a heavy chain variable domain; (CH1 or CK)c dimerizes with the (CH1 or CK)a on the central chain, and the Va-1 and Vb-1 form a first antigen binding domain; and (CH1 or CK)d dimerizes with the (CH1 or CK)b unit on the central chain, and the Va-2 and Vb-2 form a second antigen binding domain, wherein either the first or the second antigen binding domain binds to human NKp46, and the other binds to the cancer antigen; or
   (2) is a heterodimeric polypeptide which comprises the following domain arrangement:

(Va-1—Vb-1—CK)—(hinge or linker)—CH2—CH3
   (Va-2—Vb-2—CH1)—(hinge or linker)—CH2—CH3 wherein Va-1, Vb-1, Va-2 and Vb-2 are each a VH domain or a VL domain, and wherein one of Va-1 and Vb-1 is a VH and the other is a VL such that Va-1 and Vb-1 form a first antigen binding domain (ABD), wherein one of Va-2 and Vb-2 is a VH and the other is a VL such that Va-2 and Vb-2 form a second antigen binding domain, wherein one of the ABDs monovalently binds NKp46 and the other binds to a cancer antigen, wherein either the first or the second antigen binding domain binds to human NKp46, and the other binds to the cancer antigen; or
   (3) is a multispecific protein comprises the following domain arrangement:

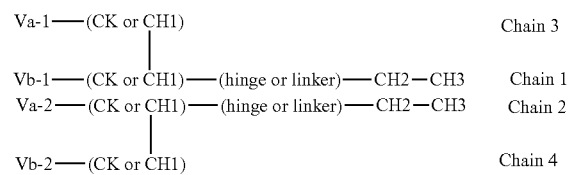

wherein Va-1, Vb-1, Va-2 and Vb-2 are each a VH domain or a VL domain, and wherein one of Va-1 and Vb-1 is a VH and the other is a VL such that Va-1 and Vb-1 form a first antigen binding domain (ABD), wherein one of Va-2 and Vb-2 is a VH and the other is a VL and wherein Va-2 and Vb-2 form a second antigen binding domain, wherein chain 1 and 2 associate by CH3-CH3 dimerization and CH1 and CK are selected such that chain 3 associates with chain 1 and chain 4 associates with chain 2, wherein either the first or the second antigen binding domain binds to human NKp46, and the other binds to the cancer antigen.

9. The method of treating cancer of claim 1, wherein the cancer is head and neck cancer.

10. The method of treating cancer of claim 1, wherein the cancer is a CD19 or CD20 expressing cancer.

11. The method of treating cancer of claim 1, wherein the multispecific protein comprises:
   (1) a first (central) polypeptide chain having domains arranged as follows (N- to C-terminal):
   Va-1-CH1-CH2-CH3-VH$^{anti\text{-}NKp46}$-CK;
   (2) a second polypeptide chain having domains arranged as follows (N- to C-terminal):
   Va-1-CK-CH2-CH3 and
   (3) a third polypeptide chain having domains arranged as follows (N- to C-terminal):
   VK$^{anti\text{-}NKp46}$-CH1;
   wherein one of Va-1 is a light chain variable domain, and the other Va-1 is a heavy chain variable domain, and they together form an ABD which binds to the cancer antigen.

12. The method of treating cancer of claim 1, wherein the cancer antigen bound by the first or second ABD is selected from CD19, CD20, EGFR, ROR1, and KIR3DL2.

* * * * *

SEQUENCE LISTING

```
<160> NUMBER OF SEQ ID NOS: 202

<210> SEQ ID NO 1
<211> LENGTH: 304
<212> TYPE: PRT
<213> ORGANISM: homo sapiens

<400> SEQUENCE: 1

Met Ser Ser Thr Leu Pro Ala Leu Leu Cys Val Gly Leu Cys Leu Ser
1               5                   10                  15

Gln Arg Ile Ser Ala Gln Gln Thr Leu Pro Lys Pro Phe Ile Trp
            20                  25                  30

Ala Glu Pro His Phe Met Val Pro Lys Glu Lys Gln Val Thr Ile Cys
            35                  40                  45

Cys Gln Gly Asn Tyr Gly Ala Val Glu Tyr Gln Leu His Phe Glu Gly
        50                  55                  60

Ser Leu Phe Ala Val Asp Arg Pro Lys Pro Glu Arg Ile Asn Lys
65                  70                  75                  80

Val Lys Phe Tyr Ile Pro Asp Met Asn Ser Arg Met Ala Gly Gln Tyr
                    85                  90                  95

Ser Cys Ile Tyr Arg Val Gly Glu Leu Trp Ser Glu Pro Ser Asn Leu
                100                 105                 110

Leu Asp Leu Val Val Thr Glu Met Tyr Asp Thr Pro Thr Leu Ser Val
            115                 120                 125

His Pro Gly Pro Glu Val Ile Ser Gly Glu Lys Val Thr Phe Tyr Cys
    130                 135                 140

Arg Leu Asp Thr Ala Thr Ser Met Phe Leu Leu Leu Lys Glu Gly Arg
145                 150                 155                 160

Ser Ser His Val Gln Arg Gly Tyr Gly Lys Val Gln Ala Glu Phe Pro
                165                 170                 175

Leu Gly Pro Val Thr Thr Ala His Arg Gly Thr Tyr Arg Cys Phe Gly
            180                 185                 190

Ser Tyr Asn Asn His Ala Trp Ser Phe Pro Ser Glu Pro Val Lys Leu
        195                 200                 205

Leu Val Thr Gly Asp Ile Glu Asn Thr Ser Leu Ala Pro Glu Asp Pro
    210                 215                 220

Thr Phe Pro Ala Asp Thr Trp Gly Thr Tyr Leu Leu Thr Thr Glu Thr
225                 230                 235                 240

Gly Leu Gln Lys Asp His Ala Leu Trp Asp His Thr Ala Gln Asn Leu
                245                 250                 255

Leu Arg Met Gly Leu Ala Phe Leu Val Leu Val Ala Leu Val Trp Phe
            260                 265                 270

Leu Val Glu Asp Trp Leu Ser Arg Lys Arg Thr Arg Glu Arg Ala Ser
        275                 280                 285

Arg Ala Ser Thr Trp Glu Gly Arg Arg Arg Leu Asn Thr Gln Thr Leu
```

```
            290                 295                 300
```

<210> SEQ ID NO 2
<211> LENGTH: 216
<212> TYPE: PRT
<213> ORGANISM: homo sapiens

<400> SEQUENCE: 2

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Thr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215
```

<210> SEQ ID NO 3
<211> LENGTH: 120
<212> TYPE: PRT
<213> ORGANISM: Mus musculus

<400> SEQUENCE: 3

```
Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Asn Trp Gly Lys Gln Arg Ser Gly Gln Gly Leu Glu Trp Ile
        35                  40                  45

Gly Glu Ile Tyr Pro Gly Ser Gly Thr Asn Tyr Tyr Asn Glu Lys Phe
    50                  55                  60

Lys Ala Lys Ala Thr Leu Thr Ala Asp Lys Ser Ser Asn Ile Ala Tyr
65                  70                  75                  80

Met Gln Leu Ser Ser Leu Thr Ser Glu Asp Ser Ala Val Tyr Phe Cys
                85                  90                  95

Ala Arg Arg Gly Arg Tyr Gly Leu Tyr Ala Met Asp Tyr Trp Gly Gln
```

```
                100                 105                 110

Gly Thr Ser Val Thr Val Ser Ser
            115                 120

<210> SEQ ID NO 4
<211> LENGTH: 107
<212> TYPE: PRT
<213> ORGANISM: Mus musculus

<400> SEQUENCE: 4

Asp Ile Gln Met Thr Gln Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Asn Asn Leu Glu Gln
65                  70                  75                  80

Glu Asp Ile Ala Thr Tyr Phe Cys Gln Gln Gly Asn Thr Arg Pro Trp
                85                  90                  95

Thr Phe Gly Gly Gly Thr Lys Leu Glu Ile Lys
            100                 105

<210> SEQ ID NO 5
<211> LENGTH: 122
<212> TYPE: PRT
<213> ORGANISM: Mus musculus

<400> SEQUENCE: 5

Glu Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Ser Thr Ser Tyr Asn Pro Ser Leu
    50                  55                  60

Glu Ser Arg Ile Ser Ile Thr Arg Asp Thr Ser Thr Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Gly Tyr Tyr Gly Ser Ser Trp Gly Val Phe Ala Tyr Trp
            100                 105                 110

Gly Gln Gly Thr Leu Val Thr Val Ser Ala
        115                 120

<210> SEQ ID NO 6
<211> LENGTH: 107
<212> TYPE: PRT
<213> ORGANISM: Mus musculus

<400> SEQUENCE: 6

Asp Ile Gln Met Thr Gln Ser Pro Ala Ser Leu Ser Ala Ser Val Gly
1               5                   10                  15

Glu Thr Val Thr Ile Thr Cys Arg Val Ser Glu Asn Ile Tyr Ser Tyr
            20                  25                  30
```

```
Leu Ala Trp Tyr Gln Gln Lys Gln Gly Lys Ser Pro Gln Leu Leu Val
            35                  40                  45

Tyr Asn Ala Lys Thr Leu Ala Glu Gly Val Pro Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Trp
                85                  90                  95

Thr Phe Gly Gly Gly Thr Lys Leu Glu Ile Lys
                100                 105

<210> SEQ ID NO 7
<211> LENGTH: 116
<212> TYPE: PRT
<213> ORGANISM: Mus musculus

<400> SEQUENCE: 7

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Ser Pro Asn Ile Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Gly Gly Ser Phe Asp Tyr Trp Gly Gln Gly Thr Thr Leu
                100                 105                 110

Thr Val Ser Ser
        115

<210> SEQ ID NO 8
<211> LENGTH: 107
<212> TYPE: PRT
<213> ORGANISM: Mus musculus

<400> SEQUENCE: 8

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
                100                 105

<210> SEQ ID NO 9
```

```
<211> LENGTH: 117
<212> TYPE: PRT
<213> ORGANISM: Mus musculus

<400> SEQUENCE: 9

Gln Val Gln Leu Gln Gln Ser Ala Val Glu Leu Ala Arg Pro Gly Ala
1               5                   10                  15

Ser Val Lys Met Ser Cys Lys Ala Ser Gly Tyr Thr Phe Thr Ser Phe
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Glu Tyr Asn Gln Lys Phe
    50                  55                  60

Lys Asp Lys Thr Thr Leu Thr Ala Asp Lys Ser Ser Ser Thr Ala Tyr
65                  70                  75                  80

Met Gln Leu Asp Ser Leu Thr Ser Asp Asp Ser Ala Val Tyr Tyr Cys
                85                  90                  95

Val Arg Gly Ser Ser Arg Gly Phe Asp Tyr Trp Gly Gln Gly Thr Leu
            100                 105                 110

Val Thr Val Ser Ala
            115

<210> SEQ ID NO 10
<211> LENGTH: 107
<212> TYPE: PRT
<213> ORGANISM: Mus musculus

<400> SEQUENCE: 10

Asp Ile Gln Met Ile Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Phe Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ile Tyr Tyr Cys Gln His Phe Trp Gly Thr Pro Arg
                85                  90                  95

Thr Phe Gly Gly Gly Thr Lys Leu Glu Ile Lys
            100                 105

<210> SEQ ID NO 11
<211> LENGTH: 115
<212> TYPE: PRT
<213> ORGANISM: Mus musculus

<400> SEQUENCE: 11

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Ser
            20                  25                  30

Trp Met His Trp Ala Lys Gln Arg Pro Gly Gln Gly Leu Glu Trp Ile
        35                  40                  45

Gly His Ile His Pro Asn Ser Gly Ile Ser Asn Tyr Asn Glu Lys Phe
    50                  55                  60
```

```
Lys Gly Lys Ala Thr Leu Thr Val Asp Thr Ser Ser Thr Ala Tyr
 65                  70                  75                  80

Val Asp Leu Ser Ser Leu Thr Ser Glu Asp Ser Ala Val Tyr Tyr Cys
                 85                  90                  95

Ala Arg Gly Gly Arg Phe Asp Asp Trp Gly Ala Gly Thr Thr Val Thr
            100                 105                 110

Val Ser Ser
        115
```

<210> SEQ ID NO 12
<211> LENGTH: 108
<212> TYPE: PRT
<213> ORGANISM: Mus musculus

<400> SEQUENCE: 12

```
Asp Ile Val Met Thr Gln Ser Pro Ala Thr Leu Ser Val Thr Pro Gly
 1               5                  10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
 50                  55                  60

Ser Gly Ser Gly Ser Asp Phe Thr Leu Ser Ile Asn Ser Val Glu Pro
 65                  70                  75                  80

Glu Asp Val Gly Val Tyr Tyr Cys Gln Asn Gly His Ser Phe Leu Met
                 85                  90                  95

Tyr Thr Phe Gly Gly Gly Thr Lys Leu Glu Ile Lys
            100                 105
```

<210> SEQ ID NO 13
<211> LENGTH: 120
<212> TYPE: PRT
<213> ORGANISM: Mus musculus

<400> SEQUENCE: 13

```
Asp Val Gln Leu Gln Glu Ser Gly Pro Gly Leu Val Lys Pro Ser Gln
 1               5                  10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Lys Leu Glu Trp
            35                  40                  45

Met Gly Tyr Ile Thr Tyr Ser Gly Ser Thr Asn Tyr Asn Pro Ser Leu
 50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Ala Arg Cys Trp Asp Tyr Ala Leu Tyr Ala Met Asp Cys Trp Gly Gln
            100                 105                 110

Gly Thr Ser Val Thr Val Ser Ser
            115                 120
```

<210> SEQ ID NO 14
<211> LENGTH: 107
<212> TYPE: PRT
<213> ORGANISM: Mus musculus -continued

```
<400> SEQUENCE: 14

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Ile Tyr Ser Tyr
            20                  25                  30

Leu Ala Trp Cys Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr His Phe Ser Leu Lys Ile Asn Ser Leu Gln Pro
65                  70                  75                  80

Glu Asp Phe Gly Ile Tyr Tyr Cys Gln His Tyr Asp Thr Pro Leu
                85                  90                  95

Thr Phe Gly Ala Gly Thr Lys Leu Glu Leu Lys
            100                 105

<210> SEQ ID NO 15
<211> LENGTH: 5
<212> TYPE: PRT
<213> ORGANISM: mus musculus

<400> SEQUENCE: 15

Asp Tyr Val Ile Asn
1               5

<210> SEQ ID NO 16
<211> LENGTH: 7
<212> TYPE: PRT
<213> ORGANISM: mus musculus

<400> SEQUENCE: 16

Gly Tyr Thr Phe Thr Asp Tyr
1               5

<210> SEQ ID NO 17
<211> LENGTH: 8
<212> TYPE: PRT
<213> ORGANISM: mus musculus

<400> SEQUENCE: 17

Gly Tyr Thr Phe Thr Asp Tyr Val
1               5

<210> SEQ ID NO 18
<211> LENGTH: 17
<212> TYPE: PRT
<213> ORGANISM: mus musculus

<400> SEQUENCE: 18

Glu Ile Tyr Pro Gly Ser Gly Thr Asn Tyr Tyr Asn Glu Lys Phe Lys
1               5                   10                  15

Ala

<210> SEQ ID NO 19
<211> LENGTH: 4
<212> TYPE: PRT
<213> ORGANISM: mus musculus

<400> SEQUENCE: 19

Pro Gly Ser Gly
1
```

<210> SEQ ID NO 20
<211> LENGTH: 16
<212> TYPE: PRT
<213> ORGANISM: mus musculus

<400> SEQUENCE: 20

Gly Tyr Thr Phe Thr Asp Tyr Val Ile Tyr Pro Gly Ser Gly Thr Asn
1               5                   10                  15

<210> SEQ ID NO 21
<211> LENGTH: 11
<212> TYPE: PRT
<213> ORGANISM: mus musculus

<400> SEQUENCE: 21

Arg Gly Arg Tyr Gly Leu Tyr Ala Met Asp Tyr
1               5                   10

<210> SEQ ID NO 22
<211> LENGTH: 9
<212> TYPE: PRT
<213> ORGANISM: mus musculus

<400> SEQUENCE: 22

Gly Arg Tyr Gly Leu Tyr Ala Met Asp
1               5

<210> SEQ ID NO 23
<211> LENGTH: 13
<212> TYPE: PRT
<213> ORGANISM: mus musculus

<400> SEQUENCE: 23

Ala Arg Arg Gly Arg Tyr Gly Leu Tyr Ala Met Asp Tyr
1               5                   10

<210> SEQ ID NO 24
<211> LENGTH: 11
<212> TYPE: PRT
<213> ORGANISM: mus musculus

<400> SEQUENCE: 24

Arg Ala Ser Gln Asp Ile Ser Asn Tyr Leu Asn
1               5                   10

<210> SEQ ID NO 25
<211> LENGTH: 7
<212> TYPE: PRT
<213> ORGANISM: Mus musculus

<400> SEQUENCE: 25

Ser Gln Asp Ile Ser Asn Tyr
1               5

<210> SEQ ID NO 26
<211> LENGTH: 6
<212> TYPE: PRT
<213> ORGANISM: mus musculus

<400> SEQUENCE: 26

Gln Asp Ile Ser Asn Tyr
1               5

-continued

```
<210> SEQ ID NO 27
<211> LENGTH: 7
<212> TYPE: PRT
<213> ORGANISM: Mus musculus

<400> SEQUENCE: 27

Tyr Thr Ser Arg Leu His Ser
1               5

<210> SEQ ID NO 28
<211> LENGTH: 9
<212> TYPE: PRT
<213> ORGANISM: mus musculus

<400> SEQUENCE: 28

Gln Gln Gly Asn Thr Arg Pro Trp Thr
1               5

<210> SEQ ID NO 29
<211> LENGTH: 9
<212> TYPE: PRT
<213> ORGANISM: Mus musculus

<400> SEQUENCE: 29

Tyr Thr Ser Gly Asn Thr Arg Pro Trp
1               5

<210> SEQ ID NO 30
<211> LENGTH: 12
<212> TYPE: PRT
<213> ORGANISM: Mus musculus

<400> SEQUENCE: 30

Tyr Thr Ser Gln Gln Gly Asn Thr Arg Pro Trp Thr
1               5                   10

<210> SEQ ID NO 31
<211> LENGTH: 6
<212> TYPE: PRT
<213> ORGANISM: Mus musculus

<400> SEQUENCE: 31

Ser Asp Tyr Ala Trp Asn
1               5

<210> SEQ ID NO 32
<211> LENGTH: 8
<212> TYPE: PRT
<213> ORGANISM: Mus musculus

<400> SEQUENCE: 32

Gly Tyr Ser Ile Thr Ser Asp Tyr
1               5

<210> SEQ ID NO 33
<211> LENGTH: 9
<212> TYPE: PRT
<213> ORGANISM: Mus musculus

<400> SEQUENCE: 33

Gly Tyr Ser Ile Thr Ser Asp Tyr Ala
1               5

<210> SEQ ID NO 34
<211> LENGTH: 16
```

-continued

```
<212> TYPE: PRT
<213> ORGANISM: Mus musculus

<400> SEQUENCE: 34

Tyr Ile Thr Tyr Ser Gly Ser Thr Ser Tyr Asn Pro Ser Leu Glu Ser
1               5                   10                  15

<210> SEQ ID NO 35
<211> LENGTH: 7
<212> TYPE: PRT
<213> ORGANISM: Mus musculus

<400> SEQUENCE: 35

Ile Thr Tyr Ser Gly Ser Thr
1               5

<210> SEQ ID NO 36
<211> LENGTH: 13
<212> TYPE: PRT
<213> ORGANISM: Mus musculus

<400> SEQUENCE: 36

Gly Gly Tyr Tyr Gly Ser Ser Trp Gly Val Phe Ala Tyr
1               5                   10

<210> SEQ ID NO 37
<211> LENGTH: 11
<212> TYPE: PRT
<213> ORGANISM: Mus musculus

<400> SEQUENCE: 37

Gly Tyr Tyr Gly Ser Ser Trp Gly Val Phe Ala
1               5                   10

<210> SEQ ID NO 38
<211> LENGTH: 15
<212> TYPE: PRT
<213> ORGANISM: Mus musculus

<400> SEQUENCE: 38

Ala Arg Gly Gly Tyr Tyr Gly Ser Ser Trp Gly Val Phe Ala Tyr
1               5                   10                  15

<210> SEQ ID NO 39
<211> LENGTH: 11
<212> TYPE: PRT
<213> ORGANISM: Mus musculus

<400> SEQUENCE: 39

Arg Val Ser Glu Asn Ile Tyr Ser Tyr Leu Ala
1               5                   10

<210> SEQ ID NO 40
<211> LENGTH: 7
<212> TYPE: PRT
<213> ORGANISM: Mus musculus

<400> SEQUENCE: 40

Ser Glu Asn Ile Tyr Ser Tyr
1               5

<210> SEQ ID NO 41
<211> LENGTH: 6
<212> TYPE: PRT
<213> ORGANISM: Mus musculus
```

```
<400> SEQUENCE: 41

Glu Asn Ile Tyr Ser Tyr
1               5

<210> SEQ ID NO 42
<211> LENGTH: 7
<212> TYPE: PRT
<213> ORGANISM: Mus musculus

<400> SEQUENCE: 42

Asn Ala Lys Thr Leu Ala Glu
1               5

<210> SEQ ID NO 43
<211> LENGTH: 9
<212> TYPE: PRT
<213> ORGANISM: Mus musculus

<400> SEQUENCE: 43

Gln His His Tyr Gly Thr Pro Trp Thr
1               5

<210> SEQ ID NO 44
<211> LENGTH: 6
<212> TYPE: PRT
<213> ORGANISM: Mus musculus

<400> SEQUENCE: 44

His Tyr Gly Thr Pro Trp
1               5

<210> SEQ ID NO 45
<211> LENGTH: 9
<212> TYPE: PRT
<213> ORGANISM: mus musculus

<400> SEQUENCE: 45

Gln His His Tyr Gly Thr Pro Trp Thr
1               5

<210> SEQ ID NO 46
<211> LENGTH: 5
<212> TYPE: PRT
<213> ORGANISM: Mus musculus

<400> SEQUENCE: 46

Glu Tyr Thr Met His
1               5

<210> SEQ ID NO 47
<211> LENGTH: 7
<212> TYPE: PRT
<213> ORGANISM: Mus musculus

<400> SEQUENCE: 47

Gly Tyr Thr Phe Thr Glu Tyr
1               5

<210> SEQ ID NO 48
<211> LENGTH: 8
<212> TYPE: PRT
<213> ORGANISM: Mus musculus

<400> SEQUENCE: 48
```

Gly Tyr Thr Phe Thr Glu Tyr Thr
1               5

<210> SEQ ID NO 49
<211> LENGTH: 17
<212> TYPE: PRT
<213> ORGANISM: Mus musculus

<400> SEQUENCE: 49

Gly Ile Ser Pro Asn Ile Gly Gly Thr Ser Tyr Asn Gln Lys Phe Lys
1               5                   10                  15
Gly

<210> SEQ ID NO 50
<211> LENGTH: 8
<212> TYPE: PRT
<213> ORGANISM: Mus musculus

<400> SEQUENCE: 50

Ile Ser Pro Asn Ile Gly Gly Thr
1               5

<210> SEQ ID NO 51
<211> LENGTH: 7
<212> TYPE: PRT
<213> ORGANISM: Mus musculus

<400> SEQUENCE: 51

Arg Gly Gly Ser Phe Asp Tyr
1               5

<210> SEQ ID NO 52
<211> LENGTH: 5
<212> TYPE: PRT
<213> ORGANISM: Mus musculus

<400> SEQUENCE: 52

Gly Gly Ser Phe Asp
1               5

<210> SEQ ID NO 53
<211> LENGTH: 9
<212> TYPE: PRT
<213> ORGANISM: Mus musculus

<400> SEQUENCE: 53

Ala Arg Arg Gly Gly Ser Phe Asp Tyr
1               5

<210> SEQ ID NO 54
<211> LENGTH: 11
<212> TYPE: PRT
<213> ORGANISM: Mus musculus

<400> SEQUENCE: 54

Arg Ala Ser Gln Ser Ile Ser Asp Tyr Leu His
1               5                   10

<210> SEQ ID NO 55
<211> LENGTH: 7
<212> TYPE: PRT
<213> ORGANISM: Mus musculus

<400> SEQUENCE: 55

Ser Gln Ser Ile Ser Asp Tyr
1               5

<210> SEQ ID NO 56
<211> LENGTH: 6
<212> TYPE: PRT
<213> ORGANISM: Mus musculus

<400> SEQUENCE: 56

Gln Ser Ile Ser Asp Tyr
1               5

<210> SEQ ID NO 57
<211> LENGTH: 7
<212> TYPE: PRT
<213> ORGANISM: Mus musculus

<400> SEQUENCE: 57

Tyr Ala Ser Gln Ser Ile Ser
1               5

<210> SEQ ID NO 58
<211> LENGTH: 9
<212> TYPE: PRT
<213> ORGANISM: Mus musculus

<400> SEQUENCE: 58

Gln Asn Gly His Ser Phe Pro Leu Thr
1               5

<210> SEQ ID NO 59
<211> LENGTH: 6
<212> TYPE: PRT
<213> ORGANISM: Mus musculus

<400> SEQUENCE: 59

Gly His Ser Phe Pro Leu
1               5

<210> SEQ ID NO 60
<211> LENGTH: 5
<212> TYPE: PRT
<213> ORGANISM: Mus musculus

<400> SEQUENCE: 60

Ser Phe Thr Met His
1               5

<210> SEQ ID NO 61
<211> LENGTH: 7
<212> TYPE: PRT
<213> ORGANISM: Mus musculus

<400> SEQUENCE: 61

Gly Tyr Thr Phe Thr Ser Phe
1               5

<210> SEQ ID NO 62
<211> LENGTH: 8
<212> TYPE: PRT
<213> ORGANISM: Mus musculus

<400> SEQUENCE: 62

Gly Tyr Thr Phe Thr Ser Phe Thr

```
1               5
```

<210> SEQ ID NO 63
<211> LENGTH: 17
<212> TYPE: PRT
<213> ORGANISM: Mus musculus

<400> SEQUENCE: 63

```
Tyr Ile Asn Pro Ser Ser Gly Tyr Thr Glu Tyr Asn Gln Lys Phe Lys
1               5                   10                  15

Asp
```

<210> SEQ ID NO 64
<211> LENGTH: 8
<212> TYPE: PRT
<213> ORGANISM: Mus musculus

<400> SEQUENCE: 64

```
Ile Asn Pro Ser Ser Gly Tyr Thr
1               5
```

<210> SEQ ID NO 65
<211> LENGTH: 8
<212> TYPE: PRT
<213> ORGANISM: Mus musculus

<400> SEQUENCE: 65

```
Gly Ser Ser Arg Gly Phe Asp Tyr
1               5
```

<210> SEQ ID NO 66
<211> LENGTH: 6
<212> TYPE: PRT
<213> ORGANISM: Mus musculus

<400> SEQUENCE: 66

```
Ser Ser Arg Gly Phe Asp
1               5
```

<210> SEQ ID NO 67
<211> LENGTH: 10
<212> TYPE: PRT
<213> ORGANISM: Mus musculus

<400> SEQUENCE: 67

```
Val Arg Gly Ser Ser Arg Gly Phe Asp Tyr
1               5                   10
```

<210> SEQ ID NO 68
<211> LENGTH: 11
<212> TYPE: PRT
<213> ORGANISM: Mus musculus

<400> SEQUENCE: 68

```
Arg Ala Ser Glu Asn Ile Tyr Ser Asn Leu Ala
1               5                   10
```

<210> SEQ ID NO 69
<211> LENGTH: 6
<212> TYPE: PRT
<213> ORGANISM: Mus musculur

<400> SEQUENCE: 69

```
Glu Asn Ile Tyr Ser Asn
```

-continued

```
1               5

<210> SEQ ID NO 70
<211> LENGTH: 7
<212> TYPE: PRT
<213> ORGANISM: mus musculur

<400> SEQUENCE: 70

Ala Ala Thr Asn Leu Ala Asp
1               5

<210> SEQ ID NO 71
<211> LENGTH: 9
<212> TYPE: PRT
<213> ORGANISM: Mus musculus

<400> SEQUENCE: 71

Gln His Phe Trp Gly Thr Pro Arg Thr
1               5

<210> SEQ ID NO 72
<211> LENGTH: 6
<212> TYPE: PRT
<213> ORGANISM: Mus musculus

<400> SEQUENCE: 72

Phe Trp Gly Thr Pro Arg
1               5

<210> SEQ ID NO 73
<211> LENGTH: 5
<212> TYPE: PRT
<213> ORGANISM: Mus musculus

<400> SEQUENCE: 73

Ser Ser Trp Met His
1               5

<210> SEQ ID NO 74
<211> LENGTH: 7
<212> TYPE: PRT
<213> ORGANISM: Mus musculus

<400> SEQUENCE: 74

Gly Tyr Thr Phe Thr Ser Ser
1               5

<210> SEQ ID NO 75
<211> LENGTH: 8
<212> TYPE: PRT
<213> ORGANISM: Mus musculus

<400> SEQUENCE: 75

Gly Tyr Thr Phe Thr Ser Ser Trp
1               5

<210> SEQ ID NO 76
<211> LENGTH: 17
<212> TYPE: PRT
<213> ORGANISM: Mus musculus

<400> SEQUENCE: 76

His Ile His Pro Asn Ser Gly Ile Ser Asn Tyr Asn Glu Lys Phe Lys
1               5                   10                  15
```

Gly

```
<210> SEQ ID NO 77
<211> LENGTH: 8
<212> TYPE: PRT
<213> ORGANISM: Mus musculus

<400> SEQUENCE: 77

Ile His Pro Asn Ser Gly Ile Ser
1               5

<210> SEQ ID NO 78
<211> LENGTH: 6
<212> TYPE: PRT
<213> ORGANISM: Mus musculus

<400> SEQUENCE: 78

Gly Gly Arg Phe Asp Asp
1               5

<210> SEQ ID NO 79
<211> LENGTH: 8
<212> TYPE: PRT
<213> ORGANISM: Mus musculus

<400> SEQUENCE: 79

Ala Arg Gly Gly Arg Phe Asp Asp
1               5

<210> SEQ ID NO 80
<211> LENGTH: 11
<212> TYPE: PRT
<213> ORGANISM: Mus musculus

<400> SEQUENCE: 80

Arg Ala Ser Gln Ser Ile Ser Asp Tyr Leu His
1               5                   10

<210> SEQ ID NO 81
<211> LENGTH: 11
<212> TYPE: PRT
<213> ORGANISM: Mus musculus

<400> SEQUENCE: 81

Gly Arg Phe Asp Ser Gln Ser Ile Ser Asp Tyr
1               5                   10

<210> SEQ ID NO 82
<211> LENGTH: 10
<212> TYPE: PRT
<213> ORGANISM: Mus musculus

<400> SEQUENCE: 82

Gln Asn Gly His Ser Phe Leu Met Tyr Thr
1               5                   10

<210> SEQ ID NO 83
<211> LENGTH: 7
<212> TYPE: PRT
<213> ORGANISM: Mus musculus

<400> SEQUENCE: 83

Gly His Ser Phe Leu Met Tyr
1               5
```

<210> SEQ ID NO 84
<211> LENGTH: 13
<212> TYPE: PRT
<213> ORGANISM: Mus musculus

<400> SEQUENCE: 84

Tyr Ala Ser Gln Asn Gly His Ser Phe Leu Met Tyr Thr
1               5                   10

<210> SEQ ID NO 85
<211> LENGTH: 6
<212> TYPE: PRT
<213> ORGANISM: mus musculus

<400> SEQUENCE: 85

Ser Asp Tyr Ala Trp Asn
1               5

<210> SEQ ID NO 86
<211> LENGTH: 8
<212> TYPE: PRT
<213> ORGANISM: Mus musculus

<400> SEQUENCE: 86

Gly Tyr Ser Ile Thr Ser Asp Tyr
1               5

<210> SEQ ID NO 87
<211> LENGTH: 9
<212> TYPE: PRT
<213> ORGANISM: Mus musculus

<400> SEQUENCE: 87

Gly Tyr Ser Ile Thr Ser Asp Tyr Ala
1               5

<210> SEQ ID NO 88
<211> LENGTH: 16
<212> TYPE: PRT
<213> ORGANISM: Mus musculus

<400> SEQUENCE: 88

Tyr Ile Thr Tyr Ser Gly Ser Thr Asn Tyr Asn Pro Ser Leu Lys Ser
1               5                   10                  15

<210> SEQ ID NO 89
<211> LENGTH: 11
<212> TYPE: PRT
<213> ORGANISM: Mus musculus

<400> SEQUENCE: 89

Cys Trp Asp Tyr Ala Leu Tyr Ala Met Asp Cys
1               5                   10

<210> SEQ ID NO 90
<211> LENGTH: 9
<212> TYPE: PRT
<213> ORGANISM: mus musculus

<400> SEQUENCE: 90

Trp Asp Tyr Ala Leu Tyr Ala Met Asp
1               5

<210> SEQ ID NO 91

```
<211> LENGTH: 13
<212> TYPE: PRT
<213> ORGANISM: Mus musculus

<400> SEQUENCE: 91

Ala Arg Cys Trp Asp Tyr Ala Leu Tyr Ala Met Asp Cys
1               5                   10

<210> SEQ ID NO 92
<211> LENGTH: 11
<212> TYPE: PRT
<213> ORGANISM: Mus musculus

<400> SEQUENCE: 92

Arg Thr Ser Glu Asn Ile Tyr Ser Tyr Leu Ala
1               5                   10

<210> SEQ ID NO 93
<211> LENGTH: 7
<212> TYPE: PRT
<213> ORGANISM: Mus musculus

<400> SEQUENCE: 93

Asn Ala Lys Thr Leu Ala Glu
1               5

<210> SEQ ID NO 94
<211> LENGTH: 9
<212> TYPE: PRT
<213> ORGANISM: Mus musculus

<400> SEQUENCE: 94

Gln His His Tyr Asp Thr Pro Leu Thr
1               5

<210> SEQ ID NO 95
<211> LENGTH: 9
<212> TYPE: PRT
<213> ORGANISM: mus musculus

<400> SEQUENCE: 95

Asn Ala Lys His Tyr Asp Thr Pro Leu
1               5

<210> SEQ ID NO 96
<211> LENGTH: 9
<212> TYPE: PRT
<213> ORGANISM: Mus musculus

<400> SEQUENCE: 96

Gln His His Tyr Asp Thr Pro Leu Thr
1               5

<210> SEQ ID NO 97
<211> LENGTH: 5
<212> TYPE: PRT
<213> ORGANISM: Mus musculus

<400> SEQUENCE: 97

Asn Tyr Gly Met Asn
1               5

<210> SEQ ID NO 98
<211> LENGTH: 7
<212> TYPE: PRT
```

<213> ORGANISM: mus musculus

<400> SEQUENCE: 98

Gly Tyr Thr Phe Thr Asn Tyr
1               5

<210> SEQ ID NO 99
<211> LENGTH: 8
<212> TYPE: PRT
<213> ORGANISM: mus musculus

<400> SEQUENCE: 99

Gly Tyr Thr Phe Thr Asn Tyr Gly
1               5

<210> SEQ ID NO 100
<211> LENGTH: 17
<212> TYPE: PRT
<213> ORGANISM: mus musculus

<400> SEQUENCE: 100

Trp Ile Asn Thr Asn Thr Gly Glu Pro Thr Tyr Ala Glu Glu Phe Lys
1               5                   10                  15
Gly

<210> SEQ ID NO 101
<211> LENGTH: 8
<212> TYPE: PRT
<213> ORGANISM: Mus musculus

<400> SEQUENCE: 101

Ile Asn Thr Asn Thr Gly Glu Pro
1               5

<210> SEQ ID NO 102
<211> LENGTH: 8
<212> TYPE: PRT
<213> ORGANISM: Mus musculus

<400> SEQUENCE: 102

Asp Tyr Leu Tyr Tyr Phe Asp Tyr
1               5

<210> SEQ ID NO 103
<211> LENGTH: 6
<212> TYPE: PRT
<213> ORGANISM: mus musculus

<400> SEQUENCE: 103

Tyr Leu Tyr Tyr Phe Asp
1               5

<210> SEQ ID NO 104
<211> LENGTH: 10
<212> TYPE: PRT
<213> ORGANISM: Mus musculus

<400> SEQUENCE: 104

Ala Arg Asp Tyr Leu Tyr Tyr Phe Asp Tyr
1               5                   10

<210> SEQ ID NO 105
<211> LENGTH: 11
<212> TYPE: PRT

<213> ORGANISM: Mus musculus

<400> SEQUENCE: 105

Lys Ala Ser Glu Asn Val Val Thr Tyr Val Ser
1               5                   10

<210> SEQ ID NO 106
<211> LENGTH: 7
<212> TYPE: PRT
<213> ORGANISM: Mus musculus

<400> SEQUENCE: 106

Ser Glu Asn Val Val Thr Tyr
1               5

<210> SEQ ID NO 107
<211> LENGTH: 6
<212> TYPE: PRT
<213> ORGANISM: Mus musculus

<400> SEQUENCE: 107

Glu Asn Val Val Thr Tyr
1               5

<210> SEQ ID NO 108
<211> LENGTH: 7
<212> TYPE: PRT
<213> ORGANISM: Mus musculus

<400> SEQUENCE: 108

Gly Ala Ser Asn Arg Tyr Thr
1               5

<210> SEQ ID NO 109
<211> LENGTH: 9
<212> TYPE: PRT
<213> ORGANISM: mus musculus

<400> SEQUENCE: 109

Gly Gln Gly Tyr Ser Tyr Pro Tyr Thr
1               5

<210> SEQ ID NO 110
<211> LENGTH: 6
<212> TYPE: PRT
<213> ORGANISM: mus musculus

<400> SEQUENCE: 110

Gly Tyr Ser Tyr Pro Tyr
1               5

<210> SEQ ID NO 111
<211> LENGTH: 9
<212> TYPE: PRT
<213> ORGANISM: mus musculus

<400> SEQUENCE: 111

Gly Gln Gly Tyr Ser Tyr Pro Tyr Thr
1               5

<210> SEQ ID NO 112
<211> LENGTH: 227
<212> TYPE: PRT
<213> ORGANISM: homo sapiens

<400> SEQUENCE: 112

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Gly Gly Gly Ser Gly
            100                 105                 110

Gly Gly Gly Ser Gly Gly Gly Ser Gly Gln Pro Arg Glu Pro Gln
                115                 120                 125

Val Tyr Thr Leu Pro Pro Ser Arg Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225

<210> SEQ ID NO 113
<211> LENGTH: 333
<212> TYPE: DNA
<213> ORGANISM: mus musculus

<400> SEQUENCE: 113
gacattcagc tgacccaatc tccagcttct ttggctgtgt ctctagggca gagggccacc      60
atctcctgca aggccagcca aagtgttgat tatgatggtg atagttattt gaactggtac     120
caacagatac aggacagcc acccaaactc ctcatctatg atgcatccaa tctagtatct     180
gggattccac ccaggtttag tggcagtggg tctgggacag acttcaccct caacatccat     240
cctgtggaga aggtggatgc tgcaacctat cactgtcagc aaagtactga ggacccttgg     300
acgttcggtg aggcaccaa gctggaaatc aaa                                    333

<210> SEQ ID NO 114
<211> LENGTH: 111
<212> TYPE: PRT
<213> ORGANISM: mus musculus

<400> SEQUENCE: 114

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp

```
                    20                  25                  30
Gly Asp Ser Tyr Leu Asn Trp Tyr Gln Gln Ile Pro Gly Gln Pro Pro
                35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
                100                 105                 110

<210> SEQ ID NO 115
<211> LENGTH: 372
<212> TYPE: DNA
<213> ORGANISM: mus musculus

<400> SEQUENCE: 115
caggttcagc tgcagcagtc tggggctgag ctggtgcggc ctgggtcctc agtgaagatt      60
tcctgcaaag catctggcta cgcattcagt agctactgga tgaactgggt gaagcagagg     120
cctggacagg gtcttgagtg gattggacag atttggcctg agatggtga tactaactac      180 aacggaaagt tcaagggcaa ggccacactg actgcagacg aatcctccag cacagcctac     240
atgcagctca gcagcctggc ctctgaggac tctgcggtct atttctgtgc aagacgagaa     300
acgaccactg tcgggcgtta ttactatgct atggactact ggggtcaagg aaccacagtc     360
accgtctcct ca                                                         372

<210> SEQ ID NO 116
<211> LENGTH: 124
<212> TYPE: PRT
<213> ORGANISM: Mus musculus

<400> SEQUENCE: 116

Gln Val Gln Leu Gln Gln Ser Gly Ala Glu Leu Val Arg Pro Gly Ser
 1               5                  10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
                35                  40                  45

Gly Gln Ile Trp Pro Gly Asp Gly Asp Thr Asn Tyr Asn Gly Lys Phe
 50                  55                  60

Lys Gly Lys Ala Thr Leu Thr Ala Asp Glu Ser Ser Ser Thr Ala Tyr
 65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
                100                 105                 110

Tyr Trp Gly Gln Gly Thr Thr Val Thr Val Ser Ser
                115                 120

<210> SEQ ID NO 117
<211> LENGTH: 648
<212> TYPE: DNA
<213> ORGANISM: homo sapiens

<400> SEQUENCE: 117
```

```
gcacctgaac tcctgggggg accgtcagtc ttcctcttcc ccccaaaacc caaggacacc    60
ctcatgatct cccggacccc tgaggtcaca tgcgtggtgg tggacgtgag ccacgaagac   120
cctgaggtca agttcaactg gtacgtggac ggcgtggagg tgcataatgc caagacaaag   180
ccgcgggagg agcagtacaa cagcacgtac cgtgtggtca gcgtcctcac cgtcctgcac   240
caggactggc tgaatggcaa ggagtacaag tgcaaggtct ccaacaaagc cctcccagcc   300
cccatcgaga aaaccatctc caaagccaaa gggcagcccc gagaaccaca ggtgtacacc   360 aagccccat cccgggagga tgaccaag aaccaggtca gcctgtcctg cctggtcaaa     420
ggcttctatc ccagcgacat cgccgtggag tgggagagca atgggcagcc ggagaacaac   480
tacaagacca cggttcccgt gctggactcc gacggctcct tccgcctcgc tagctacctc   540
accgtggaca agagcaggtg gcagcagggg aacgtcttct catgctccgt gatgcatgag   600
gctctgcaca accactacac gcagaagagc ctctccctgt ccccgggg               648

<210> SEQ ID NO 118
<211> LENGTH: 718
<212> TYPE: PRT
<213> ORGANISM: Artificial
<220> FEATURE:
<223> OTHER INFORMATION: Chimeric homo sapiens mus musculus

<400> SEQUENCE: 118

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Ser Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255
```

```
Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Lys Pro Pro Ser Arg Glu Glu Met Thr
    370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Val Pro Val Leu Asp Ser Asp Gly Ser Phe Arg Leu Ala
            420                 425                 430

Ser Tyr Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Ser Thr Gly Ser Asp Ile Lys Leu Gln
465                 470                 475                 480

Gln Ser Gly Ala Glu Leu Ala Arg Pro Gly Ala Ser Val Lys Met Ser
                485                 490                 495

Cys Lys Thr Ser Gly Tyr Thr Phe Thr Arg Tyr Thr Met His Trp Val
            500                 505                 510

Lys Gln Arg Pro Gly Gln Gly Leu Glu Trp Ile Gly Tyr Ile Asn Pro
        515                 520                 525

Ser Arg Gly Tyr Thr Asn Tyr Asn Gln Lys Phe Lys Asp Lys Ala Thr
    530                 535                 540

Leu Thr Thr Asp Lys Ser Ser Ser Thr Ala Tyr Met Gln Leu Ser Ser
545                 550                 555                 560

Leu Thr Ser Glu Asp Ser Ala Val Tyr Tyr Cys Ala Arg Tyr Tyr Asp
                565                 570                 575

Asp His Tyr Cys Leu Asp Tyr Trp Gly Gln Gly Thr Thr Leu Thr Val
            580                 585                 590

Ser Ser Val Glu Gly Gly Ser Gly Gly Ser Gly Gly Ser Gly Gly Ser
        595                 600                 605

Gly Gly Val Asp Asp Ile Gln Leu Thr Gln Ser Pro Ala Ile Met Ser
    610                 615                 620

Ala Ser Pro Gly Glu Lys Val Thr Met Thr Cys Arg Ala Ser Ser Ser
625                 630                 635                 640

Val Ser Tyr Met Asn Trp Tyr Gln Gln Lys Ser Gly Thr Ser Pro Lys
                645                 650                 655

Arg Trp Ile Tyr Asp Thr Ser Lys Val Ala Ser Gly Val Pro Tyr Arg
            660                 665                 670
```

```
Phe Ser Gly Ser Gly Ser Gly Thr Ser Tyr Ser Leu Thr Ile Ser Ser
            675                 680                 685

Met Glu Ala Glu Asp Ala Ala Thr Tyr Tyr Cys Gln Gln Trp Ser Ser
            690                 695                 700

Asn Pro Leu Thr Phe Gly Ala Gly Thr Lys Leu Glu Leu Lys
705                 710                 715

<210> SEQ ID NO 119
<211> LENGTH: 249
<212> TYPE: PRT
<213> ORGANISM: mus musculus

<400> SEQUENCE: 119

Ser Thr Gly Ser Gln Val Gln Leu Gln Gln Ser Gly Pro Glu Leu Val
1               5                   10                  15

Lys Pro Gly Ala Ser Val Lys Met Ser Cys Lys Ala Ser Gly Tyr Thr
            20                  25                  30

Phe Thr Asp Tyr Val Ile Asn Trp Gly Lys Gln Arg Ser Gly Gln Gly
        35                  40                  45

Leu Glu Trp Ile Gly Glu Ile Tyr Pro Gly Ser Gly Thr Asn Tyr Tyr
    50                  55                  60

Asn Glu Lys Phe Lys Ala Lys Ala Thr Leu Thr Ala Asp Lys Ser Ser
65                  70                  75                  80

Asn Ile Ala Tyr Met Gln Leu Ser Ser Leu Thr Ser Glu Asp Ser Ala
                85                  90                  95

Val Tyr Phe Cys Ala Arg Arg Gly Arg Tyr Gly Leu Tyr Ala Met Asp
            100                 105                 110

Tyr Trp Gly Gln Gly Thr Ser Val Thr Val Ser Ser Val Glu Gly Gly
        115                 120                 125

Ser Gly Gly Ser Gly Gly Ser Gly Gly Val Asp Asp Ile
    130                 135                 140

Gln Met Thr Gln Thr Thr Ser Ser Leu Ser Ala Ser Leu Gly Asp Arg
145                 150                 155                 160

Val Thr Ile Ser Cys Arg Ala Ser Gln Asp Ile Ser Asn Tyr Leu Asn
                165                 170                 175

Trp Tyr Gln Gln Lys Pro Asp Gly Thr Val Lys Leu Leu Ile Tyr Tyr
            180                 185                 190

Thr Ser Arg Leu His Ser Gly Val Pro Ser Arg Phe Ser Gly Ser Gly
        195                 200                 205

Ser Gly Thr Asp Tyr Ser Leu Thr Ile Asn Asn Leu Glu Gln Glu Asp
    210                 215                 220

Ile Ala Thr Tyr Phe Cys Gln Gln Gly Asn Thr Arg Pro Trp Thr Phe
225                 230                 235                 240

Gly Gly Gly Thr Lys Leu Glu Ile Lys
                245

<210> SEQ ID NO 120
<211> LENGTH: 251
<212> TYPE: PRT
<213> ORGANISM: mus musculus

<400> SEQUENCE: 120

Ser Thr Gly Ser Glu Val Gln Leu Gln Glu Ser Gly Pro Gly Leu Val
1               5                   10                  15

Lys Pro Ser Gln Ser Leu Ser Leu Thr Cys Thr Val Thr Gly Tyr Ser
            20                  25                  30
```

Ile Thr Ser Asp Tyr Ala Trp Asn Trp Ile Arg Gln Phe Pro Gly Asn
            35                  40                  45

Lys Leu Glu Trp Met Gly Tyr Ile Thr Tyr Ser Gly Ser Thr Ser Tyr
 50                  55                  60

Asn Pro Ser Leu Glu Ser Arg Ile Ser Ile Thr Arg Asp Thr Ser Thr
 65                  70                  75                  80

Asn Gln Phe Phe Leu Gln Leu Asn Ser Val Thr Thr Glu Asp Thr Ala
                 85                  90                  95

Thr Tyr Tyr Cys Ala Arg Gly Gly Tyr Gly Ser Ser Trp Gly Val
            100                 105                 110

Phe Ala Tyr Trp Gly Gln Gly Thr Leu Val Thr Val Ser Ala Val Glu
            115                 120                 125

Gly Gly Ser Gly Gly Ser Gly Gly Ser Gly Gly Ser Gly Gly Val Asp
130                 135                 140

Asp Ile Gln Met Thr Gln Ser Pro Ala Ser Leu Ser Ala Ser Val Gly
145                 150                 155                 160

Glu Thr Val Thr Ile Thr Cys Arg Val Ser Glu Asn Ile Tyr Ser Tyr
                165                 170                 175

Leu Ala Trp Tyr Gln Gln Lys Gln Gly Lys Ser Pro Gln Leu Leu Val
            180                 185                 190

Tyr Asn Ala Lys Thr Leu Ala Glu Gly Val Pro Ser Arg Phe Ser Gly
            195                 200                 205

Ser Gly Ser Gly Thr Gln Phe Ser Leu Lys Ile Asn Ser Leu Gln Pro
            210                 215                 220

Glu Asp Phe Gly Ser Tyr Tyr Cys Gln His His Tyr Gly Thr Pro Trp
225                 230                 235                 240

Thr Phe Gly Gly Gly Thr Lys Leu Glu Ile Lys
                245                 250

<210> SEQ ID NO 121
<211> LENGTH: 245
<212> TYPE: PRT
<213> ORGANISM: mus musculus

<400> SEQUENCE: 121

Ser Thr Gly Ser Glu Val Gln Leu Gln Gln Ser Gly Pro Glu Leu Val
 1               5                  10                  15

Lys Pro Gly Ala Ser Val Lys Ile Ser Cys Lys Thr Ser Gly Tyr Thr
             20                  25                  30

Phe Thr Glu Tyr Thr Met His Trp Val Lys Gln Ser His Gly Lys Ser
             35                  40                  45

Leu Glu Trp Ile Gly Gly Ile Ser Pro Asn Ile Gly Gly Thr Ser Tyr
 50                  55                  60

Asn Gln Lys Phe Lys Gly Lys Ala Thr Leu Thr Val Asp Lys Ser Ser
 65                  70                  75                  80

Ser Thr Ala Tyr Met Glu Leu Arg Ser Leu Thr Ser Glu Asp Ser Ala
                 85                  90                  95

Val Tyr Tyr Cys Ala Arg Arg Gly Gly Ser Phe Asp Tyr Trp Gly Gln
            100                 105                 110

Gly Thr Thr Leu Thr Val Ser Ser Val Glu Gly Gly Ser Gly Gly Ser
            115                 120                 125

Gly Gly Ser Gly Gly Ser Gly Gly Val Asp Asp Ile Val Met Thr Gln
130                 135                 140

Ser Pro Ala Thr Leu Ser Val Thr Pro Gly Asp Arg Val Ser Leu Ser
145                 150                 155                 160

```
Cys Arg Ala Ser Gln Ser Ile Ser Asp Tyr Leu His Trp Tyr Gln Gln
                165                 170                 175

Lys Ser His Glu Ser Pro Arg Leu Leu Ile Lys Tyr Ala Ser Gln Ser
            180                 185                 190

Ile Ser Gly Ile Pro Ser Arg Phe Ser Gly Ser Gly Ser Gly Ser Asp
        195                 200                 205

Phe Thr Leu Ser Ile Asn Ser Val Glu Pro Glu Asp Val Gly Val Tyr
    210                 215                 220

Tyr Cys Gln Asn Gly His Ser Phe Pro Leu Thr Phe Gly Ala Gly Thr
225                 230                 235                 240

Lys Leu Glu Leu Lys
            245

<210> SEQ ID NO 122
<211> LENGTH: 246
<212> TYPE: PRT
<213> ORGANISM: Mus musculus

<400> SEQUENCE: 122

Ser Thr Gly Ser Gln Val Gln Leu Gln Gln Ser Ala Val Glu Leu Ala
1               5                   10                  15

Arg Pro Gly Ala Ser Val Lys Met Ser Cys Lys Ala Ser Gly Tyr Thr
            20                  25                  30

Phe Thr Ser Phe Thr Met His Trp Val Lys Gln Arg Pro Gly Gln Gly
        35                  40                  45

Leu Glu Trp Ile Gly Tyr Ile Asn Pro Ser Ser Gly Tyr Thr Glu Tyr
    50                  55                  60

Asn Gln Lys Phe Lys Asp Lys Thr Thr Leu Thr Ala Asp Lys Ser Ser
65                  70                  75                  80

Ser Thr Ala Tyr Met Gln Leu Asp Ser Leu Thr Ser Asp Asp Ser Ala
                85                  90                  95

Val Tyr Tyr Cys Val Arg Gly Ser Arg Gly Phe Asp Tyr Trp Gly
            100                 105                 110

Gln Gly Thr Leu Val Thr Val Ser Ala Val Glu Gly Gly Ser Gly Gly
        115                 120                 125

Ser Gly Gly Ser Gly Gly Ser Gly Val Asp Asp Ile Gln Met Ile
    130                 135                 140

Gln Ser Pro Ala Ser Leu Ser Val Ser Val Gly Glu Thr Val Thr Ile
145                 150                 155                 160

Thr Cys Arg Ala Ser Glu Asn Ile Tyr Ser Asn Leu Ala Trp Phe Gln
                165                 170                 175

Gln Lys Gln Gly Lys Ser Pro Gln Leu Leu Val Tyr Ala Ala Thr Asn
            180                 185                 190

Leu Ala Asp Gly Val Pro Ser Arg Phe Ser Gly Ser Gly Ser Gly Thr
        195                 200                 205

Gln Tyr Ser Leu Lys Ile Asn Ser Leu Gln Ser Glu Asp Phe Gly Ile
    210                 215                 220

Tyr Tyr Cys Gln His Phe Trp Gly Thr Pro Arg Thr Phe Gly Gly Gly
225                 230                 235                 240

Thr Lys Leu Glu Ile Lys
            245

<210> SEQ ID NO 123
<211> LENGTH: 245
<212> TYPE: PRT
```

<213> ORGANISM: Mus musculus

<400> SEQUENCE: 123

```
Ser Thr Gly Ser Gln Val Gln Leu Gln Gln Pro Gly Ser Val Leu Val
1               5                   10                  15
Arg Pro Gly Ala Ser Val Lys Leu Ser Cys Lys Ala Ser Gly Tyr Thr
                20                  25                  30
Phe Thr Ser Ser Trp Met His Trp Ala Lys Gln Arg Pro Gly Gln Gly
            35                  40                  45
Leu Glu Trp Ile Gly His Ile His Pro Asn Ser Gly Ile Ser Asn Tyr
        50                  55                  60
Asn Glu Lys Phe Lys Gly Lys Ala Thr Leu Thr Val Asp Thr Ser Ser
65                  70                  75                  80
Ser Thr Ala Tyr Val Asp Leu Ser Ser Leu Thr Ser Glu Asp Ser Ala
                85                  90                  95
Val Tyr Tyr Cys Ala Arg Gly Gly Arg Phe Asp Asp Trp Gly Ala Gly
                100                 105                 110
Thr Thr Val Thr Val Ser Ser Val Glu Gly Ser Gly Gly Ser Gly Ser
            115                 120                 125
Gly Ser Gly Gly Ser Gly Gly Val Asp Asp Ile Val Met Thr Gln Ser
        130                 135                 140
Pro Ala Thr Leu Ser Val Thr Pro Gly Asp Arg Val Ser Leu Ser Cys
145                 150                 155                 160
Arg Ala Ser Gln Ser Ile Ser Asp Tyr Leu His Trp Tyr Gln Gln Lys
                165                 170                 175
Ser His Glu Ser Pro Arg Leu Leu Ile Lys Tyr Ala Ser Gln Ser Ile
                180                 185                 190
Ser Gly Ile Pro Ser Arg Phe Ser Gly Ser Gly Ser Gly Ser Asp Phe
            195                 200                 205
Thr Leu Ser Ile Asn Ser Val Glu Pro Glu Asp Val Gly Val Tyr Tyr
        210                 215                 220
Cys Gln Asn Gly His Ser Phe Leu Met Tyr Thr Phe Gly Gly Gly Thr
225                 230                 235                 240
Lys Leu Glu Ile Lys
                245
```

<210> SEQ ID NO 124
<211> LENGTH: 249
<212> TYPE: PRT
<213> ORGANISM: Mus musculus

<400> SEQUENCE: 124

```
Ser Thr Gly Ser Asp Val Gln Leu Gln Glu Ser Gly Pro Gly Leu Val
1               5                   10                  15
Lys Pro Ser Gln Ser Leu Ser Leu Thr Cys Thr Val Thr Gly Tyr Ser
                20                  25                  30
Ile Thr Ser Asp Tyr Ala Trp Asn Trp Ile Arg Gln Phe Pro Gly Asn
            35                  40                  45
Lys Leu Glu Trp Met Gly Tyr Ile Thr Tyr Ser Gly Ser Thr Asn Tyr
        50                  55                  60
Asn Pro Ser Leu Lys Ser Arg Ile Ser Ile Thr Arg Asp Thr Ser Lys
65                  70                  75                  80
Asn Gln Phe Phe Leu Gln Leu Asn Ser Val Thr Thr Glu Asp Thr Ala
                85                  90                  95
Thr Tyr Tyr Cys Ala Arg Cys Trp Asp Tyr Ala Leu Tyr Ala Met Asp
```

```
            100                 105                 110
Cys Trp Gly Gln Gly Thr Ser Val Thr Val Ser Ser Val Glu Gly Gly
            115                 120                 125

Ser Gly Gly Ser Gly Gly Ser Gly Gly Ser Gly Gly Val Asp Asp Ile
            130                 135                 140

Gln Met Thr Gln Ser Pro Ala Ser Leu Ser Ala Ser Val Gly Glu Thr
145                 150                 155                 160

Val Thr Ile Thr Cys Arg Thr Ser Glu Asn Ile Tyr Ser Tyr Leu Ala
                165                 170                 175

Trp Cys Gln Gln Lys Gln Gly Lys Ser Pro Gln Leu Leu Val Tyr Asn
                180                 185                 190

Ala Lys Thr Leu Ala Glu Gly Val Pro Ser Arg Phe Ser Gly Ser Gly
            195                 200                 205

Ser Gly Thr His Phe Ser Leu Lys Ile Asn Ser Leu Gln Pro Glu Asp
            210                 215                 220

Phe Gly Ile Tyr Tyr Cys Gln His His Tyr Asp Thr Pro Leu Thr Phe
225                 230                 235                 240

Gly Ala Gly Thr Lys Leu Glu Leu Lys
                245

<210> SEQ ID NO 125
<211> LENGTH: 246
<212> TYPE: PRT
<213> ORGANISM: Mus musculus

<400> SEQUENCE: 125

Ser Thr Gly Ser Gln Ile Gln Leu Val Gln Ser Gly Pro Glu Leu Gln
1               5                   10                  15

Lys Pro Gly Glu Thr Val Lys Ile Ser Cys Lys Ala Ser Gly Tyr Thr
            20                  25                  30

Phe Thr Asn Tyr Gly Met Asn Trp Val Lys Gln Ala Pro Gly Lys Gly
        35                  40                  45

Leu Lys Trp Met Gly Trp Ile Asn Thr Asn Thr Gly Glu Pro Thr Tyr
    50                  55                  60

Ala Glu Glu Phe Lys Gly Arg Phe Ala Phe Ser Leu Glu Thr Ser Ala
65                  70                  75                  80

Ser Thr Ala Tyr Leu Gln Ile Asn Asn Leu Lys Asn Glu Asp Thr Ala
                85                  90                  95

Thr Tyr Phe Cys Ala Arg Asp Tyr Leu Tyr Tyr Phe Asp Tyr Trp Gly
            100                 105                 110

Gln Gly Thr Thr Leu Thr Val Ser Ser Val Glu Gly Gly Ser Gly Gly
            115                 120                 125

Ser Gly Gly Ser Gly Gly Ser Gly Gly Val Asp Asn Ile Val Met Thr
            130                 135                 140

Gln Ser Pro Lys Ser Met Ser Met Ser Val Gly Glu Arg Val Thr Leu
145                 150                 155                 160

Thr Cys Lys Ala Ser Glu Asn Val Val Thr Tyr Val Ser Trp Tyr Gln
                165                 170                 175

Gln Lys Pro Glu Gln Ser Pro Lys Leu Leu Ile Tyr Gly Ala Ser Asn
            180                 185                 190

Arg Tyr Thr Gly Val Pro Asp Arg Phe Thr Gly Ser Gly Ser Ala Thr
        195                 200                 205

Asp Phe Thr Leu Thr Ile Ser Ser Val Gln Ala Glu Asp Leu Ala Asp
    210                 215                 220
```

```
Tyr His Cys Gly Gln Gly Tyr Ser Tyr Pro Tyr Thr Phe Gly Gly Gly
225                 230                 235                 240

Thr Lys Leu Glu Ile Lys
            245

<210> SEQ ID NO 126
<211> LENGTH: 751
<212> TYPE: DNA
<213> ORGANISM: mus musculus

<400> SEQUENCE: 126
gtcgactgga agccaggtac agctgcagca gtctggccct gaactcgtca aaccaggagc      60
ttccgtgaag atgtcctgca aggcttcagg gtacacgttt accgactatg tgatcaattg     120
gggtaagcag cgctctgggc aaggcttgga gtggattggc gagatctatc ctggagtgg     180
gaccaactat tacaacgaga gttcaaggc caaagccact ttgactgcag acaagagctc     240
aaacattgcc tacatgcaac tgagctccct gacatcagag gattctgctg tgtacttctg     300
tgcacgtaga ggtcggtacg gtctgtatgc catggactat tggggccaag gcacttccgt     360
gacagtcagc tctgtggaag gaggaagtgg cggttcagga ggtagcggag gtccggagg      420
agtggatgac attcagatga cacagaccac ttctagcctc tccgcatccc ttggggatag     480
ggtcaccatc agttgtaggg ctagccagga catttccaat tacctgaact ggtatcagca     540
gaaacccgat ggcacagtta agcttctgat ctactacaca agcagactgc actcaggggt     600
tccatctcgg tttagtggaa gtggctctgg taccgactat tccctgacca tcaacaatct     660
ggaacaggaa gatatcgcca cctacttctg ccaacagggc aatactcgac cctggacatt     720
tggtggcggc acgaaactcg agataaaata a                                    751

<210> SEQ ID NO 127
<211> LENGTH: 757
<212> TYPE: DNA
<213> ORGANISM: Mus musculus

<400> SEQUENCE: 127
gtcgactgga tccgaggtac agttgcagga gagtgggcct ggactggtca aaccctccca     60
atctctgagc ttgacatgca cagtcacagg ctacagcatc acctccgact acgcttggaa    120
ttggattcga cagtttcccg caacaagct ggaatggatg ggctacatca cctatagtgg     180
tagcacttcc tataatccct cacttgagag ccggatttcc atcactaggg atacgagcac    240
caaccagttc ttcctgcagc tgaatagcgt caccaccgaa gatactgcca cctattactg    300
cgcaagaggc ggttactatg cagttcatg gggtgtattc gcctattggg acaggggac      360
acttgtgaca gtgtctgctg ttgaaggtgg atccggcgga tcaggaggga gtggtggcag    420
tggaggtgtt gacgacattc agatgaccca atccctgct tctctctcag cctctgtggg    480
agagactgtg accataacct gtcgtgttag cgagaacatc tactcctatc tcgcctggta    540
tcagcagaaa caggggaaat ccccacaact gctcgtgtac aatgccaaga ctctggcaga    600
aggagtgcca agccgctttt ccgggtctgg gtctgggaca cagttctcac tgaagatcaa    660
ctcttttgcaa cctgaggatt ttggctctta ctactgtcag catcactatg gcacaccatg    720
gacgtttggt ggcggcacta agctggagat taagtaa                            757

<210> SEQ ID NO 128
<211> LENGTH: 739
<212> TYPE: DNA
<213> ORGANISM: Mus musculus
```

<400> SEQUENCE: 128

```
gtcgactggg tccgaagtgc aactgcaaca gtctggccct gagctggtca aacccggtgc    60
ttcagtgaag atctcctgca agacatccgg ctacaccttc actgagtaca ccatgcactg   120
ggtcaaacag tctcacggta agagcctgga gtggataggc ggaatttcac caacattgg   180
agggacctcc tataaccaga gttcaaggg caaagccacc cttacagttg acaagagcag    240
ttcaactgcc tacatggaac tgcgctcatt gacctccgag gattcagccg tgtattactg    300
cgctagaagg ggaggatcct tcgattattg gggccaaggc actacgctta ccgtgagcag    360
cgttgaaggt ggttctggcg gctctggtgg aagtggaggg agtggcgggg tagacgacat    420
cgtgatgact cagagtccag caactctgtc cgttacacct ggagatcgag tgtctctgag    480
ttgtcgtgca agccagtcta tctctgacta tctgcactgg tatcagcaga gagccatga    540
gtcacctagg ctgttgatca agtacgcctc tcagtccatt agcgggattc catcccggtt    600
tagtggctct ggctccggta gtgacttcac actcagcatc aatagcgtcg aaccagagga    660
tgtaggggtg tactactgtc agaatgggca ttccttctcc ctcacatttg gagctggtac    720
caaactcgag ctgaaataa                                                739
```

<210> SEQ ID NO 129
<211> LENGTH: 742
<212> TYPE: DNA
<213> ORGANISM: Mus musculus

<400> SEQUENCE: 129

```
gtcgactggc tcccaagtac agcttcagca gtctgccgtc gaacttgctc gaccaggagc    60
ttcagtgaag atgagctgca aagcctctgg ttacaccttc acgtcctta ccatgcattg    120
ggtgaagcag cgtcctggcc aaggcctgga gtggattggc tacatcaatc cctccagcgg    180
gtataccgag tacaaccaga gttcaaggga caaaacaacc ctgactgccg ataagtcaag    240
tagcacagcc tatatgcagc tggattccct gacatcagac gatagcgctg tgtattactg    300
cgttaggggc tctagcagag ggttcgacta ttggggtcaa ggcacactgg tcacggttag    360
tgccgttgaa ggaggctctg gaggcagtgg aggttctgga gggtcaggcg gtgtggatga    420
cattcagatg attcagagtc ccgctagctt gagtgtaagc gtcggtgaga cagtgaccat    480
cacttgtcgc gcatccgaaa acatctactc caatctcgca tggttccagc agaaacaggg    540
caaatcaccc caattgctcg tgtatgccgc aactaatctg gctgatggtg tgccttccag    600
gtttagcggg tctggatctg ggactcagta ctccctgaag atcaactccc tccagtctga    660
ggacttcggg atctattact gtcagcactt ttggggaact ccacggacct tggaggcgg    720
gaccaaactg gagataaagt aa                                           742
```

<210> SEQ ID NO 130
<211> LENGTH: 696
<212> TYPE: DNA
<213> ORGANISM: Mus musculus

<400> SEQUENCE: 130

```
ctggtgaggc aggtgcatc tgtgaagctg tcatgcaaag catccgggta cacgttcacc    60
tcttcatgga tgcattgggc caaacagcgt ccaggccagg gccttgagtg gattggacac    120
attcacccca atagcggcat atccaactac aacgagaagt tcaagggcaa agccacactg    180
acagtggata cttccagctc tacagcctat gtggaccta gtagcttgac cagtgaggat    240
```

```
tctgccgtat actactgtgc tagaggtggg cggtttgacg attggggtgc tgggaccaca    300
gtcaccgtga gcagtgtcga aggtggatca ggtggatctg gaggctcagg cggttctggc    360
ggtgttgacg acatcgtgat gactcaaagc cctgctactc tctctgtcac acccggagat    420
agggtaagcc tcagttgtcg agcaagccag tcaatcagcg actatctgca ctggtatcag    480
cagaagtccc atgaatcccc acgcttgctc atcaagtacg ccagtcagtc catcagtggc    540
attccttccc ggttttctgg gtctggatcc gggtcagact tcactctgag cattaactcc    600
gtcgaacccg aggatgttgg cgtgtattat tgccagaatg acattccttt cctgatgtac    660
acctttggcg agggaccaa actggagatc aagtaa                               696

<210> SEQ ID NO 131
<211> LENGTH: 751
<212> TYPE: DNA
<213> ORGANISM: Mus musculus

<400> SEQUENCE: 131
gtcgactggg tctgatgtgc agttgcagga gtcaggacct gggcttgtca agccaagcca     60
gagcctcagt ctcacttgca ctgtcacagg ctatagcatc acatccgact atgcttggaa    120
ttggattagg cagtttcctg caataagct ggaatggatg gggtacatca cctattccgg     180
cagtaccaac tacaatccca gcttgaaatc tcggatttcc ataacacgcg atactagcaa    240
gaaccagttc ttccttcagc tgaactctgt gacaacagag gataccgcta cgtactattg    300
cgccagatgc tgggattacg ccctgtatgc catggactgt gggggtcaag gtaccagcgt    360
tactgtgtct agcgtcgaag gcggaagtgg cggctcagga gggtcaggag ctcaggcgg    420 agtggatgac attcagatga cccaatctcc cgcatccctg tccgcatcag taggggagac    480
agtgaccatt acctgtcgta cttccgagaa catctactcc tatcttgcct ggtgtcaaca    540
gaaacagggg aaaagtccac agctgctggt gtataacgcc aagaccttgg cagaaggtgt    600
tcccagtcga ttctctggtt ccggatccgg tacacacttc agcctgaaga tcaattctct    660
gcaaccagag gactttggaa tctactactg ccagcatcac tacgacactc ctctgacgtt    720
tggcgctggt accaagctcg aactgaaata a                                   751

<210> SEQ ID NO 132
<211> LENGTH: 742
<212> TYPE: DNA
<213> ORGANISM: Mus musculus

<400> SEQUENCE: 132
gtcgactggt agccagatac agctggtaca gtcaggacca gagctgcaga aacctggaga     60
gacagtgaag atcagctgca aggctagcgg gtacaccttc acgaattacg ggatgaactg    120
ggtcaagcag gctccaggca aagggctgaa gtggatgggc tggattaaca ccaatactgg    180
ggaaccaacc tatgccgagg aattcaaggg agatttgcc ttttccctcg aaaccagcgc     240
ctcaaccgcc tatctccaga tcaacaacct gaagaatgag gataccgcta cctacttctg    300
tgcaagggac tacctctact acttcgacta ttggggccaa ggtacgactc ttacagtctc    360
tagtgttgag ggaggggagtg gaggttctgg aggctctggt ggctctggag gcgttgacaa    420
catcgtgatg actcagtctc ccaaaagcat gagtatgagt gtgggtgaac gagttacctt    480
gacatgcaaa gcctccgaga atgtcgtgac atacgtgtcc tggtatcagc agaaacccga    540
gcaatcccct aagctgctga tctatggcgc tagcaatcgc tatactggcg tacctgatcg    600
gttcacagga tcaggctcag ccactgactt tactcttacc atttcctccg tgcaggcaga    660
```

-continued

```
agatttggca gattaccact gtgggcaagg ttactcttat ccctatacat ttggaggcgg    720
cacaaagctg gagattaagt aa                                             742
```

<210> SEQ ID NO 133
<211> LENGTH: 720
<212> TYPE: PRT
<213> ORGANISM: Artificial
<220> FEATURE:
<223> OTHER INFORMATION: Chimeric homo sapiens mus musculus

<400> SEQUENCE: 133

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
```

```
                    340                 345                 350
Leu Pro Ala Pro Ile Glu Lys Thr Ile Ser Lys Ala Lys Gly Gln Pro
                355                 360                 365

Arg Glu Pro Gln Val Tyr Thr Lys Pro Pro Ser Arg Glu Glu Met Thr
            370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Val Pro Val Leu Asp Ser Asp Gly Ser Phe Arg Leu Ala
            420                 425                 430

Ser Tyr Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
            450                 455                 460

Ser Leu Ser Leu Ser Pro Gly Ser Thr Gly Ser Gln Val Gln Leu Gln
465                 470                 475                 480

Gln Ser Gly Pro Glu Leu Val Lys Pro Gly Ala Ser Val Lys Met Ser
                485                 490                 495

Cys Lys Ala Ser Gly Tyr Thr Phe Thr Asp Tyr Val Ile Asn Trp Gly
            500                 505                 510

Lys Gln Arg Ser Gly Gln Gly Leu Glu Trp Ile Gly Glu Ile Tyr Pro
            515                 520                 525

Gly Ser Gly Thr Asn Tyr Tyr Asn Glu Lys Phe Lys Ala Lys Ala Thr
        530                 535                 540

Leu Thr Ala Asp Lys Ser Ser Asn Ile Ala Tyr Met Gln Leu Ser Ser
545                 550                 555                 560

Leu Thr Ser Glu Asp Ser Ala Val Tyr Phe Cys Ala Arg Arg Gly Arg
                565                 570                 575

Tyr Gly Leu Tyr Ala Met Asp Tyr Trp Gly Gln Gly Thr Ser Val Thr
            580                 585                 590

Val Ser Ser Val Glu Gly Gly Ser Gly Gly Ser Gly Gly Ser Gly Gly
            595                 600                 605

Ser Gly Gly Val Asp Asp Ile Gln Met Thr Gln Thr Thr Ser Ser Leu
    610                 615                 620

Ser Ala Ser Leu Gly Asp Arg Val Thr Ile Ser Cys Arg Ala Ser Gln
625                 630                 635                 640

Asp Ile Ser Asn Tyr Leu Asn Trp Tyr Gln Gln Lys Pro Asp Gly Thr
                645                 650                 655

Val Lys Leu Leu Ile Tyr Tyr Thr Ser Arg Leu His Ser Gly Val Pro
            660                 665                 670

Ser Arg Phe Ser Gly Ser Gly Ser Gly Thr Asp Tyr Ser Leu Thr Ile
            675                 680                 685

Asn Asn Leu Glu Gln Glu Asp Ile Ala Thr Tyr Phe Cys Gln Gln Gly
            690                 695                 700

Asn Thr Arg Pro Trp Thr Phe Gly Gly Gly Thr Lys Leu Glu Ile Lys
705                 710                 715                 720
```

<210> SEQ ID NO 134
<211> LENGTH: 722
<212> TYPE: PRT
<213> ORGANISM: Artificial
<220> FEATURE:
<223> OTHER INFORMATION: Chimeric homo sapiens mus musculus

```
<400> SEQUENCE: 134

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Ser Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
    195                 200                 205

Leu Ser Ser Leu Ala Ser Glu Asp Ser Ala Val Tyr Phe Cys Ala Arg
210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
    275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
    355                 360                 365

Arg Glu Pro Gln Val Tyr Thr Lys Pro Pro Ser Arg Glu Glu Met Thr
370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415
```

```
Lys Thr Thr Val Pro Val Leu Asp Ser Asp Gly Ser Phe Arg Leu Ala
            420                 425                 430

Ser Tyr Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Ser Thr Gly Ser Glu Val Gln Leu Gln
465                 470                 475                 480

Glu Ser Gly Pro Gly Leu Val Lys Pro Ser Gln Ser Leu Ser Leu Thr
                485                 490                 495

Cys Thr Val Thr Gly Tyr Ser Ile Thr Ser Asp Tyr Ala Trp Asn Trp
                500                 505                 510

Ile Arg Gln Phe Pro Gly Asn Lys Leu Glu Trp Met Gly Tyr Ile Thr
            515                 520                 525

Tyr Ser Gly Ser Thr Ser Tyr Asn Pro Ser Leu Glu Ser Arg Ile Ser
        530                 535                 540

Ile Thr Arg Asp Thr Ser Thr Asn Gln Phe Phe Leu Gln Leu Asn Ser
545                 550                 555                 560

Val Thr Thr Glu Asp Thr Ala Thr Tyr Tyr Cys Ala Arg Gly Gly Tyr
                565                 570                 575

Tyr Gly Ser Ser Trp Gly Val Phe Ala Tyr Trp Gly Gln Gly Thr Leu
            580                 585                 590

Val Thr Val Ser Ala Val Glu Gly Gly Ser Gly Gly Ser Gly Gly Ser
        595                 600                 605

Gly Gly Ser Gly Gly Val Asp Asp Ile Gln Met Thr Gln Ser Pro Ala
            610                 615                 620

Ser Leu Ser Ala Ser Val Gly Glu Thr Val Thr Ile Thr Cys Arg Val
625                 630                 635                 640

Ser Glu Asn Ile Tyr Ser Tyr Leu Ala Trp Tyr Gln Gln Lys Gln Gly
                645                 650                 655

Lys Ser Pro Gln Leu Leu Val Tyr Asn Ala Lys Thr Leu Ala Glu Gly
            660                 665                 670

Val Pro Ser Arg Phe Ser Gly Ser Gly Ser Gly Thr Gln Phe Ser Leu
        675                 680                 685

Lys Ile Asn Ser Leu Gln Pro Glu Asp Phe Gly Ser Tyr Tyr Cys Gln
            690                 695                 700

His His Tyr Gly Thr Pro Trp Thr Phe Gly Gly Gly Thr Lys Leu Glu
705                 710                 715                 720

Ile Lys

<210> SEQ ID NO 135
<211> LENGTH: 716
<212> TYPE: PRT
<213> ORGANISM: Artificial
<220> FEATURE:
<223> OTHER INFORMATION: Chimeric homo sapiens mus musculus

<400> SEQUENCE: 135

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45
```

```
Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Gly
                100                 105                 110

Gly Gly Gly Ser Gly Gly Gly Ser Gly Gly Gly Ser Gln Val
            115                 120                 125

Gln Leu Gln Gln Ser Gly Ala Glu Leu Val Arg Pro Gly Ser Ser Val
130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
                180                 185                 190

Lys Ala Thr Leu Thr Ala Asp Glu Ser Ser Ser Thr Ala Tyr Met Gln
                195                 200                 205

Leu Ser Ser Leu Ala Ser Glu Asp Ser Ala Val Tyr Phe Cys Ala Arg
210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
                275                 280                 285

Val Asp Val Ser His Glu Asp Pro Glu Val Lys Phe Asn Trp Tyr Val
                290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
                355                 360                 365

Arg Glu Pro Gln Val Tyr Thr Lys Pro Pro Ser Arg Glu Glu Met Thr
                370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Val Pro Val Leu Asp Ser Asp Gly Ser Phe Arg Leu Ala
                420                 425                 430

Ser Tyr Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
450                 455                 460

Ser Leu Ser Leu Ser Pro Gly Ser Thr Gly Ser Glu Val Gln Leu Gln
```

```
                  465                 470                 475                 480
        Gln Ser Gly Pro Glu Leu Val Lys Pro Gly Ala Ser Val Lys Ile Ser
                        485                 490                 495

Cys Lys Thr Ser Gly Tyr Thr Phe Thr Glu Tyr Thr Met His Trp Val
                        500                 505                 510

Lys Gln Ser His Gly Lys Ser Leu Glu Trp Ile Gly Ile Ser Pro
                        515                 520                 525

Asn Ile Gly Gly Thr Ser Tyr Asn Gln Lys Phe Lys Gly Lys Ala Thr
                        530                 535                 540

Leu Thr Val Asp Lys Ser Ser Thr Ala Tyr Met Glu Leu Arg Ser
        545                 550                 555                 560

Leu Thr Ser Glu Asp Ser Ala Val Tyr Tyr Cys Ala Arg Arg Gly Gly
                        565                 570                 575

Ser Phe Asp Tyr Trp Gly Gln Gly Thr Thr Leu Thr Val Ser Ser Val
                        580                 585                 590

Glu Gly Gly Ser Gly Gly Ser Gly Gly Ser Gly Gly Ser Gly Gly Val
                        595                 600                 605

Asp Asp Ile Val Met Thr Gln Ser Pro Ala Thr Leu Ser Val Thr Pro
        610                 615                 620

Gly Asp Arg Val Ser Leu Ser Cys Arg Ala Ser Gln Ser Ile Ser Asp
        625                 630                 635                 640

Tyr Leu His Trp Tyr Gln Gln Lys Ser His Glu Ser Pro Arg Leu Leu
                        645                 650                 655

Ile Lys Tyr Ala Ser Gln Ser Ile Ser Gly Ile Pro Ser Arg Phe Ser
                        660                 665                 670

Gly Ser Gly Ser Gly Ser Asp Phe Thr Leu Ser Ile Asn Ser Val Glu
                        675                 680                 685

Pro Glu Asp Val Gly Val Tyr Tyr Cys Gln Asn Gly His Ser Phe Pro
                        690                 695                 700

Leu Thr Phe Gly Ala Gly Thr Lys Leu Glu Leu Lys
        705                 710                 715

<210> SEQ ID NO 136
<211> LENGTH: 717
<212> TYPE: PRT
<213> ORGANISM: Artificial
<220> FEATURE:
<223> OTHER INFORMATION: Chimeric homo sapiens mus musculus

<400> SEQUENCE: 136

Asp Ile Gln Leu Thr Gln Ser Pro Ala Ser Leu Ala Val Ser Leu Gly
        1               5                   10                  15

Gln Arg Ala Thr Ile Ser Cys Lys Ala Ser Gln Ser Val Asp Tyr Asp
                        20                  25                  30

Gly Asp Ser Tyr Leu Asn Trp Tyr Gln Gln Ile Pro Gly Gln Pro Pro
                        35                  40                  45

Lys Leu Leu Ile Tyr Asp Ala Ser Asn Leu Val Ser Gly Ile Pro Pro
                        50                  55                  60

Arg Phe Ser Gly Ser Gly Ser Gly Thr Asp Phe Thr Leu Asn Ile His
        65                  70                  75                  80

Pro Val Glu Lys Val Asp Ala Ala Thr Tyr His Cys Gln Gln Ser Thr
                        85                  90                  95

Glu Asp Pro Trp Thr Phe Gly Gly Gly Thr Lys Leu Glu Ile Lys Gly
                        100                 105                 110

Gly Gly Gly Ser Gly Gly Gly Gly Ser Gly Gly Gly Gly Ser Gln Val
```

```
            115                 120                 125
Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
                180                 185                 190

Lys Ala Thr Leu Thr Ala Asp Glu Ser Ser Ser Thr Ala Tyr Met Gln
                195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
                275                 280                 285

Val Asp Val Ser His Glu Asp Pro Glu Val Lys Phe Asn Trp Tyr Val
                290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
                355                 360                 365

Arg Glu Pro Gln Val Tyr Thr Lys Pro Pro Ser Arg Glu Glu Met Thr
                370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Val Pro Val Leu Asp Ser Asp Gly Ser Phe Arg Leu Ala
                420                 425                 430

Ser Tyr Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
                450                 455                 460

Ser Leu Ser Leu Ser Pro Gly Ser Thr Gly Ser Gln Val Gln Leu Gln
                465                 470                 475                 480

Gln Ser Ala Val Glu Leu Ala Arg Pro Gly Ala Ser Val Lys Met Ser
                485                 490                 495

Cys Lys Ala Ser Gly Tyr Thr Phe Thr Ser Phe Thr Met His Trp Val
                500                 505                 510

Lys Gln Arg Pro Gly Gln Gly Leu Glu Trp Ile Gly Tyr Ile Asn Pro
                515                 520                 525

Ser Ser Gly Tyr Thr Glu Tyr Asn Gln Lys Phe Lys Asp Lys Thr Thr
                530                 535                 540
```

Leu Thr Ala Asp Lys Ser Ser Thr Ala Tyr Met Gln Leu Asp Ser
545                 550                 555                 560

Leu Thr Ser Asp Asp Ser Ala Val Tyr Tyr Cys Val Arg Gly Ser Ser
                565                 570                 575

Arg Gly Phe Asp Tyr Trp Gly Gln Gly Thr Leu Val Thr Val Ser Ala
            580                 585                 590

Val Glu Gly Gly Ser Gly Gly Ser Gly Gly Ser Gly Gly Ser Gly Gly
        595                 600                 605

Val Asp Asp Ile Gln Met Ile Gln Ser Pro Ala Ser Leu Ser Val Ser
610                 615                 620

Val Gly Glu Thr Val Thr Ile Thr Cys Arg Ala Ser Glu Asn Ile Tyr
625                 630                 635                 640

Ser Asn Leu Ala Trp Phe Gln Gln Lys Gln Gly Lys Ser Pro Gln Leu
                645                 650                 655

Leu Val Tyr Ala Ala Thr Asn Leu Ala Asp Gly Val Pro Ser Arg Phe
            660                 665                 670

Ser Gly Ser Gly Ser Gly Thr Gln Tyr Ser Leu Lys Ile Asn Ser Leu
        675                 680                 685

Gln Ser Glu Asp Phe Gly Ile Tyr Tyr Cys Gln His Phe Trp Gly Thr
690                 695                 700

Pro Arg Thr Phe Gly Gly Gly Thr Lys Leu Glu Ile Lys
705                 710                 715

<210> SEQ ID NO 137
<211> LENGTH: 716
<212> TYPE: PRT
<213> ORGANISM: Artificial
<220> FEATURE:
<223> OTHER INFORMATION: Chimeric homo sapiens mus musculus

<400> SEQUENCE: 137

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
        50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

```
Lys Ala Thr Leu Thr Ala Asp Glu Ser Ser Thr Ala Tyr Met Gln
            195                 200                 205

Leu Ser Ser Leu Ala Ser Glu Asp Ser Ala Val Tyr Phe Cys Ala Arg
        210                 215                 220

Arg Glu Thr Thr Thr Val Gly Arg Tyr Tyr Ala Met Asp Tyr Trp
225                 230                 235                 240

Gly Gln Gly Thr Thr Val Thr Val Ser Ser Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
        290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Lys Pro Pro Ser Arg Glu Glu Met Thr
            370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Val Pro Val Leu Asp Ser Asp Gly Ser Phe Arg Leu Ala
            420                 425                 430

Ser Tyr Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
        450                 455                 460

Ser Leu Ser Leu Ser Pro Gly Ser Thr Gly Ser Gln Val Gln Leu Gln
465                 470                 475                 480

Gln Pro Gly Ser Val Leu Val Arg Pro Gly Ala Ser Val Lys Leu Ser
                485                 490                 495

Cys Lys Ala Ser Gly Tyr Thr Phe Thr Ser Ser Trp Met His Trp Ala
            500                 505                 510

Lys Gln Arg Pro Gly Gln Gly Leu Glu Trp Ile Gly His Ile His Pro
            515                 520                 525

Asn Ser Gly Ile Ser Asn Tyr Asn Glu Lys Phe Lys Gly Lys Ala Thr
            530                 535                 540

Leu Thr Val Asp Thr Ser Ser Thr Ala Tyr Val Asp Leu Ser Ser
545                 550                 555                 560

Leu Thr Ser Glu Asp Ser Ala Val Tyr Tyr Cys Ala Arg Gly Gly Arg
                565                 570                 575

Phe Asp Asp Trp Gly Ala Gly Thr Thr Val Thr Val Ser Ser Val Glu
            580                 585                 590

Gly Gly Ser Gly Gly Ser Gly Ser Gly Gly Ser Gly Gly Val Asp
            595                 600                 605
```

```
Asp Ile Val Met Thr Gln Ser Pro Ala Thr Leu Ser Val Thr Pro Gly
    610                 615                 620

Asp Arg Val Ser Leu Ser Cys Arg Ala Ser Gln Ser Ile Ser Asp Tyr
625                 630                 635                 640

Leu His Trp Tyr Gln Gln Lys Ser His Glu Ser Pro Arg Leu Leu Ile
                645                 650                 655

Lys Tyr Ala Ser Gln Ser Ile Ser Gly Ile Pro Ser Arg Phe Ser Gly
                660                 665                 670

Ser Gly Ser Gly Ser Asp Phe Thr Leu Ser Ile Asn Ser Val Glu Pro
            675                 680                 685

Glu Asp Val Gly Val Tyr Tyr Cys Gln Asn Gly His Ser Phe Leu Met
690                 695                 700

Tyr Thr Phe Gly Gly Gly Thr Lys Leu Glu Ile Lys
705                 710                 715

<210> SEQ ID NO 138
<211> LENGTH: 720
<212> TYPE: PRT
<213> ORGANISM: Artificial
<220> FEATURE:
<223> OTHER INFORMATION: Chimeric homo sapiens mus musculus

<400> SEQUENCE: 138

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255
```

-continued

```
Pro Glu Leu Leu Gly Gly Pro Ser Val Phe Leu Phe Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
            325                 330                 335

Asp Trp Leu Asn Gly Lys Glu Tyr Lys Cys Lys Val Ser Asn Lys Ala
        340                 345                 350

Leu Pro Ala Pro Ile Glu Lys Thr Ile Ser Lys Ala Lys Gly Gln Pro
    355                 360                 365

Arg Glu Pro Gln Val Tyr Thr Lys Pro Pro Ser Arg Glu Glu Met Thr
370                 375                 380

Lys Asn Gln Val Ser Leu Ser Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Val Pro Val Leu Asp Ser Asp Gly Ser Phe Arg Leu Ala
        420                 425                 430

Ser Tyr Leu Thr Val Asp Lys Ser Arg Trp Gln Gln Gly Asn Val Phe
    435                 440                 445

Ser Cys Ser Val Met His Glu Ala Leu His Asn His Tyr Thr Gln Lys
450                 455                 460

Ser Leu Ser Leu Ser Pro Gly Ser Thr Gly Ser Asp Val Gln Leu Gln
465                 470                 475                 480

Glu Ser Gly Pro Gly Leu Val Lys Pro Ser Gln Ser Leu Ser Leu Thr
            485                 490                 495

Cys Thr Val Thr Gly Tyr Ser Ile Thr Ser Asp Tyr Ala Trp Asn Trp
        500                 505                 510

Ile Arg Gln Phe Pro Gly Asn Lys Leu Glu Trp Met Gly Tyr Ile Thr
    515                 520                 525

Tyr Ser Gly Ser Thr Asn Tyr Asn Pro Ser Leu Lys Ser Arg Ile Ser
530                 535                 540

Ile Thr Arg Asp Thr Ser Lys Asn Gln Phe Phe Leu Gln Leu Asn Ser
545                 550                 555                 560

Val Thr Thr Glu Asp Thr Ala Thr Tyr Tyr Cys Ala Arg Cys Trp Asp
            565                 570                 575

Tyr Ala Leu Tyr Ala Met Asp Cys Trp Gly Gln Gly Thr Ser Val Thr
        580                 585                 590

Val Ser Ser Val Glu Gly Gly Ser Gly Gly Ser Gly Gly Ser Gly Gly
    595                 600                 605

Ser Gly Gly Val Asp Asp Ile Gln Met Thr Gln Ser Pro Ala Ser Leu
610                 615                 620

Ser Ala Ser Val Gly Glu Thr Val Thr Ile Thr Cys Arg Thr Ser Glu
625                 630                 635                 640

Asn Ile Tyr Ser Tyr Leu Ala Trp Cys Gln Gln Lys Gln Gly Lys Ser
            645                 650                 655

Pro Gln Leu Leu Val Tyr Asn Ala Lys Thr Leu Ala Glu Gly Val Pro
        660                 665                 670

Ser Arg Phe Ser Gly Ser Gly Ser Gly Thr His Phe Ser Leu Lys Ile
```

-continued

```
              675                 680                 685
Asn Ser Leu Gln Pro Glu Asp Phe Gly Ile Tyr Tyr Cys Gln His His
        690                 695                 700
Tyr Asp Thr Pro Leu Thr Phe Gly Ala Gly Thr Lys Leu Glu Leu Lys
705                 710                 715                 720

<210> SEQ ID NO 139
<211> LENGTH: 717
<212> TYPE: PRT
<213> ORGANISM: Artificial
<220> FEATURE:
<223> OTHER INFORMATION: Chimeric homo sapiens mus musculus

<400> SEQUENCE: 139

Asp Ile Gln Leu Thr Gln Ser Pro Ala Ser Leu Ala Val Ser Leu Gly
1               5                   10                  15
Gln Arg Ala Thr Ile Ser Cys Lys Ala Ser Gln Ser Val Asp Tyr Asp
            20                  25                  30
Gly Asp Ser Tyr Leu Asn Trp Tyr Gln Gln Ile Pro Gly Gln Pro Pro
        35                  40                  45
Lys Leu Leu Ile Tyr Asp Ala Ser Asn Leu Val Ser Gly Ile Pro Pro
    50                  55                  60
Arg Phe Ser Gly Ser Gly Ser Gly Thr Asp Phe Thr Leu Asn Ile His
65                  70                  75                  80
Pro Val Glu Lys Val Asp Ala Ala Thr Tyr His Cys Gln Gln Ser Thr
                85                  90                  95
Glu Asp Pro Trp Thr Phe Gly Gly Gly Thr Lys Leu Glu Ile Lys Gly
            100                 105                 110
Gly Gly Gly Ser Gly Gly Gly Gly Ser Gly Gly Gly Gly Ser Gln Val
        115                 120                 125
Gln Leu Gln Gln Ser Gly Ala Glu Leu Val Arg Pro Gly Ser Ser Val
    130                 135                 140
Lys Ile Ser Cys Lys Ala Ser Gly Tyr Ala Phe Ser Ser Tyr Trp Met
145                 150                 155                 160
Asn Trp Val Lys Gln Arg Pro Gly Gln Gly Leu Glu Trp Ile Gly Gln
                165                 170                 175
Ile Trp Pro Gly Asp Gly Asp Thr Asn Tyr Asn Gly Lys Phe Lys Gly
            180                 185                 190
Lys Ala Thr Leu Thr Ala Asp Glu Ser Ser Ser Thr Ala Tyr Met Gln
        195                 200                 205
Leu Ser Ser Leu Ala Ser Glu Asp Ser Ala Val Tyr Phe Cys Ala Arg
    210                 215                 220
Arg Glu Thr Thr Thr Val Gly Arg Tyr Tyr Tyr Ala Met Asp Tyr Trp
225                 230                 235                 240
Gly Gln Gly Thr Thr Val Thr Val Ser Ser Gly Gly Gly Ser Ser Ala
                245                 250                 255
Pro Glu Leu Leu Gly Gly Pro Ser Val Phe Leu Phe Pro Pro Lys Pro
            260                 265                 270
Lys Asp Thr Leu Met Ile Ser Arg Thr Pro Glu Val Thr Cys Val Val
        275                 280                 285
Val Asp Val Ser His Glu Asp Pro Glu Val Lys Phe Asn Trp Tyr Val
    290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
```

```
                    325                 330                 335
Asp Trp Leu Asn Gly Lys Glu Tyr Lys Cys Lys Val Ser Asn Lys Ala
                340                 345                 350
Leu Pro Ala Pro Ile Glu Lys Thr Ile Ser Lys Ala Lys Gly Gln Pro
            355                 360                 365
Arg Glu Pro Gln Val Tyr Thr Lys Pro Pro Ser Arg Glu Glu Met Thr
        370                 375                 380
Lys Asn Gln Val Ser Leu Ser Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Val Pro Val Leu Asp Ser Asp Gly Ser Phe Arg Leu Ala
            420                 425                 430
Ser Tyr Leu Thr Val Asp Lys Ser Arg Trp Gln Gln Gly Asn Val Phe
        435                 440                 445
Ser Cys Ser Val Met His Glu Ala Leu His Asn His Tyr Thr Gln Lys
        450                 455                 460
Ser Leu Ser Leu Ser Pro Gly Ser Thr Gly Ser Gln Ile Gln Leu Val
465                 470                 475                 480
Gln Ser Gly Pro Glu Leu Gln Lys Pro Gly Glu Thr Val Lys Ile Ser
                485                 490                 495
Cys Lys Ala Ser Gly Tyr Thr Phe Thr Asn Tyr Gly Met Asn Trp Val
            500                 505                 510
Lys Gln Ala Pro Gly Lys Gly Leu Lys Trp Met Gly Trp Ile Asn Thr
        515                 520                 525
Asn Thr Gly Glu Pro Thr Tyr Ala Glu Glu Phe Lys Gly Arg Phe Ala
530                 535                 540
Phe Ser Leu Glu Thr Ser Ala Ser Thr Ala Tyr Leu Gln Ile Asn Asn
545                 550                 555                 560
Leu Lys Asn Glu Asp Thr Ala Thr Tyr Phe Cys Ala Arg Asp Tyr Leu
                565                 570                 575
Tyr Tyr Phe Asp Tyr Trp Gly Gln Gly Thr Thr Leu Thr Val Ser Ser
            580                 585                 590
Val Glu Gly Gly Ser Gly Gly Ser Gly Gly Ser Gly Gly Ser Gly Gly
        595                 600                 605
Val Asp Asn Ile Val Met Thr Gln Ser Pro Lys Ser Met Ser Met Ser
    610                 615                 620
Val Gly Glu Arg Val Thr Leu Thr Cys Lys Ala Ser Glu Asn Val Val
625                 630                 635                 640
Thr Tyr Val Ser Trp Tyr Gln Gln Lys Pro Glu Gln Ser Pro Lys Leu
                645                 650                 655
Leu Ile Tyr Gly Ala Ser Asn Arg Tyr Thr Gly Val Pro Asp Arg Phe
            660                 665                 670
Thr Gly Ser Gly Ser Ala Thr Asp Phe Thr Leu Thr Ile Ser Ser Val
        675                 680                 685
Gln Ala Glu Asp Leu Ala Asp Tyr His Cys Gly Gln Gly Tyr Ser Tyr
    690                 695                 700
Pro Tyr Thr Phe Gly Gly Gly Thr Lys Leu Glu Ile Lys
705                 710                 715

<210> SEQ ID NO 140
<211> LENGTH: 698
<212> TYPE: PRT
<213> ORGANISM: Artificial
```

<220> FEATURE:
<223> OTHER INFORMATION: Chimeric homo sapiens mus musculus

<400> SEQUENCE: 140

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Ala Met Asp Tyr Trp
225                 230                 235                 240

Gly Gln Gly Thr Thr Val Thr Val Ser Ser Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Lys Pro Pro Ser Arg Glu Glu Met Thr
    370                 375                 380

Lys Asn Gln Val Ser Leu Ser Cys Leu Val Lys Gly Phe Tyr Pro Ser
385                 390                 395                 400
```

```
Asp Ile Ala Val Glu Trp Glu Ser Asn Gly Gln Pro Glu Asn Asn Tyr
                405                 410                 415

Lys Thr Thr Val Pro Val Leu Asp Ser Asp Gly Ser Phe Arg Leu Ala
            420                 425                 430

Ser Tyr Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Ser Thr Gly Ser Glu Val Gln Leu Gln
465                 470                 475                 480

Gln Ser Gly Pro Glu Leu Val Lys Pro Gly Ala Ser Val Lys Ile Ser
                485                 490                 495

Cys Lys Thr Ser Gly Tyr Thr Phe Thr Glu Tyr Thr Met His Trp Val
            500                 505                 510

Lys Gln Ser His Gly Lys Ser Leu Glu Trp Ile Gly Gly Ile Ser Pro
        515                 520                 525

Asn Ile Gly Gly Thr Ser Tyr Asn Gln Lys Phe Lys Gly Lys Ala Thr
    530                 535                 540

Leu Thr Val Asp Lys Ser Ser Thr Ala Tyr Met Glu Leu Arg Ser
545                 550                 555                 560

Leu Thr Ser Glu Asp Ser Ala Val Tyr Tyr Cys Ala Arg Arg Gly Gly
                565                 570                 575

Ser Phe Asp Tyr Trp Gly Gln Gly Thr Thr Leu Thr Val Ser Ser Ala
            580                 585                 590

Ser Thr Lys Gly Pro Ser Val Phe Pro Leu Ala Pro Ser Ser Lys Ser
        595                 600                 605

Thr Ser Gly Gly Thr Ala Ala Leu Gly Cys Leu Val Lys Asp Tyr Phe
    610                 615                 620

Pro Glu Pro Val Thr Val Ser Trp Asn Ser Gly Ala Leu Thr Ser Gly
625                 630                 635                 640

Val His Thr Phe Pro Ala Val Leu Gln Ser Ser Gly Leu Tyr Ser Leu
                645                 650                 655

Ser Ser Val Val Thr Val Pro Ser Ser Ser Leu Gly Thr Gln Thr Tyr
            660                 665                 670

Ile Cys Asn Val Asn His Lys Pro Ser Asn Thr Lys Val Asp Lys Arg
        675                 680                 685

Val Glu Pro Lys Ser Cys Asp Lys Thr His
690                 695

<210> SEQ ID NO 141
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 141

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60
```

```
Ser Gly Ser Gly Ser Asp Phe Thr Leu Ser Ile Asn Ser Val Glu Pro
 65                  70                  75                  80

Glu Asp Val Gly Val Tyr Tyr Cys Gln Asn Gly His Ser Phe Pro Leu
                 85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 142
<211> LENGTH: 837
<212> TYPE: PRT
<213> ORGANISM: Artificial
<220> FEATURE:
<223> OTHER INFORMATION: Chimeric homo sapiens mus musculus

<400> SEQUENCE: 142

Asp Ile Gln Leu Thr Gln Ser Pro Ala Ser Leu Ala Val Ser Leu Gly
  1               5                  10                  15

Gln Arg Ala Thr Ile Ser Cys Lys Ala Ser Gln Ser Val Asp Tyr Asp
             20                  25                  30

Gly Asp Ser Tyr Leu Asn Trp Tyr Gln Gln Ile Pro Gly Gln Pro Pro
         35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
            115                 120                 125

Gln Leu Gln Gln Ser Gly Ala Glu Leu Val Arg Pro Gly Ser Ser Val
130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
            195                 200                 205
```

```
Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
450                 455                 460

Ser Leu Ser Leu Ser Pro Gly Gly Gly Gly Ser Gly Gly Gly Gly
465                 470                 475                 480

Ser Gly Gly Gly Ser Gly Gln Pro Arg Glu Pro Gln Val Tyr Thr
                485                 490                 495

Leu Pro Pro Ser Arg Glu Glu Met Thr Lys Asn Gln Val Ser Leu Thr
            500                 505                 510

Cys Leu Val Lys Gly Phe Tyr Pro Ser Asp Ile Ala Val Glu Trp Glu
            515                 520                 525

Ser Asn Gly Gln Pro Glu Asn Asn Tyr Lys Thr Thr Pro Pro Val Leu
530                 535                 540

Asp Ser Asp Gly Ser Phe Phe Leu Tyr Ser Lys Leu Thr Val Asp Lys
545                 550                 555                 560

Ser Arg Trp Gln Gln Gly Asn Val Phe Ser Cys Ser Val Met His Glu
                565                 570                 575

Ala Leu His Asn His Tyr Thr Gln Lys Ser Leu Ser Leu Ser Pro Gly
            580                 585                 590

Ser Thr Gly Ser Glu Val Gln Leu Gln Gln Ser Gly Pro Glu Leu Val
            595                 600                 605

Lys Pro Gly Ala Ser Val Lys Ile Ser Cys Lys Thr Ser Gly Tyr Thr
610                 615                 620
```

```
Phe Thr Glu Tyr Thr Met His Trp Val Lys Gln Ser His Gly Lys Ser
625                 630                 635                 640

Leu Glu Trp Ile Gly Gly Ile Ser Pro Asn Ile Gly Gly Thr Ser Tyr
            645                 650                 655

Asn Gln Lys Phe Lys Gly Lys Ala Thr Leu Thr Val Asp Lys Ser Ser
        660                 665                 670

Ser Thr Ala Tyr Met Glu Leu Arg Ser Leu Thr Ser Glu Asp Ser Ala
    675                 680                 685

Val Tyr Tyr Cys Ala Arg Arg Gly Gly Ser Phe Asp Tyr Trp Gly Gln
690                 695                 700

Gly Thr Thr Leu Thr Val Ser Ser Val Glu Gly Gly Ser Gly Gly Ser
705                 710                 715                 720

Gly Gly Ser Gly Gly Ser Gly Gly Val Asp Asp Ile Val Met Thr Gln
            725                 730                 735

Ser Pro Ala Thr Leu Ser Val Thr Pro Gly Asp Arg Val Ser Leu Ser
                740                 745                 750

Cys Arg Ala Ser Gln Ser Ile Ser Asp Tyr Leu His Trp Tyr Gln Gln
            755                 760                 765

Lys Ser His Glu Ser Pro Arg Leu Leu Ile Lys Tyr Ala Ser Gln Ser
770                 775                 780

Ile Ser Gly Ile Pro Ser Arg Phe Ser Gly Ser Gly Ser Gly Ser Asp
785                 790                 795                 800

Phe Thr Leu Ser Ile Asn Ser Val Glu Pro Glu Asp Val Gly Val Tyr
                805                 810                 815

Tyr Cys Gln Asn Gly His Ser Phe Pro Leu Thr Phe Gly Ala Gly Thr
            820                 825                 830

Lys Leu Glu Leu Lys
        835

<210> SEQ ID NO 143
<211> LENGTH: 837
<212> TYPE: PRT
<213> ORGANISM: Artificial
<220> FEATURE:
<223> OTHER INFORMATION: Chimeric homo sapiens mus musculus

<400> SEQUENCE: 143

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140
```

-continued

```
Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
            165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Thr Ala Tyr Met Gln
            195                 200                 205

Leu Ser Ser Leu Ala Ser Glu Asp Ser Ala Val Tyr Phe Cys Ala Arg
210                 215                 220

Arg Glu Thr Thr Thr Val Gly Arg Tyr Tyr Ala Met Asp Tyr Trp
225                 230                 235                 240

Gly Gln Gly Thr Thr Val Thr Val Ser Ser Gly Gly Ser Ser Ala
            245                 250                 255

Pro Glu Leu Leu Gly Gly Pro Ser Val Phe Leu Phe Pro Pro Lys Pro
        260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Ser Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
450                 455                 460

Ser Leu Ser Leu Ser Pro Gly Gly Gly Gly Ser Gly Gly Gly Gly
465                 470                 475                 480

Ser Gly Gly Gly Gly Ser Gly Gln Pro Arg Glu Pro Gln Val Tyr Thr
            485                 490                 495

Leu Pro Pro Ser Arg Glu Glu Met Thr Lys Asn Gln Val Ser Leu Thr
            500                 505                 510

Cys Leu Val Lys Gly Phe Tyr Pro Ser Asp Ile Ala Val Glu Trp Glu
            515                 520                 525

Ser Asn Gly Gln Pro Glu Asn Asn Tyr Lys Thr Thr Pro Pro Val Leu
            530                 535                 540

Asp Ser Asp Gly Ser Phe Phe Leu Tyr Ser Lys Leu Thr Val Asp Lys
545                 550                 555                 560

Ser Arg Trp Gln Gln Gly Asn Val Phe Ser Cys Ser Val Met His Glu
```

```
                    565                 570                 575
Ala Leu His Asn His Tyr Thr Gln Lys Ser Leu Ser Leu Ser Pro Gly
            580                 585                 590

Ser Thr Gly Ser Glu Val Gln Leu Gln Gln Ser Gly Pro Glu Leu Val
        595                 600                 605

Lys Pro Gly Ala Ser Val Lys Ile Ser Cys Lys Thr Ser Gly Tyr Thr
        610                 615                 620

Phe Thr Glu Tyr Thr Met His Trp Val Lys Gln Ser His Gly Lys Ser
625                 630                 635                 640

Leu Glu Trp Ile Gly Gly Ile Ser Pro Asn Ile Gly Gly Thr Ser Tyr
                645                 650                 655

Asn Gln Lys Phe Lys Gly Lys Ala Thr Leu Thr Val Asp Lys Ser Ser
            660                 665                 670

Ser Thr Ala Tyr Met Glu Leu Arg Ser Leu Thr Ser Glu Asp Ser Ala
        675                 680                 685

Val Tyr Tyr Cys Ala Arg Arg Gly Gly Ser Phe Asp Tyr Trp Gly Gln
    690                 695                 700

Gly Thr Thr Leu Thr Val Ser Ser Val Glu Gly Ser Gly Gly Ser
705                 710                 715                 720

Gly Gly Ser Gly Gly Ser Gly Gly Val Asp Asp Ile Val Met Thr Gln
                725                 730                 735

Ser Pro Ala Thr Leu Ser Val Thr Pro Gly Asp Arg Val Ser Leu Ser
            740                 745                 750

Cys Arg Ala Ser Gln Ser Ile Ser Asp Tyr Leu His Trp Tyr Gln Gln
        755                 760                 765

Lys Ser His Glu Ser Pro Arg Leu Leu Ile Lys Tyr Ala Ser Gln Ser
        770                 775                 780

Ile Ser Gly Ile Pro Ser Arg Phe Ser Gly Ser Gly Ser Gly Ser Asp
785                 790                 795                 800

Phe Thr Leu Ser Ile Asn Ser Val Glu Pro Glu Asp Val Gly Val Tyr
                805                 810                 815

Tyr Cys Gln Asn Gly His Ser Phe Pro Leu Thr Phe Gly Ala Gly Thr
            820                 825                 830

Lys Leu Glu Leu Lys
        835

<210> SEQ ID NO 144
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 144

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
```

```
                    85                  90                  95
Glu Asp Pro Trp Thr Phe Gly Gly Thr Lys Leu Glu Ile Lys Arg
                100                 105                 110

Thr Val Ala Ala Pro Ser Val Phe Ile Phe Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
                210                 215

<210> SEQ ID NO 145
<211> LENGTH: 675
<212> TYPE: PRT
<213> ORGANISM: Artificial
<220> FEATURE:
<223> OTHER INFORMATION: Chimeric homo sapiens mus musculus

<400> SEQUENCE: 145

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Ala Met Asp
                100                 105                 110

Tyr Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Arg Val Glu Pro
            210                 215                 220

Lys Ser Cys Gly Gly Gly Ser Ser Ala Pro Glu Leu Leu Gly Gly Pro
```

-continued

```
              225                 230                 235                 240
Ser Val Phe Leu Phe Pro Pro Lys Pro Lys Asp Thr Leu Met Ile Ser
                  245                 250                 255
Arg Thr Pro Glu Val Thr Cys Val Val Val Asp Val Ser His Glu Asp
                  260                 265                 270
Pro Glu Val Lys Phe Asn Trp Tyr Val Asp Gly Val Glu Val His Asn
                  275                 280                 285
Ala Lys Thr Lys Pro Arg Glu Glu Gln Tyr Ser Ser Thr Tyr Arg Val
          290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                  325                 330                 335
Thr Ile Ser Lys Ala Lys Gly Gln Pro Arg Glu Pro Gln Val Tyr Thr
                  340                 345                 350
Lys Pro Pro Ser Arg Glu Glu Met Thr Lys Asn Gln Val Ser Leu Ser
                  355                 360                 365
Cys Leu Val Lys Gly Phe Tyr Pro Ser Asp Ile Ala Val Glu Trp Glu
          370                 375                 380
Ser Asn Gly Gln Pro Glu Asn Asn Tyr Lys Thr Thr Pro Val Leu
385                 390                 395                 400
Asp Ser Asp Gly Ser Phe Arg Leu Ala Ser Tyr Leu Thr Val Asp Lys
                  405                 410                 415
Ser Arg Trp Gln Gln Gly Asn Val Phe Ser Cys Ser Val Met His Glu
                  420                 425                 430
Ala Leu His Asn His Tyr Thr Gln Lys Ser Leu Ser Leu Ser Pro Gly
                  435                 440                 445
Ser Thr Gly Ser Glu Val Gln Leu Gln Gln Ser Gly Pro Glu Leu Val
          450                 455                 460
Lys Pro Gly Ala Ser Val Lys Ile Ser Cys Lys Thr Ser Gly Tyr Thr
465                 470                 475                 480
Phe Thr Glu Tyr Thr Met His Trp Val Lys Gln Ser His Gly Lys Ser
                  485                 490                 495
Leu Glu Trp Ile Gly Gly Ile Ser Pro Asn Ile Gly Gly Thr Ser Tyr
                  500                 505                 510
Asn Gln Lys Phe Lys Gly Lys Ala Thr Leu Thr Val Asp Lys Ser Ser
                  515                 520                 525
Ser Thr Ala Tyr Met Glu Leu Arg Ser Leu Thr Ser Glu Asp Ser Ala
          530                 535                 540
Val Tyr Tyr Cys Ala Arg Arg Gly Gly Ser Phe Asp Tyr Trp Gly Gln
545                 550                 555                 560
Gly Thr Thr Leu Thr Val Ser Ser Arg Thr Val Ala Ala Pro Ser Val
                  565                 570                 575
Phe Ile Phe Pro Pro Ser Asp Glu Gln Leu Lys Ser Gly Thr Ala Ser
                  580                 585                 590
Val Val Cys Leu Leu Asn Asn Phe Tyr Pro Arg Glu Ala Lys Val Gln
                  595                 600                 605
Trp Lys Val Asp Asn Ala Leu Gln Ser Gly Asn Ser Gln Glu Ser Val
          610                 615                 620
Thr Glu Gln Asp Ser Lys Asp Ser Thr Tyr Ser Leu Ser Ser Thr Leu
625                 630                 635                 640
Thr Leu Ser Lys Ala Asp Tyr Glu Lys His Lys Val Tyr Ala Cys Glu
                  645                 650                 655
```

```
Val Thr His Gln Gly Leu Ser Ser Pro Val Thr Lys Ser Phe Asn Arg
            660                 665                 670

Gly Glu Cys
        675

<210> SEQ ID NO 146
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 146

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 147
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 147

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
```

```
            50                  55                  60
Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
            210                 215

<210> SEQ ID NO 148
<211> LENGTH: 801
<212> TYPE: PRT
<213> ORGANISM: Artificial
<220> FEATURE:
<223> OTHER INFORMATION: Chimeric homo sapiens mus musculus

<400> SEQUENCE: 148

Gln Val Gln Leu Gln Gln Ser Gly Ala Glu Leu Val Arg Pro Gly Ser
  1               5                  10                  15

Ser Val Lys Ile Ser Cys Lys Ala Ser Gly Tyr Ala Phe Ser Ser Tyr
                 20                  25                  30

Trp Met Asn Trp Val Lys Gln Arg Pro Gly Gln Gly Leu Glu Trp Ile
             35                  40                  45

Gly Gln Ile Trp Pro Gly Asp Gly Asp Thr Asn Tyr Asn Gly Lys Phe
         50                  55                  60

Lys Gly Lys Ala Thr Leu Thr Ala Asp Glu Ser Ser Ser Thr Ala Tyr
 65                  70                  75                  80

Met Gln Leu Ser Ser Leu Ala Ser Glu Asp Ser Ala Val Tyr Phe Cys
                 85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
```

-continued

```
            195                 200                 205
Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Ser
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Gly Gly Gly Ser Gly Gly Gly Gly Ser Gly
        450                 455                 460

Gly Gly Gly Ser Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
                500                 505                 510

Gly Gln Pro Glu Asn Asn Tyr Lys Thr Thr Pro Pro Val Leu Asp Ser
            515                 520                 525

Asp Gly Ser Phe Phe Leu Tyr Ser Lys Leu Thr Val Asp Lys Ser Arg
        530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Ser Thr
                565                 570                 575

Gly Ser Glu Val Gln Leu Gln Gln Ser Gly Pro Glu Leu Val Lys Pro
                580                 585                 590

Gly Ala Ser Val Lys Ile Ser Cys Lys Thr Ser Gly Tyr Thr Phe Thr
            595                 600                 605

Glu Tyr Thr Met His Trp Val Lys Gln Ser His Gly Lys Ser Leu Glu
        610                 615                 620
```

-continued

```
Trp Ile Gly Gly Ile Ser Pro Asn Ile Gly Gly Thr Ser Tyr Asn Gln
625                 630                 635                 640

Lys Phe Lys Gly Lys Ala Thr Leu Thr Val Asp Lys Ser Ser Ser Thr
            645                 650                 655

Ala Tyr Met Glu Leu Arg Ser Leu Thr Ser Glu Asp Ser Ala Val Tyr
        660                 665                 670

Tyr Cys Ala Arg Arg Gly Gly Ser Phe Asp Tyr Trp Gly Gln Gly Thr
    675                 680                 685

Thr Leu Thr Val Ser Ser Arg Thr Val Ala Ala Pro Ser Val Phe Ile
690                 695                 700

Phe Pro Pro Ser Asp Glu Gln Leu Lys Ser Gly Thr Ala Ser Val Val
705                 710                 715                 720

Cys Leu Leu Asn Asn Phe Tyr Pro Arg Glu Ala Lys Val Gln Trp Lys
                725                 730                 735

Val Asp Asn Ala Leu Gln Ser Gly Asn Ser Gln Glu Ser Val Thr Glu
            740                 745                 750

Gln Asp Ser Lys Asp Ser Thr Tyr Ser Leu Ser Ser Thr Leu Thr Leu
        755                 760                 765

Ser Lys Ala Asp Tyr Glu Lys His Lys Val Tyr Ala Cys Glu Val Thr
    770                 775                 780

His Gln Gly Leu Ser Ser Pro Val Thr Lys Ser Phe Asn Arg Gly Glu
785                 790                 795                 800

Cys

<210> SEQ ID NO 149
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 149

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175
```

```
Thr Val Pro Ser Ser Leu Gly Thr Gln Thr Tyr Ile Cys Asn Val
        180                 185                 190

Asn His Lys Pro Ser Asn Thr Lys Val Asp Lys Arg Val Glu Pro Lys
            195                 200                 205

Ser Cys Asp Lys Thr His
        210
```

<210> SEQ ID NO 150
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 150

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 151
<211> LENGTH: 801
<212> TYPE: PRT
<213> ORGANISM: Artificial
<220> FEATURE:
<223> OTHER INFORMATION: Chimeric homo sapiens mus musculus

<400> SEQUENCE: 151

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45
```

```
Gly Gln Ile Trp Pro Gly Asp Gly Asp Thr Asn Tyr Asn Gly Lys Phe
    50                  55                  60
Lys Gly Lys Ala Thr Leu Thr Ala Asp Glu Ser Ser Ser Thr Ala Tyr
65                  70                  75                  80
Met Gln Leu Ser Ser Leu Ala Ser Glu Asp Ser Ala Val Tyr Phe Cys
                85                  90                  95
Ala Arg Arg Glu Thr Thr Thr Val Gly Arg Tyr Tyr Tyr Ala Met Asp
                100                 105                 110
Tyr Trp Gly Gln Gly Thr Thr Val Thr Val Ser Ser Ala Ser Thr Lys
            115                 120                 125
Gly Pro Ser Val Phe Pro Leu Ala Pro Ser Ser Lys Ser Thr Ser Gly
    130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
                180                 185                 190
Val Thr Val Pro Ser Ser Ser Leu Gly Thr Gln Thr Tyr Ile Cys Asn
            195                 200                 205
Val Asn His Lys Pro Ser Asn Thr Lys Val Asp Lys Arg Val Glu Pro
    210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
                260                 265                 270
Val Ser His Glu Asp Pro Glu Val Lys Phe Asn Trp Tyr Val Asp Gly
            275                 280                 285
Val Glu Val His Asn Ala Lys Thr Lys Pro Arg Glu Glu Gln Tyr Ser
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
                340                 345                 350
Pro Gln Val Tyr Thr Leu Pro Pro Ser Arg Glu Glu Met Thr Lys Asn
            355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
                420                 425                 430
Ser Val Met His Glu Ala Leu His Asn His Tyr Thr Gln Lys Ser Leu
            435                 440                 445
Ser Leu Ser Pro Gly Gly Gly Gly Ser Gly Gly Gly Ser Gly
    450                 455                 460
```

Gly Gly Gly Ser Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
            485                 490                 495

Val Lys Gly Phe Tyr Pro Ser Asp Ile Ala Val Glu Trp Glu Ser Asn
        500                 505                 510

Gly Gln Pro Glu Asn Asn Tyr Lys Thr Thr Pro Pro Val Leu Asp Ser
    515                 520                 525

Asp Gly Ser Phe Phe Leu Tyr Ser Lys Leu Thr Val Asp Lys Ser Arg
530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Ser Thr
                565                 570                 575

Gly Ser Glu Val Gln Leu Gln Gln Ser Gly Pro Glu Leu Val Lys Pro
            580                 585                 590

Gly Ala Ser Val Lys Ile Ser Cys Lys Thr Ser Gly Tyr Thr Phe Thr
        595                 600                 605

Glu Tyr Thr Met His Trp Val Lys Gln Ser His Gly Lys Ser Leu Glu
    610                 615                 620

Trp Ile Gly Gly Ile Ser Pro Asn Ile Gly Gly Thr Ser Tyr Asn Gln
625                 630                 635                 640

Lys Phe Lys Gly Lys Ala Thr Leu Thr Val Asp Lys Ser Ser Ser Thr
                645                 650                 655

Ala Tyr Met Glu Leu Arg Ser Leu Thr Ser Glu Asp Ser Ala Val Tyr
            660                 665                 670

Tyr Cys Ala Arg Arg Gly Gly Ser Phe Asp Tyr Trp Gly Gln Gly Thr
        675                 680                 685

Thr Leu Thr Val Ser Ser Arg Thr Val Ala Ala Pro Ser Val Phe Ile
    690                 695                 700

Phe Pro Pro Ser Asp Glu Gln Leu Lys Ser Gly Thr Ala Ser Val Val
705                 710                 715                 720

Cys Leu Leu Asn Asn Phe Tyr Pro Arg Glu Ala Lys Val Gln Trp Lys
                725                 730                 735

Val Asp Asn Ala Leu Gln Ser Gly Asn Ser Gln Glu Ser Val Thr Glu
            740                 745                 750

Gln Asp Ser Lys Asp Ser Thr Tyr Ser Leu Ser Ser Thr Leu Thr Leu
        755                 760                 765

Ser Lys Ala Asp Tyr Glu Lys His Lys Val Tyr Ala Cys Glu Val Thr
    770                 775                 780

His Gln Gly Leu Ser Ser Pro Val Thr Lys Ser Phe Asn Arg Gly Glu
785                 790                 795                 800

Cys

<210> SEQ ID NO 152
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 152

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr

```
                20                  25                  30
Leu His Trp Tyr Gln Gln Lys Ser His Glu Ser Pro Arg Leu Leu Ile
            35                  40                  45
Lys Tyr Ala Ser Gln Ser Ile Ser Gly Ile Pro Ser Arg Phe Ser Gly
50                  55                  60
Ser Gly Ser Gly Ser Asp Phe Thr Leu Ser Ile Asn Ser Val Glu Pro
65                  70                  75                  80
Glu Asp Val Gly Val Tyr Tyr Cys Gln Asn Gly His Ser Phe Pro Leu
                85                  90                  95
Thr Phe Gly Ala Gly Thr Lys Leu Glu Leu Lys Ala Ser Thr Lys Gly
                100                 105                 110
Pro Ser Val Phe Pro Leu Ala Pro Ser Ser Lys Ser Thr Ser Gly Gly
                115                 120                 125
Thr Ala Ala Leu Gly Cys Leu Val Lys Asp Tyr Phe Pro Glu Pro Val
            130                 135                 140
Thr Val Ser Trp Asn Ser Gly Ala Leu Thr Ser Gly Val His Thr Phe
145                 150                 155                 160
Pro Ala Val Leu Gln Ser Ser Gly Leu Tyr Ser Leu Ser Ser Val Val
                165                 170                 175
Thr Val Pro Ser Ser Ser Leu Gly Thr Gln Thr Tyr Ile Cys Asn Val
            180                 185                 190
Asn His Lys Pro Ser Asn Thr Lys Val Asp Lys Arg Val Glu Pro Lys
            195                 200                 205
Ser Cys Asp Lys Thr His
        210

<210> SEQ ID NO 153
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 153

Asp Ile Gln Leu Thr Gln Ser Pro Ala Ser Leu Ala Val Ser Leu Gly
1               5                   10                  15
Gln Arg Ala Thr Ile Ser Cys Lys Ala Ser Gln Ser Val Asp Tyr Asp
                20                  25                  30
Gly Asp Ser Tyr Leu Asn Trp Tyr Gln Gln Ile Pro Gly Gln Pro Pro
            35                  40                  45
Lys Leu Leu Ile Tyr Asp Ala Ser Asn Leu Val Ser Gly Ile Pro Pro
50                  55                  60
Arg Phe Ser Gly Ser Gly Ser Gly Thr Asp Phe Thr Leu Asn Ile His
65                  70                  75                  80
Pro Val Glu Lys Val Asp Ala Ala Thr Tyr His Cys Gln Gln Ser Thr
                85                  90                  95
Glu Asp Pro Trp Thr Phe Gly Gly Gly Thr Lys Leu Glu Ile Lys Arg
                100                 105                 110
Thr Val Ala Ala Pro Ser Val Phe Ile Phe Pro Pro Ser Asp Glu Gln
            115                 120                 125
Leu Lys Ser Gly Thr Ala Ser Val Val Cys Leu Leu Asn Asn Phe Tyr
            130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
```

```
                    165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 154
<211> LENGTH: 796
<212> TYPE: PRT
<213> ORGANISM: Artificial
<220> FEATURE:
<223> OTHER INFORMATION: Chimeric homo sapiens mus musculus

<400> SEQUENCE: 154

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Gly Gly Gly Ser Ser Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ser Ser Thr Tyr Arg Val
    290                 295                 300

Val Ser Val Leu Thr Val Leu His Gln Asp Trp Leu Asn Gly Lys Glu
```

-continued

```
            305                 310                 315                 320
        Tyr Lys Cys Lys Val Ser Asn Lys Ala Leu Pro Ala Pro Ile Glu Lys
                        325                 330                 335

Thr Ile Ser Lys Ala Lys Gly Gln Pro Arg Glu Pro Gln Val Tyr Thr
                        340                 345                 350

Leu Pro Pro Ser Arg Glu Glu Met Thr Lys Asn Gln Val Ser Leu Thr
                        355                 360                 365

Cys Leu Val Lys Gly Phe Tyr Pro Ser Asp Ile Ala Val Glu Trp Glu
                    370                 375                 380

Ser Asn Gly Gln Pro Glu Asn Asn Tyr Lys Thr Thr Pro Pro Val Leu
        385                 390                 395                 400

Asp Ser Asp Gly Ser Phe Phe Leu Tyr Ser Lys Leu Thr Val Asp Lys
                            405                 410                 415

Ser Arg Trp Gln Gln Gly Asn Val Phe Ser Cys Ser Val Met His Glu
                        420                 425                 430

Ala Leu His Asn His Tyr Thr Gln Lys Ser Leu Ser Leu Ser Pro Gly
                        435                 440                 445

Gly Gly Gly Gly Ser Gly Gly Gly Ser Gly Gly Gly Gly Ser Gly
                    450                 455                 460

Gln Pro Arg Glu Pro Gln Val Tyr Thr Leu Pro Pro Ser Arg Glu Glu
        465                 470                 475                 480

Met Thr Lys Asn Gln Val Ser Leu Thr Cys Leu Val Lys Gly Phe Tyr
                        485                 490                 495

Pro Ser Asp Ile Ala Val Glu Trp Glu Ser Asn Gly Gln Pro Glu Asn
                    500                 505                 510

Asn Tyr Lys Thr Thr Pro Pro Val Leu Asp Ser Asp Gly Ser Phe Phe
                    515                 520                 525

Leu Tyr Ser Lys Leu Thr Val Asp Lys Ser Arg Trp Gln Gln Gly Asn
                    530                 535                 540

Val Phe Ser Cys Ser Val Met His Glu Ala Leu His Asn His Tyr Thr
        545                 550                 555                 560

Gln Lys Ser Leu Ser Leu Ser Pro Gly Ser Thr Gly Ser Glu Val Gln
                        565                 570                 575

Leu Gln Gln Ser Gly Pro Glu Leu Val Lys Pro Gly Ala Ser Val Lys
                    580                 585                 590

Ile Ser Cys Lys Thr Ser Gly Tyr Thr Phe Thr Glu Tyr Thr Met His
                    595                 600                 605

Trp Val Lys Gln Ser His Gly Lys Ser Leu Glu Trp Ile Gly Gly Ile
                    610                 615                 620

Ser Pro Asn Ile Gly Gly Thr Ser Tyr Asn Gln Lys Phe Lys Gly Lys
        625                 630                 635                 640

Ala Thr Leu Thr Val Asp Lys Ser Ser Thr Ala Tyr Met Glu Leu
                            645                 650                 655

Arg Ser Leu Thr Ser Glu Asp Ser Ala Val Tyr Tyr Cys Ala Arg Arg
                        660                 665                 670

Gly Gly Ser Phe Asp Tyr Trp Gly Gln Gly Thr Thr Leu Thr Val Ser
                    675                 680                 685

Ser Arg Thr Val Ala Ala Pro Ser Val Phe Ile Phe Pro Pro Ser Asp
        690                 695                 700

Glu Gln Leu Lys Ser Gly Thr Ala Ser Val Val Cys Leu Leu Asn Asn
                        705                 710                 715                 720

Phe Tyr Pro Arg Glu Ala Lys Val Gln Trp Lys Val Asp Asn Ala Leu
                        725                 730                 735
```

Gln Ser Gly Asn Ser Gln Glu Ser Val Thr Glu Gln Asp Ser Lys Asp
            740                 745                 750

Ser Thr Tyr Ser Leu Ser Ser Thr Leu Thr Leu Ser Lys Ala Asp Tyr
            755                 760                 765

Glu Lys His Lys Val Tyr Ala Cys Glu Val Thr His Gln Gly Leu Ser
            770                 775                 780

Ser Pro Val Thr Lys Ser Phe Asn Arg Gly Glu Cys
785                 790                 795

<210> SEQ ID NO 155
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 155

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 156
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 156

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp

```
                  20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 157
<211> LENGTH: 819
<212> TYPE: PRT
<213> ORGANISM: Artificial
<220> FEATURE:
<223> OTHER INFORMATION: Chimeric homo sapiens mus musculus

<400> SEQUENCE: 157

Gln Val Gln Leu Gln Gln Ser Gly Ala Glu Leu Val Arg Pro Gly Ser
 1               5                  10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
 65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
```

```
            165                 170                 175
Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr Ser
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
                355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Gly Gly Gly Ser Gly Gly Gly Gly Ser Gly
            450                 455                 460

Gly Gly Gly Ser Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
                500                 505                 510

Gly Gln Pro Glu Asn Asn Tyr Lys Thr Thr Pro Pro Val Leu Asp Ser
                515                 520                 525

Asp Gly Ser Phe Phe Leu Tyr Ser Lys Leu Thr Val Asp Lys Ser Arg
                530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Ser Thr
                565                 570                 575

Gly Ser Glu Val Gln Leu Gln Gln Ser Gly Pro Glu Leu Val Lys Pro
            580                 585                 590
```

-continued

```
Gly Ala Ser Val Lys Ile Ser Cys Lys Thr Ser Gly Tyr Thr Phe Thr
            595                 600                 605

Glu Tyr Thr Met His Trp Val Lys Gln Ser His Gly Lys Ser Leu Glu
        610                 615                 620

Trp Ile Gly Gly Ile Ser Pro Asn Ile Gly Gly Thr Ser Tyr Asn Gln
625                 630                 635                 640

Lys Phe Lys Gly Lys Ala Thr Leu Thr Val Asp Lys Ser Ser Ser Thr
                645                 650                 655

Ala Tyr Met Glu Leu Arg Ser Leu Thr Ser Glu Asp Ser Ala Val Tyr
            660                 665                 670

Tyr Cys Ala Arg Arg Gly Gly Ser Phe Asp Tyr Trp Gly Gln Gly Thr
        675                 680                 685

Thr Leu Thr Val Ser Ser Val Glu Gly Gly Ser Gly Gly Ser Gly Gly
    690                 695                 700

Ser Gly Gly Ser Gly Gly Val Asp Asp Ile Val Met Thr Gln Ser Pro
705                 710                 715                 720

Ala Thr Leu Ser Val Thr Pro Gly Asp Arg Val Ser Leu Ser Cys Arg
                725                 730                 735

Ala Ser Gln Ser Ile Ser Asp Tyr Leu His Trp Tyr Gln Gln Lys Ser
            740                 745                 750

His Glu Ser Pro Arg Leu Leu Ile Lys Tyr Ala Ser Gln Ser Ile Ser
        755                 760                 765

Gly Ile Pro Ser Arg Phe Ser Gly Ser Gly Ser Asp Phe Thr
    770                 775                 780

Leu Ser Ile Asn Ser Val Glu Pro Glu Asp Val Gly Val Tyr Tyr Cys
785                 790                 795                 800

Gln Asn Gly His Ser Phe Pro Leu Thr Phe Gly Ala Gly Thr Lys Leu
                805                 810                 815

Glu Leu Lys
```

<210> SEQ ID NO 158
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 158

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215
```

<210> SEQ ID NO 159  
<211> LENGTH: 819  
<212> TYPE: PRT  
<213> ORGANISM: Artificial  
<220> FEATURE:  
<223> OTHER INFORMATION: Chimeric homo sapiens mus musculus

<400> SEQUENCE: 159

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Ser Pro Pro Ser Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270
```

```
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Ser
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Glu Glu Met Thr Lys Asn
        355                 360                 365
Gln Val Ser Leu Thr Cys Leu Val Lys Gly Phe Tyr Pro Ser Asp Ile
370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Gly Gly Gly Ser Gly Gly Gly Ser Gly
450                 455                 460
Gly Gly Ser Gly Gln Pro Arg Glu Pro Gln Val Tyr Thr Leu Pro
465                 470                 475                 480
Pro Ser Arg Glu Glu Met Thr Lys Asn Gln Val Ser Leu Thr Cys Leu
                485                 490                 495
Val Lys Gly Phe Tyr Pro Ser Asp Ile Ala Val Glu Trp Glu Ser Asn
            500                 505                 510
Gly Gln Pro Glu Asn Asn Tyr Lys Thr Thr Pro Pro Val Leu Asp Ser
        515                 520                 525
Asp Gly Ser Phe Phe Leu Tyr Ser Lys Leu Thr Val Asp Lys Ser Arg
530                 535                 540
Trp Gln Gln Gly Asn Val Phe Ser Cys Ser Val Met His Glu Ala Leu
545                 550                 555                 560
His Asn His Tyr Thr Gln Lys Ser Leu Ser Leu Ser Pro Gly Ser Thr
                565                 570                 575
Gly Ser Glu Val Gln Leu Gln Gln Ser Gly Pro Glu Leu Val Lys Pro
            580                 585                 590
Gly Ala Ser Val Lys Ile Ser Cys Lys Thr Ser Gly Tyr Thr Phe Thr
        595                 600                 605
Glu Tyr Thr Met His Trp Val Lys Gln Ser His Gly Lys Ser Leu Glu
610                 615                 620
Trp Ile Gly Gly Ile Ser Pro Asn Ile Gly Gly Thr Ser Tyr Asn Gln
625                 630                 635                 640
Lys Phe Lys Gly Lys Ala Thr Leu Thr Val Asp Lys Ser Ser Ser Thr
                645                 650                 655
Ala Tyr Met Glu Leu Arg Ser Leu Thr Ser Glu Asp Ser Ala Val Tyr
            660                 665                 670
Tyr Cys Ala Arg Arg Gly Gly Ser Phe Asp Tyr Trp Gly Gln Gly Thr
        675                 680                 685
Thr Leu Thr Val Ser Ser Val Glu Gly Gly Ser Gly Gly Ser Gly Gly
```

```
                690                 695                 700
Ser Gly Gly Ser Gly Gly Val Asp Asp Ile Val Met Thr Gln Ser Pro
705                 710                 715                 720

Ala Thr Leu Ser Val Thr Pro Gly Asp Arg Val Ser Leu Ser Cys Arg
                725                 730                 735

Ala Ser Gln Ser Ile Ser Asp Tyr Leu His Trp Tyr Gln Gln Lys Ser
                740                 745                 750

His Glu Ser Pro Arg Leu Leu Ile Lys Tyr Ala Ser Gln Ser Ile Ser
                755                 760                 765

Gly Ile Pro Ser Arg Phe Ser Gly Ser Gly Ser Gly Ser Asp Phe Thr
770                 775                 780

Leu Ser Ile Asn Ser Val Glu Pro Glu Asp Val Gly Val Tyr Tyr Cys
785                 790                 795                 800

Gln Asn Gly His Ser Phe Pro Leu Thr Phe Gly Ala Gly Thr Lys Leu
                805                 810                 815

Glu Leu Lys

<210> SEQ ID NO 160
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 160

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 161
```

```
<211> LENGTH: 815
<212> TYPE: PRT
<213> ORGANISM: Artificial
<220> FEATURE:
<223> OTHER INFORMATION: Chimeric homo sapiens mus musculus

<400> SEQUENCE: 161
```

| | | | | | | | | | | | | | | |
|---|---|---|---|---|---|---|---|---|---|---|---|---|---|---|
| Gln | Val | Gln | Leu | Gln | Gln | Ser | Gly | Ala | Glu | Leu | Val | Arg | Pro | Gly |  Ser |
| 1 | | | | 5 | | | | | 10 | | | | | 15 |
| Ser | Val | Lys | Ile | Ser | Cys | Lys | Ala | Ser | Gly | Tyr | Ala | Phe | Ser | Ser | Tyr |
| | | | 20 | | | | | 25 | | | | | 30 | | |
| Trp | Met | Asn | Trp | Val | Lys | Gln | Arg | Pro | Gly | Gln | Gly | Leu | Glu | Trp | Ile |
| | | 35 | | | | | 40 | | | | | 45 | | | |
| Gly | Gln | Ile | Trp | Pro | Gly | Asp | Gly | Asp | Thr | Asn | Tyr | Asn | Gly | Lys | Phe |
| | 50 | | | | | 55 | | | | | 60 | | | | |
| Lys | Gly | Lys | Ala | Thr | Leu | Thr | Ala | Asp | Glu | Ser | Ser | Thr | Ala | Tyr |
| 65 | | | | | 70 | | | | | 75 | | | | | 80 |
| Met | Gln | Leu | Ser | Ser | Leu | Ala | Ser | Glu | Asp | Ser | Ala | Val | Tyr | Phe | Cys |
| | | | | 85 | | | | | 90 | | | | | 95 | |
| Ala | Arg | Arg | Glu | Thr | Thr | Thr | Val | Gly | Arg | Tyr | Tyr | Tyr | Ala | Met | Asp |
| | | | | 100 | | | | | 105 | | | | | 110 | |
| Tyr | Trp | Gly | Gln | Gly | Thr | Thr | Val | Thr | Val | Ser | Ser | Ala | Ser | Thr | Lys |
| | | | 115 | | | | | 120 | | | | | 125 | | |
| Gly | Pro | Ser | Val | Phe | Pro | Leu | Ala | Pro | Ser | Ser | Lys | Ser | Thr | Ser | Gly |
| | 130 | | | | | 135 | | | | | 140 | | | | |
| Gly | Thr | Ala | Ala | Leu | Gly | Cys | Leu | Val | Lys | Asp | Tyr | Phe | Pro | Glu | Pro |
| 145 | | | | | 150 | | | | | 155 | | | | | 160 |
| Val | Thr | Val | Ser | Trp | Asn | Ser | Gly | Ala | Leu | Thr | Ser | Gly | Val | His | Thr |
| | | | | 165 | | | | | 170 | | | | | 175 | |
| Phe | Pro | Ala | Val | Leu | Gln | Ser | Ser | Gly | Leu | Tyr | Ser | Leu | Ser | Ser | Val |
| | | | 180 | | | | | 185 | | | | | 190 | | |
| Val | Thr | Val | Pro | Ser | Ser | Leu | Gly | Thr | Gln | Thr | Tyr | Ile | Cys | Asn |
| | | 195 | | | | | 200 | | | | | 205 | | | |
| Val | Asn | His | Lys | Pro | Ser | Asn | Thr | Lys | Val | Asp | Lys | Arg | Val | Glu | Pro |
| | 210 | | | | | 215 | | | | | 220 | | | | |
| Lys | Ser | Cys | Gly | Gly | Gly | Ser | Ser | Pro | Ala | Pro | Glu | Leu | Leu | Gly | Gly |
| 225 | | | | | 230 | | | | | 235 | | | | | 240 |
| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |
| Ser | Arg | Thr | Pro | Glu | Val | Thr | Cys | Val | Val | Val | Asp | Val | Ser | His | Glu |
| | | | 260 | | | | | 265 | | | | | 270 | | |
| Asp | Pro | Glu | Val | Lys | Phe | Asn | Trp | Tyr | Val | Asp | Gly | Val | Glu | Val | His |
| | | 275 | | | | | 280 | | | | | 285 | | | |
| Asn | Ala | Lys | Thr | Lys | Pro | Arg | Glu | Glu | Gln | Tyr | Ser | Ser | Thr | Tyr | Arg |
| | 290 | | | | | 295 | | | | | 300 | | | | |
| Val | Val | Ser | Val | Leu | Thr | Val | Leu | His | Gln | Asp | Trp | Leu | Asn | Gly | Lys |
| 305 | | | | | 310 | | | | | 315 | | | | | 320 |
| Glu | Tyr | Lys | Cys | Lys | Val | Ser | Asn | Lys | Ala | Leu | Pro | Ala | Pro | Ile | Glu |
| | | | | 325 | | | | | 330 | | | | | 335 | |
| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |
| Thr | Leu | Pro | Pro | Ser | Arg | Glu | Glu | Met | Thr | Lys | Asn | Gln | Val | Ser | Leu |
| | | 355 | | | | | 360 | | | | | 365 | | | |
| Thr | Cys | Leu | Val | Lys | Gly | Phe | Tyr | Pro | Ser | Asp | Ile | Ala | Val | Glu | Trp |
| | 370 | | | | | 375 | | | | | 380 | | | | |

-continued

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
        405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Gly Gly Gly Gly Ser Gly Gly Gly Ser Gly Gly Gly Gly Ser
                    455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
                500                 505                 510

Asn Asn Tyr Lys Thr Thr Pro Pro Val Leu Asp Ser Asp Gly Ser Phe
            515                 520                 525

Phe Leu Tyr Ser Lys Leu Thr Val Asp Lys Ser Arg Trp Gln Gln Gly
                530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Ser Thr Gly Ser Glu Val
                565                 570                 575

Gln Leu Gln Gln Ser Gly Pro Glu Leu Val Lys Pro Gly Ala Ser Val
                580                 585                 590

Lys Ile Ser Cys Lys Thr Ser Gly Tyr Thr Phe Thr Glu Tyr Thr Met
                595                 600                 605

His Trp Val Lys Gln Ser His Gly Lys Ser Leu Glu Trp Ile Gly Gly
        610                 615                 620

Ile Ser Pro Asn Ile Gly Gly Thr Ser Tyr Asn Gln Lys Phe Lys Gly
625                 630                 635                 640

Lys Ala Thr Leu Thr Val Asp Lys Ser Ser Ser Thr Ala Tyr Met Glu
                645                 650                 655

Leu Arg Ser Leu Thr Ser Glu Asp Ser Ala Val Tyr Tyr Cys Ala Arg
                660                 665                 670

Arg Gly Gly Ser Phe Asp Tyr Trp Gly Gln Gly Thr Thr Leu Thr Val
        675                 680                 685

Ser Ser Val Glu Gly Gly Ser Gly Gly Ser Gly Gly Ser Gly Gly Ser
690                 695                 700

Gly Gly Val Asp Asp Ile Val Met Thr Gln Ser Pro Ala Thr Leu Ser
705                 710                 715                 720

Val Thr Pro Gly Asp Arg Val Ser Leu Ser Cys Arg Ala Ser Gln Ser
        725                 730                 735

Ile Ser Asp Tyr Leu His Trp Tyr Gln Gln Lys Ser His Glu Ser Pro
            740                 745                 750

Arg Leu Leu Ile Lys Tyr Ala Ser Gln Ser Ile Ser Gly Ile Pro Ser
            755                 760                 765

Arg Phe Ser Gly Ser Gly Ser Gly Ser Asp Phe Thr Leu Ser Ile Asn
        770                 775                 780

Ser Val Glu Pro Glu Asp Val Gly Val Tyr Tyr Cys Gln Asn Gly His
785                 790                 795                 800

-continued

Ser Phe Pro Leu Thr Phe Gly Ala Gly Thr Lys Leu Glu Leu Lys
             805                 810                 815

<210> SEQ ID NO 162
<211> LENGTH: 819
<212> TYPE: PRT
<213> ORGANISM: Artificial
<220> FEATURE:
<223> OTHER INFORMATION: Chimeric homo sapiens mus musculus

<400> SEQUENCE: 162

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Ser Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

```
Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Gly Gly Gly Ser Gly Gly Gly Gly
465                 470                 475                 480

Ser Gly Gly Gly Gly Ser Gly Gln Pro Arg Glu Pro Gln Val Tyr Thr
                485                 490                 495

Leu Pro Pro Ser Arg Glu Glu Met Thr Lys Asn Gln Val Ser Leu Thr
            500                 505                 510

Cys Leu Val Lys Gly Phe Tyr Pro Ser Asp Ile Ala Val Glu Trp Glu
        515                 520                 525

Ser Asn Gly Gln Pro Glu Asn Asn Tyr Lys Thr Thr Pro Pro Val Leu
    530                 535                 540

Asp Ser Asp Gly Ser Phe Phe Leu Tyr Ser Lys Leu Thr Val Asp Lys
545                 550                 555                 560

Ser Arg Trp Gln Gln Gly Asn Val Phe Ser Cys Ser Val Met His Glu
                565                 570                 575

Ala Leu His Asn His Tyr Thr Gln Lys Ser Leu Ser Leu Ser Pro Gly
            580                 585                 590

Ser Thr Gly Ser Glu Val Gln Leu Gln Gln Ser Gly Pro Glu Leu Val
        595                 600                 605

Lys Pro Gly Ala Ser Val Lys Ile Ser Cys Lys Thr Ser Gly Tyr Thr
    610                 615                 620

Phe Thr Glu Tyr Thr Met His Trp Val Lys Gln Ser His Gly Lys Ser
625                 630                 635                 640

Leu Glu Trp Ile Gly Gly Ile Ser Pro Asn Ile Gly Gly Thr Ser Tyr
                645                 650                 655

Asn Gln Lys Phe Lys Gly Lys Ala Thr Leu Thr Val Asp Lys Ser Ser
            660                 665                 670

Ser Thr Ala Tyr Met Glu Leu Arg Ser Leu Thr Ser Glu Asp Ser Ala
        675                 680                 685

Val Tyr Tyr Cys Ala Arg Arg Gly Gly Ser Phe Asp Tyr Trp Gly Gln
    690                 695                 700

Gly Thr Thr Leu Thr Val Ser Ser Arg Thr Val Ala Ala Pro Ser Val
705                 710                 715                 720

Phe Ile Phe Pro Pro Ser Asp Glu Gln Leu Lys Ser Gly Thr Ala Ser
                725                 730                 735

Val Val Cys Leu Leu Asn Asn Phe Tyr Pro Arg Glu Ala Lys Val Gln
            740                 745                 750

Trp Lys Val Asp Asn Ala Leu Gln Ser Gly Asn Ser Gln Glu Ser Val
        755                 760                 765

Thr Glu Gln Asp Ser Lys Asp Ser Thr Tyr Ser Leu Ser Ser Thr Leu
```

```
                770               775                780
Thr Leu Ser Lys Ala Asp Tyr Glu Lys His Lys Val Tyr Ala Cys Glu
785                 790                 795                800

Val Thr His Gln Gly Leu Ser Ser Pro Val Thr Lys Ser Phe Asn Arg
                    805                 810                 815

Gly Glu Cys

<210> SEQ ID NO 163
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 163

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 164
<211> LENGTH: 819
<212> TYPE: PRT
<213> ORGANISM: Artificial
<220> FEATURE:
<223> OTHER INFORMATION: Chimeric homo sapiens mus musculus

<400> SEQUENCE: 164

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
```

```
                35                  40                  45
Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Gly
                100                 105                 110

Gly Gly Gly Ser Gly Gly Gly Gly Ser Gly Gly Gly Gly Ser Gln Val
                115                 120                 125

Gln Leu Gln Gln Ser Gly Ala Glu Leu Val Arg Pro Gly Ser Ser Val
130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
                180                 185                 190

Lys Ala Thr Leu Thr Ala Asp Glu Ser Ser Ser Thr Ala Tyr Met Gln
                195                 200                 205

Leu Ser Ser Leu Ala Ser Glu Asp Ser Ala Val Tyr Phe Cys Ala Arg
210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Ser Ser Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
                275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
                355                 360                 365

Arg Glu Pro Gln Val Tyr Thr Leu Pro Pro Ser Arg Glu Glu Met Thr
                370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
                450                 455                 460
```

Ser Leu Ser Leu Ser Pro Gly Gly Gly Gly Ser Gly Gly Gly
465                 470                 475                 480

Ser Gly Gly Gly Ser Gly Gln Pro Arg Glu Pro Gln Val Tyr Thr
            485                 490                 495

Leu Pro Pro Ser Arg Glu Glu Met Thr Lys Asn Gln Val Ser Leu Thr
        500                 505                 510

Cys Leu Val Lys Gly Phe Tyr Pro Ser Asp Ile Ala Val Glu Trp Glu
            515                 520                 525

Ser Asn Gly Gln Pro Glu Asn Asn Tyr Lys Thr Thr Pro Pro Val Leu
530                 535                 540

Asp Ser Asp Gly Ser Phe Phe Leu Tyr Ser Lys Leu Thr Val Asp Lys
545                 550                 555                 560

Ser Arg Trp Gln Gln Gly Asn Val Phe Ser Cys Ser Val Met His Glu
                565                 570                 575

Ala Leu His Asn His Tyr Thr Gln Lys Ser Leu Ser Leu Ser Pro Gly
            580                 585                 590

Ser Thr Gly Ser Glu Val Gln Leu Gln Gln Ser Gly Pro Glu Leu Val
        595                 600                 605

Lys Pro Gly Ala Ser Val Lys Ile Ser Cys Lys Thr Ser Gly Tyr Thr
    610                 615                 620

Phe Thr Glu Tyr Thr Met His Trp Val Lys Gln Ser His Gly Lys Ser
625                 630                 635                 640

Leu Glu Trp Ile Gly Gly Ile Ser Pro Asn Ile Gly Gly Thr Ser Tyr
                645                 650                 655

Asn Gln Lys Phe Lys Gly Lys Ala Thr Leu Thr Val Asp Lys Ser Ser
            660                 665                 670

Ser Thr Ala Tyr Met Glu Leu Arg Ser Leu Thr Ser Glu Asp Ser Ala
        675                 680                 685

Val Tyr Tyr Cys Ala Arg Arg Gly Gly Ser Phe Asp Tyr Trp Gly Gln
    690                 695                 700

Gly Thr Thr Leu Thr Val Ser Ser Ala Ser Thr Lys Gly Pro Ser Val
705                 710                 715                 720

Phe Pro Leu Ala Pro Ser Ser Lys Ser Thr Ser Gly Gly Thr Ala Ala
                725                 730                 735

Leu Gly Cys Leu Val Lys Asp Tyr Phe Pro Glu Pro Val Thr Val Ser
            740                 745                 750

Trp Asn Ser Gly Ala Leu Thr Ser Gly Val His Thr Phe Pro Ala Val
        755                 760                 765

Leu Gln Ser Ser Gly Leu Tyr Ser Leu Ser Ser Val Val Thr Val Pro
    770                 775                 780

Ser Ser Ser Leu Gly Thr Gln Thr Tyr Ile Cys Asn Val Asn His Lys
785                 790                 795                 800

Pro Ser Asn Thr Lys Val Asp Lys Arg Val Glu Pro Lys Ser Cys Asp
                805                 810                 815

Lys Thr His

<210> SEQ ID NO 165
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 165

```
Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 166
<211> LENGTH: 218
<212> TYPE: PRT
<213> ORGANISM: Artificial
<220> FEATURE:
<223> OTHER INFORMATION: Chimeric homo sapiens mus musculus

<400> SEQUENCE: 166

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140
```

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 167
<211> LENGTH: 792
<212> TYPE: PRT
<213> ORGANISM: Artificial
<220> FEATURE:
<223> OTHER INFORMATION: Chimeric homo sapiens mus musculus

<400> SEQUENCE: 167

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Lys Ala Thr Leu Thr Ala Asp Glu Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Ser Pro Pro Ser Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285
```

```
Val Glu Val His Asn Ala Lys Thr Lys Pro Arg Glu Glu Gln Tyr Ser
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
                355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Gly Gly Gly Ser Gly Gly Gly Gly Ser Gly
450                 455                 460

Gly Gly Ser Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
                500                 505                 510

Gly Gln Pro Glu Asn Asn Tyr Lys Thr Thr Pro Pro Val Leu Asp Ser
                515                 520                 525

Asp Gly Ser Phe Phe Leu Tyr Ser Lys Leu Thr Val Asp Lys Ser Arg
                530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Ser Thr
                565                 570                 575

Gly Ser Asp Ile Val Met Thr Gln Ser Pro Ala Thr Leu Ser Val Thr
                580                 585                 590

Pro Gly Asp Arg Val Ser Leu Ser Cys Arg Ala Ser Gln Ser Ile Ser
                595                 600                 605

Asp Tyr Leu His Trp Tyr Gln Gln Lys Ser His Glu Ser Pro Arg Leu
                610                 615                 620

Leu Ile Lys Tyr Ala Ser Gln Ser Ile Ser Gly Ile Pro Ser Arg Phe
625                 630                 635                 640

Ser Gly Ser Gly Ser Gly Ser Asp Phe Thr Leu Ser Ile Asn Ser Val
                645                 650                 655

Glu Pro Glu Asp Val Gly Val Tyr Tyr Cys Gln Asn Gly His Ser Phe
                660                 665                 670

Pro Leu Thr Phe Gly Ala Gly Thr Lys Leu Glu Leu Lys Ala Ser Thr
                675                 680                 685

Lys Gly Pro Ser Val Phe Pro Leu Ala Pro Ser Ser Lys Ser Thr Ser
                690                 695                 700

Gly Gly Thr Ala Ala Leu Gly Cys Leu Val Lys Asp Tyr Phe Pro Glu
```

```
705                 710                 715                 720
Pro Val Thr Val Ser Trp Asn Ser Gly Ala Leu Thr Ser Gly Val His
                725                 730                 735

Thr Phe Pro Ala Val Leu Gln Ser Ser Gly Leu Tyr Ser Leu Ser Ser
                740                 745                 750

Val Val Thr Val Pro Ser Ser Leu Gly Thr Gln Thr Tyr Ile Cys
                755                 760                 765

Asn Val Asn His Lys Pro Ser Asn Thr Lys Val Asp Lys Arg Val Glu
                770                 775                 780

Pro Lys Ser Cys Asp Lys Thr His
785                 790
```

<210> SEQ ID NO 168
<211> LENGTH: 223
<212> TYPE: PRT
<213> ORGANISM: Artificial
<220> FEATURE:
<223> OTHER INFORMATION: Chimeric homo sapiens mus musculus

<400> SEQUENCE: 168

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
                20                  25                  30

Thr Met His Trp Val Lys Gln Ser His Gly Lys Ser Leu Glu Trp Ile
            35                  40                  45

Gly Gly Ile Ser Pro Asn Ile Gly Gly Thr Ser Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Gly Gly Ser Phe Asp Tyr Trp Gly Gln Gly Thr Thr Leu
                100                 105                 110

Thr Val Ser Ser Arg Thr Val Ala Ala Pro Ser Val Phe Ile Phe Pro
            115                 120                 125

Pro Ser Asp Glu Gln Leu Lys Ser Gly Thr Ala Ser Val Val Cys Leu
        130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
                180                 185                 190

Ala Asp Tyr Glu Lys His Lys Val Tyr Ala Cys Glu Val Thr His Gln
            195                 200                 205

Gly Leu Ser Ser Pro Val Thr Lys Ser Phe Asn Arg Gly Glu Cys
        210                 215                 220
```

<210> SEQ ID NO 169
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 169

-continued

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
```

-continued

```
                420             425             430
His Tyr Thr Gln Lys Ser Leu Ser Leu Ser Pro Gly Lys
            435             440             445

<210> SEQ ID NO 170
<211> LENGTH: 680
<212> TYPE: PRT
<213> ORGANISM: Artificial
<220> FEATURE:
<223> OTHER INFORMATION: Chimeric homo sapiens mus musculus

<400> SEQUENCE: 170

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
```

```
                    340                 345                 350

Pro Gln Val Tyr Thr Leu Pro Pro Ser Arg Glu Glu Met Thr Lys Asn
                355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Ser Thr Gly Ser Glu Val Gln Leu Gln Gln Ser
    450                 455                 460

Gly Pro Glu Leu Val Lys Pro Gly Ala Ser Val Lys Ile Ser Cys Lys
465                 470                 475                 480

Thr Ser Gly Tyr Thr Phe Thr Glu Tyr Thr Met His Trp Val Lys Gln
                485                 490                 495

Ser His Gly Lys Ser Leu Glu Trp Ile Gly Gly Ile Ser Pro Asn Ile
            500                 505                 510

Gly Gly Thr Ser Tyr Asn Gln Lys Phe Lys Gly Lys Ala Thr Leu Thr
        515                 520                 525

Val Asp Lys Ser Ser Ser Thr Ala Tyr Met Glu Leu Arg Ser Leu Thr
    530                 535                 540

Ser Glu Asp Ser Ala Val Tyr Tyr Cys Ala Arg Arg Gly Gly Ser Phe
545                 550                 555                 560

Asp Tyr Trp Gly Gln Gly Thr Thr Leu Thr Val Ser Ser Arg Thr Val
                565                 570                 575

Ala Ala Pro Ser Val Phe Ile Phe Pro Pro Ser Asp Glu Gln Leu Lys
            580                 585                 590

Ser Gly Thr Ala Ser Val Val Cys Leu Leu Asn Asn Phe Tyr Pro Arg
        595                 600                 605

Glu Ala Lys Val Gln Trp Lys Val Asp Asn Ala Leu Gln Ser Gly Asn
    610                 615                 620

Ser Gln Glu Ser Val Thr Glu Gln Asp Ser Lys Asp Ser Thr Tyr Ser
625                 630                 635                 640

Leu Ser Ser Thr Leu Thr Leu Ser Lys Ala Asp Tyr Glu Lys His Lys
                645                 650                 655

Val Tyr Ala Cys Glu Val Thr His Gln Gly Leu Ser Ser Pro Val Thr
            660                 665                 670

Lys Ser Phe Asn Arg Gly Glu Cys
        675                 680

<210> SEQ ID NO 171
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 171

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
```

```
                20                  25                  30
Leu His Trp Tyr Gln Gln Lys Ser His Glu Ser Pro Arg Leu Leu Ile
             35                  40                  45

Lys Tyr Ala Ser Gln Ser Ile Ser Gly Ile Pro Ser Arg Phe Ser Gly
         50                  55                  60

Ser Gly Ser Gly Ser Asp Phe Thr Leu Ser Ile Asn Ser Val Glu Pro
 65                  70                  75                  80

Glu Asp Val Gly Val Tyr Tyr Cys Gln Asn Gly His Ser Phe Pro Leu
                 85                  90                  95

Thr Phe Gly Ala Gly Thr Lys Leu Glu Leu Lys Ala Ser Thr Lys Gly
                100                 105                 110

Pro Ser Val Phe Pro Leu Ala Pro Ser Ser Lys Ser Thr Ser Gly Gly
            115                 120                 125

Thr Ala Ala Leu Gly Cys Leu Val Lys Asp Tyr Phe Pro Glu Pro Val
        130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
                180                 185                 190

Asn His Lys Pro Ser Asn Thr Lys Val Asp Lys Arg Val Glu Pro Lys
            195                 200                 205

Ser Cys Asp Lys Thr His
            210

<210> SEQ ID NO 172
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 172

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
```

165                 170                 175
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys Asp Lys Thr His Thr Cys
            210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Ser Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 173
<211> LENGTH: 680
<212> TYPE: PRT
<213> ORGANISM: Artificial
<220> FEATURE:
<223> OTHER INFORMATION: Chimeric homo sapiens mus musculus

<400> SEQUENCE: 173

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
            50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys

```
                    85                  90                  95
Ala Arg Arg Glu Thr Thr Thr Val Gly Arg Tyr Tyr Ala Met Asp
                100                 105                 110
Tyr Trp Gly Gln Gly Thr Thr Val Thr Val Ser Ser Ala Ser Thr Lys
            115                 120                 125
Gly Pro Ser Val Phe Pro Leu Ala Pro Ser Ser Lys Ser Thr Ser Gly
        130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
                180                 185                 190
Val Thr Val Pro Ser Ser Ser Leu Gly Thr Gln Thr Tyr Ile Cys Asn
            195                 200                 205
Val Asn His Lys Pro Ser Asn Thr Lys Val Asp Lys Arg Val Glu Pro
        210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
                260                 265                 270
Val Ser His Glu Asp Pro Glu Val Lys Phe Asn Trp Tyr Val Asp Gly
            275                 280                 285
Val Glu Val His Asn Ala Lys Thr Lys Pro Arg Glu Glu Gln Tyr Ser
        290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
                340                 345                 350
Pro Gln Val Tyr Thr Leu Pro Pro Ser Arg Glu Glu Met Thr Lys Asn
            355                 360                 365
Gln Val Ser Leu Thr Cys Leu Val Lys Gly Phe Tyr Pro Ser Asp Ile
        370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
                420                 425                 430
Ser Val Met His Glu Ala Leu His Asn His Tyr Thr Gln Lys Ser Leu
            435                 440                 445
Ser Leu Ser Pro Gly Ser Thr Gly Ser Glu Val Gln Leu Gln Gln Ser
        450                 455                 460
Gly Pro Glu Leu Val Lys Pro Gly Ala Ser Val Lys Ile Ser Cys Lys
465                 470                 475                 480
Thr Ser Gly Tyr Thr Phe Thr Glu Tyr Thr Met His Trp Val Lys Gln
                485                 490                 495
Ser His Gly Lys Ser Leu Glu Trp Ile Gly Gly Ile Ser Pro Asn Ile
                500                 505                 510
```

```
Gly Gly Thr Ser Tyr Asn Gln Lys Phe Lys Gly Lys Ala Thr Leu Thr
            515                 520                 525

Val Asp Lys Ser Ser Ser Thr Ala Tyr Met Glu Leu Arg Ser Leu Thr
    530                 535                 540

Ser Glu Asp Ser Ala Val Tyr Tyr Cys Ala Arg Arg Gly Gly Ser Phe
545                 550                 555                 560

Asp Tyr Trp Gly Gln Gly Thr Thr Leu Thr Val Ser Ser Arg Thr Val
                565                 570                 575

Ala Ala Pro Ser Val Phe Ile Phe Pro Pro Ser Asp Glu Gln Leu Lys
                580                 585                 590

Ser Gly Thr Ala Ser Val Val Cys Leu Leu Asn Asn Phe Tyr Pro Arg
            595                 600                 605

Glu Ala Lys Val Gln Trp Lys Val Asp Asn Ala Leu Gln Ser Gly Asn
            610                 615                 620

Ser Gln Glu Ser Val Thr Glu Gln Asp Ser Lys Asp Ser Thr Tyr Ser
625                 630                 635                 640

Leu Ser Ser Thr Leu Thr Leu Ser Lys Ala Asp Tyr Glu Lys His Lys
                645                 650                 655

Val Tyr Ala Cys Glu Val Thr His Gln Gly Leu Ser Ser Pro Val Thr
                660                 665                 670

Lys Ser Phe Asn Arg Gly Glu Cys
            675                 680

<210> SEQ ID NO 174
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 174

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
                100                 105                 110

Pro Ser Val Phe Pro Leu Ala Pro Ser Ser Lys Ser Thr Ser Gly Gly
            115                 120                 125

Thr Ala Ala Leu Gly Cys Leu Val Lys Asp Tyr Phe Pro Glu Pro Val
        130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190
```

```
Asn His Lys Pro Ser Asn Thr Lys Val Asp Lys Arg Val Glu Pro Lys
        195                 200                 205
Ser Cys Asp Lys Thr His
    210
```

<210> SEQ ID NO 175
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 175

```
Asp Ile Gln Leu Thr Gln Ser Pro Ala Ser Leu Ala Val Ser Leu Gly
1               5                   10                  15
Gln Arg Ala Thr Ile Ser Cys Lys Ala Ser Gln Ser Val Asp Tyr Asp
            20                  25                  30
Gly Asp Ser Tyr Leu Asn Trp Tyr Gln Gln Ile Pro Gly Gln Pro Pro
        35                  40                  45
Lys Leu Leu Ile Tyr Asp Ala Ser Asn Leu Val Ser Gly Ile Pro Pro
    50                  55                  60
Arg Phe Ser Gly Ser Gly Ser Gly Thr Asp Phe Thr Leu Asn Ile His
65                  70                  75                  80
Pro Val Glu Lys Val Asp Ala Ala Thr Tyr His Cys Gln Gln Ser Thr
                85                  90                  95
Glu Asp Pro Trp Thr Phe Gly Gly Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Ser Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Ser Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
```

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 176
<211> LENGTH: 680
<212> TYPE: PRT
<213> ORGANISM: Artificial
<220> FEATURE:
<223> OTHER INFORMATION: Chimeric homo sapiens mus musculus

<400> SEQUENCE: 176

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Ser Asp Lys Thr His Thr Cys Pro Cys Pro Ala Pro Glu
225                 230                 235                 240

Leu Leu Gly Gly Pro Ser Val Phe Leu Phe Pro Pro Lys Pro Lys Asp
                245                 250                 255

-continued

```
Thr Leu Met Ile Ser Arg Thr Pro Glu Val Thr Cys Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Ser Thr Gly Ser Glu Val Gln Leu Gln Gln Ser
    450                 455                 460

Gly Pro Glu Leu Val Lys Pro Gly Ala Ser Val Lys Ile Ser Cys Lys
465                 470                 475                 480

Thr Ser Gly Tyr Thr Phe Thr Glu Tyr Thr Met His Trp Val Lys Gln
                485                 490                 495

Ser His Gly Lys Ser Leu Glu Trp Ile Gly Gly Ile Ser Pro Asn Ile
            500                 505                 510

Gly Gly Thr Ser Tyr Asn Gln Lys Phe Lys Gly Lys Ala Thr Leu Thr
        515                 520                 525

Val Asp Lys Ser Ser Ser Thr Ala Tyr Met Glu Leu Arg Ser Leu Thr
    530                 535                 540

Ser Glu Asp Ser Ala Val Tyr Tyr Cys Ala Arg Arg Gly Gly Ser Phe
545                 550                 555                 560

Asp Tyr Trp Gly Gln Gly Thr Thr Leu Thr Val Ser Ser Arg Thr Val
                565                 570                 575

Ala Ala Pro Ser Val Phe Ile Phe Pro Pro Ser Asp Glu Gln Leu Lys
            580                 585                 590

Ser Gly Thr Ala Ser Val Val Cys Leu Leu Asn Asn Phe Tyr Pro Arg
        595                 600                 605

Glu Ala Lys Val Gln Trp Lys Val Asp Asn Ala Leu Gln Ser Gly Asn
    610                 615                 620

Ser Gln Glu Ser Val Thr Glu Gln Asp Ser Lys Asp Ser Thr Tyr Ser
625                 630                 635                 640

Leu Ser Ser Thr Leu Thr Leu Ser Lys Ala Asp Tyr Glu Lys His Lys
                645                 650                 655

Val Tyr Ala Cys Glu Val Thr His Gln Gly Leu Ser Ser Pro Val Thr
            660                 665                 670
```

```
Lys Ser Phe Asn Arg Gly Glu Cys
        675                 680
```

<210> SEQ ID NO 177
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 177

```
Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110

Pro Ser Val Phe Pro Leu Ala Pro Ser Ser Lys Ser Thr Ser Gly Gly
        115                 120                 125

Thr Ala Ala Leu Gly Cys Leu Val Lys Asp Tyr Phe Pro Glu Pro Val
    130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210
```

<210> SEQ ID NO 178
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 178

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80
```

```
Pro Val Glu Lys Val Asp Ala Ala Thr Tyr His Cys Gln Gln Ser Thr
                85                  90                  95
Glu Asp Pro Trp Thr Phe Gly Gly Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445

<210> SEQ ID NO 179
<211> LENGTH: 698
<212> TYPE: PRT
<213> ORGANISM: Artificial
<220> FEATURE:
<223> OTHER INFORMATION: Chimeric homo sapiens mus musculus

<400> SEQUENCE: 179
```

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Thr Ala Tyr
65              70                  75                  80

Met Gln Leu Ser Ser Leu Ala Ser Glu Asp Ser Ala Val Tyr Phe Cys
            85                  90                  95

Ala Arg Arg Glu Thr Thr Thr Val Gly Arg Tyr Tyr Tyr Ala Met Asp
                100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415
```

```
Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Ser Thr Gly Ser Glu Val Gln Leu Gln Gln Ser
    450                 455                 460

Gly Pro Glu Leu Val Lys Pro Gly Ala Ser Val Lys Ile Ser Cys Lys
465                 470                 475                 480

Thr Ser Gly Tyr Thr Phe Thr Glu Tyr Thr Met His Trp Val Lys Gln
                485                 490                 495

Ser His Gly Lys Ser Leu Glu Trp Ile Gly Gly Ile Ser Pro Asn Ile
            500                 505                 510

Gly Gly Thr Ser Tyr Asn Gln Lys Phe Lys Gly Lys Ala Thr Leu Thr
        515                 520                 525

Val Asp Lys Ser Ser Ser Thr Ala Tyr Met Glu Leu Arg Ser Leu Thr
    530                 535                 540

Ser Glu Asp Ser Ala Val Tyr Tyr Cys Ala Arg Arg Gly Gly Ser Phe
545                 550                 555                 560

Asp Tyr Trp Gly Gln Gly Thr Thr Leu Thr Val Ser Ser Val Glu Gly
                565                 570                 575

Gly Ser Gly Gly Ser Gly Gly Ser Gly Gly Ser Gly Gly Val Asp Asp
            580                 585                 590

Ile Val Met Thr Gln Ser Pro Ala Thr Leu Ser Val Thr Pro Gly Asp
        595                 600                 605

Arg Val Ser Leu Ser Cys Arg Ala Ser Gln Ser Ile Ser Asp Tyr Leu
    610                 615                 620

His Trp Tyr Gln Gln Lys Ser His Glu Ser Pro Arg Leu Leu Ile Lys
625                 630                 635                 640

Tyr Ala Ser Gln Ser Ile Ser Gly Ile Pro Ser Arg Phe Ser Gly Ser
                645                 650                 655

Gly Ser Gly Ser Asp Phe Thr Leu Ser Ile Asn Ser Val Glu Pro Glu
            660                 665                 670

Asp Val Gly Val Tyr Tyr Cys Gln Asn Gly His Ser Phe Pro Leu Thr
        675                 680                 685

Phe Gly Ala Gly Thr Lys Leu Glu Leu Lys
    690                 695
```

<210> SEQ ID NO 180
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 180

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80
```

Pro Val Glu Lys Val Asp Ala Ala Thr Tyr His Cys Gln Gln Ser Thr
             85                  90                  95

Glu Asp Pro Trp Thr Phe Gly Gly Thr Lys Leu Glu Ile Lys Arg
        100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Ser Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 181
<211> LENGTH: 698
<212> TYPE: PRT
<213> ORGANISM: Artificial
<220> FEATURE:
<223> OTHER INFORMATION: Chimeric homo sapiens mus musculus

<400> SEQUENCE: 181

-continued

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Thr Ala Tyr
65                  70                  75                  80

Met Gln Leu Ser Ser Leu Ala Ser Glu Asp Ser Ala Val Tyr Phe Cys
            85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Ser
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys

```
                420                 425                 430
Ser Val Met His Glu Ala Leu His Asn His Tyr Thr Gln Lys Ser Leu
            435                 440                 445

Ser Leu Ser Pro Gly Ser Thr Gly Ser Glu Val Gln Leu Gln Gln Ser
450                 455                 460

Gly Pro Glu Leu Val Lys Pro Gly Ala Ser Val Lys Ile Ser Cys Lys
465                 470                 475                 480

Thr Ser Gly Tyr Thr Phe Thr Glu Tyr Thr Met His Trp Val Lys Gln
                485                 490                 495

Ser His Gly Lys Ser Leu Glu Trp Ile Gly Gly Ile Ser Pro Asn Ile
            500                 505                 510

Gly Gly Thr Ser Tyr Asn Gln Lys Phe Lys Gly Lys Ala Thr Leu Thr
        515                 520                 525

Val Asp Lys Ser Ser Ser Thr Ala Tyr Met Glu Leu Arg Ser Leu Thr
    530                 535                 540

Ser Glu Asp Ser Ala Val Tyr Tyr Cys Ala Arg Arg Gly Gly Ser Phe
545                 550                 555                 560

Asp Tyr Trp Gly Gln Gly Thr Thr Leu Thr Val Ser Ser Val Glu Gly
                565                 570                 575

Gly Ser Gly Gly Ser Gly Gly Ser Gly Gly Ser Gly Gly Val Asp Asp
            580                 585                 590

Ile Val Met Thr Gln Ser Pro Ala Thr Leu Ser Val Thr Pro Gly Asp
        595                 600                 605

Arg Val Ser Leu Ser Cys Arg Ala Ser Gln Ser Ile Ser Asp Tyr Leu
    610                 615                 620

His Trp Tyr Gln Gln Lys Ser His Glu Ser Pro Arg Leu Leu Ile Lys
625                 630                 635                 640

Tyr Ala Ser Gln Ser Ile Ser Gly Ile Pro Ser Arg Phe Ser Gly Ser
                645                 650                 655

Gly Ser Gly Ser Asp Phe Thr Leu Ser Ile Asn Ser Val Glu Pro Glu
            660                 665                 670

Asp Val Gly Val Tyr Tyr Cys Gln Asn Gly His Ser Phe Pro Leu Thr
        675                 680                 685

Phe Gly Ala Gly Thr Lys Leu Glu Leu Lys
    690                 695

<210> SEQ ID NO 182
<211> LENGTH: 454
<212> TYPE: PRT
<213> ORGANISM: Artificial
<220> FEATURE:
<223> OTHER INFORMATION: Chimeric homo sapiens mus musculus

<400> SEQUENCE: 182

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
```

```
            85                  90                  95
Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Ser
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Lys
        450

<210> SEQ ID NO 183
<211> LENGTH: 670
<212> TYPE: PRT
<213> ORGANISM: Artificial
<220> FEATURE:
<223> OTHER INFORMATION: Chimeric homo sapiens mus musculus
```

```
<400> SEQUENCE: 183

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Ser Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415
```

```
Gly Asn Val Phe Ser Cys Ser Val Met His Glu Ala Leu His Asn His
            420                 425                 430

Tyr Thr Gln Lys Ser Leu Ser Leu Ser Pro Gly Ser Thr Gly Ser Glu
            435                 440                 445

Val Gln Leu Gln Gln Ser Gly Pro Glu Leu Val Lys Pro Gly Ala Ser
450                 455                 460

Val Lys Ile Ser Cys Lys Thr Ser Gly Tyr Thr Phe Thr Glu Tyr Thr
465                 470                 475                 480

Met His Trp Val Lys Gln Ser His Gly Lys Ser Leu Glu Trp Ile Gly
            485                 490                 495

Gly Ile Ser Pro Asn Ile Gly Gly Thr Ser Tyr Asn Gln Lys Phe Lys
            500                 505                 510

Gly Lys Ala Thr Leu Thr Val Asp Lys Ser Ser Ser Thr Ala Tyr Met
            515                 520                 525

Glu Leu Arg Ser Leu Thr Ser Glu Asp Ser Ala Val Tyr Tyr Cys Ala
            530                 535                 540

Arg Arg Gly Gly Ser Phe Asp Tyr Trp Gly Gln Gly Thr Thr Leu Thr
545                 550                 555                 560

Val Ser Ser Arg Thr Val Ala Ala Pro Ser Val Phe Ile Phe Pro Pro
            565                 570                 575

Ser Asp Glu Gln Leu Lys Ser Gly Thr Ala Ser Val Val Cys Leu Leu
            580                 585                 590

Asn Asn Phe Tyr Pro Arg Glu Ala Lys Val Gln Trp Lys Val Asp Asn
            595                 600                 605

Ala Leu Gln Ser Gly Asn Ser Gln Glu Ser Val Thr Glu Gln Asp Ser
            610                 615                 620

Lys Asp Ser Thr Tyr Ser Leu Ser Ser Thr Leu Thr Leu Ser Lys Ala
625                 630                 635                 640

Asp Tyr Glu Lys His Lys Val Tyr Ala Cys Glu Val Thr His Gln Gly
            645                 650                 655

Leu Ser Ser Pro Val Thr Lys Ser Phe Asn Arg Gly Glu Cys
            660                 665                 670

<210> SEQ ID NO 184
<211> LENGTH: 214
<212> TYPE: PRT
<213> ORGANISM: Artificial
<220> FEATURE:
<223> OTHER INFORMATION: Chimeric homo sapiens mus musculus

<400> SEQUENCE: 184

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys Ala Ser Thr Lys Gly
            100                 105                 110
```

Pro Ser Val Phe Pro Leu Ala Pro Ser Ser Lys Ser Thr Ser Gly Gly
            115                 120                 125

Thr Ala Ala Leu Gly Cys Leu Val Lys Asp Tyr Phe Pro Glu Pro Val
        130                 135                 140

Thr Val Ser Trp Asn Ser Gly Ala Leu Thr Ser Gly Val His Thr Phe
145                 150                 155                 160

Pro Ala Val Leu Gln Ser Ser Gly Leu Tyr Ser Leu Ser Ser Val Val
                165                 170                 175

Thr Val Pro Ser Ser Ser Leu Gly Thr Gln Thr Tyr Ile Cys Asn Val
            180                 185                 190

Asn His Lys Pro Ser Asn Thr Lys Val Asp Lys Arg Val Glu Pro Lys
        195                 200                 205

Ser Cys Asp Lys Thr His
    210

<210> SEQ ID NO 185
<211> LENGTH: 445
<212> TYPE: PRT
<213> ORGANISM: Artificial
<220> FEATURE:
<223> OTHER INFORMATION: Chimeric homo sapiens mus musculus

<400> SEQUENCE: 185

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

```
Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Ser Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 186
<211> LENGTH: 671
<212> TYPE: PRT
<213> ORGANISM: Artificial
<220> FEATURE:
<223> OTHER INFORMATION: Chimeric homo sapiens mus musculus

<400> SEQUENCE: 186

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175
```

```
Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Ser
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Ser Thr Gly Ser Asp Ile Val Met Thr Gln Ser
    450                 455                 460

Pro Ala Thr Leu Ser Val Thr Pro Gly Asp Arg Val Ser Leu Ser Cys
465                 470                 475                 480

Arg Ala Ser Gln Ser Ile Ser Asp Tyr Leu His Trp Tyr Gln Gln Lys
                485                 490                 495

Ser His Glu Ser Pro Arg Leu Leu Ile Lys Tyr Ala Ser Gln Ser Ile
            500                 505                 510

Ser Gly Ile Pro Ser Arg Phe Ser Gly Ser Gly Ser Gly Ser Asp Phe
        515                 520                 525

Thr Leu Ser Ile Asn Ser Val Glu Pro Glu Asp Val Gly Val Tyr Tyr
    530                 535                 540

Cys Gln Asn Gly His Ser Phe Pro Leu Thr Phe Gly Ala Gly Thr Lys
545                 550                 555                 560

Leu Glu Leu Lys Ala Ser Thr Lys Gly Pro Ser Val Phe Pro Leu Ala
                565                 570                 575

Pro Ser Ser Lys Ser Thr Ser Gly Gly Thr Ala Ala Leu Gly Cys Leu
            580                 585                 590
```

```
Val Lys Asp Tyr Phe Pro Glu Pro Val Thr Val Ser Trp Asn Ser Gly
        595                 600                 605

Ala Leu Thr Ser Gly Val His Thr Phe Pro Ala Val Leu Gln Ser Ser
    610                 615                 620

Gly Leu Tyr Ser Leu Ser Ser Val Val Thr Val Pro Ser Ser Ser Leu
625                 630                 635                 640

Gly Thr Gln Thr Tyr Ile Cys Asn Val Asn His Lys Pro Ser Asn Thr
                645                 650                 655

Lys Val Asp Lys Arg Val Glu Pro Lys Ser Cys Asp Lys Thr His
        660                 665                 670
```

<210> SEQ ID NO 187
<211> LENGTH: 223
<212> TYPE: PRT
<213> ORGANISM: Artificial
<220> FEATURE:
<223> OTHER INFORMATION: Chimeric homo sapiens mus musculus

<400> SEQUENCE: 187

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Ser Pro Asn Ile Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Gly Gly Ser Phe Asp Tyr Trp Gly Gln Gly Thr Thr Leu
            100                 105                 110

Thr Val Ser Ser Arg Thr Val Ala Ala Pro Ser Val Phe Ile Phe Pro
        115                 120                 125

Pro Ser Asp Glu Gln Leu Lys Ser Gly Thr Ala Ser Val Val Cys Leu
    130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
    210                 215                 220
```

<210> SEQ ID NO 188
<211> LENGTH: 18
<212> TYPE: PRT
<213> ORGANISM: Artificial Sequence
<220> FEATURE:
<223> OTHER INFORMATION: Flexible Linker

<400> SEQUENCE: 188

```
Gly Glu Gly Thr Ser Thr Gly Ser Gly Gly Ser Gly Gly Ser Gly Gly
1               5                   10                  15
```

Ala Asp

<210> SEQ ID NO 189
<211> LENGTH: 15
<212> TYPE: PRT
<213> ORGANISM: Artificial Sequence
<220> FEATURE:
<223> OTHER INFORMATION: Flexible Linker

<400> SEQUENCE: 189

Gly Gly Gly Gly Ser Gly Gly Gly Gly Ser Gly Gly Gly Gly Ser
1               5                   10                  15

<210> SEQ ID NO 190
<211> LENGTH: 5
<212> TYPE: PRT
<213> ORGANISM: Artificial Sequence
<220> FEATURE:
<223> OTHER INFORMATION: Linker Sequence

<400> SEQUENCE: 190

Gly Gly Gly Ser Ser
1               5

<210> SEQ ID NO 191
<211> LENGTH: 4
<212> TYPE: PRT
<213> ORGANISM: Artificial Sequence
<220> FEATURE:
<223> OTHER INFORMATION: Linker Sequence

<400> SEQUENCE: 191

Arg Thr Val Ala
1

<210> SEQ ID NO 192
<211> LENGTH: 5
<212> TYPE: PRT
<213> ORGANISM: Artificial Sequence
<220> FEATURE:
<223> OTHER INFORMATION: Linker Sequence

<400> SEQUENCE: 192

Pro Ala Ala Ala Pro
1               5

<210> SEQ ID NO 193
<211> LENGTH: 5
<212> TYPE: PRT
<213> ORGANISM: Artificial Sequence
<220> FEATURE:
<223> OTHER INFORMATION: Linker Sequence

<400> SEQUENCE: 193

Pro Ala Ala Ala Ser
1               5

<210> SEQ ID NO 194
<211> LENGTH: 5
<212> TYPE: PRT
<213> ORGANISM: Artificial Sequence
<220> FEATURE:
<223> OTHER INFORMATION: Linker Sequence

<400> SEQUENCE: 194

Ser Ala Ala Ala Ser

```
<210> SEQ ID NO 195
<211> LENGTH: 10
<212> TYPE: PRT
<213> ORGANISM: Artificial Sequence
<220> FEATURE:
<223> OTHER INFORMATION: Linker Sequence

<400> SEQUENCE: 195

Asp Lys Thr His Thr Cys Pro Pro Cys Pro
1               5                   10

<210> SEQ ID NO 196
<211> LENGTH: 15
<212> TYPE: PRT
<213> ORGANISM: Artificial Sequence
<220> FEATURE:
<223> OTHER INFORMATION: Linker Sequence

<400> SEQUENCE: 196

Gly Gly Gly Gly Ser Gly Gly Gly Gly Ser Gly Gly Gly Gly Ser
1               5                   10                  15

<210> SEQ ID NO 197
<211> LENGTH: 5
<212> TYPE: PRT
<213> ORGANISM: Artificial Sequence
<220> FEATURE:
<223> OTHER INFORMATION: Linker Sequence

<400> SEQUENCE: 197

Gly Gly Gly Gly Ser
1               5

<210> SEQ ID NO 198
<211> LENGTH: 18
<212> TYPE: PRT
<213> ORGANISM: Artificial Sequence
<220> FEATURE:
<223> OTHER INFORMATION: Linker Sequence

<400> SEQUENCE: 198

Val Glu Gly Gly Ser Gly Gly Ser Gly Gly Ser Gly Gly Ser Gly Gly
1               5                   10                  15

Val Asp

<210> SEQ ID NO 199
<211> LENGTH: 4
<212> TYPE: PRT
<213> ORGANISM: Artificial Sequence
<220> FEATURE:
<223> OTHER INFORMATION: Linker Sequence

<400> SEQUENCE: 199

Ser Thr Gly Ser
1

<210> SEQ ID NO 200
<211> LENGTH: 15
<212> TYPE: PRT
<213> ORGANISM: Artificial Sequence
<220> FEATURE:
<223> OTHER INFORMATION: Linker Sequence

<400> SEQUENCE: 200
```

-continued

```
Gly Gly Gly Gly Ser Gly Gly Gly Ser Gly Gly Gly Ser
1               5                   10                  15

<210> SEQ ID NO 201
<211> LENGTH: 5
<212> TYPE: PRT
<213> ORGANISM: Artificial Sequence
<220> FEATURE:
<223> OTHER INFORMATION: Linker Sequence

<400> SEQUENCE: 201

Gly Gly Gly Gly Ser
1               5

<210> SEQ ID NO 202
<211> LENGTH: 18
<212> TYPE: PRT
<213> ORGANISM: Artificial Sequence
<220> FEATURE:
<223> OTHER INFORMATION: Linker Sequence

<400> SEQUENCE: 202

Val Glu Gly Gly Ser Gly Gly Ser Gly Gly Ser Gly Gly Ser Gly Gly
1               5                   10                  15

Val Asp
```